United States Patent
Caulfield et al.

(10) Patent No.: US 9,738,688 B2
(45) Date of Patent: Aug. 22, 2017

(54) HIV-1 ENVELOPE GLYCOPROTEIN

(71) Applicants: INTERNATIONAL AIDS VACCINE INITIATIVE, New York, NY (US); CORNELL UNIVERSITY, Ithaca, NY (US); THE SCRIPPS RESEARCH INSTITUTE, La Jolla, CA (US)

(72) Inventors: Michael Caulfield, Fort Washington, PA (US); Albert Cupo, Stamford, CT (US); Hansi Dean, New York, NY (US); Simon Hoffenberg, Hartsdale, NY (US); C. Richter King, Washington, DC (US); P. J. Klasse, New York, NY (US); Andre Marozsan, Milford, CT (US); John P. Moore, New York, NY (US); Rogier W. Sanders, New York, NY (US); Andrew Ward, San Diego, CA (US); Ian Wilson, La Jolla, CA (US); Jean-Philippe Julien, San Diego, CA (US)

(73) Assignees: INTERNATIONAL AIDS VACCINE INITIATIVE, New York, NY (US); THE SCRIPPS RESEARCH INSTITUTE, La Jolla, CA (US); CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/072,209

(22) Filed: Nov. 5, 2013

(65) Prior Publication Data

US 2014/0212458 A1 Jul. 31, 2014

Related U.S. Application Data

(60) Provisional application No. 61/722,739, filed on Nov. 5, 2012.

(51) Int. Cl.
*A61K 39/21* (2006.01)
*C07K 14/005* (2006.01)
*A61K 39/39* (2006.01)
*A61K 39/12* (2006.01)

(52) U.S. Cl.
CPC ............ *C07K 14/005* (2013.01); *A61K 39/12* (2013.01); *A61K 39/21* (2013.01); *A61K 39/39* (2013.01);
(Continued)

(58) Field of Classification Search
None
See application file for complete search history.

(56) References Cited

U.S. PATENT DOCUMENTS

2005/0089526 A1* 4/2005 Moore et al. ............ 424/188.1
2006/0275897 A1* 12/2006 Nabel et al. ............. 435/320.1
2008/0274134 A1* 11/2008 Schulke et al. ......... 424/196.11

FOREIGN PATENT DOCUMENTS

EP         2765138 A2    8/2014
WO    WO 2006/002079    1/2006
(Continued)

OTHER PUBLICATIONS

Dey et al. Specific amino acids in the N-terminus of the gp41 ectodomain contribute to the stabilization of a soluble, cleaved gp140 envelope glycoprotein from human immunodeficiency virus type 1. Virol. 2007; 360(1): 199-208.*

(Continued)

*Primary Examiner* — Janet L Andres
*Assistant Examiner* — Stuart W Snyder
(74) *Attorney, Agent, or Firm* — Vedder Price P.C.; Thomas J. Kowalski; Deborah L. Lu

(57) ABSTRACT

The present application relates to novel HIV-1 envelope glycoproteins, which may be utilized as HIV-1 vaccine immunogens, and antigens for crystallization, electron
(Continued)

microscopy and other biophysical, biochemical and immunological studies for the identification of broad neutralizing antibodies. The present invention encompasses the preparation and purification of immunogenic compositions, which are formulated into the vaccines of the present invention.

19 Claims, 50 Drawing Sheets

(52) U.S. Cl.
CPC .............. *C12N 2740/16034* (2013.01); *C12N 2740/16122* (2013.01)

(56) References Cited

FOREIGN PATENT DOCUMENTS

| WO | WO 2007/149490 | 12/2007 | |
|---|---|---|---|
| WO | WO 2011/109511 | 9/2011 | |
| WO | WO 2011/109511 A2 * | 9/2011 | .............. C12Q 1/70 |

OTHER PUBLICATIONS

Sanders et al. Stabilization of the Soluble, Cleaved, Trimeric Form of the Envelope Glycoprotein Complex of Human Immunodeficiency Virus Type 1. J. Virol. 2002; 76(17): 8875-8889.*

Fisher et al. Isolation and Characterization of the Human Tissue-type Plasminogen Activator Structural Gene Including Its 5' Flanking Region. J. Biol. Chem. 1985; 260(20): 11223-11230.*

Beddows, et al., Construction and Characterization of Soluble, Cleaved, and Stabilized Trimeric Env Proteins Based on HIV Type 1 Env Subtype A, AIDS Research and Human Retroviruses (2006) vol. 22, No. 6, p. 569-579.

Hoffenberg, et al., Identification of a Clade a HIV Envelope Immunogen from Protocol G that Elicits Neutralizing Antibodies to Tier 2 Viruses, Retrovirology (2012) vol. 9, Suppl. 2.

Klasse, et al., Influences on Trimerization and Aggregation of Soluble, Cleaved HIV-1 SOSIP Envelope Glycoprotein, Journal of Virology (2013) vol. 87, No. 17, p. 9873-9885.

Melchers, et al., A Stabilized HIV-1 Envelope Glycoprotein Trimer Fused to CD40 Ligand Targets and Activates Dendritic Cells, Retrovirology (2011) vol. 8, No. 48, p. 1-15.

Sanders, et al., A Next-Generation Cleaved, Soluble HIV-1 Env. Trimer, BG505 SOSIP.664 gp140, Expressing Multiple Epitopes for Broadly Neutralizing but not Non-Neutralizing Antibodies, PLOS Pathogens (2013) vol. 9, Issue 9, e1003618, p. 1-20.

Extended EP Search Report dated Aug. 7, 2014 for EP Application No. 13191697.5.

* cited by examiner

FIG. 1
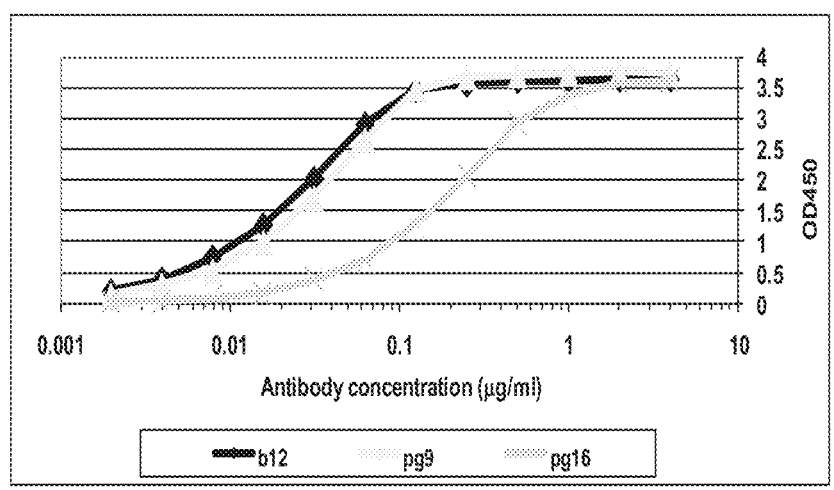
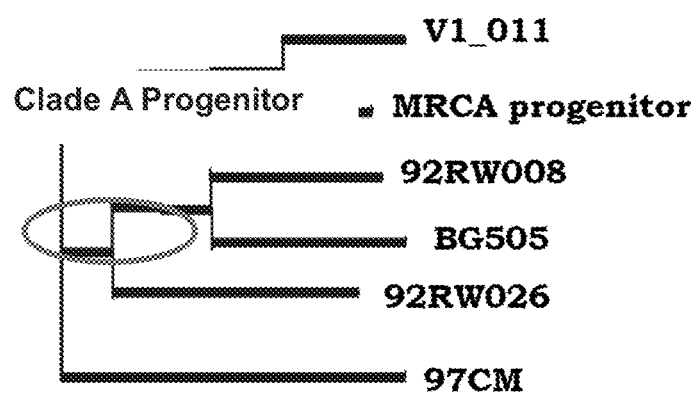

FIG. 2A

```
     BssHII
   AscI     EcoRI                              PstI                    BspMI
     GGCGCGCCGAATTCGCCACCATGCCTATGGGCAGCCTGCAGCCTCTGGCCACACTGTACC
  1  ---------+---------+---------+---------+---------+---------+
     CCGCGCGGCTTAAGCGGTGGTACGGATACCCGTCGGACGTCGGAGACCGGTGTGACATGG
                         M  P  M  G  S  L  Q  P  L  A  T  L  Y  L
                         1     3     5     7     9     11    13

SphI
     TGCTGGGCATGCTGGTGGCCTCTGTGCTGGCCGCCGAGAACCTGTGGGTGACAGTGTACT
 61  ---------+---------+---------+---------+---------+---------+
     ACGACCCGTACGACCACCGGAGACACGACCGGCGGCTCTTGGACACCCACTGTCACATGA
      L  G  M  L  V  A  S  V  L  A  A  E  N  L  W  V  T  V  Y  Y
      15    17    19    21    23    25    27    29    31    33

StuI
     ACGGCGTGCCCGTGTGGAAGGACGCCGAGACAACCCTGTTCTGCGCCAGCGACGCCAAGG
121  ---------+---------+---------+---------+---------+---------+
     TGCCGCACGGGCACACCTTCCTGCGGCTCTGTTGGGACAAGACGCGGTCGCTGCGGTTCC
      G  V  P  V  W  K  D  A  E  T  T  L  F  C  A  S  D  A  K  A
      35    37    39    41    43    45    47    49    51    53

CCTACGAGACAGAGAAGCACAACGTGTGGGCCACCCACGCCTGCGTGCCAACCGACCCTA
181  ---------+---------+---------+---------+---------+---------+
     GGATGCTCTGTCTCTTCGTGTTGCACACCCGGTGGGTGCGGACGCACGGTTGGCTGGGAT
      Y  E  T  E  K  H  N  V  W  A  T  H  A  C  V  P  T  D  P  N
      55    57    59    61    63    65    67    69    71    73

ACCCCAGGAAATCCACCTGGAAAACGTGACCGAAGAGTTCAACATGTGGAAGAACAACA
241  ---------+---------+---------+---------+---------+---------+
     TGGGGGTCCTTTAGGTGGACCTTTTGCACTGGCTTCTCAAGTTGTACACCTTCTTGTTGT
      P  Q  E  I  H  L  E  N  V  T  E  E  F  N  M  W  K  N  N  M
      75    77    79    81    83    85    87    89    91    93
```

FIG. 2B

```
      TGGTGGAACAGATGCACACCGACATCATCAGCCTGTGGGACCAGAGCCTGAAGCCCTGCG
301   ---------+---------+---------+---------+---------+---------+
      ACCACCTTGTCTACGTGTGGCTGTAGTAGTCGGACACCCTGGTCTCGGACTTCGGGACGC
       V   E   Q   M   H   T   D   I   I   S   L   W   D   Q   S   L   K   P   C   V
        95      97      99     101     103     105     107     109     111     113

PstI
      TGAAGCTGACCCCCCTGTGCGTGACCCTGCAGTGCACCAACGTGACCAACAACATCACCG
361   ---------+---------+---------+---------+---------+---------+
      ACTTCGACTGGGGGGACACGCACTGGGACGTCACGTGGTTGCACTGGTTGTTGTAGTGGC
       K   L   T   P   L   C   V   T   L   Q   C   T   N   V   T   N   N   I   T   D
       115     117     119     121     123     125     127     129     131     133

PstI
      ACGACATGCGGGGCGAGCTGAAGAACTGCAGCTTCAACATGACCACCGAGCTGCGGGACA
421   ---------+---------+---------+---------+---------+---------+
      TGCTGTACGCCCCGCTCGACTTCTTGACGTCGAAGTTGTACTGGTGGCTCGACGCCCTGT
       D   M   R   G   E   L   K   N   C   S   F   N   M   T   T   E   L   R   D   K
       135     137     139     141     143     145     147     149     151     153

AGAAACAGAAGGTGTACAGCCTGTTCTACCGGCTGGACGTGGTGCAGATCAACGAGAACC
481   ---------+---------+---------+---------+---------+---------+
      TCTTTGTCTTCCACATGTCGGACAAGATGGCCGACCTGCACCACGTCTAGTTGCTCTTGG
       K   Q   K   V   Y   S   L   F   Y   R   L   D   V   V   Q   I   N   E   N   Q
       155     157     159     161     163     165     167     169     171     173

BclI
      AGGGCAACAGAAGCAACAACAGCAACAAAGAGTACCGGCTGATCAACTGCAACACCAGCG
541   ---------+---------+---------+---------+---------+---------+
      TCCCGTTGTCTTCGTTGTTGTCGTTGTTTCTCATGGCCGACTAGTTGACGTTGTGGTCGC
       G   N   R   S   N   N   S   N   K   E   Y   R   L   I   N   C   N   T   S   A
       175     177     179     181     183     185     187     189     191     193

StuI
      CCATCACCCAGGCCTGCCCCAAGGTGTCCTTCGAGCCCATCCCCATCCACTACTGCGCCC
601   ---------+---------+---------+---------+---------+---------+
      GGTAGTGGGTCCGGACGGGGTTCCACAGGAAGCTCGGGTAGGGGTAGGTGATGACGCGGG
       I   T   Q   A   C   P   K   V   S   F   E   P   I   P   I   H   Y   C   A   P
       195     197     199     201     203     205     207     209     211     213

CTGCCGGCTTCGCCATCCTGAAGTGCAAGGACAAGAAGTTCAACGGCACCGGCCCCTGCC
661   ---------+---------+---------+---------+---------+---------+
      GACGGCCGAAGCGGTAGGACTTCACGTTCCTGTTCTTCAAGTTGCCGTGGCCGGGGACGG
       A   G   F   A   I   L   K   C   K   D   K   K   F   N   G   T   G   P   C   P
       215     217     219     221     223     225     227     229     231     233

PvuII
      CCAGCGTGTCCACAGTGCAGTGTACCCACGGCATCAAGCCCGTGGTGTCCACCCAGCTGC
721   ---------+---------+---------+---------+---------+---------+
      GGTCGCACAGGTGTCACGTCACATGGGTGCCGTAGTTCGGGCACCACAGGTGGGTCGACG
       S   V   S   T   V   Q   C   T   H   G   I   K   P   V   V   S   T   Q   L   L
       235     237     239     241     243     245     247     249     251     253

BclI
      TGCTGAACGGCAGCCTGGCCGAAGAGGAAGTGATGATCAGAAGCGAGAACATCACCAACA
781   ---------+---------+---------+---------+---------+---------+
      ACGACTTGCCGTCGGACCGGCTTCTCCTTCACTACTAGTCTTCGCTCTTGTAGTGGTTGT
       L   N   G   S   L   A   E   E   E   V   M   I   R   S   E   N   I   T   N   N
       255     257     259     261     263     265     267     269     271     273
```

FIG. 2C

```
     ACGCCAAGAACATCCTGGTGCAGTTCAACACCCCCGTGCAGATTAACTGCACCCGGCCCA
841  ---------+---------+---------+---------+---------+---------+
     TGCGGTTCTTGTAGGACCACGTCAAGTTGTGGGGGCACGTCTAATTGACGTGGGCCGGGT
      A   K   N   I   L   V   Q   F   N   T   P   V   Q   I   N   C   T   R   P   N
         275     277     279     281     283     285     287     289     291     293

StuI
     ACAACAACACCAGAAAGAGCATCCGGATCGGCCCAGGCCAGGCCTTCTACGCCACCGGCG
901  ---------+---------+---------+---------+---------+---------+
     TGTTGTTGTGGTCTTTCTCGTAGGCCTAGCCGGGTCCGGTCCGGAAGATGCGGTGGCCGC
      N   N   T   R   K   S   I   R   I   G   P   G   Q   A   F   Y   A   T   G   D
         295     297     299     301     303     305     307     309     311     313

ACATCATCGGCGACATCCGGCAGGCCCACTGCACCGTGTCCAAGGCCACCTGGAACGAGA
961  ---------+---------+---------+---------+---------+---------+
     TGTAGTAGCCGCTGTAGGCCGTCCGGGTGACGTGGCACAGGTTCCGGTGGACCTTGCTCT
      I   I   G   D   I   R   Q   A   H   C   T   V   S   K   A   T   W   N   E   T
         315     317     319     321     323     325     327     329     331     333

PvuII
     CACTGGGCAAGGTGGTGAAACAGCTGCGGAAGCACTTCGGGAACAACACCATCATCCGCT
1021 ---------+---------+---------+---------+---------+---------+
     GTGACCCGTTCCACCACTTTGTCGACGCCTTCGTGAAGCCCTTGTTGTGGTAGTAGGCGA
      L   G   K   V   V   K   Q   L   R   K   H   F   G   N   N   T   I   I   R   F
         335     337     339     341     343     345     347     349     351     353

TCGCCAACAGCTCTGGCGGCGACCTGGAAGTGACCACCCACAGCTTCAACTGTGGCGGCG
1081 ---------+---------+---------+---------+---------+---------+
     AGCGGTTGTCGAGACCGCCGCTGGACCTTCACTGGTGGGTGTCGAAGTTGACACCGCCGC
      A   N   S   S   G   G   D   L   E   V   T   T   H   S   F   N   C   G   G   E
         355     357     359     361     363     365     367     369     371     373

AGTTCTTCTACTGCAATACCTCCGGCCTGTTCAACAGCACCTGGATCAGCAATACCAGCG
1141 ---------+---------+---------+---------+---------+---------+
     TCAAGAAGATGACGTTATGGAGGCCGGACAAGTTGTCGTGGACCTAGTCGTTATGGTCGC
      F   F   Y   C   N   T   S   G   L   F   N   S   T   W   I   S   N   T   S   V
         375     377     379     381     383     385     387     389     391     393

TGCAGGGCAGCAACAGCACCGGCAGCAACGACAGCATCACCCTGCCCTGCCGGATCAAGC
1201 ---------+---------+---------+---------+---------+---------+
     ACGTCCCGTCGTTGTCGTGGCCGTCGTTGCTGTCGTAGTGGGACGGGACGGCCTAGTTCG
      Q   G   S   N   S   T   G   S   N   D   S   I   T   L   P   C   R   I   K   Q
         395     397     399     401     403     405     407     409     411     413

AGATCATCAATATGTGGCAGCGGATTGGCCAGGCTATGTACGCCCCACCCATCCAGGGCG
1261 ---------+---------+---------+---------+---------+---------+
     TCTAGTAGTTATACACCGTCGCCTAACCGGTCCGATACATGCGGGGTGGGTAGGTCCCGC
      I   I   N   M   W   Q   R   I   G   Q   A   M   Y   A   P   P   I   Q   G   V
         415     417     419     421     423     425     427     429     431     433

BclI                                 SmaI
     TGATCAGATGCGTGTCCAATATCACCGGCCTGATCCTGACCCGGGACGGCGGCTCTACCA
1321 ---------+---------+---------+---------+---------+---------+
     ACTAGTCTACGCACAGGTTATAGTGGCCGGACTAGGACTGGGCCCTGCCGCCGAGATGGT
      I   R   C   V   S   N   I   T   G   L   I   L   T   R   D   G   G   S   T   N
         435     437     439     441     443     445     447     449     451     453

ACAGCACCACCGAAACCTTCAGACCCGGCGGAGGCGACATGAGAGACAACTGGCGGAGCG
1381 ---------+---------+---------+---------+---------+---------+
     TGTCGTGGTGGCTTTGGAAGTCTGGGCCGCCTCCGCTGTACTCTCTGTTGACCGCCTCGC
      S   T   T   E   T   F   R   P   G   G   G   D   M   R   D   N   W   R   S   E
         455     457     459     461     463     465     467     469     471     473
```

FIG. 2D

```
     AGCTGTACAAGTACAAAGTGGTGAAAATCGAGCCCCTGGGCGTGGCCCCCACCAGAGCCA
1441 ---------+---------+---------+---------+---------+---------+
     TCGACATGTTCATGTTTCACCACTTTTAGCTCGGGGACCCGCACCGGGGGTGGTCTCGGT
      L   Y   K   Y   K   V   V   K   I   E   P   L   G   V   A   P   T   R   A   K
       475     477     479     481     483     485     487     489     491     493
```

```
                                                              NotI
                                                              EagI
     AGAGAAGAGTGGTCGGAAGCGAGAAGTCCGGCCACCACCACCATCACCACTGAGCGGCCG
1501 ---------+---------+---------+---------+---------+---------+
     TCTCTTCTCACCAGCCTTCGCTCTTCAGGCCGGTGGTGGTGGTAGTGGTGACTCGCCGGC
      R   R   V   V   G   S   E   K   S   G   H   H   H   H   H   *
       495     497     499     501     503     505     507     509     511
```

```
     PacI
     CTTAATTAA
1561 ---------
     GAATTAATT
```

FIG. 3A

```
     BssHII
     AscI      EcoRI                              PstI                    BspMI
     GGCGCGCCGAATTCGCCACCATGCCTATGGGCAGCCTGCAGCCTCTGGCCACACTGTACC
  1  ---------+---------+---------+---------+---------+---------+
     CCGCGCGGCTTAAGCGGTGGTACGGATACCCGTCGGACGTCGGAGACCGGTGTGACATGG
                           M  P  M  G  S  L  Q  P  L  A  T  L  Y  L
                           1     3     5     7     9    11    13

SphI
     TGCTGGGCATGCTGGTGGCCTCTGTGCTGGCCGCCGAGAACCTGTGGGTGACAGTGTACT
 61  ---------+---------+---------+---------+---------+---------+
     ACGACCCGTACGACCACCGGAGACACGACCGGCGGCTCTTGGACACCCACTGTCACATGA
      L  G  M  L  V  A  S  V  L  A  A  E  N  L  W  V  T  V  Y  Y
        15    17    19    21    23    25    27    29    31    33

StuI
     ACGGCGTGCCCGTGTGGAAGGACGCCGAGACAACCCTGTTCTGCGCCAGCGACGCCAAGG
121  ---------+---------+---------+---------+---------+---------+
     TGCCGCACGGGCACACCTTCCTGCGGCTCTGTTGGGACAAGACGCGGTCGCTGCGGTTCC
        G  V  P  V  W  K  D  A  E  T  T  L  F  C  A  S  D  A  K  A
        35    37    39    41    43    45    47    49    51    53

CCTACGAGACAGAGAAGCACAACGTGTGGGCCACCCACGCCTGCGTGCCAACCGACCCTA
181  ---------+---------+---------+---------+---------+---------+
     GGATGCTCTGTCTCTTCGTGTTGCACACCCGGTGGGTGCGGACGCACGGTTGGCTGGGAT
        Y  E  T  E  K  H  N  V  W  A  T  H  A  C  V  P  T  D  P  N
        55    57    59    61    63    65    67    69    71    73

ACCCCCAGGAAATCCACCTGGAAAACGTGACCGAAGAGTTCAACATGTGGAAGAACAACA
241  ---------+---------+---------+---------+---------+---------+
     TGGGGGTCCTTTAGGTGGACCTTTTGCACTGGCTTCTCAAGTTGTACACCTTCTTGTTGT
        P  Q  E  I  H  L  E  N  V  T  E  E  F  N  M  W  K  N  N  M
        75    77    79    81    83    85    87    89    91    93
```

FIG. 3B

```
     TGGTGGAACAGATGCACACCGACATCATCAGCCTGTGGGACCAGAGCCTGAAGCCCTGCG
301  ---------+---------+---------+---------+---------+---------+
     ACCACCTTGTCTACGTGTGGCTGTAGTAGTCGGACACCCTGGTCTCGGACTTCGGGACGC
      V   E   Q   M   H   T   D   I   I   S   L   W   D   Q   S   L   K   P   C   V
       95      97      99     101     103     105     107     109     111     113
                                    PstI
     TGAAGCTGACCCCCCTGTGCGTGACCCTGCAGTGCACCAACGTGACCAACAACATCACCG
361  ---------+---------+---------+---------+---------+---------+
     ACTTCGACTGGGGGGACACGCACTGGGACGTCACGTGGTTGCACTGGTTGTTGTAGTGGC
      K   L   T   P   L   C   V   T   L   Q   C   T   N   V   T   N   N   I   T   D
      115     117     119     121     123     125     127     129     131     133
                                    PstI
     ACGACATGCGGGGCGAGCTGAAGAACTGCAGCTTCAACATGACCACCGAGCTGCGGGACA
421  ---------+---------+---------+---------+---------+---------+
     TGCTGTACGCCCCGCTCGACTTCTTGACGTCGAAGTTGTACTGGTGGCTCGACGCCCTGT
      D   M   R   G   E   L   K   N   C   S   F   N   M   T   T   E   L   R   D   K
      135     137     139     141     143     145     147     149     151     153

AGAAACAGAAGGTGTACAGCCTGTTCTACCGGCTGGACGTGGTGCAGATCAACGAGAACC
481  ---------+---------+---------+---------+---------+---------+
     TCTTTGTCTTCCACATGTCGGACAAGATGGCCGACCTGCACCACGTCTAGTTGCTCTTGG
      K   Q   K   V   Y   S   L   F   Y   R   L   D   V   V   Q   I   N   E   N   Q
      155     157     159     161     163     165     167     169     171     173
                                              BclI
     AGGGCAACAGAAGCAACAACAGCAACAAAGAGTACCGGCTGATCAACTGCAACACCAGCG
541  ---------+---------+---------+---------+---------+---------+
     TCCCGTTGTCTTCGTTGTTGTCGTTGTTTCTCATGGCCGACTAGTTGACGTTGTGGTCGC
      G   N   R   S   N   N   S   N   K   E   Y   R   L   I   N   C   N   T   S   A
      175     177     179     181     183     185     187     189     191     193
          StuI
     CCATCACCCAGGCCTGCCCCAAGGTGTCCTTCGAGCCCATCCCCATCCACTACTGCGCCC
601  ---------+---------+---------+---------+---------+---------+
     GGTAGTGGGTCCGGACGGGGTTCCACAGGAAGCTCGGGTAGGGGTAGGTGATGACGCGGG
      I   T   Q   A   C   P   K   V   S   F   E   P   I   P   I   H   Y   C   A   P
      195     197     199     201     203     205     207     209     211     213

CTGCCGGCTTCGCCATCCTGAAGTGCAAGGACAAGAAGTTCAACGGCACCGGCCCCTGCC
661  ---------+---------+---------+---------+---------+---------+
     GACGGCCGAAGCGGTAGGACTTCACGTTCCTGTTCTTCAAGTTGCCGTGGCCGGGGACGG
      A   G   F   A   I   L   K   C   K   D   K   K   F   N   G   T   G   P   C   P
      215     217     219     221     223     225     227     229     231     233
                                                            PvuII
     CCAGCGTGTCCACAGTGCAGTGTACCCACGGCATCAAGCCCGTGGTGTCCACCCAGCTGC
721  ---------+---------+---------+---------+---------+---------+
     GGTCGCACAGGTGTCACGTCACATGGGTGCCGTAGTTCGGGCACCACAGGTGGGTCGACG
      S   V   S   T   V   Q   C   T   H   G   I   K   P   V   V   S   T   Q   L   L
      235     237     239     241     243     245     247     249     251     253
                                    BclI
     TGCTGAACGGCAGCCTGGCCGAAGAGGAAGTGATGATCAGAAGCGAGAACATCACCAACA
781  ---------+---------+---------+---------+---------+---------+
     ACGACTTGCCGTCGGACCGGCTTCTCCTTCACTACTAGTCTTCGCTCTTGTAGTGGTTGT
      L   N   G   S   L   A   E   E   E   V   M   I   R   S   E   N   I   T   N   N
      255     257     259     261     263     265     267     269     271     273
```

FIG. 3C

```
     ACGCCAAGAACATCCTGGTGCAGTTCAACACCCCCGTGCAGATTAACTGCACCCGGCCCA
841  ---------+---------+---------+---------+---------+---------+
     TGCGGTTCTTGTAGGACCACGTCAAGTTGTGGGGCACGTCTAATTGACGTGGGCCGGGT
      A   K   N   I   L   V   Q   F   N   T   P   V   Q   I   N   C   T   R   P   N
       275     277     279     281     283     285     287     289     291     293

StuI
     ACAACAACACCAGAAAGAGCATCCGGATCGGCCCAGGCCAGGCCTTCTACGCCACCGGCG
901  ---------+---------+---------+---------+---------+---------+
     TGTTGTTGTGGTCTTTCTCGTAGGCCTAGCCGGGTCCGGTCCGGAAGATGCGGTGGCCGC
      N   N   T   R   K   S   I   R   I   G   P   G   Q   A   F   Y   A   T   G   D
       295     297     299     301     303     305     307     309     311     313

ACATCATCGGCGACATCCGGCAGGCCCACTGCACCGTGTCCAAGGCCACCTGGAACGAGA
961  ---------+---------+---------+---------+---------+---------+
     TGTAGTAGCCGCTGTAGGCCGTCCGGGTGACGTGGCACAGGTTCCGGTGGACCTTGCTCT
      I   I   G   D   I   R   Q   A   H   C   T   V   S   K   A   T   W   N   E   T
       315     317     319     321     323     325     327     329     331     333

PvuII
     CACTGGGCAAGGTGGTGAAACAGCTGCGGAAGCACTTCGGGAACAACACCATCATCCGCT
1021 ---------+---------+---------+---------+---------+---------+
     GTGACCCGTTCCACCACTTTGTCGACGCCTTCGTGAAGCCCTTGTTGTGGTAGTAGGCGA
      L   G   K   V   V   K   Q   L   R   K   H   F   G   N   N   T   I   I   R   F
       335     337     339     341     343     345     347     349     351     353

TCGCCAACAGCTCTGGCGGCGACCTGGAAGTGACCACCCACAGCTTCAACTGTGGCGGCG
1081 ---------+---------+---------+---------+---------+---------+
     AGCGGTTGTCGAGACCGCCGCTGGACCTTCACTGGTGGGTGTCGAAGTTGACACCGCCGC
      A   N   S   S   G   G   D   L   E   V   T   T   H   S   F   N   C   G   G   E
       355     357     359     361     363     365     367     369     371     373

AGTTCTTCTACTGCAATACCTCCGGCCTGTTCAACAGCACCTGGATCAGCAATACCAGCG
1141 ---------+---------+---------+---------+---------+---------+
     TCAAGAAGATGACGTTATGGAGGCCGGACAAGTTGTCGTGGACCTAGTCGTTATGGTCGC
      F   F   Y   C   N   T   S   G   L   F   N   S   T   W   I   S   N   T   S   V
       375     377     379     381     383     385     387     389     391     393

TGCAGGGCAGCAACAGCACCGGCAGCAACGACAGCATCACCCTGCCCTGCCGGATCAAGC
1201 ---------+---------+---------+---------+---------+---------+
     ACGTCCCGTCGTTGTCGTGGCCGTCGTTGCTGTCGTAGTGGGACGGGACGGCCTAGTTCG
      Q   G   S   N   S   T   G   S   N   D   S   I   T   L   P   C   R   I   K   Q
       395     397     399     401     403     405     407     409     411     413

AGATCATCAATATGTGGCAGCGGATTGGCCAGGCTATGTACGCCCCACCCATCCAGGGCG
1261 ---------+---------+---------+---------+---------+---------+
     TCTAGTAGTTATACACCGTCGCCTAACCGGTCCGATACATGCGGGGTGGGTAGGTCCCGC
      I   I   N   M   W   Q   R   I   G   Q   A   M   Y   A   P   P   I   Q   G   V
       415     417     419     421     423     425     427     429     431     433

BclI                              SmaI
     TGATCAGATGCGTGTCCAATATCACCGGCCTGATCCTGACCCGGGACGGCGGCTCTACCA
1321 ---------+---------+---------+---------+---------+---------+
     ACTAGTCTACGCACAGGTTATAGTGGCCGGACTAGGACTGGGCCCTGCCGCCGAGATGGT
      I   R   C   V   S   N   I   T   G   L   I   L   T   R   D   G   G   S   T   N
       435     437     439     441     443     445     447     449     451     453

ACAGCACCACCGAAACCTTCAGACCCGGCGGAGGCGACATGAGAGACAACTGGCGGAGCG
1381 ---------+---------+---------+---------+---------+---------+
     TGTCGTGGTGGCTTTGGAAGTCTGGGCCGCCTCCGCTGTACTCTCTGTTGACCGCCTCGC
      S   T   T   E   T   F   R   P   G   G   G   D   M   R   D   N   W   R   S   E
       455     457     459     461     463     465     467     469     471     473
```

FIG. 3D

```
      AGCTGTACAAGTACAAAGTGGTGAAAATCGAGCCCCTGGGCGTGGCCCCCACCAGAGCCA
1441  ---------+---------+---------+---------+---------+---------+
      TCGACATGTTCATGTTTCACCACTTTTAGCTCGGGGACCCGCACCGGGGTGGTCTCGGT
       L   Y   K   Y   K   V   V   K   I   E   P   L   G   V   A   P   T   R   A   K
       475     477     479     481     483     485     487     489     491     493

NarI
                                            KasI
      AGAGAAGAGTGGTCGGAAGCGAGAAGTCCGCCGTGGGCATCGGCGCCGTGTTTCTGGGAT
1501  ---------+---------+---------+---------+---------+---------+
      TCTCTTCTCACCAGCCTTCGCTCTTCAGGCGGCACCCGTAGCCGCGGCACAAAGACCCTA
       R   R   V   V   G   S   E   K   S   A   V   G   I   G   A   V   F   L   G   F
       495     497     499     501     503     505     507     509     511     513

TCCTGGGCGCTGCCGGCTCTACAATGGGAGCCGCCAGCATGACACTGACCGTGCAGGCCA
1561  ---------+---------+---------+---------+---------+---------+
      AGGACCCGCGACGGCCGAGATGTTACCCTCGGCGGTCGTACTGTGACTGGCACGTCCGGT
       L   G   A   A   G   S   T   M   G   A   A   S   M   T   L   T   V   Q   A   R
       515     517     519     521     523     525     527     529     531     533

BspMI                                    BspMI
      GAAACCTGCTGTCCGGCATCGTGCAGCAGCAGAGCAACCTGCTGAGAGCCATCGAGGCCC
1621  ---------+---------+---------+---------+---------+---------+
      CTTTGGACGACAGGCCGTAGCACGTCGTCGTCTCGTTGGACGACTCTCGGTAGCTCCGGG
       N   L   L   S   G   I   V   Q   Q   Q   S   N   L   L   R   A   I   E   A   Q
       535     537     539     541     543     545     547     549     551     553

PvuII
                                            PstI
      AGCAGCATCTCCTCAAACTCACAGTCTGGGGCATCAAGCAGCTGCAGGCCAGGGTGCTGG
1681  ---------+---------+---------+---------+---------+---------+
      TCGTCGTAGAGGAGTTTGAGTGTCAGACCCCGTAGTTCGTCGACGTCCGGTCCCACGACC
       Q   H   L   L   K   L   T   V   W   G   I   K   Q   L   Q   A   R   V   L   A
       555     557     559     561     563     565     567     569     571     573

BspMI                                    PstI
      CCGTGGAGAGATACCTGCGGGATCAGCAGCTCCTCGGCATCTGGGGCTGCAGCGGCAAGC
1741  ---------+---------+---------+---------+---------+---------+
      GGCACCTCTCTATGGACGCCCTAGTCGTCGAGGAGCCGTAGACCCCGACGTCGCCGTTCG
       V   E   R   Y   L   R   D   Q   Q   L   L   G   I   W   G   C   S   G   K   L
       575     577     579     581     583     585     587     589     591     593

PvuII                        BglII
      TGATCTGCACCACCAACGTGCCCTGGAACTCCAGCTGGTCCAACCGGAACCTGAGCGAGA
1801  ---------+---------+---------+---------+---------+---------+
      ACTAGACGTGGTGGTTGCACGGGACCTTGAGGTCGACCAGGTTGGCCTTGGACTCGCTCT
       I   C   T   T   N   V   P   W   N   S   S   W   S   N   R   N   L   S   E   I
       595     597     599     601     603     605     607     609     611     613

PstI
      TCTGGGACAACATGACCTGGCTGCAGTGGGACAAAGAGATCAGCAACTACACCCAGATCA
1861  ---------+---------+---------+---------+---------+---------+
      AGACCCTGTTGTACTGGACCGACGTCACCCTGTTTCTCTAGTCGTTGATGTGGGTCTAGT
       W   D   N   M   T   W   L   Q   W   D   K   E   I   S   N   Y   T   Q   I   I
       615     617     619     621     623     625     627     629     631     633

TCTACGGCCTGCTGGAAGAGAGCCAGAACCAGCAGGAAAAGAACGAACAGGATCTCCTGG
1921  ---------+---------+---------+---------+---------+---------+
      AGATGCCGGACGACCTTCTCTCGGTCTTGGTCGTCCTTTTCTTGCTTGTCCTAGAGGACC
       Y   G   L   L   E   E   S   Q   N   Q   Q   E   K   N   E   Q   D   L   L   A
       635     637     639     641     643     645     647     649     651     653
```

FIG. 3E

```
                 PflMI
      CTCTCGATAAGTGGGCCAGCCTGTGGAATTGGTTCGACATCAGCAACTGGCTGTGGTACA
1981  ---------+---------+---------+---------+---------+---------+
      GAGAGCTATTCACCCGGTCGGACACCTTAACCAAGCTGTAGTCGTTGACCGACACCATGT
       L  D  K  W  A  S  L  W  N  W  F  D  I  S  N  W  L  W  Y  I
       655   657   659   661   663   665   667   669   671   673

NotI
                                          EagI    PacI
      TCAAGGGCAGCGGCCACCACCACCATCACCACTGAGCGGCCGCTTAATTAA
2041  ---------+---------+---------+---------+---------+-
      AGTTCCCGTCGCCGGTGGTGGTGGTAGTGGTGACTCGCCGGCGAATTAATT
       K  G  S  G  H  H  H  H  H  H  *
       675   677   679   681   683   685
```

FIG. 4A

```
    BssHII
  AscI       EcoRI              NcoI BamHI PstI
  GGCGCGCCGAATTCGCCACCATGCCCATGGGATCCCTGCAGCCTCTGGCCACACTGTATC
1 ---------+---------+---------+---------+---------+---------+
  CCGCGCGGCTTAAGCGGTGGTACGGGTACCCTAGGGACGTCGGAGACCGGTGTGACATAG
                       M   P   M   G   S   L   Q   P   L   A   T   L   Y   L
                       1       3       5       7       9      11      13

SphI                                              BstEII
   TGCTGGGCATGCTGGTGGCCTCTGTGCTGGCCGCTGGCAATCTGTGGGTCACCGTGTACT
61 ---------+---------+---------+---------+---------+---------+
   ACGACCCGTACGACCACCGGAGACACGACCGGCGACCGTTAGACACCCAGTGGCACATGA
     L   G   M   L   V   A   S   V   L   A   A   G   N   L   W   V   T   V   Y   Y
    15      17      19      21      23      25      27      29      31      33

StuI
    ACGGCGTGCCCGTGTGGAAGGACGCCGAGACAACCCTGTTCTGCGCCAGCGACGCCAAGG
121 ---------+---------+---------+---------+---------+---------+
    TGCCGCACGGGCACACCTTCCTGCGGCTCTGTTGGGACAAGACGCGGTCGCTGCGGTTCC
      G   V   P   V   W   K   D   A   E   T   T   L   F   C   A   S   D   A   K   A
     35      37      39      41      43      45      47      49      51      53

CCTACGAGACAGAGAAGCACAACGTGTGGGCCACCCACGCCTGCGTGCCAACCGACCCTA
181 ---------+---------+---------+---------+---------+---------+
    GGATGCTCTGTCTCTTCGTGTTGCACACCCGGTGGGTGCGGACGCACGGTTGGCTGGGAT
      Y   E   T   E   K   H   N   V   W   A   T   H   A   C   V   P   T   D   P   N
     55      57      59      61      63      65      67      69      71      73

ACCCCCAGGAAATCCACCTGGAAAACGTGACCGAAGAGTTCAACATGTGGAAGAACAACA
241 ---------+---------+---------+---------+---------+---------+
    TGGGGGTCCTTTAGGTGGACCTTTTGCACTGGCTTCTCAAGTTGTACACCTTCTTGTTGT
      P   Q   E   I   H   L   E   N   V   T   E   E   F   N   M   W   K   N   N   M
     75      77      79      81      83      85      87      89      91      93

TGGTGGAACAGATGCACACCGACATCATCAGCCTGTGGGACCAGAGCCTGAAGCCCTGCG
301 ---------+---------+---------+---------+---------+---------+
    ACCACCTTGTCTACGTGTGGCTGTAGTAGTCGGACACCCTGGTCTCGGACTTCGGGACGC
      V   E   Q   M   H   T   D   I   I   S   L   W   D   Q   S   L   K   P   C   V
     95      97      99     101     103     105     107     109     111     113
```

FIG. 4B

```
                         PstI
     TGAAGCTGACCCCCCTGTGCGTGACCCTGCAGTGCACCAACGTGACCAACAACATCACCG
361  ---------+---------+---------+---------+---------+---------+
     ACTTCGACTGGGGGGACACGCACTGGGACGTCACGTGGTTGCACTGGTTGTTGTAGTGGC
      K   L   T   P   L   C   V   T   L   Q   C   T   N   V   T   N   N   I   T   D
        115     117     119     121     123     125     127     129     131     133

PstI
     ACGACATGCGGGGCGAGCTGAAGAACTGCAGCTTCAACATGACCACCGAGCTGCGGGACA
421  ---------+---------+---------+---------+---------+---------+
     TGCTGTACGCCCCGCTCGACTTCTTGACGTCGAAGTTGTACTGGTGGCTCGACGCCCTGT
      D   M   R   G   E   L   K   N   C   S   F   N   M   T   T   E   L   R   D   K
        135     137     139     141     143     145     147     149     151     153

AGAAACAGAAGGTGTACAGCCTGTTCTACCGGCTGGACGTGGTGCAGATCAACGAGAACC
481  ---------+---------+---------+---------+---------+---------+
     TCTTTGTCTTCCACATGTCGGACAAGATGGCCGACCTGCACCACGTCTAGTTGCTCTTGG
      K   Q   K   V   Y   S   L   F   Y   R   L   D   V   V   Q   I   N   E   N   Q
        155     157     159     161     163     165     167     169     171     173

BclI
     AGGGCAACAGAAGCAACAACAGCAACAAAGAGTACCGGCTGATCAACTGCAACACCAGCG
541  ---------+---------+---------+---------+---------+---------+
     TCCCGTTGTCTTCGTTGTTGTCGTTGTTTCTCATGGCCGACTAGTTGACGTTGTGGTCGC
      G   N   R   S   N   N   S   N   K   E   Y   R   L   I   N   C   N   T   S   A
        175     177     179     181     183     185     187     189     191     193

StuI
     CCATCACCCAGGCCTGCCCCAAGGTGTCCTTCGAGCCCATCCCCATCCACTACTGCGCCC
601  ---------+---------+---------+---------+---------+---------+
     GGTAGTGGGTCCGGACGGGGTTCCACAGGAAGCTCGGGTAGGGGTAGGTGATGACGCGGG
      I   T   Q   A   C   P   K   V   S   F   E   P   I   P   I   H   Y   C   A   P
        195     197     199     201     203     205     207     209     211     213

CTGCCGGCTTCGCCATCCTGAAGTGCAAGGACAAGAAGTTCAACGGCACCGGCCCCTGCC
661  ---------+---------+---------+---------+---------+---------+
     GACGGCCGAAGCGGTAGGACTTCACGTTCCTGTTCTTCAAGTTGCCGTGGCCGGGGACGG
      A   G   F   A   I   L   K   C   K   D   K   K   F   N   G   T   G   P   C   P
        215     217     219     221     223     225     227     229     231     233

PvuII
     CCAGCGTGTCCACAGTGCAGTGTACCCACGGCATCAAGCCCGTGGTGTCCACCCAGCTGC
721  ---------+---------+---------+---------+---------+---------+
     GGTCGCACAGGTGTCACGTCACATGGGTGCCGTAGTTCGGGCACCACAGGTGGGTCGACG
      S   V   S   T   V   Q   C   T   H   G   I   K   P   V   V   S   T   Q   L   L
        235     237     239     241     243     245     247     249     251     253

BclI
     TGCTGAACGGCAGCCTGGCCGAAGAGGAAGTGATGATCAGAAGCGAGAACATCACCAACA
781  ---------+---------+---------+---------+---------+---------+
     ACGACTTGCCGTCGGACCGGCTTCTCCTTCACTACTAGTCTTCGCTCTTGTAGTGGTTGT
      L   N   G   S   L   A   E   E   E   V   M   I   R   S   E   N   I   T   N   N
        255     257     259     261     263     265     267     269     271     273

ACGCCAAGAACATCCTGGTGCAGTTCAACACCCCCGTGCAGATTAACTGCACCCGGCCCA
841  ---------+---------+---------+---------+---------+---------+
     TGCGGTTCTTGTAGGACCACGTCAAGTTGTGGGGGCACGTCTAATTGACGTGGGCCGGGT
      A   K   N   I   L   V   Q   F   N   T   P   V   Q   I   N   C   T   R   P   N
        275     277     279     281     283     285     287     289     291     293
```

FIG. 4C

```
                                              StuI
      ACAACAACACCAGAAAGAGCATCCGGATCGGCCCAGGCCAGGCCTTCTACGCCACCGGCG
 901  ---------+---------+---------+---------+---------+---------+
      TGTTGTTGTGGTCTTTCTCGTAGGCCTAGCCGGGTCCGGTCCGGAAGATGCGGTGGCCGC
       N  N  T  R  K  S  I  R  I  G  P  G  Q  A  F  Y  A  T  G  D
       295   297   299   301   303   305   307   309   311   313

ACATCATCGGCGACATCCGGCAGGCCCACTGCACCGTGTCCAAGGCCACCTGGAACGAGA
 961  ---------+---------+---------+---------+---------+---------+
      TGTAGTAGCCGCTGTAGGCCGTCCGGGTGACGTGGCACAGGTTCCGGTGGACCTTGCTCT
       I  I  G  D  I  R  Q  A  H  C  T  V  S  K  A  T  W  N  E  T
       315   317   319   321   323   325   327   329   331   333

PvuII
      CACTGGGCAAGGTGGTGAAACAGCTGCGGAAGCACTTCGGGAACAACACCATCATCCGCT
1021  ---------+---------+---------+---------+---------+---------+
      GTGACCCGTTCCACCACTTTGTCGACGCCTTCGTGAAGCCCTTGTTGTGGTAGTAGGCGA
       L  G  K  V  V  K  Q  L  R  K  H  F  G  N  N  T  I  I  R  F
       335   337   339   341   343   345   347   349   351   353

TCGCCAACAGCTCTGGCGGCGACCTGGAAGTGACCACCCACAGCTTCAACTGTGGCGGCG
1081  ---------+---------+---------+---------+---------+---------+
      AGCGGTTGTCGAGACCGCCGCTGGACCTTCACTGGTGGGTGTCGAAGTTGACACCGCCGC
       A  N  S  S  G  G  D  L  E  V  T  T  H  S  F  N  C  G  G  E
       355   357   359   361   363   365   367   369   371   373

AGTTCTTCTACTGCAATACCTCCGGCCTGTTCAACAGCACCTGGATCAGCAATACCAGCG
1141  ---------+---------+---------+---------+---------+---------+
      TCAAGAAGATGACGTTATGGAGGCCGGACAAGTTGTCGTGGACCTAGTCGTTATGGTCGC
       F  F  Y  C  N  T  S  G  L  F  N  S  T  W  I  S  N  T  S  V
       375   377   379   381   383   385   387   389   391   393

TGCAGGGCAGCAACAGCACCGGCAGCAACGACAGCATCACCCTGCCCTGCCGGATCAAGC
1201  ---------+---------+---------+---------+---------+---------+
      ACGTCCCGTCGTTGTCGTGGCCGTCGTTGCTGTCGTAGTGGGACGGGACGGCCTAGTTCG
       Q  G  S  N  S  T  G  S  N  D  S  I  T  L  P  C  R  I  K  Q
       395   397   399   401   403   405   407   409   411   413

AGATCATCAATATGTGGCAGCGGATTGGCCAGGCTATGTACGCCCCACCCATCCAGGGCG
1261  ---------+---------+---------+---------+---------+---------+
      TCTAGTAGTTATACACCGTCGCCTAACCGGTCCGATACATGCGGGGTGGGTAGGTCCCGC
       I  I  N  M  W  Q  R  I  G  Q  A  M  Y  A  P  P  I  Q  G  V
       415   417   419   421   423   425   427   429   431   433

BclI                                  SmaI
      TGATCAGATGCGTGTCCAATATCACCGGCCTGATCCTGACCCGGGACGGCGGCTCTACCA
1321  ---------+---------+---------+---------+---------+---------+
      ACTAGTCTACGCACAGGTTATAGTGGCCGGACTAGGACTGGGCCCTGCCGCCGAGATGGT
       I  R  C  V  S  N  I  T  G  L  I  L  T  R  D  G  G  S  T  N
       435   437   439   441   443   445   447   449   451   453

ACAGCACCACCGAAACCTTCAGACCCGGCGGAGGCGACATGAGAGACAACTGGCGGAGCG
1381  ---------+---------+---------+---------+---------+---------+
      TGTCGTGGTGGCTTTGGAAGTCTGGGCCGCCTCCGCTGTACTCTCTGTTGACCGCCTCGC
       S  T  T  E  T  F  R  P  G  G  G  D  M  R  D  N  W  R  S  E
       455   457   459   461   463   465   467   469   471   473

AGCTGTACAAGTACAAAGTGGTGAAAATCGAGCCCCTGGGCGTGGCCCCCACCAGAGCCA
1441  ---------+---------+---------+---------+---------+---------+
      TCGACATGTTCATGTTTCACCACTTTTAGCTCGGGGACCCGCACCGGGGGTGGTCTCGGT
       L  Y  K  Y  K  V  V  K  I  E  P  L  G  V  A  P  T  R  A  K
       475   477   479   481   483   485   487   489   491   493
```

FIG. 4D

```
                                                       NarI
                                                       KasI
      AGAGAAGAGTGGTCGGAAGCGAGAAGTCCGCCGTGGGAATCGGCGCCGTGTTTCTGGGAT
1501  ---------+---------+---------+---------+---------+---------+
      TCTCTTCTCACCAGCCTTCGCTCTTCAGGCGGCACCCTTAGCCGCGGCACAAAGACCCTA
       R  R  V  V  G  S  E  K  S  A  V  G  I  G  A  V  F  L  G  F
        495   497   499   501   503   505   507   509   511   513

TCCTGGGCGCTGCCGGCTCTACAATGGGAGCCGCCAGCATGACACTGACCGTGCAGGCCA
1561  ---------+---------+---------+---------+---------+---------+
      AGGACCCGCGACGGCCGAGATGTTACCCTCGGCGGTCGTACTGTGACTGGCACGTCCGGT
       L  G  A  A  G  S  T  M  G  A  A  S  M  T  L  T  V  Q  A  R
        515   517   519   521   523   525   527   529   531   533

BspMI                               BspMI
      GAAACCTGCTGTCCGGCATCGTGCAGCAGCAGAGCAACCTGCTGAGAGCCATCGAGGCCC
1621  ---------+---------+---------+---------+---------+---------+
      CTTTGGACGACAGGCCGTAGCACGTCGTCGTCTCGTTGGACGACTCTCGGTAGCTCCGGG
       N  L  L  S  G  I  V  Q  Q  Q  S  N  L  L  R  A  I  E  A  Q
        535   537   539   541   543   545   547   549   551   553

PvuII
                                        PstI
      AGCAGCATCTCCTCAAACTCACAGTCTGGGGCATCAAGCAGCTGCAGGCCAGGGTGCTGG
1681  ---------+---------+---------+---------+---------+---------+
      TCGTCGTAGAGGAGTTTGAGTGTCAGACCCCGTAGTTCGTCGACGTCCGGTCCCACGACC
       Q  H  L  L  K  L  T  V  W  G  I  K  Q  L  Q  A  R  V  L  A
        555   557   559   561   563   565   567   569   571   573

BspMI                                           PstI
      CCGTGGAGAGATACCTGCGGGATCAGCAGCTCCTCGGCATCTGGGGCTGCAGCGGCAAGC
1741  ---------+---------+---------+---------+---------+---------+
      GGCACCTCTCTATGGACGCCCTAGTCGTCGAGGAGCCGTAGACCCCGACGTCGCCGTTCG
       V  E  R  Y  L  R  D  Q  Q  L  L  G  I  W  G  C  S  G  K  L
        575   577   579   581   583   585   587   589   591   593

PvuII                BglII
      TGATCTGCACCACCAACGTGCCCTGGAACTCCAGCTGGTCCAACCGGAACCTGAGCGAGA
1801  ---------+---------+---------+---------+---------+---------+
      ACTAGACGTGGTGGTTGCACGGGACCTTGAGGTCGACCAGGTTGGCCTTGGACTCGCTCT
       I  C  T  T  N  V  P  W  N  S  S  W  S  N  R  N  L  S  E  I
        595   597   599   601   603   605   607   609   611   613

PstI
      TCTGGGACAATATGACCTGGCTGCAGTGGGACAAAGAGATCAGCAACTACACCCAGATCA
1861  ---------+---------+---------+---------+---------+---------+
      AGACCCTGTTATACTGGACCGACGTCACCCTGTTTCTCTAGTCGTTGATGTGGGTCTAGT
       W  D  N  M  T  W  L  Q  W  D  K  E  I  S  N  Y  T  Q  I  I
        615   617   619   621   623   625   627   629   631   633

BspMI
      TCTACGGCCTGCTGGAAGAGAGCCAGAACCAGCAGGAAAAGAACGAGCAGGACCTGCTGG
1921  ---------+---------+---------+---------+---------+---------+
      AGATGCCGGACGACCTTCTCTCGGTCTTGGTCGTCCTTTTCTTGCTCGTCCTGGACGACC
       Y  G  L  L  E  E  S  Q  N  Q  Q  E  K  N  E  Q  D  L  L  A
        635   637   639   641   643   645   647   649   651   653

CCCTGGACAAGTGGGCCTCCCTGTGGAATTGGTTCGACATCTCCAACTGGCTGTGGTACA
1981  ---------+---------+---------+---------+---------+---------+
      GGGACCTGTTCACCCGGAGGGACACCTTAACCAAGCTGTAGAGGTTGACCGACACCATGT
       L  D  K  W  A  S  L  W  N  W  F  D  I  S  N  W  L  W  Y  I
        655   657   659   661   663   665   667   669   671   673
```

FIG. 4E

```
      TCAAGGGCAGCGGCGGCATGAAGCAGATCGAGGACAAGATCGAAGAGATCGAGTCTAAGA
2041  ---------+---------+---------+---------+---------+---------+
      AGTTCCCGTCGCCGCCGTACTTCGTCTAGCTCCTGTTCTAGCTTCTCTAGCTCAGATTCT
       K  G  S  G  G  M  K  Q  I  E  D  K  I  E  E  I  E  S  K  I
       675   677   679   681   683   685   687   689   691   693

TCAAGAAGATTGAGAACGAGATCGCCCGCATCAAGAAACTGATCGGCGAGAGCGGCCACC
2101  ---------+---------+---------+---------+---------+---------+
      AGTTCTTCTAACTCTTGCTCTAGCGGGCGTAGTTCTTTGACTAGCCGCTCTCGCCGGTGG
       K  K  I  E  N  E  I  A  R  I  K  K  L  I  G  E  S  G  H  H
       695   697   699   701   703   705   707   709   711   713

NotI
                    EagI   PacI
      ACCACCATCACCATTGAGCGGCCGCTTAATTAA
2161  ---------+---------+---------+---
      TGGTGGTAGTGGTAACTCGCCGGCGAATTAATT
       H  H  H  H  *
       715   717   719
```

FIG. 5A

```
      BssHII
    AscI      EcoRI                  NcoI BamHI PstI
    GGCGCGCCGAATTCGCCACCATGCCCATGGGATCCCTGCAGCCTCTGGCCACACTGTATC
  1 ---------+---------+---------+---------+---------+---------+
    CCGCGCGGCTTAAGCGGTGGTACGGGTACCCTAGGGACGTCGGAGACCGGTGTGACATAG
                         M   P   M   G   S   L   Q   P   L   A   T   L   Y   L
                         1       3       5       7       9      11      13

SphI                                              BstEII
    TGCTGGGCATGCTGGTGGCCTCTGTGCTGGCCGCTGGCAATCTGTGGGTCACCGTGTACT
 61 ---------+---------+---------+---------+---------+---------+
    ACGACCCGTACGACCACCGGAGACACGACCGGCGACCGTTAGACACCCAGTGGCACATGA
      L   G   M   L   V   A   S   V   L   A   A   G   N   L   W   V   T   V   Y   Y
     15      17      19      21      23      25      27      29      31      33

StuI
    ACGGCGTGCCCGTGTGGAAGGACGCCGAGACAACCCTGTTCTGCGCCAGCGACGCCAAGG
121 ---------+---------+---------+---------+---------+---------+
    TGCCGCACGGGCACACCTTCCTGCGGCTCTGTTGGGACAAGACGCGGTCGCTGCGGTTCC
       G   V   P   V   W   K   D   A   E   T   T   L   F   C   A   S   D   A   K   A
      35      37      39      41      43      45      47      49      51      53

CCTACGAGACAGAGAAGCACAACGTGTGGGCCACCCACGCCTGCGTGCCAACCGACCCTA
181 ---------+---------+---------+---------+---------+---------+
    GGATGCTCTGTCTCTTCGTGTTGCACACCCGGTGGGTGCGGACGCACGGTTGGCTGGGAT
       Y   E   T   E   K   H   N   V   W   A   T   H   A   C   V   P   T   D   P   N
      55      57      59      61      63      65      67      69      71      73

ACCCCCAGGAAATCCACCTGGAAAACGTGACCGAAGAGTTCAACATGTGGAAGAACAACA
241 ---------+---------+---------+---------+---------+---------+
    TGGGGGTCCTTTAGGTGGACCTTTTGCACTGGCTTCTCAAGTTGTACACCTTCTTGTTGT
       P   Q   E   I   H   L   E   N   V   T   E   E   F   N   M   W   K   N   N   M
      75      77      79      81      83      85      87      89      91      93

TGGTGGAACAGATGCACACCGACATCATCAGCCTGTGGGACCAGAGCCTGAAGCCCTGCG
301 ---------+---------+---------+---------+---------+---------+
    ACCACCTTGTCTACGTGTGGCTGTAGTAGTCGGACACCCTGGTCTCGGACTTCGGGACGC
       V   E   Q   M   H   T   D   I   I   S   L   W   D   Q   S   L   K   P   C   V
      95      97      99     101     103     105     107     109     111     113
```

FIG. 5B

```
                              PstI
     TGAAGCTGACCCCCCTGTGCGTGACCCTGCAGTGCACCAACGTGACCAACAACATCACCG
361  ---------+---------+---------+---------+---------+---------+
     ACTTCGACTGGGGGGACACGCACTGGGACGTCACGTGGTTGCACTGGTTGTTGTAGTGGC
      K   L   T   P   L   C   V   T   L   Q   C   T   N   V   T   N   N   I   T   D
      115     117     119     121     123     125     127     129     131     133

PstI
     ACGACATGCGGGGCGAGCTGAAGAACTGCAGCTTCAACATGACCACCGAGCTGCGGGACA
421  ---------+---------+---------+---------+---------+---------+
     TGCTGTACGCCCCGCTCGACTTCTTGACGTCGAAGTTGTACTGGTGGCTCGACGCCCTGT
      D   M   R   G   E   L   K   N   C   S   F   N   M   T   T   E   L   R   D   K
      135     137     139     141     143     145     147     149     151     153

AGAAACAGAAGGTGTACAGCCTGTTCTACCGGCTGGACGTGGTGCAGATCAACGAGAACC
481  ---------+---------+---------+---------+---------+---------+
     TCTTTGTCTTCCACATGTCGGACAAGATGGCCGACCTGCACCACGTCTAGTTGCTCTTGG
      K   Q   K   V   Y   S   L   F   Y   R   L   D   V   V   Q   I   N   E   N   Q
      155     157     159     161     163     165     167     169     171     173

BclI
     AGGGCAACAGAAGCAACAACAGCAACAAAGAGTACCGGCTGATCAACTGCAACACCAGCG
541  ---------+---------+---------+---------+---------+---------+
     TCCCGTTGTCTTCGTTGTTGTCGTTGTTTCTCATGGCCGACTAGTTGACGTTGTGGTCGC
      G   N   R   S   N   N   S   N   K   E   Y   R   L   I   N   C   N   T   S   A
      175     177     179     181     183     185     187     189     191     193

StuI
     CCATCACCCAGGCCTGCCCCAAGGTGTCCTTCGAGCCCATCCCCATCCACTACTGCGCCC
601  ---------+---------+---------+---------+---------+---------+
     GGTAGTGGGTCCGGACGGGGTTCCACAGGAAGCTCGGGTAGGGGTAGGTGATGACGCGGG
      I   T   Q   A   C   P   K   V   S   F   E   P   I   P   I   H   Y   C   A   P
      195     197     199     201     203     205     207     209     211     213

CTGCCGGCTTCGCCATCCTGAAGTGCAAGGACAAGAAGTTCAACGGCACCGGCCCCTGCC
661  ---------+---------+---------+---------+---------+---------+
     GACGGCCGAAGCGGTAGGACTTCACGTTCCTGTTCTTCAAGTTGCCGTGGCCGGGGACGG
      A   G   F   A   I   L   K   C   K   D   K   K   F   N   G   T   G   P   C   P
      215     217     219     221     223     225     227     229     231     233

PvuII
     CCAGCGTGTCCACAGTGCAGTGTACCCACGGCATCAAGCCCGTGGTGTCCACCCAGCTGC
721  ---------+---------+---------+---------+---------+---------+
     GGTCGCACAGGTGTCACGTCACATGGGTGCCGTAGTTCGGGCACCACAGGTGGGTCGACG
      S   V   S   T   V   Q   C   T   H   G   I   K   P   V   V   S   T   Q   L   L
      235     237     239     241     243     245     247     249     251     253

BclI
     TGCTGAACGGCAGCCTGGCCGAAGAGGAAGTGATGATCAGAAGCGAGAACATCACCAACA
781  ---------+---------+---------+---------+---------+---------+
     ACGACTTGCCGTCGGACCGGCTTCTCCTTCACTACTAGTCTTCGCTCTTGTAGTGGTTGT
      L   N   G   S   L   A   E   E   E   V   M   I   R   S   E   N   I   T   N   N
      255     257     259     261     263     265     267     269     271     273

ACGCCAAGAACATCCTGGTGCAGTTCAACACCCCCGTGCAGATTAACTGCACCCGGCCCA
841  ---------+---------+---------+---------+---------+---------+
     TGCGGTTCTTGTAGGACCACGTCAAGTTGTGGGGGCACGTCTAATTGACGTGGGCCGGGT
      A   K   N   I   L   V   Q   F   N   T   P   V   Q   I   N   C   T   R   P   N
      275     277     279     281     283     285     287     289     291     293
```

FIG. 5C

```
                                         StuI
         ACAACAACACCAGAAAGAGCATCCGGATCGGCCCAGGCCAGGCCTTCTACGCCACCGGCG
  901    ----------+---------+---------+---------+---------+---------+
         TGTTGTTGTGGTCTTTCTCGTAGGCCTAGCCGGGTCCGGTCCGGAAGATGCGGTGGCCGC
          N  N  T  R  K  S  I  R  I  G  P  G  Q  A  F  Y  A  T  G  D
          295   297   299   301   303   305   307   309   311   313

ACATCATCGGCGACATCCGGCAGGCCCACTGCACCGTGTCCAAGGCCACCTGGAACGAGA
  961    ----------+---------+---------+---------+---------+---------+
         TGTAGTAGCCGCTGTAGGCCGTCCGGGTGACGTGGCACAGGTTCCGGTGGACCTTGCTCT
          I  I  G  D  I  R  Q  A  H  C  T  V  S  K  A  T  W  N  E  T
          315   317   319   321   323   325   327   329   331   333

PvuII
         CACTGGGCAAGGTGGTGAAACAGCTGCGGAAGCACTTCGGGAACAACACCATCATCCGCT
 1021    ----------+---------+---------+---------+---------+---------+
         GTGACCCGTTCCACCACTTTGTCGACGCCTTCGTGAAGCCCTTGTTGTGGTAGTAGGCGA
          L  G  K  V  V  K  Q  L  R  K  H  F  G  N  N  T  I  I  R  F
          335   337   339   341   343   345   347   349   351   353

TCGCCAACAGCTCTGGCGGCGACCTGGAAGTGACCACCCACAGCTTCAACTGTGGCGGCG
 1081    ----------+---------+---------+---------+---------+---------+
         AGCGGTTGTCGAGACCGCCGCTGGACCTTCACTGGTGGGTGTCGAAGTTGACACCGCCGC
          A  N  S  S  G  G  D  L  E  V  T  T  H  S  F  N  C  G  G  E
          355   357   359   361   363   365   367   369   371   373

AGTTCTTCTACTGCAATACCTCCGGCCTGTTCAACAGCACCTGGATCAGCAATACCAGCG
 1141    ----------+---------+---------+---------+---------+---------+
         TCAAGAAGATGACGTTATGGAGGCCGGACAAGTTGTCGTGGACCTAGTCGTTATGGTCGC
          F  F  Y  C  N  T  S  G  L  F  N  S  T  W  I  S  N  T  S  V
          375   377   379   381   383   385   387   389   391   393

TGCAGGGCAGCAACAGCACCGGCAGCAACGACAGCATCACCCTGCCCTGCCGGATCAAGC
 1201    ----------+---------+---------+---------+---------+---------+
         ACGTCCCGTCGTTGTCGTGGCCGTCGTTGCTGTCGTAGTGGGACGGGACGGCCTAGTTCG
          Q  G  S  N  S  T  G  S  N  D  S  I  T  L  P  C  R  I  K  Q
          395   397   399   401   403   405   407   409   411   413

AGATCATCAATATGTGGCAGCGGATTGGCCAGGCTATGTACGCCCCACCCATCCAGGGCG
 1261    ----------+---------+---------+---------+---------+---------+
         TCTAGTAGTTATACACCGTCGCCTAACCGGTCCGATACATGCGGGGTGGGTAGGTCCCGC
          I  I  N  M  W  Q  R  I  G  Q  A  M  Y  A  P  P  I  Q  G  V
          415   417   419   421   423   425   427   429   431   433

BclI                                 SmaI
         TGATCAGATGCGTGTCCAATATCACCGGCCTGATCCTGACCCGGGACGGCGGCTCTACCA
 1321    ----------+---------+---------+---------+---------+---------+
         ACTAGTCTACGCACAGGTTATAGTGGCCGGACTAGGACTGGGCCCTGCCGCCGAGATGGT
          I  R  C  V  S  N  I  T  G  L  I  L  T  R  D  G  G  S  T  N
          435   437   439   441   443   445   447   449   451   453

ACAGCACCACCGAAACCTTCAGACCCGGCGGAGGCGACATGAGAGACAACTGGCGGAGCG
 1381    ----------+---------+---------+---------+---------+---------+
         TGTCGTGGTGGCTTTGGAAGTCTGGGCCGCCTCCGCTGTACTCTCTGTTGACCGCCTCGC
          S  T  T  E  T  F  R  P  G  G  G  D  M  R  D  N  W  R  S  E
          455   457   459   461   463   465   467   469   471   473

AGCTGTACAAGTACAAAGTGGTGAAAATCGAGCCCCTGGGCGTGGCCCCCACCAGAGCCA
 1441    ----------+---------+---------+---------+---------+---------+
         TCGACATGTTCATGTTTCACCACTTTTAGCTCGGGGACCCGCACCGGGGGTGGTCTCGGT
          L  Y  K  Y  K  V  V  K  I  E  P  L  G  V  A  P  T  R  A  K
          475   477   479   481   483   485   487   489   491   493
```

FIG. 5D

```
      AGAGAAGAGTGGTCGGACGCGAGAAGCGGGCCGTGGGAATTGGAGCCGTGTTTCTGGGAT
1501  ---------+---------+---------+---------+---------+---------+
      TCTCTTCTCACCAGCCTGCGCTCTTCGCCCGGCACCCTTAACCTCGGCACAAAGACCCTA
       R   R   V   V   G   R   E   K   R   A   V   G   I   G   A   V   F   L   G   F
       495     497     499     501     503     505     507     509     511     513

TCCTGGGCGCTGCCGGCTCTACAATGGGAGCCGCCAGCATGACACTGACCGTGCAGGCCA
1561  ---------+---------+---------+---------+---------+---------+
      AGGACCCGCGACGGCCGAGATGTTACCCTCGGCGGTCGTACTGTGACTGGCACGTCCGGT
       L   G   A   A   G   S   T   M   G   A   A   S   M   T   L   T   V   Q   A   R
       515     517     519     521     523     525     527     529     531     533

BspMI                                BspMI
      GAAACCTGCTGTCCGGCATCGTGCAGCAGCAGAGCAACCTGCTGAGAGCCATCGAGGCCC
1621  ---------+---------+---------+---------+---------+---------+
      CTTTGGACGACAGGCCGTAGCACGTCGTCGTCTCGTTGGACGACTCTCGGTAGCTCCGGG
       N   L   L   S   G   I   V   Q   Q   Q   S   N   L   L   R   A   I   E   A   Q
       535     537     539     541     543     545     547     549     551     553

PvuII
                                                      PstI
      AGCAGCATCTCCTCAAACTCACAGTCTGGGGCATCAAGCAGCTGCAGGCCAGGGTGCTGG
1681  ---------+---------+---------+---------+---------+---------+
      TCGTCGTAGAGGAGTTTGAGTGTCAGACCCCGTAGTTCGTCGACGTCCGGTCCCACGACC
       Q   H   L   L   K   L   T   V   W   G   I   K   Q   L   Q   A   R   V   L   A
       555     557     559     561     563     565     567     569     571     573

BspMI                                         PstI
      CCGTGGAGAGATACCTGCGGGATCAGCAGCTCCTCGGCATCTGGGGCTGCAGCGGCAAGC
1741  ---------+---------+---------+---------+---------+---------+
      GGCACCTCTCTATGGACGCCCTAGTCGTCGAGGAGCCGTAGACCCCGACGTCGCCGTTCG
       V   E   R   Y   L   R   D   Q   Q   L   L   G   I   W   G   C   S   G   K   L
       575     577     579     581     583     585     587     589     591     593

PvuII                              BglII
      TGATCTGCACCACCAACGTGCCCTGGAACTCCAGCTGGTCCAACCGGAACCTGAGCGAGA
1801  ---------+---------+---------+---------+---------+---------+
      ACTAGACGTGGTGGTTGCACGGGACCTTGAGGTCGACCAGGTTGGCCTTGGACTCGCTCT
       I   C   T   T   N   V   P   W   N   S   S   W   S   N   R   N   L   S   E   I
       595     597     599     601     603     605     607     609     611     613

PstI
      TCTGGGACAATATGACCTGGCTGCAGTGGGACAAAGAGATCAGCAACTACACCCAGATCA
1861  ---------+---------+---------+---------+---------+---------+
      AGACCCTGTTATACTGGACCGACGTCACCCTGTTTCTCTAGTCGTTGATGTGGGTCTAGT
       W   D   N   M   T   W   L   Q   W   D   K   E   I   S   N   Y   T   Q   I   I
       615     617     619     621     623     625     627     629     631     633

BspMI
      TCTACGGCCTGCTGGAAGAGAGCCAGAACCAGCAGGAAAAGAACGAGCAGGACCTGCTGG
1921  ---------+---------+---------+---------+---------+---------+
      AGATGCCGGACGACCTTCTCTCGGTCTTGGTCGTCCTTTTCTTGCTCGTCCTGGACGACC
       Y   G   L   L   E   E   S   Q   N   Q   Q   E   K   N   E   Q   D   L   L   A
       635     637     639     641     643     645     647     649     651     653

CCCTGGACAAGTGGGCCTCCCTGTGGAATTGGTTCGACATCTCCAACTGGCTGTGGTACA
1981  ---------+---------+---------+---------+---------+---------+
      GGGACCTGTTCACCCGGAGGGACACCTTAACCAAGCTGTAGAGGTTGACCGACACCATGT
       L   D   K   W   A   S   L   W   N   W   F   D   I   S   N   W   L   W   Y   I
       655     657     659     661     663     665     667     669     671     673
```

FIG. 5E

```
        BglII
      TCAAGATCTTCATCATGATCGTGGGCGGACTGATCGGCCTGCGGATCGTGTTTGCCGTGC
2041  ---------+---------+---------+---------+---------+---------+
      AGTTCTAGAAGTAGTACTAGCACCCGCCTGACTAGCCGGACGCCTAGCACAAACGGCACG
       K   I   F   I   M   I   V   G   G   L   I   G   L   R   I   V   F   A   V   L
        675     677     679     681     683     685     687     689     691     693

NotI
                                                     EagI    PacI
      TGAGCGTGATCTCCGGCCACCACCACCATCACCACTGAGCGGCCGCTTAATTAA
2101  ---------+---------+---------+---------+---------+----
      ACTCGCACTAGAGGCCGGTGGTGGTGGTAGTGGTGACTCGCCGGCGAATTAATT
       S   V   I   S   G   H   H   H   H   H   H   *
        695     697     699     701     703     705
```

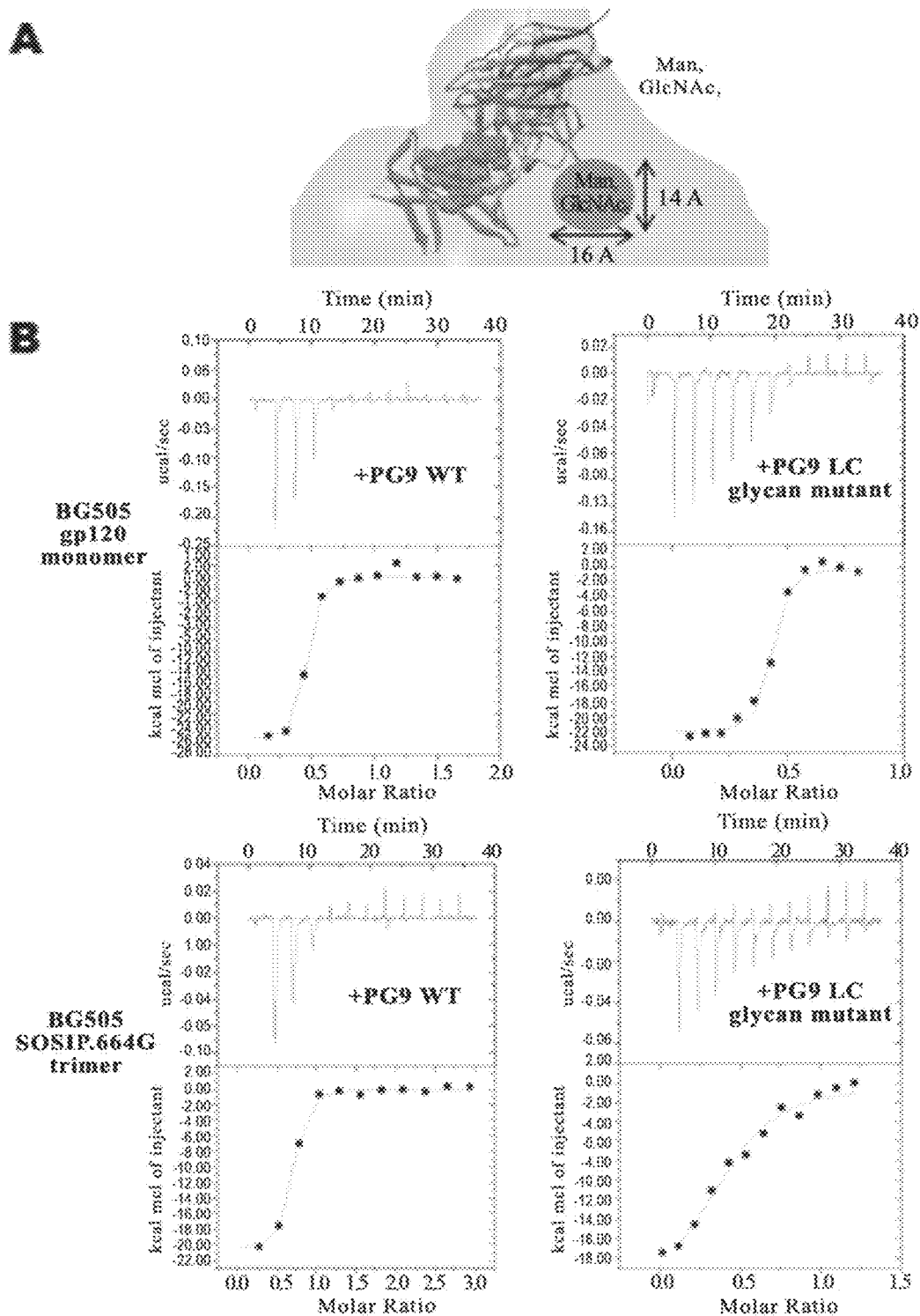

A

FIG. 9B-C
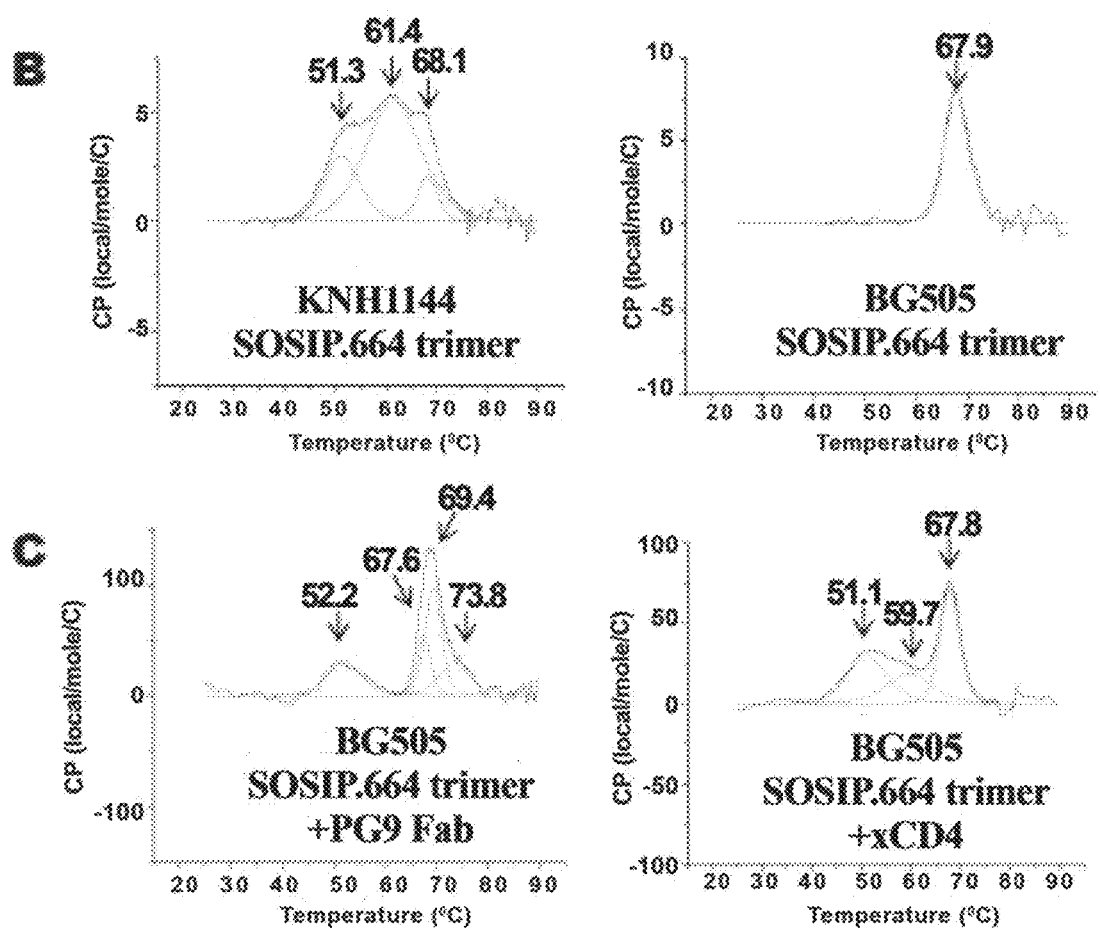

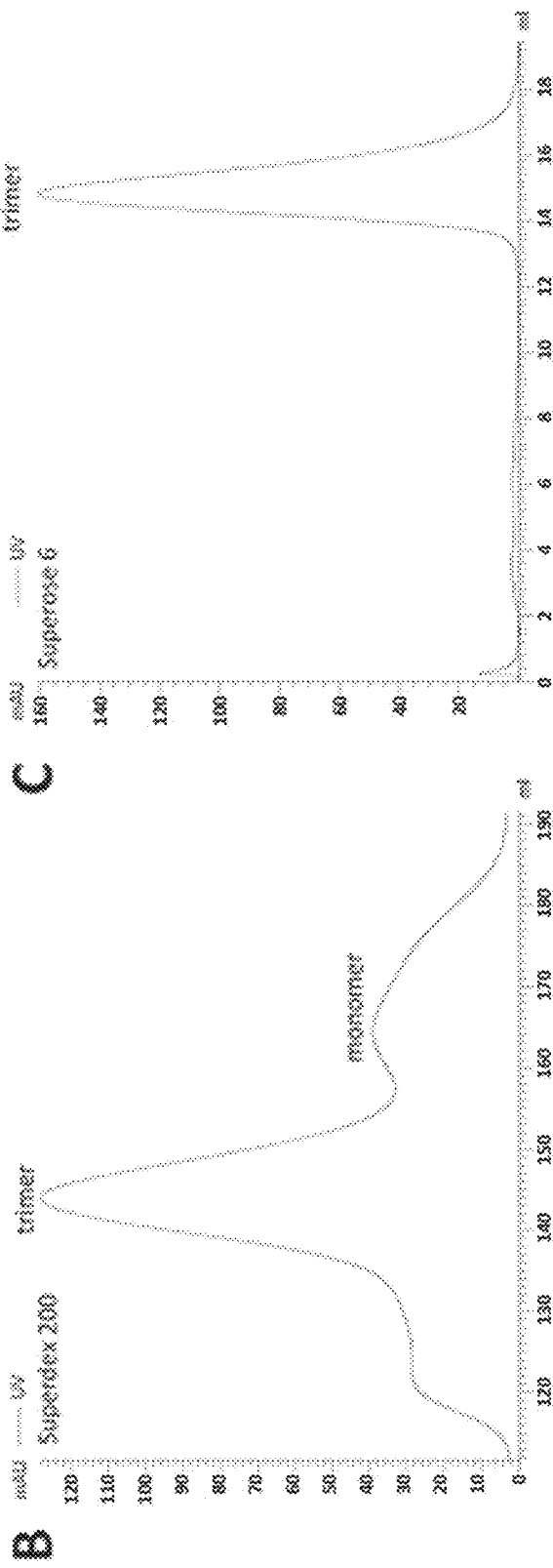
FIG. 15B-C

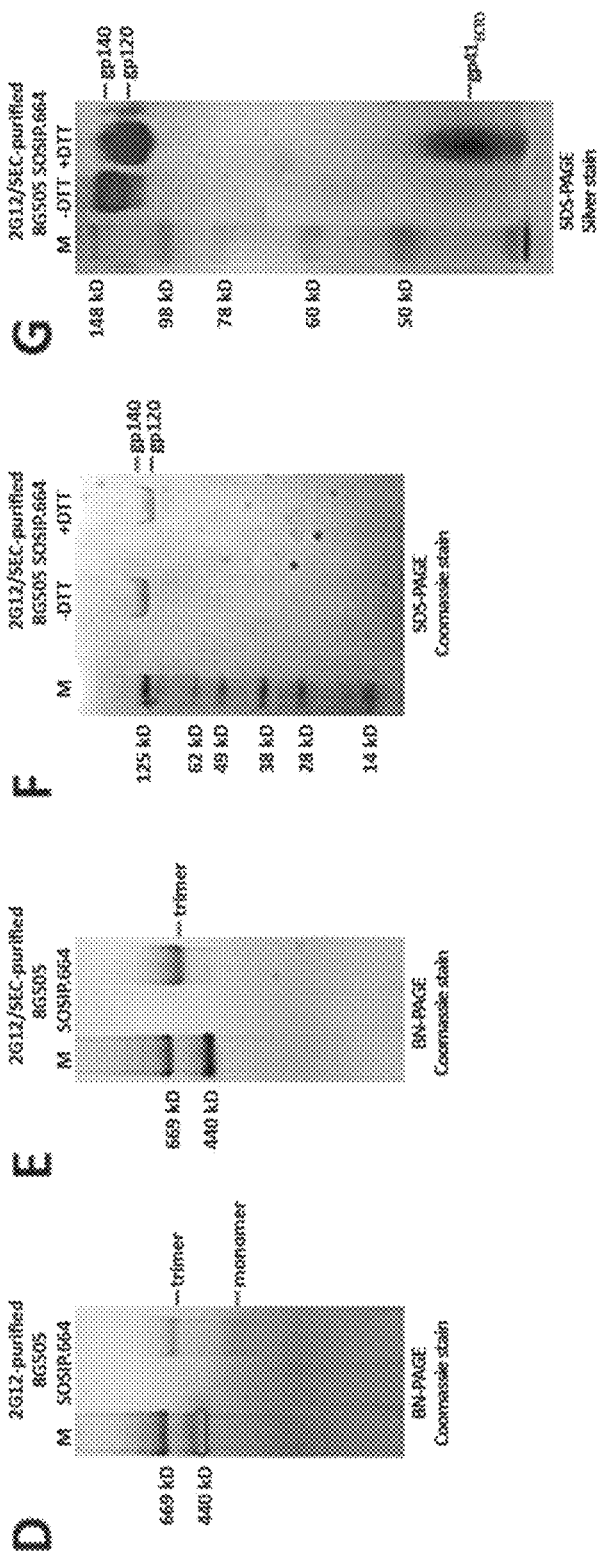
FIG. 15D-G

FIG. 17

| | epitope | antibody | IC50 | | EC50 | |
|---|---|---|---|---|---|---|
| | | | average | st. error | average | st. error |
| NAbs | CD4bs | CD4-IgG2 | 433 | 45 | 155 | 17 |
| | | VRC01 | 70 | 17 | 163 | 22 |
| | | VRC03 | 554 | 0 | 647 | 12 |
| | | VRC06 | 3316 | 220 | 1103 | 149 |
| | | VRC06b | 1106 | 105 | 345 | 32 |
| | | HJ16 | 3199 | 602 | 4375 | 1538 |
| | | 3BNC60 | 34 | 5 | 95 | 25 |
| | | 3BNC117 | 41 | 6 | 102 | 10 |
| | | 12A12 | 50 | 10 | 89 | 7 |
| | | 45-46 | 93 | 2 | 127 | 29 |
| | | 45-46W | 43 | 3 | 67 | 0 |
| | | 1NC9 | 251 | 55 | 735 | 171 |
| | | 8ANC195 | 139 | 25 | 2065 | 247 |
| | | PGV04 | 66 | 0 | 227 | 7 |
| | | CH31 | 14 | 3 | 347 | 20 |
| | | CH103 | 2572 | 405 | 792 | 24 |
| | | CH106 | 2696 | 101 | 2571 | 0 |
| | V1/V2-glycan | PG9 | 45 | 9 | 343 | 78 |
| | | PG16 | 8 | 1 | 199 | 39 |
| | | PGT145 | 83 | 10 | 114 | 29 |
| | | CH01 | 301 | 30 | 2790 | 0 |
| | V3-glycan | PGT121 | 15 | 3 | 96 | 26 |
| | | PGT122 | 112 | 32 | 159 | 27 |
| | | PGT123 | 28 | 5 | 127 | 23 |
| | | PGT125 | 7 | 1 | 47 | 5 |
| | | PGT126 | 10 | 1 | 26 | 7 |
| | | PGT127 | 37 | 5 | 66 | 2 |
| | | PGT128 | 11 | 1 | 58 | 11 |
| | | PGT130 | 87 | 2 | 524 | 205 |
| | OD-glycan | 2G12 | 790 | 133 | 27 | 3 |
| | | PGT135 | 2334 | 571 | 521 | 45 |
| | | PGT136 | 25687 | 544 | 434 | 95 |
| | unknown | 3BC176 | 175 | 14 | 5650 | 2916 |
| | | 3BC315 | 1259 | 108 | 962 | 26 |
| Non-NAbs | CD4bs | F91 | >10000 | | >10000 | |
| | | F105 | >10000 | | >10000 | |
| | | 15e | >10000 | | >10000 | |
| | | b12 | >10000 | | >10000 | |
| | | b6 | >10000 | | 871 | 144 |
| | CD4i | X5 | >10000 | | >10000 | |
| | | A32 | >10000 | | >10000 | |
| | | 17b | >10000 | | >10000 | |
| | | 412d | >10000 | | >10000 | |
| | V3 | 447-52D | >10000 | | >10000 | |
| | | 39F | >10000 | | 160 | 31 |
| | | 19b | >10000 | | 14 | 4 |
| | | 14e | >10000 | | 28 | 6 |
| | gp41 | 7B2 (I) | >10000 | | >10000 | |
| | | F240 (I) | >10000 | | >10000 | |

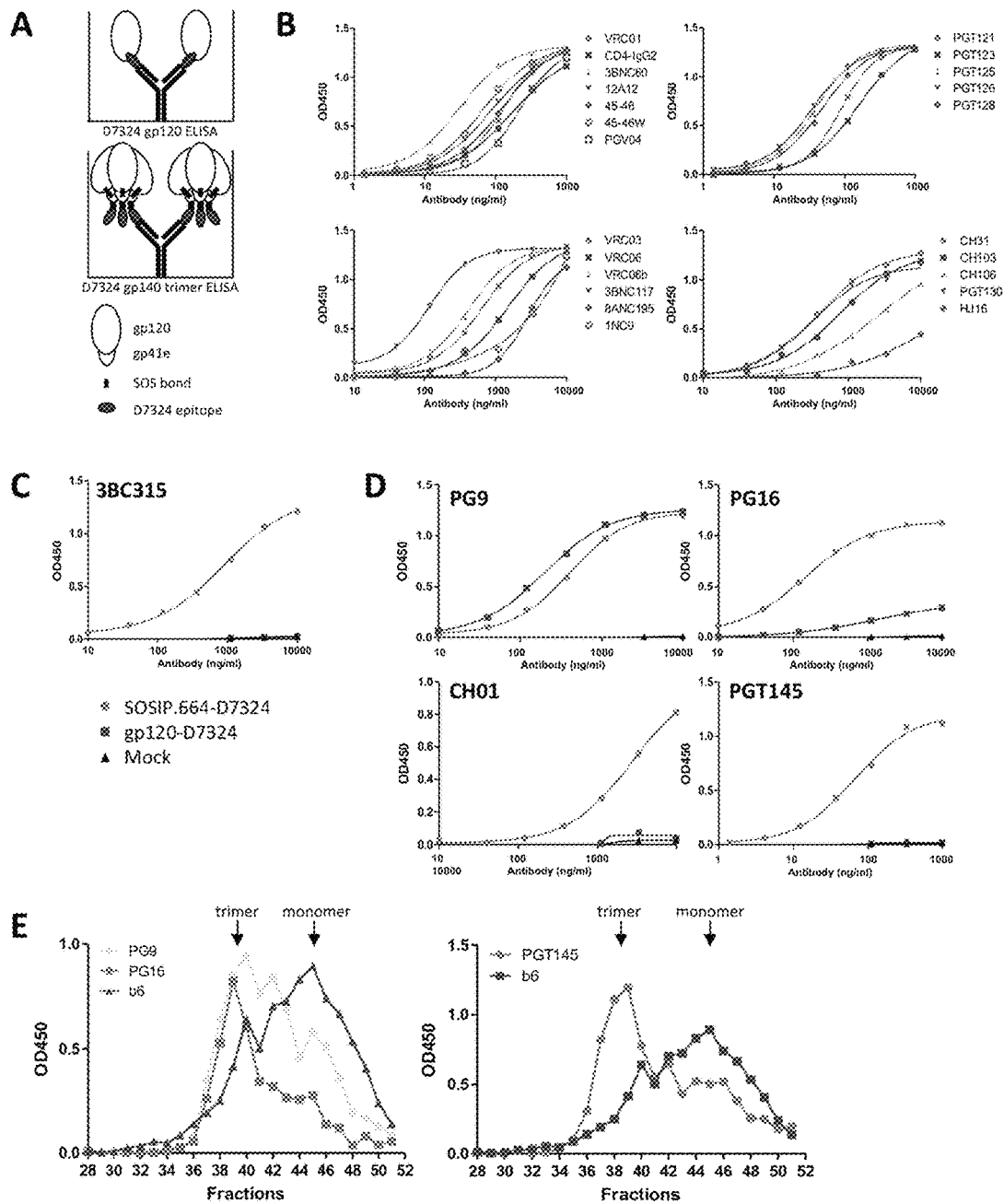

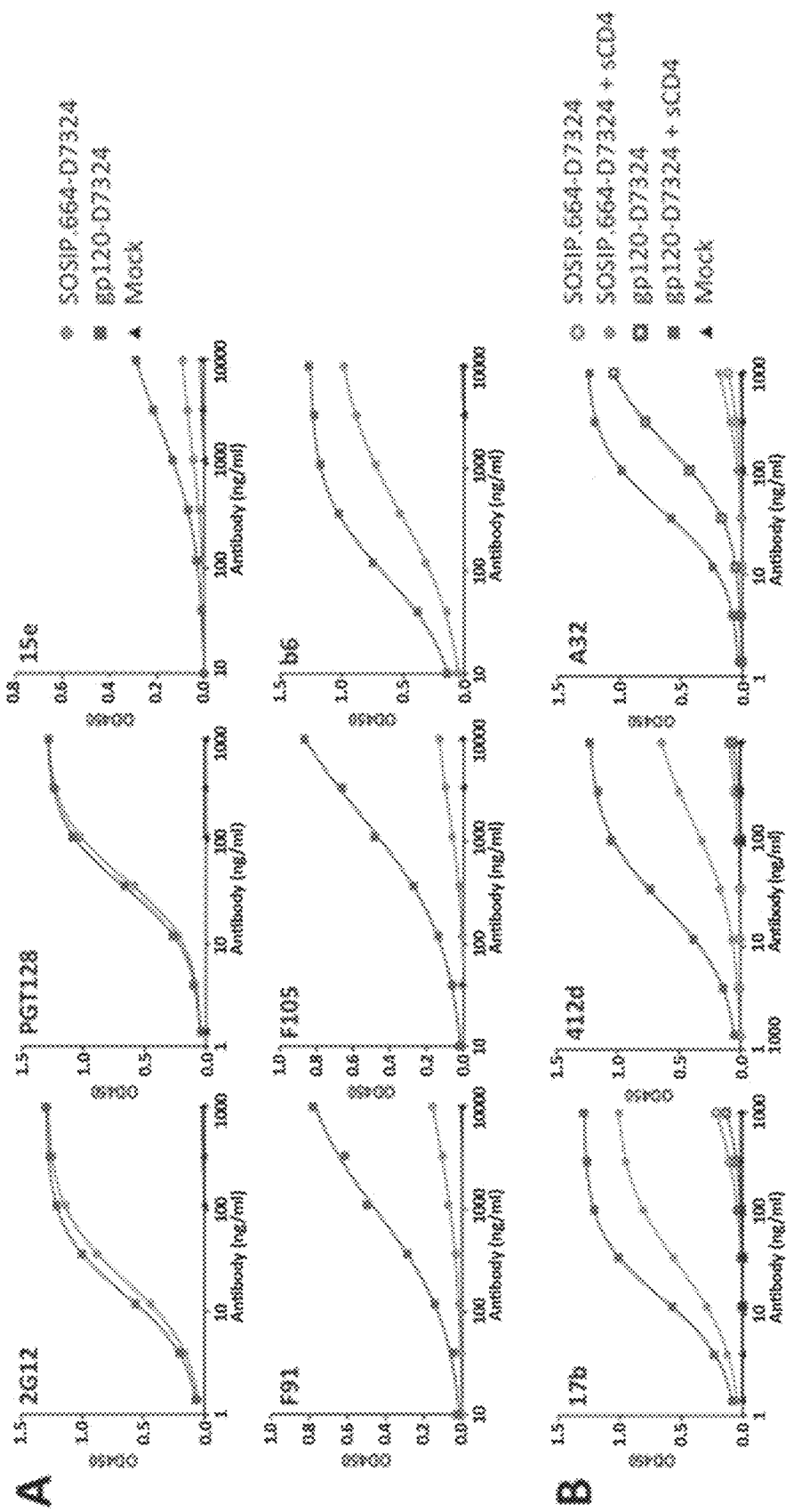
FIG. 19A-B

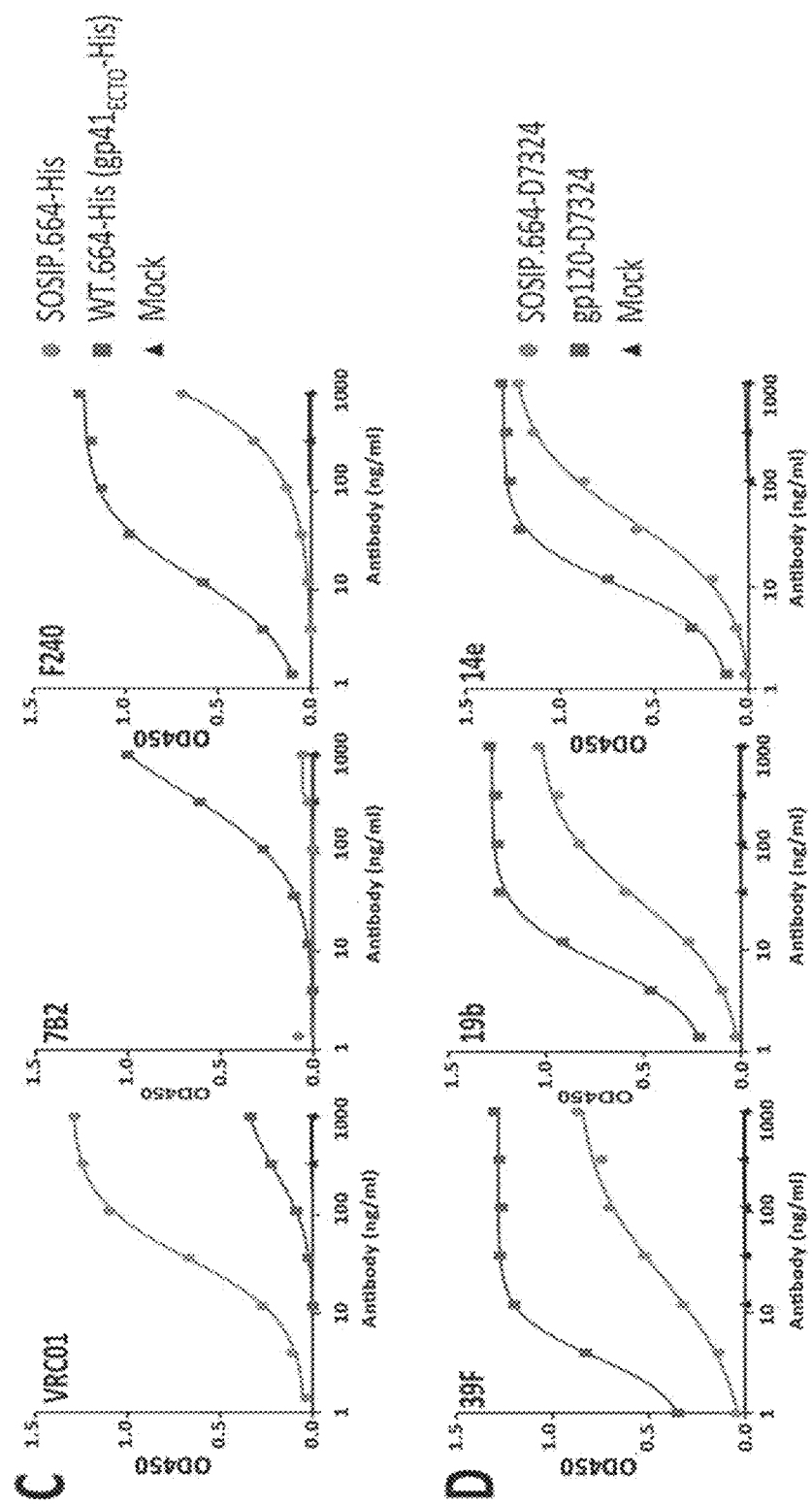
FIG. 19C-D

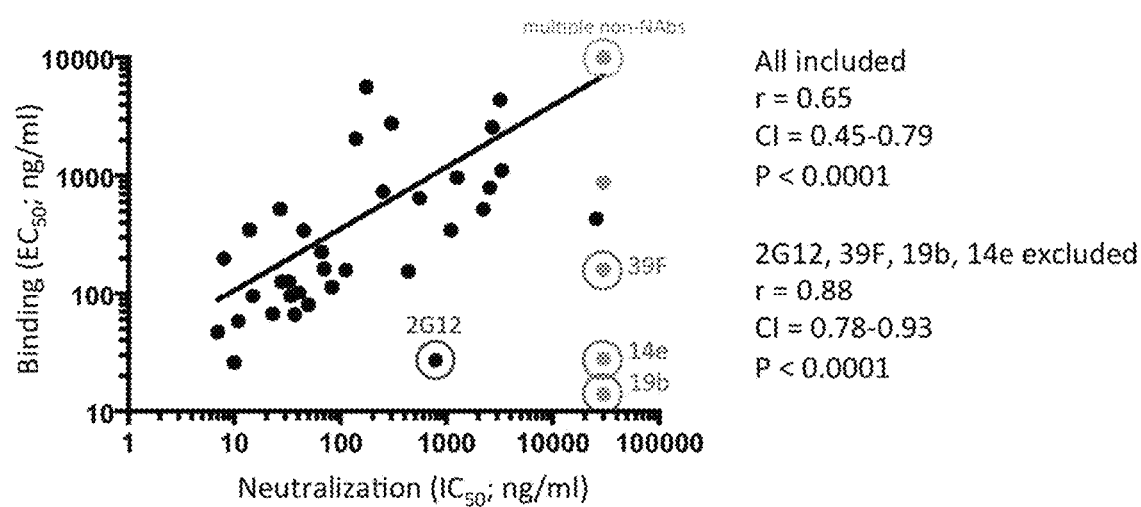

FIG. 25

| | epitope | antibody | BG505 T332N neutralization | BG505 SOSIP.664 SPR | ITC | EM | ELISA |
|---|---|---|---|---|---|---|---|
| NAbs | CD4bs | CD4-IgG2 | + | + | | | + |
| | | VRC01 | + | | | | + |
| | | VRC03 | + | | | | + |
| | | VRC06 | + | | | | + |
| | | VRC06b | + | | | | + |
| | | HJ16 | + | | | | + |
| | | 3BNC60 | + | | | | + |
| | | 3BNC117 | + | | | | + |
| | | 12A12 | + | | | | + |
| | | 45-46 | + | | | | + |
| | | 45-46W | + | | | | + |
| | | 1NC9 | + | | | | + |
| | | 8ANC195 | + | | | | + |
| | | PGV04 | + | + | + | + | + |
| | | CH31 | + | | | | + |
| | | CH103 | + | | | | + |
| | | CH106 | + | | | | + |
| | V1/V2-glycan | PG9 | + | + | + | + | + |
| | | PG16 | + | + | + | + | + |
| | | PGT145 | + | + | + | + | + |
| | | CH01 | + | | | | + |
| | V3-glycan | PGT121 | + | + | + | + | + |
| | | PGT122 | + | + | + | + | + |
| | | PGT123 | + | + | + | + | + |
| | | PGT125 | + | | | | + |
| | | PGT126 | + | | | | + |
| | | PGT127 | + | | | + | + |
| | | PGT128 | + | + | + | + | + |
| | | PGT130 | + | | | | + |
| | OD-glycan | 2G12 | + | + | + | + | + |
| | | PGT135 | + | + | | + | + |
| | | PGT136 | + | | | | + |
| | unknown | 3BC176 | + | | | + | + |
| | | 3BC315 | + | | | + | + |
| Non-NAbs | CD4bs | F91 | | | | | + |
| | | F105 | | | | | + |
| | | 15e | | | | | + |
| | | b12 | | + | | | + |
| | | b6 | | +/- | | | + |
| | CD4i | X5 | | | | | |
| | | A32 | | | | | |
| | | 17b | | | | | |
| | | 412d | | | | | |
| | V3 | 447-52D | | | | | + |
| | | 39F | | | | | + |
| | | 19b | | | | +/- | + |
| | | 14e | | +/- | | +/- | + |
| | gp41 | 7B2 | | | | | |
| | | F240 | | | | | |

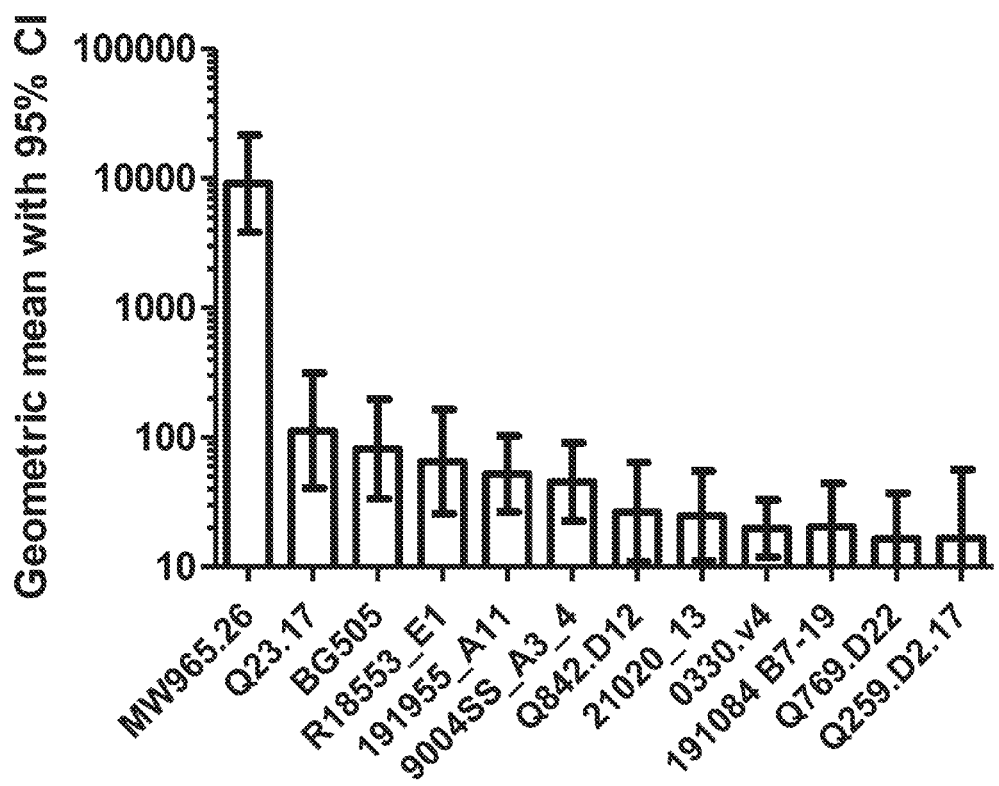

FIG. 26B

| Antibody | Specificity | Isotype | ID50 in TZM-bl Cells[1] | |
|---|---|---|---|---|
| | | | MN.3 | BG505ΔCT/T332N |
| 2219 | V3 | IgG1L | <0.01 | >25 |
| 2557 | V3 | IgG1L | <0.01 | >25 |
| 3074 | V3 | IgG1L | >25 | >25 |
| 3869 | V3 | IgG1L | 0.1 | >25 |
| 447-52D | V3 | IgG3L | <0.01 | >25 |
| 838-D | V3 | IgG1L | 0.03 | >25 |
| 1361 | V2 | IgG1K | 0.7 | >25 |
| 1393A | V2 | IgG1K | 1.6 | >25 |
| 1357D (A) | V2 | IgG1K | >25 | >25 |
| 830A | V2 | IgG3K | >17 | >17 |
| 2297 | V2 | IgG1L | 8.4 | >25 |
| 654-30D | CD4bs | IgG1L | 0.2 | >25 |
| 1008-30D | CD4bs | IgG1L | 0.9 | >25 |
| 1570D | CD4bs | IgG1L | 0.2 | >25 |
| 729-30D | CD4bs | IgG1K | 0.3 | >25 |
| 1331-160A | C5 | IgG3L | >25 | >25 |
| 670-30D | C5 | IgG1L | >25 | >25 |
| 858-30D | C5 | IgG1L | >22.4 | >22.4 |
| 181D | gp41(cluster I) | IgG2K | >25 | >25 |
| 240D | gp41(cluster I) | IgG1K | >25 | >25 |
| 50-69D | gp41(cluster I) | IgG1K | >25 | >25 |
| 126-7D | gp41(cluster II) | IgG1K | >25 | >25 |
| 167D | gp41(cluster II) | IgG1L | >25 | >25 |
| 847D | C2 | IgG1L | >25 | >25 |

FIG. 29

HIV-1 ENVELOPE GLYCOPROTEIN

INCORPORATION BY REFERENCE

This application claims benefit of and priority to U.S. provisional patent application Ser. No. 61/722,739 filed Nov. 5, 2012.

Reference is made to international patent application Serial No. PCT/US11/26862 filed Mar. 2, 2011, which published as international patent publication WO 2011/109511 on Sep. 9, 2011 and claims priority to U.S. provisional patent application Ser. No. 61/309,685 filed Mar. 2, 2010. Reference is also made to U.S. provisional patent application Ser. No. 61/664,990 filed Jun. 27, 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under Grant GM046192, No. AI082362 AI100663, AI036082, AI036214, RR017573 and RR0012000 awarded by the National Institutes of Health, and grant numbers DE-AC02-05CH11231 and DE-AC02-06CH11357 awarded by the U.S. Department of Energy. The government has certain rights in the invention.

FIELD OF THE INVENTION

This application relates to a novel HIV-1 envelope glycoprotein which may be utilized as an HIV-1 vaccine immunogen, as a native Env trimer mimic, for identification of small molecules for use as an immunogen that bind specific HIV-1 broad neutralizing antibodies, for identification of small molecules for use as an anti-viral compound that bind specific HIV-1 envelope glycoprotein monomers and/or trimers, antigens for crystallization and for the identification of broadly neutralizing antibodies.

SEQUENCE LISTING

The instant application contains a Sequence Listing which has been submitted electronically in ASCII format and is hereby incorporated by reference in its entirety. Said ASCII copy, created on Feb. 19, 2014, is named 43094.01.2026_SL.txt and is 80,976 bytes in size.

BACKGROUND OF THE INVENTION

AIDS, or Acquired Immunodeficiency Syndrome, is caused by the human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline and simian immunodeficiency viruses (SIV). Two closely related types of HIV, designated HIV-1 and HIV-2, have been identified thus far, of which HIV-1 is by far the most common cause of AIDS. However. HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4$^+$ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4$^+$ T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998; 280:1884-8). For fusion with its target cells, HIV-1 uses a trimeric Env complex containing gp120 and gp41 subunits (Burton et al., Nat Immunol. 2004; 5:233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001; 77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

Most experimental HIV-1 vaccines tested in human and/or non-human primate suggests that a successful vaccine will incorporate immunogens that elicit broad neutralizing antibodies (bNabs) and robust cell-mediated immunity. HIV-1 envelope glycoprotein (Env) is the main viral protein involved in the entry of the virus and is also the primary target for neutralizing antibodies, but due to immune evasion strategies and extreme sequence variability of Envs, generation of bNabs has been a daunting task (Phogat S, Wyatt R. Curr Pharm Des. 2007; 13:213-27, Phogat S, et al. J Intern Med. 2007 262:26-43, Karlsson Hedestam G B, et al. Nat Rev Microbiol. 2008 6:143-55).

The ability to elicit broad and potent neutralizing antibodies is a major challenge in the development of an HIV-1 vaccine. Namely, HIV-1 has evolved an impressive array of strategies to evade antibody-mediated neutralization, bNabs develop over time in a proportion of HIV-1 infected individuals, and a handful of broad neutralizing monoclonal antibodies have been isolated from clade B infected donors. These antibodies tend to display less breadth and potency against non-clade B viruses, and they recognize epitopes on the virus that so far have failed to elicit broad neutralizing responses when incorporated into a diverse range of immunogens. Presumably, this is due to the ability of these bNabs to recognize conserved recessed targets on HIV Env, which are either inaccessible by elicited antibodies or difficult to precisely redesign and present to the immune system.

Recently using a sensitive high-throughput micro-neutralization screening of supernatants from approximately 30,000 IgG+memory B cells from a HIV-1 clade A-infected African donor, two new bNabs, PG9 and PG16, that are broad and exceptionally potent neutralizing antibodies were identified (Walker L, Phogat S, et al. Science. 2009; 326: 285-9. Epub 2009 Sep. 3). These antibodies recognize a new conserved, yet accessible, vaccine target (consisting of conserved elements on the variable loops 2 and 3) on the Env and show preferential binding to HIV Env trimers (model of PG9 and PG16 epitopes on HIV-1 trimer.).

Citation or identification of any document in this application is not an admission that such document is available as prior art to the present invention.

SUMMARY OF THE INVENTION

Based on the binding property and breadth/potency of the new antibodies to neutralize >75% of the viruses tested, Applicants hypothesize that certain antibodies recognize a relevant vaccine target on the native HIV-1 Env on the surface of the virus and identification of HIV-1 envelope glycoproteins that present these targets on soluble forms of HIV-1 envelope would be good HIV-1 vaccine candidates to elicit PG9 and PG16 like antibodies and also may be used as reagents for mapping and crystallization, electron microscopy and other biophysical studies.

The envelope glycoproteins identified as a part of this invention show significantly better binding to new identified broad neutralizing antibodies PG9 and/or PG16. These are the only soluble forms of envelope identified that show such remarkable binding to PG9 and PG16. The envelope glycoproteins Envs have value (a) as reagents for screening of broad neutralizing antibodies, such as but not limited to, PG9 and PG16, (b) as reagents for screening of small molecules that compete binding of broad neutralizing antibodies, such as but not limited to, PG9 and PG16, (c) as monomer and native envelope trimer mimics for crystallization and electron microscopy studies and (d) as immunogens in different forms to use as HIV-1 vaccine components, for example, to elicit broadly neutralizing antibodies.

In an advantageous embodiment, the soluble envelope glycoproteins of the present invention may be isolated from HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus. In an advantageous embodiment, the soluble envelope glycoproteins of the present invention may be isolated from the 6535 virus, the 13095 virus, the 16055 virus, the 25710 virus, the 25925 virus, the CAAN virus, the BG505 virus or the Zm109F virus. Sequences of these viruses are available in the NCBI data base and Applicants have used them to generate recombinant Env proteins with unique sequences in which Applicants have modified the leader, added His-tag and terminated the sequence before the cleavage site for gp120 and before the transmembrane for gp140. The DNA sequences are unique as they are codon optimized based on mammalian codons for expression in mammalian cells.

In a particularly advantageous embodiment, the envelope glycoprotein may be isolated from a BG505 virus and having SOSIP mutations. In a particularly advantageous embodiment, the glycoprotein is a BG505 SOSIP.664 trimer.

In a particularly advantageous embodiment, BG505 SOSIP.664 sequence may be a modification of a BG505 gp160 sequence which may comprise (a) a replacement of signal sequence by the tPA leader to enhance secretion, (b) mutations A501C and T605C (SOS) to stabilize gp120-gp41 association, (c) mutation REKR(508-511)RRRRRR (SEQ ID NOS 1 and 2, respectively) to enhance cleavage (d) mutation I559P to facilitate trimerization, (e) a truncation at position 664 to prevent MPER-mediated aggregation and/or (f) T332N to create 2G12, PGT125-PGT131 epitopes or any combination thereof.

In a more particularly advantageous embodiment, a modified BG505 SOSIP.664 sequence may have a sequence comprising (SEQ ID NO: 3)
MDAMKRGLCCVLLLCGAVFVSPSQEIHARFRRGARAENLWVTVYYGVPVW

KDAETTLFCASDAKAYETEKHNVWATHACVPTDPNPQEIHLENVTEEFNM

WKNNMVEQMHTDIISLWDQSLKPCVKLTPLCVTLQCTNVTNNITDDMRGE

-continued

LKNCSFNMTTELRDKKQKVYSLFYRLDVVQINENQGNRSNNSNKEYRLIN

CNTSAITQACPKVSFEPIPIHYCAPAGFAILKCKDKKFNGTGPCPSVSTV

QCTHGIKPVVSTQLLLNGSLAEEEVMIRSENITNNAKNILVQFNTPVQIN

CTRPNNNTRKSIRIGPGQAFYATGDIIGDIRQAHCNVSKATWNETLGKVV

KQLRKHFGNNTIIRFANSSGGDLEVTTHSFNCGGEFFYCNTSGLFNSTWI

SNTSVQGSNSTGSNDSITLPCRIKQIINMWQRIGQAMYAPPIQGVIRCVS

NITGLILTRDGGSTNSTTETFRPGGGDMRDNWRSELYKYKVVKIEPLGVA

PTRCKRRVVGRRRRRRAVGIGAVFLGFLGAAGSTMGAASMTLTVQARNLL

SGIVQQQSNLLRAPEAQQHLLKLTVWGIKQLQARVLAVERYLRDQQLLGI

WGCSGKLICCTNVPWNSSWSNRNLSEIWDNMTWLQWDKEISNYTQIIYGL

LEESQNQQEKNEQDLLALD*.

In a particularly advantageous embodiment, the trimer protein is prepared, purified and formulated for immunization in a human.

In another particularly advantageous embodiment, the trimer protein is formulated for immunization in a human to contain an adjuvant. A number of adjuvants are well known to those investigating vaccines but could include but are not limited to those containing alum.

In another particularly advantageous embodiment, the trimer protein is further attached to a particle such that multiple copies of the trimer are attached and this material is prepared and formulated for immunization in a human.

In a particularly advantageous embodiment, the soluble envelope glycoproteins of the present invention have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to any of the sequences depicted in the figures and/or the specification.

Another advantageous embodiment encompasses a stable soluble HIV-1 envelope glycoprotein trimer mimic.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with the Electron Microscopy Data Bank will be made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 depicts recombinant HIV-1 envelope glycoprotein gp120 BG505 clade A ELISA binding and phylogeny tree. ELISA showed significant binding of PG9, PG16 and b12 antibodies to BG505 gp120. The BG505 protein sequence was selected using a bioinformatics approach that identified a close progenitor sequence to HIV-1 clade A Env from the Env protein database. The HIV-1 Env clade A sequences from the donor (V1_011) who gave rise to PG9 and PG16 antibodies were used to search the HIV-1 Env protein data base.

FIG. 2A-D depicts the sequence of BG505_gp120. Figure discloses SEQ ID NOS 10 and 11, respectively, in order of appearance.

FIG. 3A-E depicts the sequence of BG505_gp140. Figure discloses SEQ ID NOS 12 and 13, respectively, in order of appearance.

FIG. 4A-E depicts the sequence of BG505gp140GCN4L4. Figure discloses SEQ ID NOS 14 and 15, respectively, in order of appearance.

FIG. 5A-E depicts the sequence of BG505gp160ΔCT. Figure discloses SEQ ID NOS 16 and 17, respectively, in order of appearance.

(PDB ID: 3U4E) sits atop the HIV-1 spike. Glycans at position N156 and N160 are shown as spheres and colored yellow and magenta, respectively. The gp120 core monomers modeled in a trimeric configuration are shown in blue (PDB ID: 3DNN). A. SAXS reconstruction. B. Negative stain EM reconstruction. C. EM reconstruction with a low (light purple) and high (dark purple) contour level demonstrating the asymmetry of the complex and PG9 recognition of two gp120 protomers. Red, blue and yellow dots are used to portray the edges of the three different gp120 protomers. The figure was generated with UCSF Chimera (73).

Figure 7:
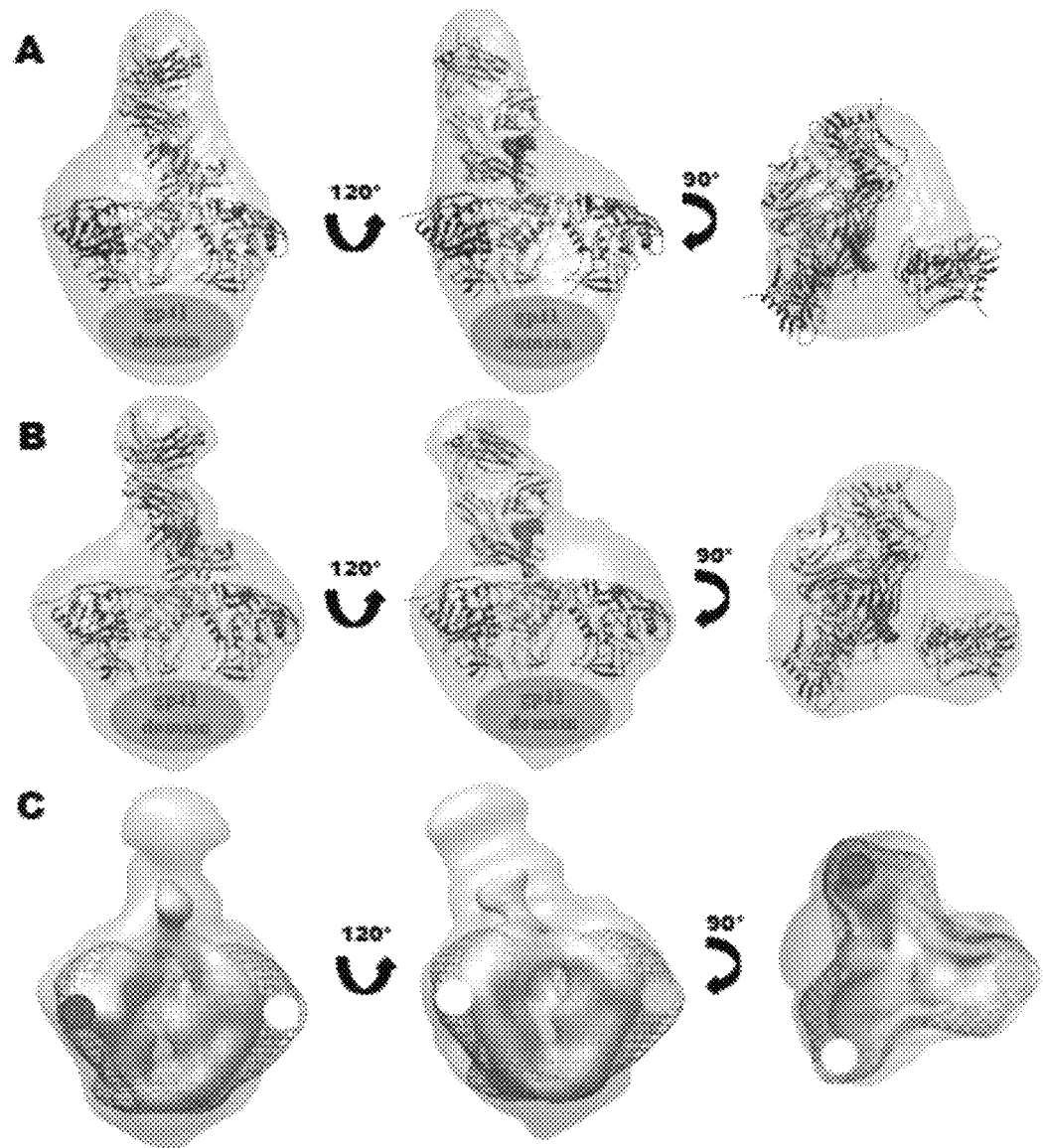
FIG. 7 depicts a structural characterization of the PG9 Fab: BG505 SOSIP.664 complex by SAXS and negative stain EM. The SAXS molecular envelope and the EM reconstruction are colored blue and red, respectively. Fitting of known protein crystal structures in the densities are shown as secondary structure cartoons. PG9 Fab (shades of gray) in complex with CAP45 gp120 V1/V2 (magenta)

FIG. 8 depicts ITC experiments for PG9 WT and a mutant binding to BG505 gp120 monomer and SOSIP.664 trimer. A. Cartoon representation of an engineered PG9 mutant that harbors a $Man_5GlcNAc_2$ glycan in the LCDR2. This mutant serves to probe the potential of additional contacts between PG9 and elements at the trimer apex. Colors are as in FIG. 7. In addition, the PG9 HCDRs and LCDRs have now been colored in shades of green and red, respectively. The figure was generated with UCSF Chimera (73). B. Representative raw data and isotherms of multiple ITC experiments demonstrating that, whereas the PG9 LC glycan mutant binds to a BG505 gp120 monomer with the same affinity as PG9 WT, it interacts with the SOSIP.664 trimer with >10× lower binding affinity. Thermodynamic parameters of binding are summarized in Table 2.

Figure 9A:
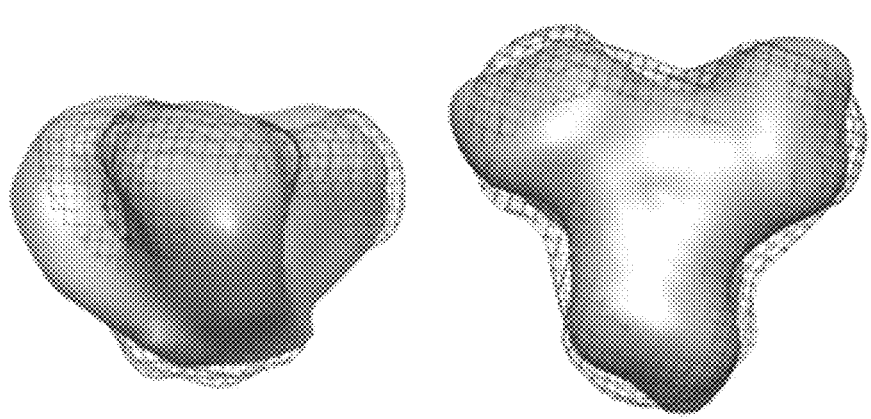

FIG. 9A-C depicts EM and DSC studies of the unliganded SOSIP.664 trimer structure and stability. A. Comparison of the EM reconstructions of the KNH1144 (blue mesh) and BG505 (orange surface) SOSIP.664 trimer, both at a 25 Å resolution. The latest appears to adopt a more compact conformation, particularly at the spike apex. The figure was generated with UCSF Chimera (73). B. The melting profile of the BG505 SOSIP.664 trimer suggests a high degree of stability in contrast to KNH1144 SOSIP.664, which initiates thermal transitions 16.6° C. sooner. Raw data are shown in black and fitted curves from which $T_m$ values were obtained for the different peaks observed and are colored in red. C. Whereas sCD4 binding destabilizes the BG505 SOSIP.664 trimer (initiation of thermal denaturation 16.8° C. prior to the unliganded sample), PG9 binding appears to both destabilize and stabilize elements of the trimer (appearance of events with Tms at 52.2° C. and 73.8° C.). Unliganded, PG9 Fab and sCD4 have $T_m$s of 67.7° C. and 61.7° C., respectively.

Figure 10:
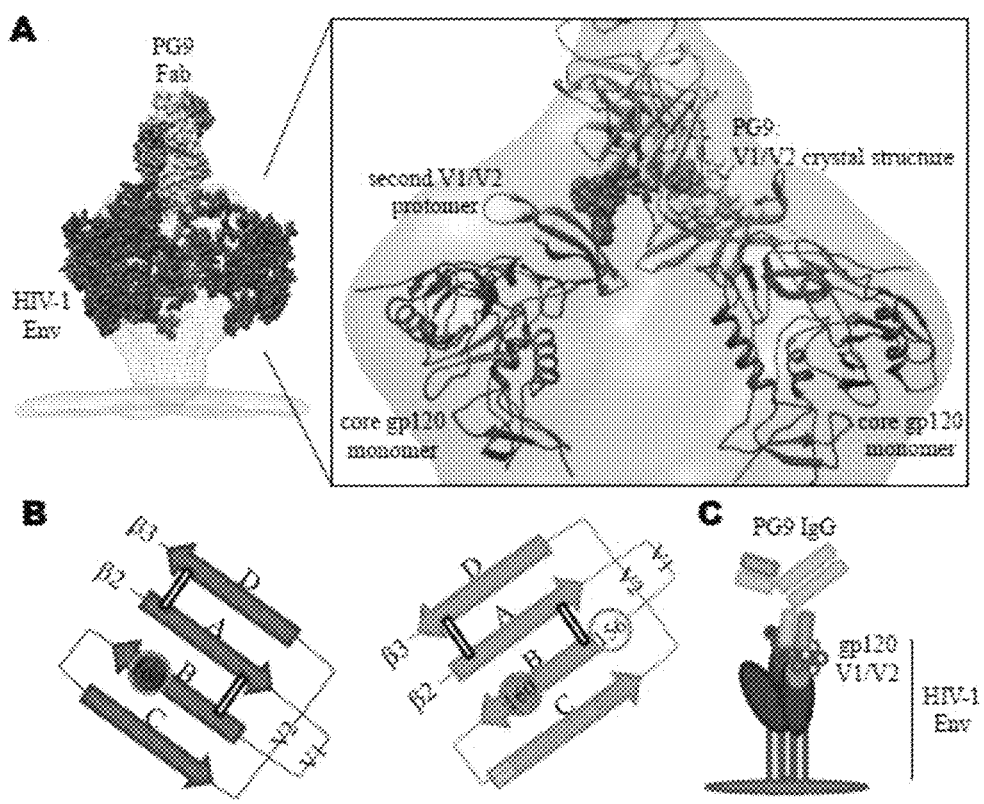

FIG. 10 depicts a model of the asymmetric recognition of the HIV-1 Env trimer by bnAb PG9. A. One PG9 Fab interacts closely with two gp120 protomers atop the HIV-1 spike. PG9 sits directly above the trimer axis and potentially accommodates additional elements to those previously identified in the PG9:V1/V2 crystal structures upon binding to Env, such as a second N160 $Man_5GlcNAc_2$ glycan. The model on the left was generated from the electron microscopy reconstruction of the unliganded membrane-anchored HIV-1 Env trimer (blue mesh, EMD ID 5019) (52) with modeled glycans and PG9 Fab shown as blue spheres and gray surface, respectively. Colors and rendering of the inset are as in FIGS. 7 and 8, and a second V1/V2 model (purple) with approximately 120° rotation related to the primary V1/V2 model (magenta) was generated to fit the density. The figure was generated with UCSF Chimera (73). B. Cartoon representation of the PG9 epitope on the HIV-1 trimer, which consists of interactions with the N156 glycan (yellow), the N160 glycan (magenta) and cationic elements of strand C (green) of a first V1/V2 gp120 protomer and possibly with a second N160 glycan (purple) from a neighboring V1/V2 gp120 protomer. The V1/V2 Greek key motif is depicted similarly to that in (45). C. Cartoon representation of PG9 interacting with two gp120 V1/V2 elements at the HIV-1 Env trimer apex, resulting in the third gp120 protomer being slightly pushed away from the trimer axis. Glycans are shown as spheres, gp41 as orange rectangles, and other elements are colored as in previous figures.

Figure 11:
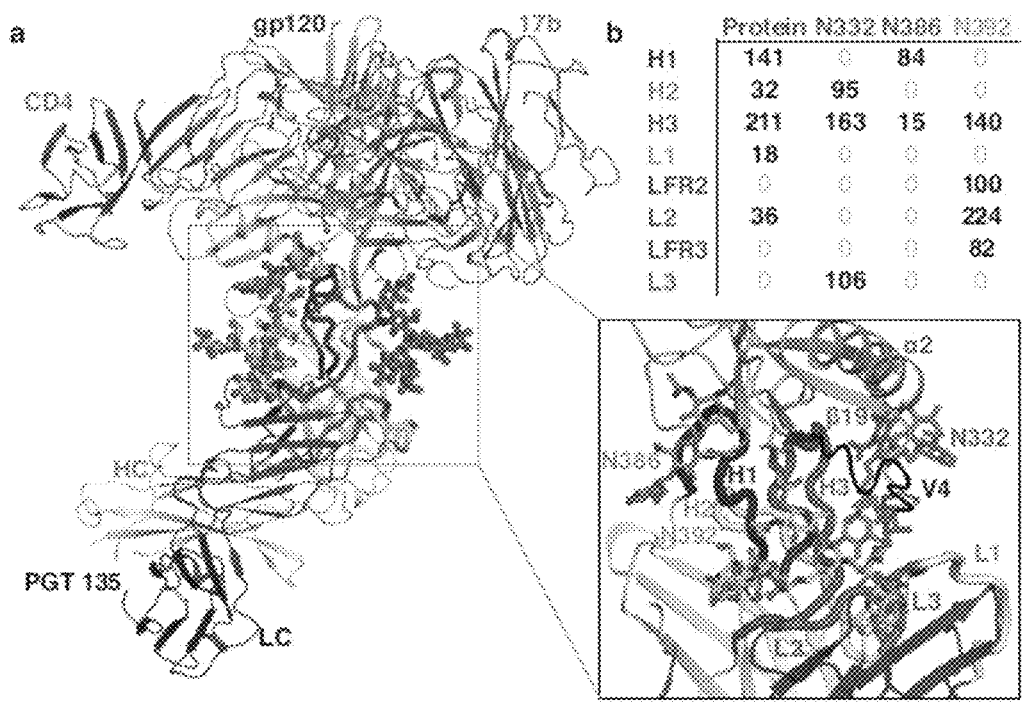

FIG. 11 depicts a crystal structure of PGT 135 in complex with HIV-1 gp120. a, The glycan-dependent interaction between PGT 135 and gp120 is presented in ribbon representation in the context of the gp120 ternary complex that contains a 2-domain CD4 and the Fab of CD4-induced antibody 17b. An enlarged display of the PGT 135/gp120 interaction is shown to the lower right. The CDR H1 and H3 loops (blue and red, respectively) penetrate deeply through the glycan canopy to contact the protein surface below, while the light chain contacts the glycans using CDR loops and framework regions. b, Buried surface on the gp120 protein surface and glycans N332, 16 N386 and N392 by CDR loops and framework regions of PGT 135. The values are in $Å^2$ and calculated using MS.

Figure 12:
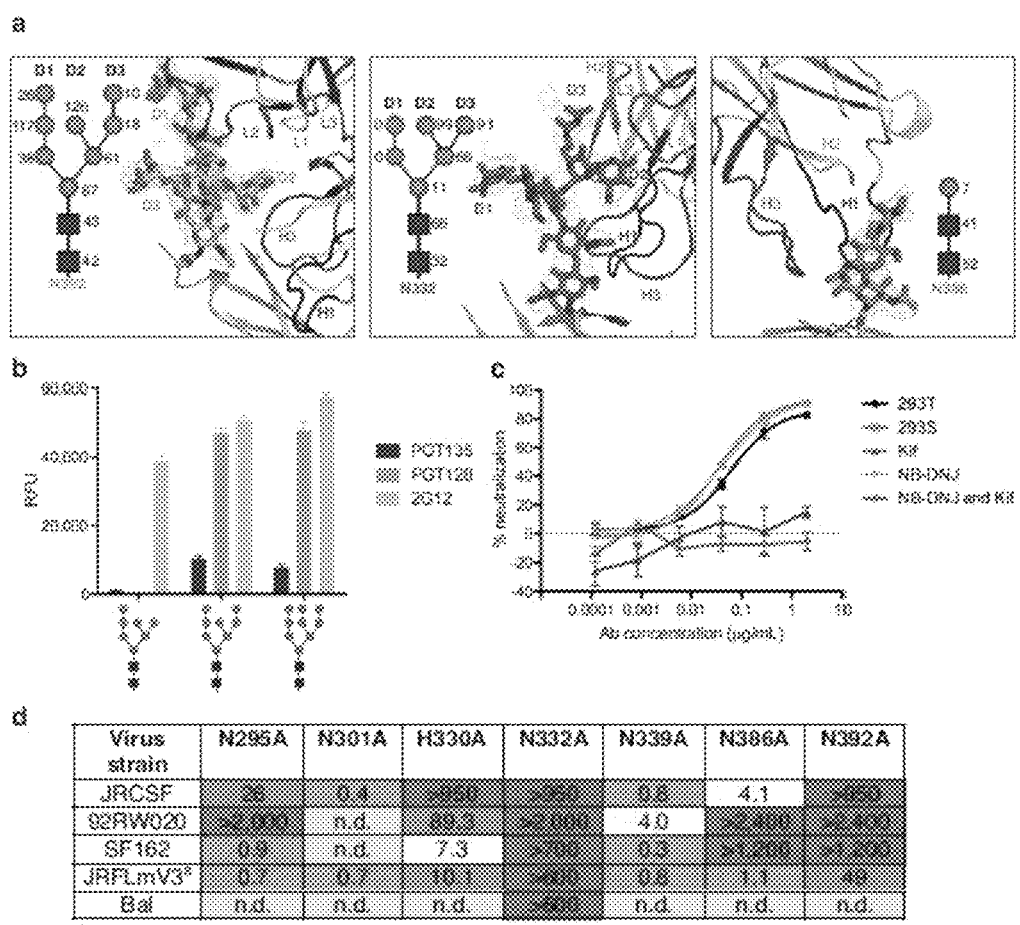

FIG. 12 depicts glycan dependency of PGT 135 binding to gp120. a, PGT 135 interactions with gp120 glycans are displayed. The 2Fo-Fc electron density (contoured at a) of N392 (left), N332 (middle) and N386 (right) glycans are shown along with contacting residues on PGT 135 colored as in FIG. 6 according to CDR loops. A schematic of each glycan is shown besides the structures for the sugars that are visible in the electron density with GlcNAc as dark blue squares and mannose residues as green circles. The buried surface area ($Å_2$) on each glycan moiety by PGT 135 is shown. b, Interactions of PGT 135, PGT 128 and 2G12 with oligomannose glycans on a high-density microarray are shown. PGT 135 binding to $Man_7GlcNAc_2$, $Man_5GlcNAc_2$ and $Man_9GlcNAc_2$ is detected. c, The glycan dependency of PGT 135 neutralization is shown using Bal pseudoviruses produced in different cell systems. Virus produced in 293T cells contains complex, hybrid and oligomannose type glycans, whereas in 293S cells only $Man_{5-9}GlcNAc_2$ glycans are present; addition of kifunensine yields only $Man_9GlcNAc_2$ glycans. NB-DNJ blocks the glycan processing at neutral glucosylated glycans. These results suggest that PGT 135 cannot neutralize viruses containing primarily $Man_9GlcNAc_2$ glycans despite being able to bind to these glycans in the context of the glycan array, suggesting that PGT135 can bind at least one but not multiple $Man_9GlcNAc_2$. d, The effect on PGT 135 neutralization of single mutations that remove specific glycans around the epitope, as well as His330, is tabulated for several HIV-1 strains. The N332 and N392 glycans are critical for neutralization in the context of all tested HIV-1 strains, while the dependency on N295 and N386 glycans is strain dependent. Values are presented as fold change in $IC_{50}$ of variant envelope compared to WT envelope (fold change=$IC_{50}$ variant $IC_{50}$ WT). Boxes are color coded for fold change; red: >100, orange 10-100, yellow 4-9 and green <4. n.d.: not determined. Values were determined by ELISA instead of neutralization.

Figure 13:
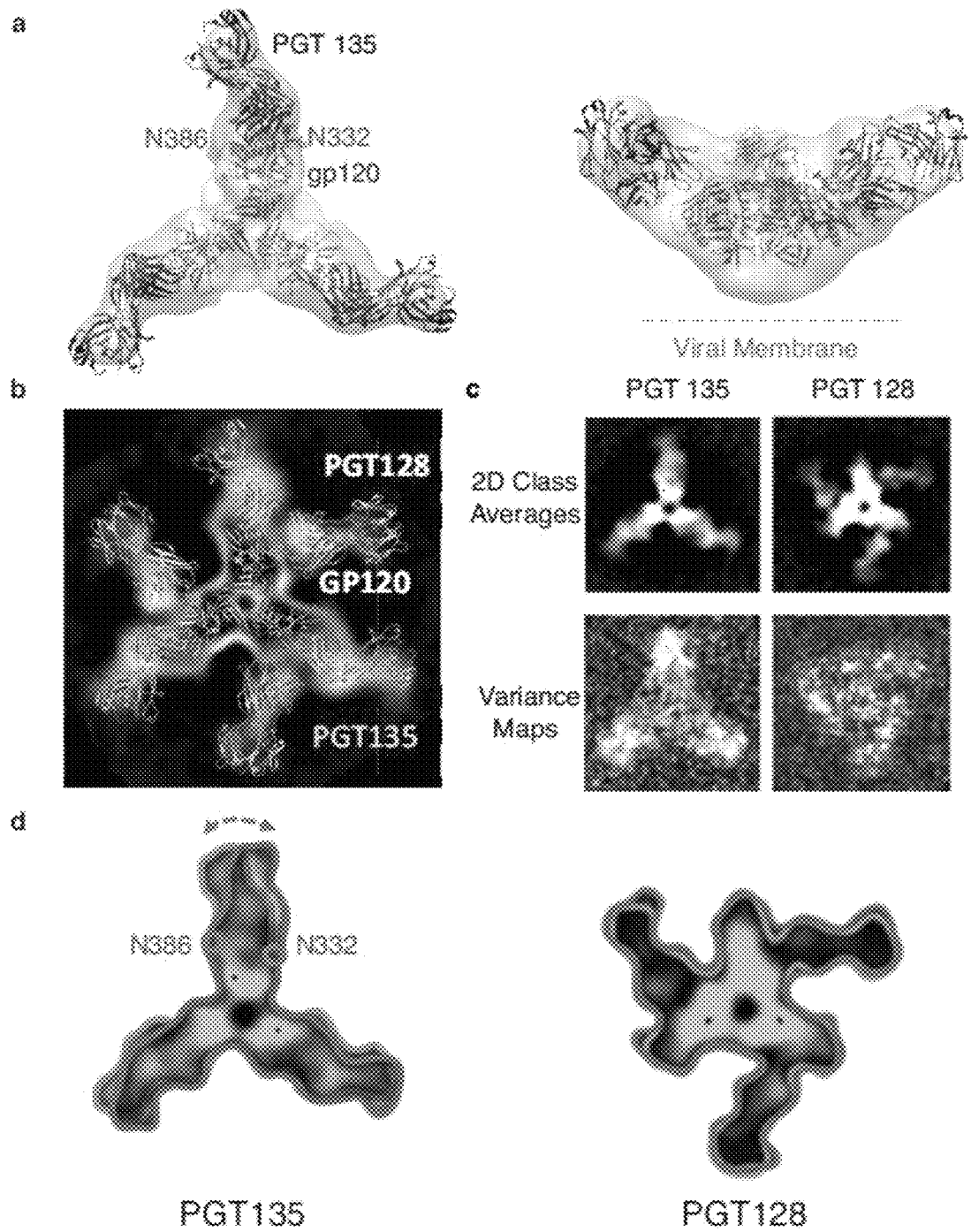

FIG. 13 depicts a gp140 BG505 SOSIP trimer binding Fab PGT135 in slightly different orientations in contrast to PGT128, which is bound in a single orientation. a, The PGT 135-gp120 structure is shown fitted into an EM density map of PGT 135 in complex with the BG505 SOSIP.664 trimer in top and side views of the trimer. b, 2D difference map of the two 2D class averages. The PGT128-SOSIP class average was subtracted from the PGT135-SOSIP class average. The overlap is shown as the black gap in the trimer region, illustrating that the trimers are equivalent and have the same relative disposition. c, Top view of the 2D class averages of the BG505 SOSIP.664 trimer in complex with PGT135 (left) and PGT128 (right). The images contributing to the class averages were aligned using a top view back projection of an undecorated SOSIP.664 trimer. On the top, the Fabs are colored cyan and yellow for PGT135 and PGT128, respectively. Below are variance maps of the trimer in complex with PGT135 (left) and PGT128 (right) indicating the variability in the images that went into the 2D class averages. Brighter pixel values correspond to a greater degree of variability in that region. Fab PGT135 exhibits a much higher degree of flexibility than PGT128. d, An overlay of the 2D class average (blue outline) and the first eigenvector (orange) of the 2D PCA analysis for PGT135 and PGT128. There is a clear distinction in the position of the Fabs between the 2D class average and the first eigenvector in the PGT135 complex, but not in the PGT128 complex.

Figure 14:
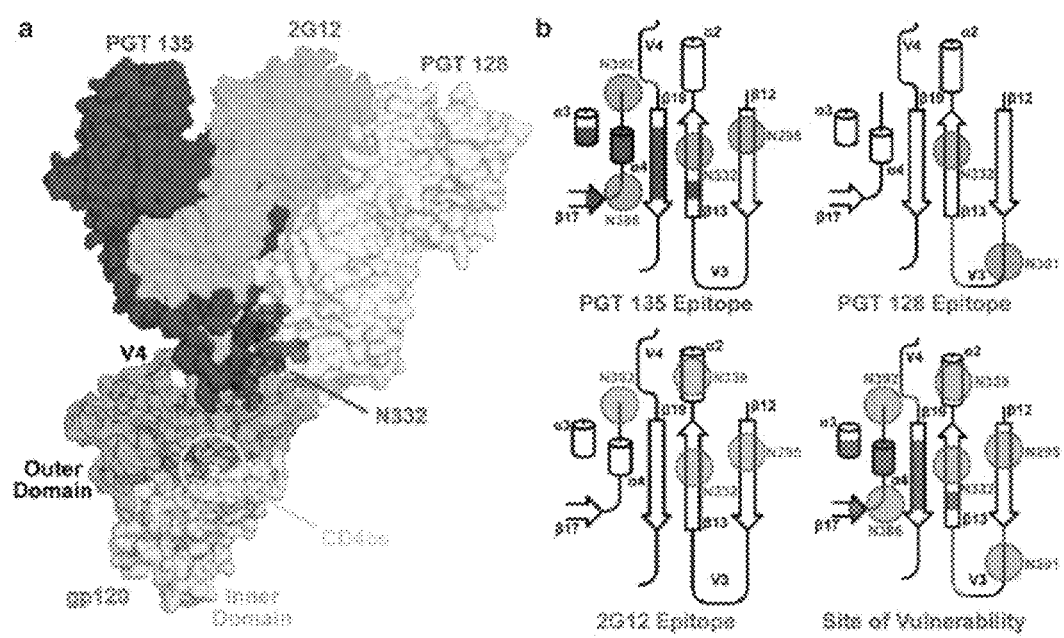

FIG. 14 depicts a supersite of vulnerability centered on the N332 glycan. a, Binding to the N332 glycan on gp120 for PGT 135, 2G12 and PGT 128 is shown with their respective structures superimposed on the N332 glycan. While 2G12 contacts the N332 glycan from the top and PGT 128 from an angle titled towards the V3 loop, PGT 135 approaches the N332 glycan from the other side closer towards the CD4 binding site. Despite all these different angles of approach and binding to different constellations of glycans and protein surfaces, these antibodies are all broad and potently neutralizing. b, The epitopes of PGT 135, PGT 128 and 2G12 are shown in topology representations in which cylinders are α-helices, arrows are β-strands and lines are loops. N-linked glycan sites are circled. Together, they define a new supersite of vulnerability containing different combinations of N-linked glycans centered on N332 and making contact with different protein elements surrounding the base of the V3 (PGT 128) and V4 (PGT135) loops. The structures of 2G12 (PDBID: 1OP5) and PGT 128 (PDBID: 3TYG) were obtained from the PDB.

FIG. 15A-G depicts a design and biochemical characterization of BG505 SOSIP.664 gp140 trimers. (A) Linear representation of the BG505 gp160, SOSIP.664 gp140, SOSIP.664-D7324 gp140 and gp120-D7324 Env proteins. Modifications compared to the original BG505 gp160 sequence are indicated in red and mentioned in the text. The following changes were made to the wild type BG505 amino acid sequence: 1) The tissue plasminogen activator (tPA) signal sequence replaced the natural one; 2) the gp41 transmembrane (TM) and cytoplasmic tail (CT) domains were deleted to create a soluble gp140; 3) the A501C and T605C substitutions were made to form a disulfide bond between gp120 and gp41ECTO [Binley J M, et al. (2000) J Virol 74: 627-643]; 4) the I559P substitution was included to promote trimerization [Sanders R W, et al. (2002) J Virol 76: 8875-8889, Sanders R W, et al. (2004) AIDS Res Hum Retroviruses 20:742-749]; 5) an optimal cleavage site (RRRRRR; R6) (SEQ ID NO: 2) replaces the natural one, REKR (SEQ ID NO: 1) [31]; 6) truncation of the MPER from residue-664 prevents aggregation [Khayat R, et al. (2013) J Virol 87:9865-72, Klasse P J, et al. (2013) J Virol 87:9873-85]; 7) the T332N substitution facilitates binding of bNabs dependent on glycan-N332. The D7324- and His-tags are indicated in yellow. Env sub-domains are indicated: 5 conserved domains (C1-C5); 5 variable domains (V1-V5); heptad repeats 1 and 2 (HR1, HR2); the membrane proximal external region (MPER); the transmembrane domain (TM); and the cytoplasmic tail (CT). The glycan assignments in Env are based on previous studies using gp120 [Cutalo J M, et al. (2004) J Am Soc Mass Spectrom 15: 1545-1555, Leonard C K, et al. (1990) J Biol Chem 265: 10373-10382, Zhu X, et al. (2000) Biochemistry 39: 11194-11204], but may be different for trimeric Env [Bonomelli C, et al. (2011) PLoS One 6: e23521]. (B) SEC profile of 2G12-purified BG505 SOSIP.664 gp140 expressed in CHO-K1 cells. A Superdex 200 26/60 column was used. (C) Analytical SEC profile of 2G12/SEC-purified BG505 SOSIP.664 trimer rerun on a Superose 6 10/30 column. (D) BN-PAGE analysis of CHO-K expressed, 2G12-purified BG505 SOSIP.664 gp140, stained by Coomassie blue. The m.w. of marker (M) proteins (thyroglobulin and ferritin) are indicated. (E) BN-PAGE analysis of 2G12/SEC-purified BG505 SOSIP.664 gp140, stained by Coomassie blue. (F) SDS-PAGE analysis using a 4-12% Bis-Tris Nu-PAGE gel of 2G12/SEC-purified BG505 SOSIP.664 gp140, under non-reducing and reducing conditions, followed by Coomassie blue staining. (G) SDS-PAGE analysis using a 10% Tris-Glycine gel of 2G12/SEC-purified BG505 SOSIP.664 gp140, under non-reducing and reducing conditions, followed by silver staining. The conversion of the gp140 band to gp120 and the appearance of a gp41 ECTO band under reducing conditions is indicative of cleavage.

Figure 16:
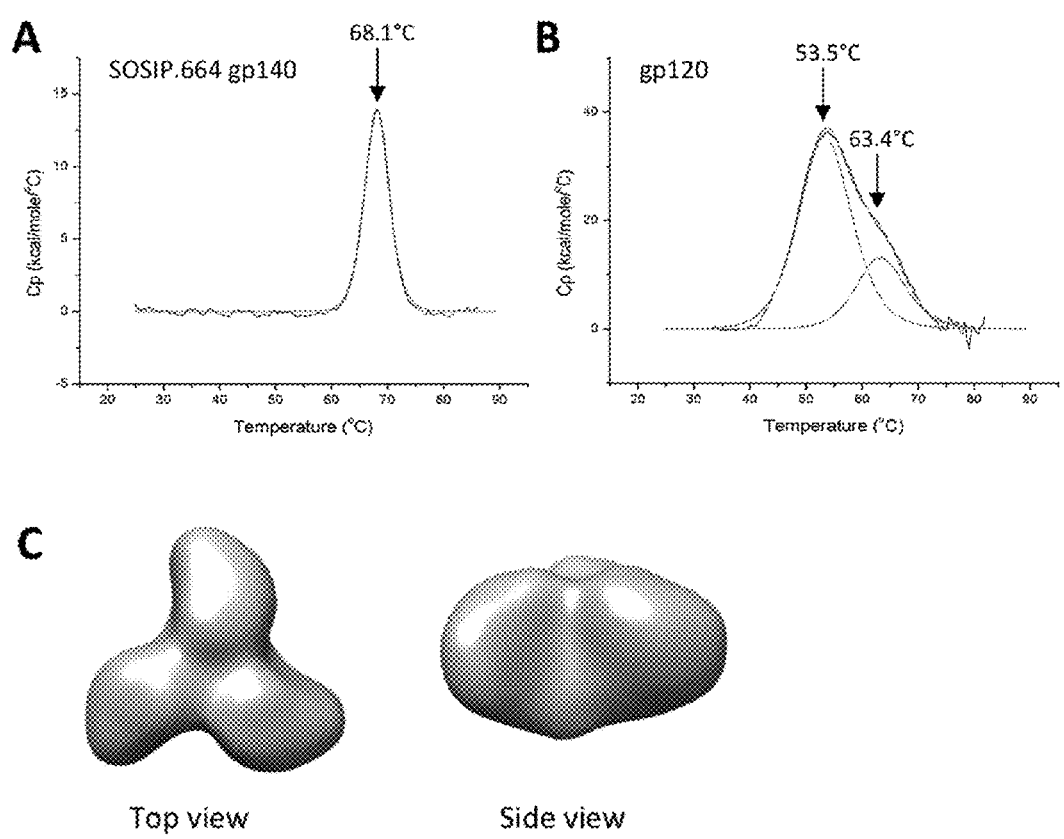

FIG. 16 depicts a biophysical characterization of BG505 SOSIP.664 gp140 trimers. DSC analysis of (A) purified BG505 SOSIP.664 gp140 trimers and (B) purified BG505 gp120 monomers. The melting profiles show that the trimer has a higher degree of stability than its monomeric counterpart, as its thermal transitions are initiated at a 14.4° C. higher temperature. Raw data are shown in black, while the fitted curves from which $T_m$ values were obtained are in red. (C) EM reconstruction of the BG505 SOSIP.664 gp140 trimer at 24-Å resolution.

FIG. 17 depicts BG505.T332N virus neutralization and ELISA binding to BG505 SOSIP.664 gp140 trimers by bNabs or non-Nabs. Midpoint neutralization concentrations ($IC_{50}$, in ng/ml) were derived from single cycle experiments involving Env-pseudovirus infection of TZM-bl cells. The values represent the averages of 2-5 independent titration experiments, each performed in duplicate, with the standard error recorded. Half-maximal binding concentrations ($EC_{50}$, in ng/ml) were derived from D7324-capture ELISAs. The values represent the averages of 2-6 independent single titration experiments, with the standard error recorded.

FIG. 18 depicts BG505 SOSIP.664 gp140 antigenicity by ELISA with bNabs. (A) Schematic representation of D7324-capture ELISAs using BG505 gp120-D7324 monomers and/or SOSIP.664-D7324 gp140 trimers. (B) Representative binding curves of bNabs VRC01, VRC03, VRC06, VRC06b, PGV04, 3BNC117, 12A12, 45-46, 45-46W, 1NC9, 8ANC195, CH31, CH103, CH106, PGT121, PGT123, PGT125, PGT126, PGT128, PGT130, and also CD4-IgG2, to purified BG505 SOSIP.664-D7324 gp140 trimers. (C) Representative binding curves of bNAb 3BC315 with purified BG505 SOSIP.664-D7324 gp140 trimers and gp120-D7324 monomers. (D) Representative binding curves of quaternary structure dependent bNabs PG9, PG16, CH01 and PGT145 to purified BG505 SOSIP.664-D7324 gp140 trimers and gp120-D7324 monomers. The legend is the same as for panel C. (E) BG505 SOSIP.664-D7324 gp140 trimers were 2G12-affinity purified and fractionated using a Superose 6 10/30 SEC column. The SEC fractions were analyzed for PG9, PG16, PGT 145 and b6 binding by D7324-capture ELISA. Note that the scales on the y-axes and x-axes vary from MAb to MAb.

FIG. 19A-D depicts BG505 SOSIP.664 gp140 antigenicity by ELISA with non-bNabs. Representative binding curves of: (A) gp120-directed non-Nabs 15e, F91, F105 and b6 to purified BG505 SOSIP.664-D7324 gp140 trimers and gp120-D7324 monomers, with bNabs 2G12 and PGT128 included as controls. (B) CD4i MAbs 17b, A32 and 412d to purified BG505 SOSIP.664-D7324 gp140 trimers and gp120-D7324 monomers in the absence (open symbols) and presence (closed symbols) of sCD4. (C) gp41-directed non-NAbs 7B2 and F240 to BG505 SOSIP.664-His and WT.664-His (=gp41 $EC_{TO}$-His) proteins. Both proteins were expressed in the presence of furin, yielding cleaved gp140. The lack of the SOS disulfide bond results in gp120 shedding from gp41$_{ECTO}$-His, as illustrated by the poor reactivity with VRC01 (left panel). (D) V3 MAbs 39F, 19b and 14e to purified BG505 SOSIP.664-D7324 gp140 trimers and gp120-D7324 monomers. Note that the scales on the y-axes and x-axes vary from MAb to MAb.

FIG. 20 depicts a correlation between MAb binding to BG505 SOSIP.664 gp140 trimers and BG505.T332N neutralization. The midpoint binding concentrations ($EC_{50}$) for MAb binding to BG505 SOSIP.664-D7324 gp140 trimers (y-axis) were plotted against the $IC_{50}$ values for neutralization of the BG505.T332N Env-pseudotype virus (x-axis). The Pearson's correlation coefficient, r, was calculated using Prism software version 5.0. When accurate midpoint concentrations could not be calculated because of lack of binding or neutralization, the highest concentration tested was included in the correlation analysis (i.e., when the $IC_{50}$ of neutralization was >30,000 ng/ml, a value of 30,000 ng/ml was used). The data points for Nabs are indicated in black, those for non-NAbs in gray. Also note that 11 data points are overlapping in the right upper corner; they were derived using MAbs that neither neutralized the virus nor bound the trimer ($IC_{50}$, of neutralization >30,000 ng/ml, $EC_{50}$ in ELISA >10,000 ng/ml). Only MAbs whose epitope could be shown to be present on at least one form of BG505 Env protein were included in this analysis; MAbs that were non-reactive, presumably because of sequence variation, were excluded. The Pearson's correlation was also calculated without the data points for 2G12, 39F, 14e and 19b, as discussed in the text. The fitted line is based on all data, i.e. including 2G12, 39F, 14e and 19b.

Figure 21:
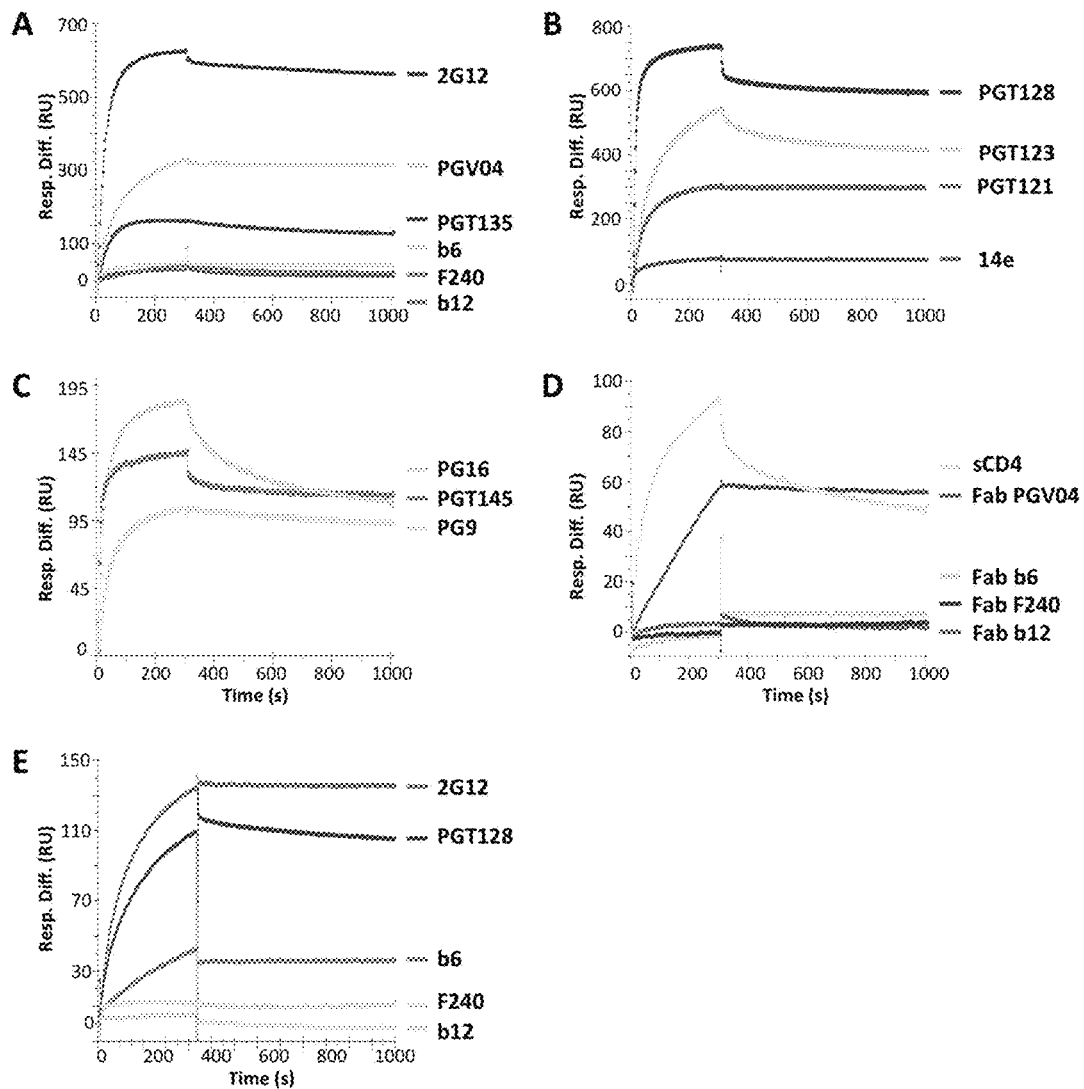

FIG. 21 depicts BG505 SOSIP.664 gp140 antigenicity by SPR. BG505 SOSIP.664-His gp140 trimers were immobilized on NTA chips (A-D). The sensorgrams show the response (RU) over time (s) using IgGs at 1,000 nM (150,000 ng/ml) (A-C) or Fabs at 500 nM (25,000 ng/ml) (D). The association phase was 300 s and dissociation was followed over 600 s. (A) 2G12 (high), PGT135 (intermediate), PGV04 (high), b6 (marginal), b12 (undetectable) and F240 (undetectable); (B) PG9, PG16, PGT145 (all intermediate); (C) PGT121 (intermediate), PGT123 (high), PGT128 (high) and 14e (low); (D) Fabs of PGV04 (intermediate), b6, b12 and F240 (undetectable). (E) In an alternative approach, Env-reactive MAb was captured by anti-Fc Ab on the chip and the responses to BG505 SOSIP.664 gp140 trimers (200 nM; 78,000 ng/ml) were followed: 2G12 (high), PGT128 (high), b6 (low), b12, F240 (undetectable). Each curve represents one of 2-3 similar replicates.

Figure 22:
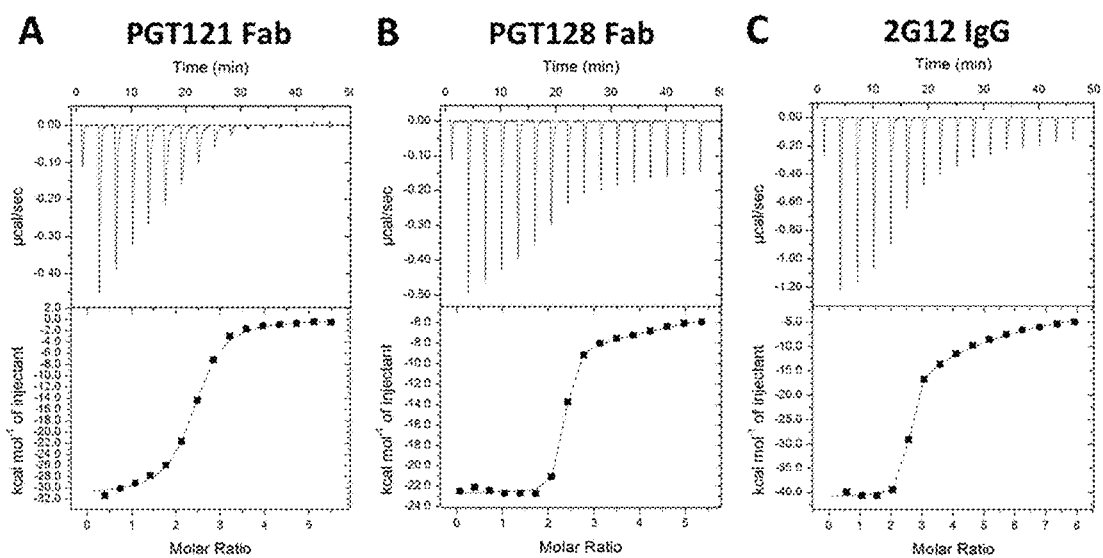

FIG. 22 depicts BG505 SOSIP.664 gp140 trimer antigenicity by ITC. The top panels show the raw data and the bottom panel the binding isotherms for representative ITC binding experiments measuring the binding of BG505 SOSIP.664 gp140 trimers to: (A) PGT121 Fab, (B) PGT 128 Fab and (C) 2G12 IgG (domain-exchanged). The thermodynamic parameters of binding are listed in Table 3.

Figure 23:
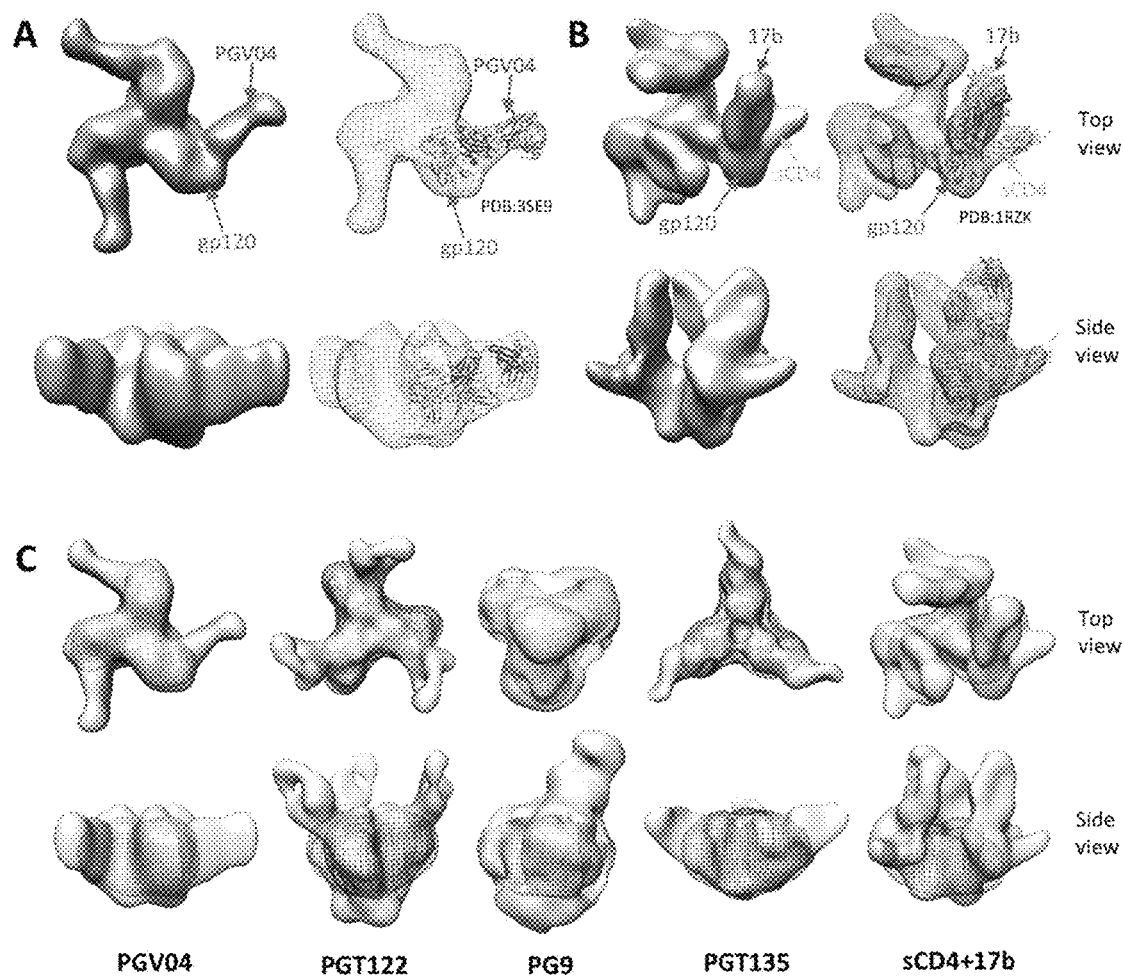

FIG. 23 depicts BG505 SOSIP.664 gp140 trimer antigenicity by negative stain EM. (A) EM reconstruction of the BG505 SOSIP.664 gp140 trimer in complex with Fab PGV04 at 23 Å resolution. The 2D class averages and the Fourier Shell Correlation (FSC) can be seen in Fig. S3 in Julien et al. (2013) Proc Natl Acad Sci USA 110: 4351-4356. The crystal structure of gp120 in complex with PGV04 (PDB:3SE9; [Wu X, et al. (2011) Science 329:811-817]) was fitted into the EM density. (B) EM reconstruction of the BG505 SOSIP.664 gp140 trimer in complex with sCD4 and Fab 17b at 22 A resolution. The 2D class averages and the Fourier Shell Correlation (FSC) are shown in Fig. S4 in Julien et al. (2013) Proc Natl Acad Sci USA 110: 4351-4356. The crystal structure of gp120 in complex with sCD4 and 17b (PDB: 1RZK; [Huang C C, et al. (2004) Proc Natl Acad Sci USA 101:2706-2711]) was fitted into the EM density. (C) Comparison of unliganded BG505 SOSIP.664 gp140 trimers with complexes of the same trimers with PGV04, PGT122, PG9, PGT135, or sCD4 with 17b. The unliganded trimer is shown in mesh. The EM reconstructions of PGT122, PG9, PGT135 with BG505 SOSIP.664 trimers, expressed in HEK293S cells, have been published elsewhere [Julien J P, et al. (2013) PLoS Pathog 9: e1003342, Kong L, et al. (2013) Nat Struct Mol Biol 20: 796-803, Julien J P, et al. (2013) Proc Natl Acad Sci USA 110: 4351-4356].

Figure 24:
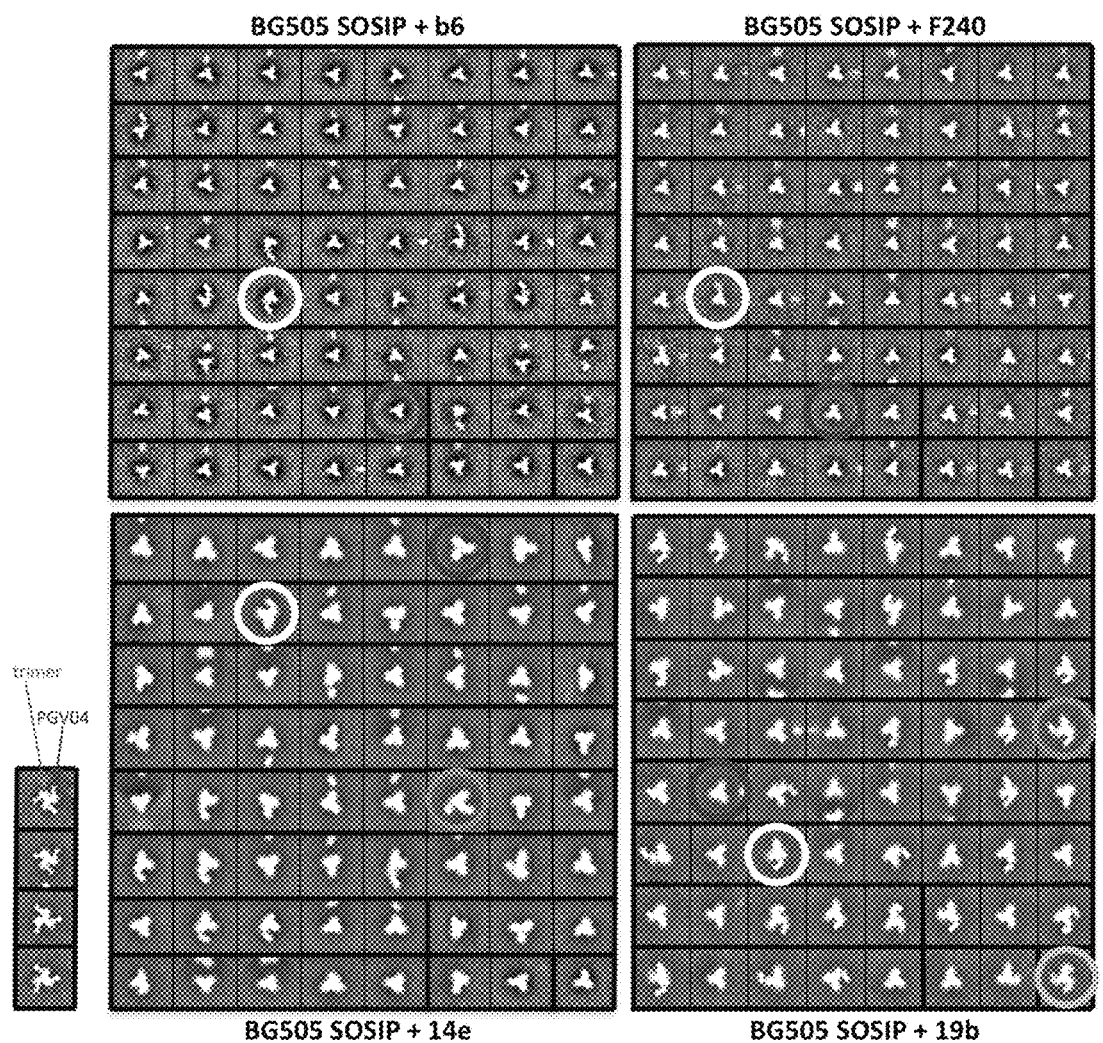

FIG. 24 depicts negative stain EM data of the BG505 SOSIP.664 gp140 trimer in complex with Fabs b6, F240, 14e or 19b. 2D class averages of trimers and trimer:Fab complexes, with 2D class averages of BG505 SOSIP.664 gp140 with PGV04 shown on the lower left panel for comparison. Examples of complexes are circled. Blue circle: no Fab bound to trimer; yellow circle: one Fab bound; red circle: two Fabs bound; green circle: three Fabs bound. For generating b6 complexes, BG505 SOSIP.664 (44 nM; 17,200 ng/ml) was incubated with Fab b6 (480 nM; 24,000 ng/ml) prior to imaging. For generating F240 complexes, BG505 SOSIP.664 (48 nM; 18,720 ng/ml) was incubated with Fab F240 (860 nM; 43,000 ng/ml) prior to imaging. For generating 14e complexes, BG505 SOSIP.664 (14 nM; 5460 ng/ml) was incubated with Fab 14e (240 nM; 12,000 ng/ml). For generating 19b images, BG505 SOSIP.664 (40 nM; 15.600 ng/ml) was incubated with Fab 19b (600 nM; 30,000 ng/ml). The results are summarized in Table 4.

FIG. 25 depicts a BG505 SOSIP.664 antigenicity summary for bNabs and non-Nabs. The following scoring was used for neutralization: +: $IC_{50}$<30,000 ng/ml; −: $IC_{50}$>30,000 ng/ml. See Table 3 for details. The following scoring was used for SPR analyses: +: >70 RU; +/−: >30 RU, <70 RU; −: <30 RU, based on plateau estimates of 1,000 nM for IgG and 500 nM for Fab. See FIG. 21 for details. In SPR CD4 binding results were obtained with sCD4 not CD4-IgG2. b6 binding was absent with b6 Fab (−) and low with b6 IgG (+/−). The following scoring was used for ITC experiments: +: N>1.2 (except for PG9, PG16 and PGT145 where N>0.4) and $K_d$<300 nM; −: N<1.2 and $K_d$<300 nM, where N is the stoichiometry of binding. See Table 3 and FIG. 22 for details. The following scoring was used for EM analyses: +: N=3 (except for PG9, PG16 and PGT145 where N=1) for <50% of the trimers; +/−: N=3 for <50% of the trimers; −: N=1, 2 or 3 for <10% of the trimers, where N is the number of Fabs bound per trimer. See Table 4, FIG. 23 and FIG. 24 for details. Note that ITC data with PG16 and PGT127 were obtained using BG505 SOSIP.664 trimers produced in GnTIdefective HEK293S cells. No ITC experiments were performed with non-Nabs. The following scoring was used for ELISA experiments: +: $EC_{50}$<10,000 ng/ml; $EC_{50}$>10,000 ng/ml. See FIGS. 17-19 for details.

FIG. 26A-B shows that HIV-1 BG505.T332N has a Tier 2 phenotype, with FIG. 26A showing assays performed with sera from 8 subtype A infected subjects and FIG. 26B showing assays with Tier 1-specific MAbs.

Figure 27:
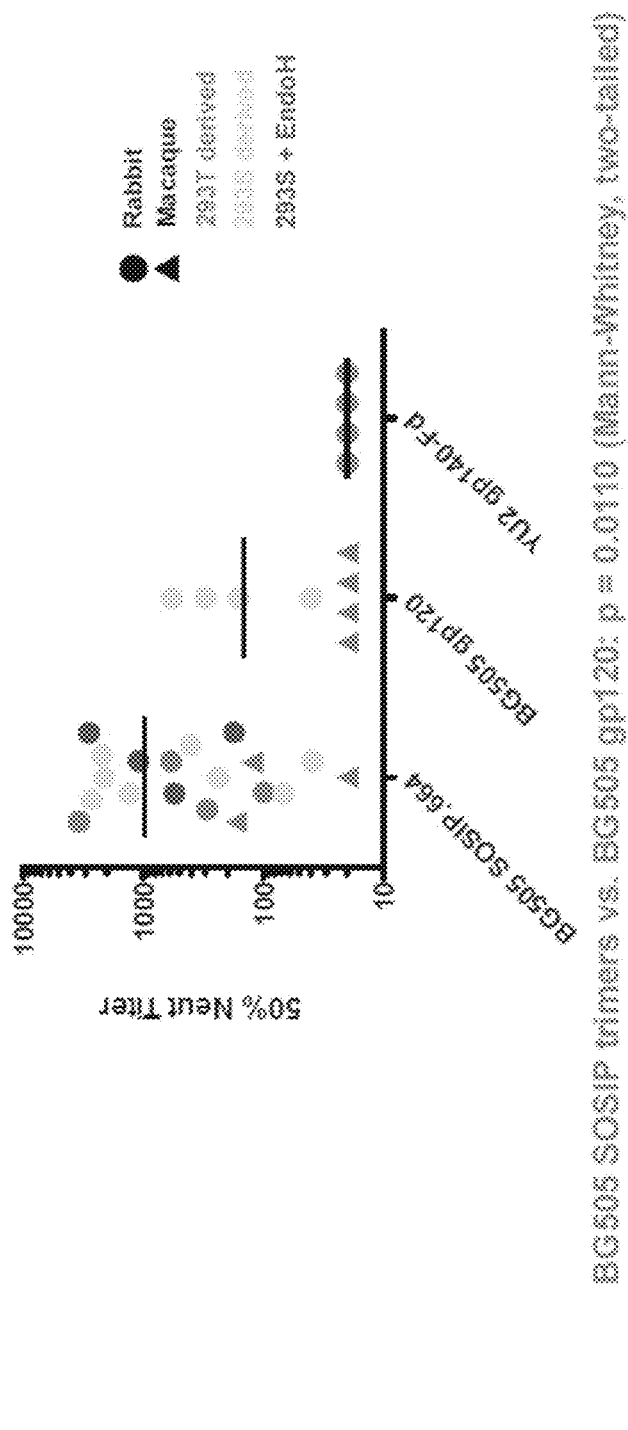

FIG. 27 depicts an autologous (BG505; Tier-2) NAbs in rabbits and macaques, specifically BG505 SOSIP.664 gp140 trimers vs. BG505 gp120 monomers (also YU2 uncleaved gp140-Foldon in rabbits) (Tzm-bl assay, Sera from weeks 20-24, after 3 or 4 immunizations).

Figure 28:
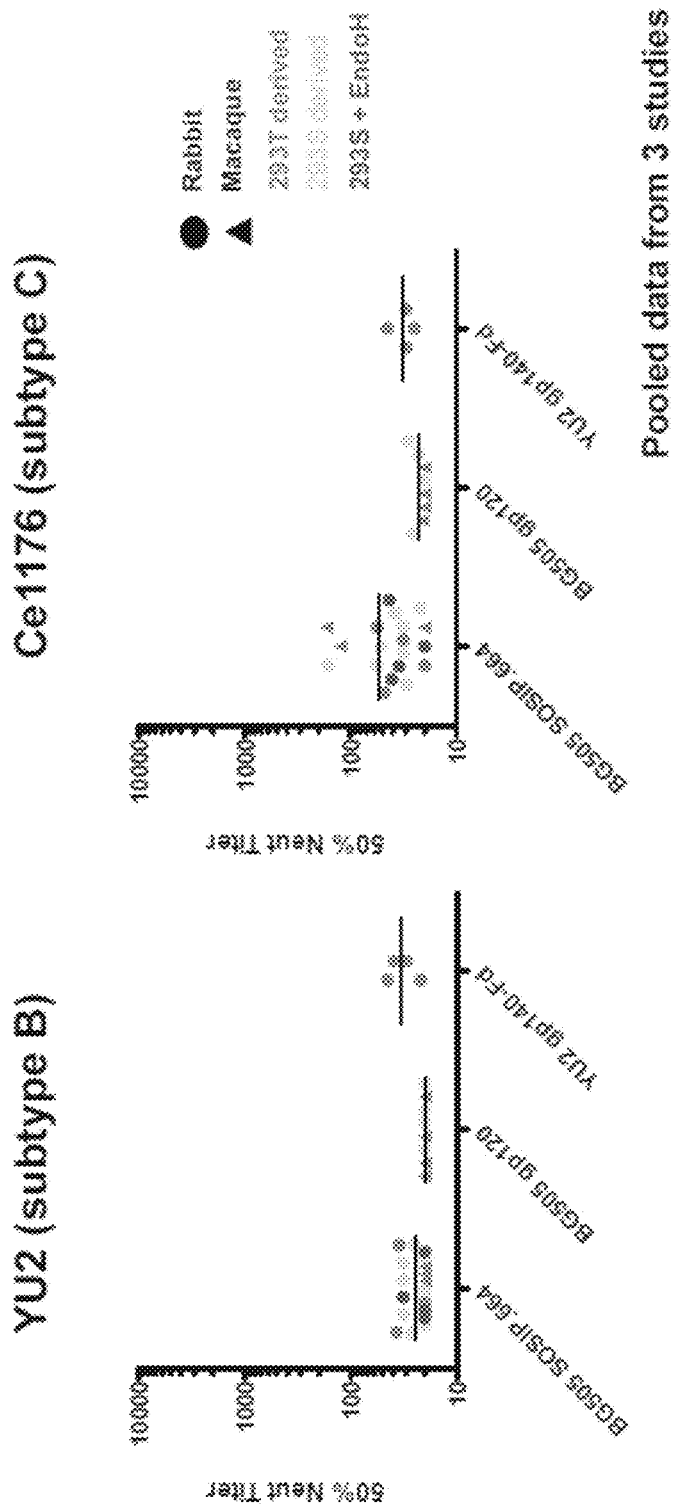

FIG. 28 depicts a heterologous Tier-2 NAb responses in rabbits and macaques, specifically BG505 SOSIP.664 gp140 trimers vs. BG505 gp120 monomers vs. YU2 uncleaved gp140-Foldon (Tzm-bl assay, Sera from week 20, after 3 immunizations).

Figure 29:
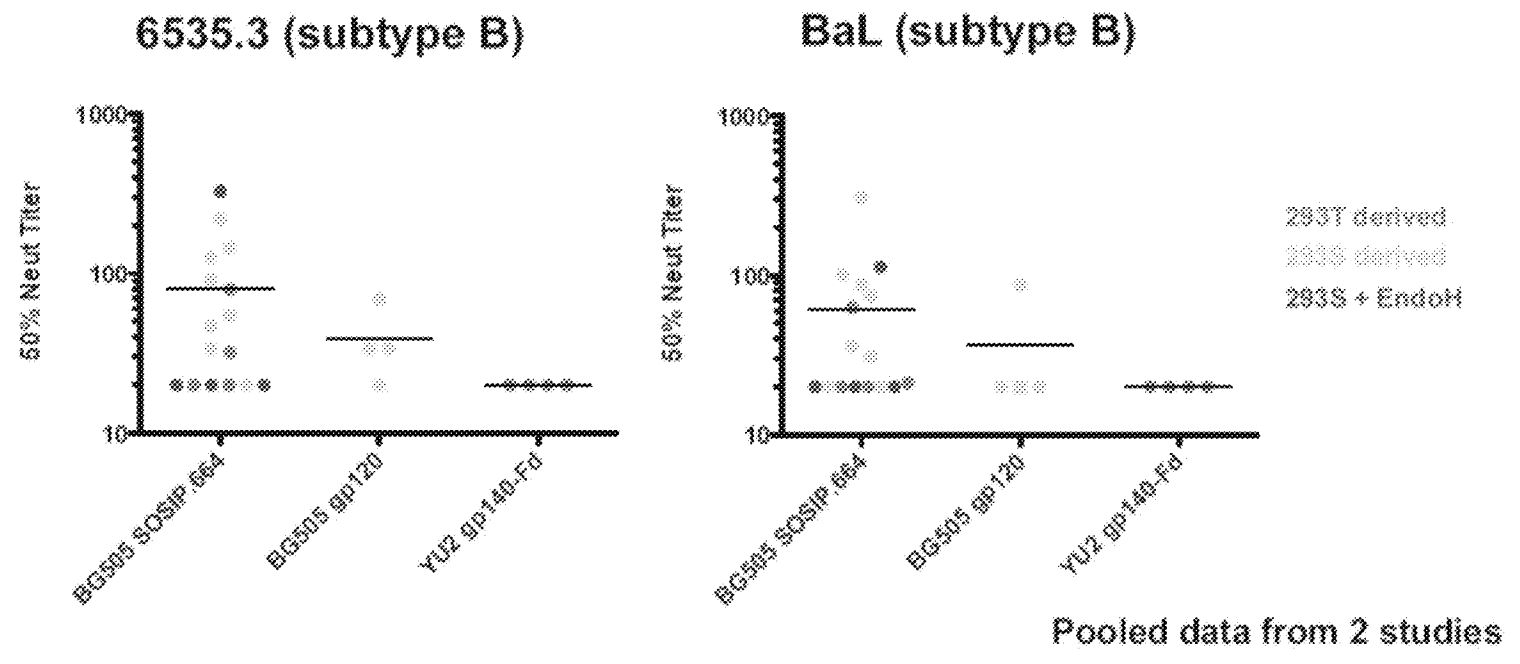

FIG. 29 depicts a heterologous Tier-1B NAb responses in rabbits, specifically BG505 SOSIP.664 gp140 trimers vs. BG505 gp120 monomers vs. YU2 uncleaved gp140-Foldon.

Figure 30:
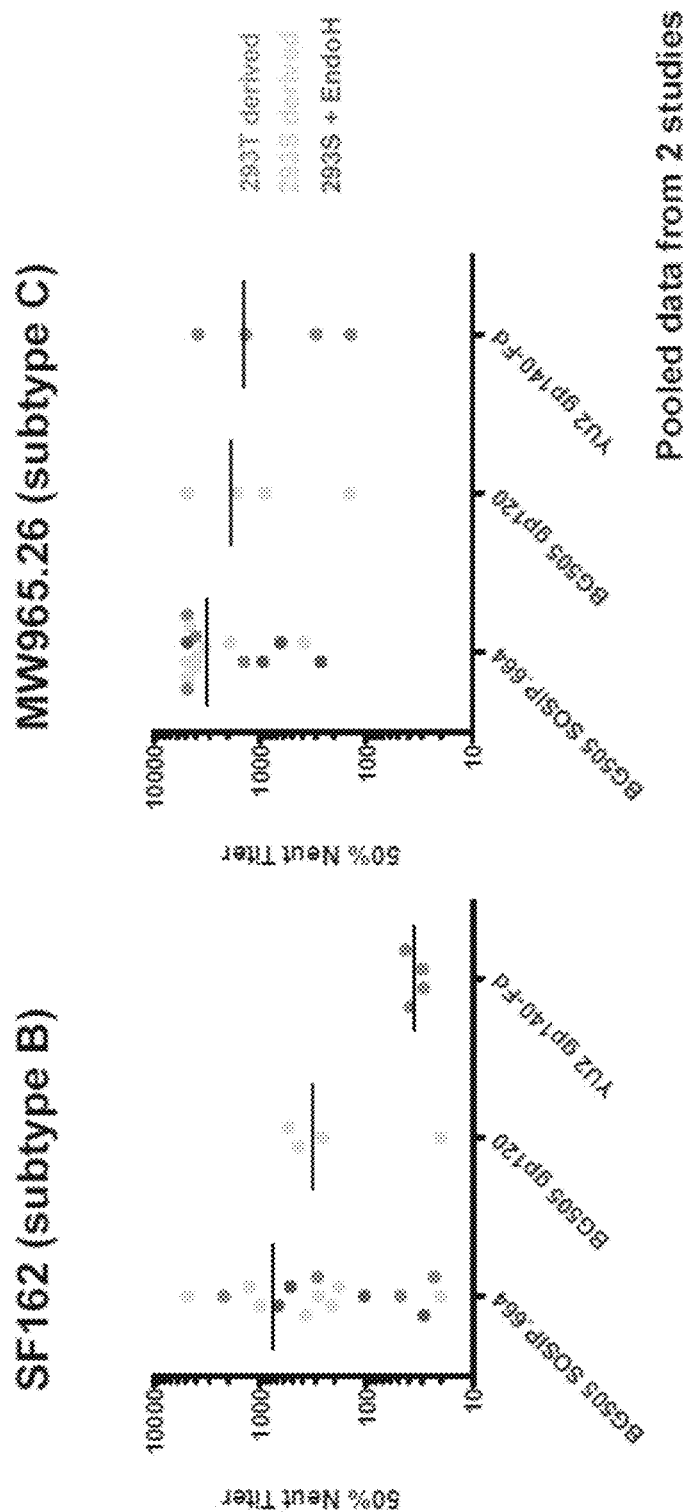

FIG. 30 depicts a heterologous Tier-1A NAb responses in rabbits, specifically BG505 SOSIP.664 gp140 trimers vs. BG505 gp120 monomers vs. YU2 uncleaved gp140-Foldon (AMC; Tzm-bl assay. Sera from week 20, after 3 immunizations).

DETAILED DESCRIPTION

Broad neutralizing antibodies PG9 and PG16 were used for screening and selecting HIV-1 isolates from a panel consisting of sixty four viral isolates from HIV-1 clades B and C for their ability to neutralize and to bind soluble forms of the HIV-1 Envelope glycoprotein. Applicants identified nine HIV-1 envelopes that were neutralized and showed binding by bNab PG9 and/or PG16. Two of the soluble HIV-1 Envs-DU422 (clade C) and YU2 (clade B) were already identified and reported (Walker L, Phogat S, et al. Science. 2009; 326:285-9. Epub 2009 Sep. 3). As a part of this invention, Applicants identified three new soluble HIV-1 Envs each from HIV-1 clade B and clade C viral isolates that show binding to bNab PG9. In addition, Applicants identified one soluble Env from HIV-1 clade C that showed binding to both bNab PG9 and PG16. The Envs identified as a part of this invention show significantly better binding to bNabs PG9 and PG16 compared to the DU422 and YU2 envelope. These newly identified Envs are the only soluble forms of Env identified to date that show such remarkable binding to PG9 and/or PG16. In addition to identification of soluble gp120 that shows significant binding to PG9, Applicants identified one native envelope trimer mimic gp140 molecule that shows significant binding to both PG9 and PG16.

Immunogens in different forms may be used as HIV-1 vaccine components to elicit bNabs. The different forms of the HIV-1 envelope may be used in a prime, as DNA/vector expressing the protein/protein and as a boost as protein. The envelopes could also be used as particulate immunogens by cross linking to virus particles like Qbeta, cow pea mosaic virus, CRM, HPV, HBsAg, etc.

In an advantageous embodiment, the soluble envelope glycoproteins of the present invention may be isolated from HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus. In an advantageous embodiment, the soluble envelope glycoproteins of the present invention may be isolated from the 6535 virus, the 13095 virus, the 16055 virus, the 25710 virus, the 25925 virus, the CAAN virus or the Zm109F virus. Applicants have generated recombinant Env proteins with unique sequences in which Applicants have modified the leader, added His-tag and cleaved the sequence before the cleavage site for gp120 and before the transmembrane for gp140. The DNA sequences are unique as they are codon optimized.

In a particularly advantageous embodiment, the envelope glycoproteins of the present invention are isolated from the 16055 and/or BG505 viruses. In a particularly advantageous embodiment, the envelope glycoprotein may be isolated from a BG505 virus and having a SOSIP mutation. In a particularly advantageous embodiment, the glycoprotein is a BG505 SOSIP.664 trimer. There may be at least one, at least two, at least three, at least four, at least five or at least six mutations in the glycoprotein.

In a particularly advantageous embodiment, the BG505 SOSIP.664 sequence may be a modification of a BG505 gp160 sequence which may comprise (a) a replacement of signal sequence by the tPA leader to enhance secretion (b) mutations A501C and T605C (SOS) to stabilize gp120-gp41 association, (c) mutation REKR(508-511) RRRRRR (SEQ ID NOS 1 and 2, respectively) to enhance cleavage (d) mutation I559P to facilitate trimerization, (e) a truncation at position 664 to prevent MPER-mediated aggregation and/or (f) T332N to create 2G12, PGT 125-PGT 131 epitopes or any combination thereof.

In a more particularly advantageous embodiment, a modified BG505 SOSIP.664 sequence may have a sequence comprising (SEQ. ID NO: 3)
MDAMKRGLCCVLLLCGAVFVSPSQEIHARFRRGARAENLWVTVYYGVPVW

KDAETTLFCASDAKAYETEKHNVWATHACVPTDPNPQEIHLENVTEEFNM

WKNNMVEQMHTDIISLWDQSLKPCVKLTPLCVTLQCTNVTNNITDDMRGE

LKNCSFNMTTELRDKKQKVYSLFYRLDVVQINENQGNRSNNSNKEYRLIN

CNTSAITQACPKVSFEPIPIHYCAPAGFAILKCKDKKFNGTGPCPSVSTV

QCTHGIKPVVSTQLLLNGSLAEEEVMIRSENITNNAKNILVQFNTPVQIN

CTRPNNNTRKSIRIGPGQAFYATGDIIGDIRQAHCNVSKATWNETLGKVV

KQLRKHFGNNTIIRFANSSGGDLEVTTHSFNCGGEFFYCNTSGLFNSTWI

SNTSVQGSNSTGSNDSITLPCRIKQIINMWQRIGQAMYAPPIQGVIRCVS

NITGLILTRDGGSTNSTTETFRPGGGDMRDNWRSELYKYKVVKIEPLGVA

PTRCKRRVVGRRRRRRAVGIGAVFLGFLGAAGSTMGAASMTLTVQARNLL

SGIVQQQSNLLRAPEAQQHLLKLTVWGIKQLQARVLAVERYLRDQQLLGI

WGCSGKLICCTNVPWNSSWSNRNLSEIWDNMTWLQWDKEISNYTQIIYGL

LEESQNQQEKNEQDLLALD\*.

HIV type 1 (HIV-1) envelope is a noncovalent trimer of gp20-gp41 heterodimers, and its lability has hindered structural studies. SOSIP gp140 is a soluble, proteolytically mature form of the HIV-1 envelope wherein gp120-gp41 interactions are stabilized via a disulfide bond and gp41 contains an additional trimer-stabilizing point mutation. The isolation of a substantially pure preparation of SOSIP gp140 trimers derived from KNH1144, a subtype A isolate was described in Iyer S P et al., AIDS Res Hum Retroviruses. 2007 23:817-28. Following initial purification, the only significant contaminants were higher-order gp140 aggregates; however, 0.05% Tween 20 quantitatively converted these aggregates into trimers. The surfactant effect was rapid, dose dependent and similarly effective for a subtype B SOSIP gp140. Surfactant-treated SOSIP gp140 retained favorable antigenicity and formed compact trimers 12-13 nm in size as determined by electron microscopy. Iyer S P et al., AIDS Res Hum Retroviruses. 2007 23:817-28 provides a description of homogeneous, cleaved HIV-1 envelope trimers.

Soluble, stabilized, proteolytically cleaved, trimeric proteins may be generated by engineering an intermolecular disulphide bond between gp120 and gp41 (SOS), combined with a single residue change, I559P, within gp41 (SOSIP). SOSIP gp140 proteins based on the subtype A HIV-1 strain KNH1144 form particularly homogenous trimers compared to a prototypical strain (JR-FL, subtype B). Described in U.S. Pat. No. 7,939,083 are the determinants of this enhanced stability which are located in the N-terminal region of KNH11144 gp41 and that, when substituted into heterologous Env sequences (e.g., JR-FL and Ba-L), have a similarly beneficial effect on trimer stability. These stabilized trimers retain the epitopes for several neutralizing antibodies and related agents (CD4-IgG2, b12, 2G12, 2F5 and 4E10) and the CD4-IgG2 molecule, so that the overall antigenic structure of the gp140 protein has not been adversely impaired by the trimer-stabilizing substitutions.

In a particularly advantageous embodiment, the soluble envelope glycoproteins of the present invention have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to any of the sequences depicted in the figures and/or specification.

Assays for screening for neutralizing antibodies are known in the art. A neutralization assay approach has been described previously (Binley J M, et al., (2004). Comprehensive Cross-Clade Neutralization Analysis of a Panel of Anti-Human Immunodeficiency Virus Type 1 Monoclonal Antibodies. *J. Virol.* 78: 13232-13252). Pseudotyped viruses may be generated by co-transfecting cells with at least two plasmids encoding the soluble Env cDNA of the present invention and the rest of the HIV genome separately. In the HIV genome-encoding vector, the Env gene may be replaced by the firefly luciferase gene. Transfectant supernatants containing pseudotyped virus may be co-incubated overnight with B cell supernatants derived from activation of an infected donor's primary peripheral blood mononuclear cells (PBMCs). Cells stably transfected with and expressing CD4 plus the CCR5 and CXCR4 coreceptors may be added to the mixture and incubated for 3 days at 37° C.

In yet another embodiment, the present invention also encompassed the use of the soluble envelope glycoproteins described herein as immunogens, advantageously as HIV-1 vaccine components.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:

Fab, the fragment which contains a monovalent antigen-binding fragment of an antibody molecule can be produced by digestion of whole antibody with the enzyme papain to yield an intact light chain and a portion of one heavy chain; two Fab fragments are obtained per antibody molecule;

Fab', the fragment of an antibody molecule, can be obtained by treating whole antibody with pepsin, followed by reduction, to yield an intact light chain and a portion of the heavy chain; two Fab' fragments are obtained per antibody molecule;

F(ab')$_2$, the fragment of the antibody that can be obtained by treating whole antibody with the enzyme pepsin without subsequent reduction; F(ab')$_2$ is a dimer of two Fab' fragments held together by two disulfide bonds;

scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-1 virus, for example SF162 and/or JRCSF with a neutralization index >1.5 or >2.0. Broad and potent neutralizing antibodies may neutralize greater than about 50% of HIV-1 viruses (from diverse clades and different strains within a clade) in a neutralization assay.

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/wblast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vector expressing a foreign epitope. Advantageously, the epitope is an HIV epitope. In an advantageous embodiment, the HIV epitope is a soluble envelope glycoprotein, however, the present invention may encompass additional HIV antigens, epitopes or immunogens. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971; 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381; 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709; 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615; 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625; 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876; 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432; 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749;

5,827,723; 5,824,497; 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707; 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406; 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610; 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The nucleotide sequences and vectors of the invention can be delivered to cells, for example if aim is to express and the HIV-1 antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68,); ISCOMs or ISCOMA-TRIX®, poly IC or poly AU acids, polyarginine with or without CpG (also known in the art as IC31; see Schellack, C. et al (2003) Proceedings of the 34$^{th}$ Annual Meeting of the German Society of Immunology Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

The invention will now be further described by way of the following non-limiting examples.

Example 1

Supersite of Immune Vulnerability on the Glycosylated Face of HIV-1 Envelope Glycoprotein gp120

PG9 is the founding member of a growing family of glycan-dependent human antibodies that preferentially bind the HIV-1 Env trimer and broadly neutralize HIV-1. Here, a soluble SOSIP.664 trimer was constructed from the Clade A BG505 sequence that binds PG9 with high affinity (~30 nM), enabling combined structural and biophysical characterization of the PG9: Env trimer complex. The BG505 SOSIP.664 trimer is remarkably stable as assessed by electron microscopy (EM) and differential scanning calorimetry. EM, SAXS, SEC-MALS and ITC indicate that one PG9 Fab binds per Env trimer near the spike apex. An ~18 Å EM reconstruction demonstrates that PG9 recognizes the Env trimer asymmetrically via contact with two of the three gp120 protomers. Molecular modeling and ITC binding experiments with an engineered PG9 mutant suggest that, in addition to the N156 and N160 glycan interactions observed in the recent crystal structures of PG9 with a scaffolded V1/V2 domain, PG9 mediates weaker secondary interactions with an N160 glycan on the adjacent V1/V2 domain of a second gp120. These integrative structural and biophysical results have direct implications for the design of HIV-1 immunogens that possess all elements of the quaternary PG9 epitope for re-eliciting bNabs against this region.

Efforts towards the development of an effective human immunodeficiency virus (HIV-1) vaccine rooted in rational design have never looked more promising. The HIV-1 vaccine field has been fueled in recent years by the discovery of several new broadly neutralizing antibodies (bNabs), which in turn have revealed a few conserved sites of vulnerability on Env, the viral surface glycoprotein responsible for mediating cell entry (Simek M D et al. (2009) J Virol 83:7337-7348, Walker L M et al. (2009) Science 326:285-289, Wu X et al. (2011) Science 333:1593-1602, Scheid J F et al. (2011) Science 333:1633-1637, Mouquet H et al. (2011) PLoS One 6:e24078, Walker L M et al. (2011) Nature 477:466-470), and recently reviewed in (Kwong P D et al. (2009) Cell Host Microbe 6:292-294, Clapham P R & Lu S (2011) Nature 477:416-417, Overbaugh J & Morris L (2012) Cold Spring Harb Perspect Med 2:a007039, Burton D R et al. (2012) Science 337:183-186). Furthermore, it has been conclusively demonstrated by passive immunization studies that if some of these bNabs are present prior to virus exposure, sterilizing immunity is attainable in animals challenged with virus (Conley A J et al. (1996) J Virol 70:6751-6758, Hessell A J et al. (2009) Nat Med 15:951-954, Hessell A J et al. (2009) PLoS Pathog 5:e1000433, Hessell A J et al. (2010) J Virol 84:1302-1313, Mascola J R (2003) Curr Mol Med 3:209-216). As such, efforts have been intensified towards design of immunogens capable of re-eliciting these types of bNabs by vaccination.

HIV-1 infection involves the Env-mediated fusion of the virus with CD4 T cells (Gallo S A et al. (2003) Biochim Biophys Acta 1614:36-50, Markovic I & Clouse K A (2004) Curr HIV Res 2:223-234). Env, one of the most heavily glycosylated proteins known, and is synthesized as a gp160 precursor, which is then cleaved in the Golgi into two subunits, gp120 and gp41 that assemble as a trimer of non-covalently associated heterodimers on the viral surface (Chan D C et al. (1997) Cell 89:263-273). Whereas gp120 mediates initial engagement with CD4 T cells through interactions with CD4 and a chemokine co-receptor (CCR5 or CXCR4), gp4 is responsible for the subsequent fusion of cell and viral membranes leading to the delivery of the viral genes and other components into the cell (Gallo S A et al. (2003) Biochim Biophys Acta 1614:36-50, Markovic I & Clouse K A (2004) Curr HIV Res 2:223-234). Interference of any of these viral entry steps by antibody recognition can lead to effective neutralization of the virus and is the sought-after correlate of protection based on successful vaccines elaborated against other pathogens (Pantaleo G & Koup R A (2004) Nat Med 10:806-810).

The major difficulty in mounting an effective antibody response against HIV-1 resides in the multiple evasion strategies used by the virus. An error-prone reverse transcriptase leads to a high degree of sequence diversity in HIV-1 Env (Karlsson Hedestam G B et al. (2008) Nat Rev Microbiol 6:143-155, Korber B et al. (2001) Br Med Bull 58:19-42, Korber B et al. (2000) Science 288:1789-1796). The few conserved regions are masked by an extensive glycan coat, as well as by the presence of hypervariable loops (McCaffrey R A et al. (2004) J Virol 78:3279-3295, Li Y et al. (2008) J Virol 82:638-651, Binley J M et al. (2010) J Virol 84:5637-5655, Johnson W E & Desrosiers R C (2002) Annu Rev Med 53:499-518, Wyatt R et al. (1998) Nature 393:705-711). In addition, it is thought that only a few functional Env molecules are present on the viral membrane and several non-functional spikes are displayed as a viral decoy strategy to overwhelm the immune system (Moore P L et al. (2006) J Virol 80:2515-2528).

Nonetheless, it has become apparent that HIV-1 infected individuals can develop bNabs over the course of a natural infection and can, therefore, overcome the evasion strategies utilized by the virus (Simek M D et al. (2009) J Virol 83:7337-7348, Doria-Rose N A et al. (2009) J Virol 83:188-199, Sather D N et al. (2009) J Virol 83:757-769, Stamatatos L et al. (2009) Nat Med 15:866-870). Although these bNabs do not seem to confer any significant advantage for disease outcome upon the individuals who produce them (Euler Z et al. (2010) J Infect Dis 201:1045-1053, Piantadosi A et al. (2009) J Virol 83:10269-10274), they would be invaluable in preventing initial infection in uninfected individuals. As such, the epitopes they recognize have been carefully scrutinized. The CD4 binding site (CD4bs) on gp120 is the Env epitope that has been the best characterized (Wu X et al. (2011) Science 333:1593-1602, Zhou T et al. (2007) Nature 445:732-737, Chen L et al. (2009) Science 326:1123-1127, Ryu S E & Hendrickson W A (2012) Mol Cells 34:231-237, Zhou T et al. (2010) Science 329:811-817). VRC01 represents one of the hallmark bNabs in this class and neutralizes approximately 90% of circulating HIV-1 viruses (Zhou T et al. (2010) Science 329:811-817). Other bNabs are directly dependent on recognition of conserved glycans, such as at position N332 near the base of the gp120 V3 loop (Walker L M et al. (2011) Nature 477:466-470). These antibodies can neutralize up to 70% of circulating isolates, but do so with exceptionally high potency (i.e. at very low concentrations) (Walker L M et al. (2011) Nature 477:466-470). The gp41 membrane proximal external region (MPER) is another epitope that is highly conserved and recognized by several bNabs (Bryson S et al. (2009) J Virol 83:11862-11875, Cardoso R M et al. (2005) Immunity 22:163-173. Ofek G et al. (2004) J Virol 78:10724-10737, Pejchal R et al. (2009) J Virol 83:8451-8462, Huang J et al. (2012) Nature 491:406-412). It appears that some of these bNabs neutralize with exceptional breadth (<98%), and as such, the highly conserved MPER also merits consideration in HIV-1 vaccine design efforts looking to induce bNabs.

Variable loops 1 and 2 (V1/V2) on gp120 are yet another target of a family of bNabs against HIV-1. As these bNabs have only recently been identified, their mode of recognition and mechanism of neutralization is only now starting to become clear. PG9 and PG16 were isolated from an African donor and neutralize approximately 70% of circulating HIV-1 isolates with high potency (Walker L M et al. (2009) Science 326:285-289). These two bNabs possess an elongated (28 residues long), hammerhead-shaped, complementarity determining region 3 of the heavy chain (HCDR3) that contains tyrosine sulfation sites (Pancera M et al. (2010) J Virol 84:8098-8110, Pejchal R et al. (2010) Proc Natl Acad Sci USA 107:11483-11488). Other isolated bNabs targeting this epitope, such as the PGT140 and CH01 series, also possess unusually long HCDR3 with potential tyrosine sulfation sites (Walker L M et al. (2011) Nature 477:466-470. McLellan J S et al. (2011) Nature 480:336-343), and it will be interesting to see whether other V1/V2 bNabs also share these characteristics (Moore P L et al. (2011) J Virol 85:3128-3141). Early functional studies revealed that the recognition of the V1/V2 epitope by these bNabs is highly dependent on the glycan at position N160, as well as the overall cationic character of protein segments in this region (Walker L M et al. (2009) Science 326:285-289). Recently, two co-crystal structures of PG9 bound to scaffolded V1/V2 loops of different isolates showed that this antibody interacts with two glycans and a 3-strand; the hammerhead-shaped HCDR3 penetrates the glycan shield to mediate mostly charged interactions with strand C of a disulfide-linked, anti-parallel β-sheet in the V1/V2 domain, while the glycans at positions N160 and N156 or N173 are accommodated in surrounding paratope pockets of the antibody (McLellan J S et al. (2011) Nature 480:336-343). Although extremely informative in revealing some of the crucial interactions between PG9 and the V1/V2 loops at an atomic level, it remained unclear why bNabs against this region of Env are mostly trimer-specific in their recognition (i.e. they do not bind to most gp120's in a monomeric context, despite neutralizing the corresponding virus).

Here, Applicants report the structural details of Env recognition by bnAb PG9 in the context of an HIV-1 trimer. Several biochemical and biophysical techniques were used singly and in combination to demonstrate that only one PG9 Fab binds the HIV-1 trimer. These results have significant implications in guiding immunogen design efforts looking to re-elicit PG9-like bNabs by vaccination as they emphasize the importance of displaying all components of an epitope that is sterically constrained in a quaternary structure environment. Finally, the SOSIP.664 trimer of Clade A BG505 sequence that enabled these structural and biophysical studies is significantly more stable than other previously described soluble Env trimers and as such might represent a good candidate for immunogen development.

Purification of a PG9:HIV-1 trimer complex and initial biophysical characterization. Recombinantly produced PG9 Fab was added in molar excess to a cleaved SOSIP.664 trimeric construct of HIV-1 Clade A BG505 sequence produced in 293S GnT I-deficient cells. Size exclusion chromatography (SEC) purification showed that the PG9 Fab: SOSIP trimer complex eluted after 14.3 ml on a Superose6 10/30 column, which is slightly earlier than the unliganded SOSIP trimer construct that elutes at 14.7 ml on the same column (FIGS. 6A and 6B). Non-reducing denaturing gel electrophoresis (SDS-PAGE) analysis of the eluting sample showed that PG9 Fab bound to the SOSIP.664 trimer in a ratio of one Fab per three gp140 monomers (FIG. 6C). Multi-angle light scattering coupled in-line with SEC (SEC-MALS) showed that the protein molar mass ($MM_{protein}$) of the eluting species was monodisperse and approximately 265 kDa (FIG. 20B and Table 3) and corresponded, within experimental error, to only one PG9 Fab bound to the SOSIP.664 trimer (FIG. 20B and Table 3). Together, these biophysical data suggested a novel mode of HIV-1 Env recognition that was amenable to structural characterization.

Molecular structure revealed by SAXS. X-ray scattering measurements were made on the SEC-MALS purified PG9 Fab: SOSIP trimer sample at three different concentrations. The linear character of the Guinier plot confirmed that the samples were almost entirely free of aggregation. Furthermore, the superimposable nature of the SAXS data collected at three different concentrations after scaling indicated that individual scattering particles were not interacting with one another and, therefore, allowed further evaluation of the data. $R_G$ and I(0) values of 56.4 Å and 174.5 Å, respectively were identical within experimental error as determined from the Guinier plot and pair-distribution function, P(r) and further confirmed the high quality of the data. $D_{max}$ derived from the P(r) function for the monodisperse PG9 Fab: SOSIP trimer complex was 196.6 Å. Analysis of the Kratky plots confirmed the sample was folded. Finally, the excluded volume was determined by analysis of the Porod invariant. The excluded volume of the sample, 786 nm$^3$, is directly related to its molar mass by a factor of two for large globular proteins (Putnam C D et al. (2007) Q Rev Biophys 40:191-285) and was, therefore, 393 kDa. Hence, the SAXS-determined molar mass of the monodisperse sample, which has a theoretical calculated mass of 392,270 Da (Table 1), corroborated the SEC-MALS data and indicated with exceptional precision that only one PG9 Fab binds to the SOSIP trimer. An ab initio molecular envelope was generated from scattering data with $q_{max}$=0.2 Å$^{-1}$ that corresponds to a ~30 Å nominal resolution for the scattering curve (Putnam C D et al. (2007) Q Rev Biophys 40:191-285). The resulting low-resolution molecular envelope allowed fitting of the previously determined crystal structure of monomeric gp120 in a trimeric arrangement, as well as the crystal structure of the PG9 Fab:gp120 V1/V2 complex (FIG. 7A). Clearly, from this low-resolution solution structure, only one PG9 Fab binds to the SOSIP trimer near the spike apex. The molecular envelope did not possess three-fold symmetry in contrast to other previously determined HIV-1 SOSIP trimer reconstructions (Pejchal R et al. (2011) Science 334:1097-1103, Depetris R S et al. (2012) J Biol Chem 287:24239-24254, Harris A et al. (2011) Proc Natl Acad Sci USA 108:11440-11445).

Molecular structure revealed by negative stain single particle EM. The PG9 Fab: SOSIP.664 BG505 complex purified by SEC-MALS was also analyzed by negative stain EM. The 2D class averages unequivocally showed that PG9 Fab recognizes the trimer in a unique way as compared to all other structurally characterized bNabs wherein one Fab bound per gp120 of the trimer in a three-fold symmetric arrangement (Pejchal R et al. (2011) Science 334:1097-1103, Tran E E et al. (2012) PLoS Pathog 8:e1002797, Liu J et al. (2008) Nature 455:109-113). A 3D-reconstruction of the PG9 Fab: SOSIP.664 BG505 complex at ~18 Å resolution provided further details of this asymmetric interaction. The lack of C3 symmetry necessitated collection of 33,431 particles in order to obtain a ~18 Å resolution reconstruction. Notably, if C3 symmetry was imposed during the reconstruction process, the resultant volume displayed discontinuous density in the region corresponding to the PG9 Fab.

In addition to corroborating the low-resolution SAXS solution structure, the EM reconstruction was sufficient to conduct high fidelity docking of crystal structures. Nearly all of the gp120 trimer core structure and the PG9:V1/V2 structure could be positioned within the envelope without significant parts protruding. The boat-shaped density of the Fab, with a dimple between the constant and variable domains, allowed unambiguous docking of the Fab atop the trimer (FIG. 7B). Further, protein G was used to unequivocally orient the Fab in the density map. In the fitted model, the glycan at position N160 sits immediately adjacent to the trimer axis, whereas the glycan at position N156/N1173 resides at the edge of the V1/V2 density (FIG. 7B). Moreover, the PG9 HCDR3 hammerhead sits directly atop the trimer axis (FIG. 7B).

Three copies of core gp120 were then fitted into the three lobes of density corresponding to each protomer of the Env trimer. Two gp120 monomers were placed in close proximity to PG9, while the remaining gp120 monomer appears to have moved away from the trimer center, which explains the loss of C3 symmetry (FIG. 7D). This observation led to the hypothesis that the preference of PG9 for a quaternary epitope might arise from additional interactions in the trimer emanating from the recognition of two out of the three gp120 V1/V2 domains at the trimer apex. This would constitute a putative secondary site of interaction that was not observed in the PG9: V1/V2 scaffold crystal structure.

High affinity for PG9 binding and putative secondary site of interaction on the Env trimer. As observed in the PG9: V1/V2 crystal structure, PG9 mediates its recognition through interactions via HCDR2, HCDR3, LCDR1, LCDR2 and LCDR3, predominantly on one side of the Fab. Upon fitting this atomic structure into the EM reconstruction, it became obvious that the other side of the PG9 variable domain consisting of HCDR1, HCDR3 and LCDR2 not participating in recognition of the V1/V2 monomer sits directly above the trimer axis. To probe whether this region comes into close contact with other V1/V2 elements at the trimer interface, a PG9 mutant was designed to insert a $Man_5GlcNAc_2$ glycan into the pocket around N160 by introduction of an NGT glycosylation sequence at the edge of LCDR2, by substitution of residues $^{56}SGV^{58}$ (FIG. 8A). A $Man_5GlcNAc_2$ glycan has dimensions of approximately 16 Å×14 Å×10 Å and, therefore, probes contacts or steric clashes within this footprint. Binding of the PG9 WT and mutant were tested with BG505 gp120 monomer and SOSIP.664 trimer by isothermal titration calorimetry (ITC). Whereas the PG9 WT and mutant bound to BG505 gp120 monomer with almost identical high affinity (~30 nM), the glycan insertion in the PG9 LCDR2 resulted in a >10-fold reduction in binding affinity on the trimer as compared to PG9 WT (FIG. 8B and Table 2). In contrast, PG9 mutant binding to the BG505 gp120 monomer was unaffected by introduction of the glycan and exhibited high binding affinity (~20 nM) (FIG. 8B and Table 2). This result indicated that indeed, the PG9 LCDR2 comes into close proximity to elements at the trimer interface, and hence was consistent with the trimer model generated from EM. However, it is noted that the binding affinity for PG9 WT to both the BG505 gp120 monomer and the SOSIP.664 trimer is similar (~20-30 nM). As such, the proximity of additional components of PG9, such as HCDR1, HCDR3 and LCDR2 to elements located at the trimer axis does not seem to lead to a significantly higher binding affinity for the SOSIP.664 trimer.

Applicants also analyzed the PG9 Fab stoichiometry of binding (N) to the monomer and SOSIP.664 trimer and found that it was identical within experimental error, providing yet another line of biophysical evidence that one PG9 binds the trimer. However, for all measurements, N<1 values were obtained from ITC measurements and these probably represent a combination of glycan heterogeneity on the glycoproteins expressed in 293 GnT 1-deficient cells, sample impurity and possible errors arising from some uncertainty in measurement of the glycoprotein concentration. Similar lower than expected N values (<3) were observed for binding of bnAb PGT127 Fab to the SOSIP.664 trimer, another bnAb possessing glycan elements in its epitope.

Increased stability of the BG505 SOSIP.664 trimer and effect of PG9 binding. In an attempt to better understand the unique nature of PG9 binding to the BG505 SOSIP.664 trimer, additional EM experiments and stability assays were performed. A comparison between the reconstructions of the unliganded BG505 SOSIP.664 trimer and that of the previously characterized unliganded KNH1144 SOSIP.664 trimer both at a 25 Å resolution (Depetris R S et al. (2012) J Biol Chem 287:24239-24254) showed that, for the same envelope volume, the BG505 SOSIP.664 appeared slightly more compact than its counterpart KNH1144 SOSIP.664G (FIG. 9A). In accord with these structural observations, the melting temperature of these two constructs (Tm), as probed by differential scanning calorimetry (DSC), varied significantly. Whereas the KNH1144 SOSIP.664 trimer showed thermal transitions at three different temperatures (51.3° C., 61.4° C. and 68.1° C.), the BG505 SOSIP.664 trimer remained surprisingly intact up to a temperature of 67.9° C. (FIG. 9B). These data therefore suggest an unusually high stability for the BG505 SOSIP.664 trimer without any signs of subunit dissociation until complete unfolding. Applicants hypothesize that this increased stability is due to the more compact nature of the trimer. Interestingly, binding of PG9 to the BG505 SOSIP.664 trimer appears to have both a destabilizing and stabilizing effect on the trimer. Upon PG9 binding, two extra thermal transitions at 52.2° C. and 73.8° C. are observed in addition to the thermal transitions of the individual components, which are hard to de-convolute because of similar Tm values (FIG. 9B). This thermal stability profile is in contrast to binding of soluble CD4, which destabilizes the trimer upon binding (FIG. 9B), possibly due to conformational changes that lead to the open conformation (Harris A et al. (2011) Proc Natl Acad Sci USA 108:11440-11445). As such, the DSC data support a mechanism by which PG9 binding stabilizes two gp140 protomers, while disrupting the trimer integrity and, therefore, the stability of the third protomer.

PG9 is a bnAb that preferentially recognizes a quaternary epitope located in the V1/V2 region of HIV-1 Env gp120. Recent crystal structures of PG9 Fab in complex with scaffolded V1/V2 clearly demonstrate close interaction between this bnAb and two glycans (N160 and N156/N173) and the cationic β-strand C of the V1/V2 region. However, recognition of the full PG9 epitope in a trimer context and its dependence on quaternary structure still need to be explained. Following the design and isolation of a stable trimeric HIV-1 Env SOSIP.664 construct of Clade A BG505 sequence, Applicants used multiple structural (EM and SAXS) and biophysical techniques (SEC-MALS, ITC and DSC) to unequivocally establish that one PG9 Fab asymmetrically interacts with V1/V2 elements at the apex of the HIV-1 Env trimer with nanomolar binding affinity. From modeling of components of gp120 core and the PG9:V1/V2 scaffold derived from crystal structures into the ~18 Å negative stain EM reconstruction and from PG9 mutant binding data, Applicants present evidence that PG9 has a larger paratope than previously identified by the X-ray crystal structures. Elements of this extended paratope, including HCDR1, HCDR3 and LCDR2 come into close proximity to neighboring V1/V2 elements at the trimer apex, such as a second glycan at position N160. Therefore, PG9 could contact a total of three glycans and a β-strand in a trimer context (FIG. 10). These additional protein and glycan elements emanating from a neighboring protomer may in part explain the quaternary nature of the PG9 epitope, in addition to the quaternary structure of elements atop the spike. Previous mixed trimer experiments had postulated that PG9 recognition was dependent on a single protomer in mediating its recognition (Walker L M et al. (2009) Science 326:285-289, Doores K J & Burton D R (2010) J Virol 84:10510-10521). It is possible that the complexity of these assays and the intrinsic assumptions of the models used to fit the data might not have been able to detect the weaker secondary interactions proposed here.

Applicants' EM data unambiguously positions N160, the central PG9 epitope glycan near the trimer axis at the apex of HIV-1 Env. These data therefore suggest that, in a trimeric configuration, the N160 $Man_5GlcNAc_2$ glycan would be a hallmark of properly folded trimers. As such, functional cleaved HIV-1 trimers would have quaternary constraints on this glycan that could explain the incomplete processing by host glycosidases of this immature oligomannose (IOM) glycan ($Man_5GlcNAc_2$). The humoral immune system would gain significant advantage in recognizing an epitope that is only displayed on functional HIV-1 trimer and, therefore, bypass decoy strategies employed by the virus that present non-functional immunogenic Env entities on the viral surface. Applicants postulate that PG9, with its elongated HCDR3 hammerhead structure, appears to not only be able to interact with and penetrate through different glycan types at N160 and N156/N173, as observed in the PG9:V1/V2 crystal structure, but also insert its extended anionic, tyrosine-sulfated HCDR3 through the dense trimeric arrangement of N160 IOM glycans to reach a secluded cationic groove in the center of the trimer apex atop the spike (FIG. 10). Together, PG9 recognition of its quaternary epitope at the HIV-1 trimer apex represents a unique asymmetric binding mode that had not yet been observed in HIV-1 or, to Applicants' knowledge, in any other viral glycoprotein antibody recognition. This structure further indicates that the BG505SOSIP retains elements of the structure of the native HIV Envelope found on HIV virus particles and thus the BG505SOSIP trimer protein is a good candidate as an immunogen and candidate vaccine.

In analyses of PG9 neutralization sensitivity and escape, several studies have reported key residues that play a significant role in mediating PG9 recognition (Walker L M et al. (2009) Science 326:285-289, Doores K J & Burton D R (2010) J Virol 84:10510-10521, O'Rourke S M et al. (2012) J Virol 86:12105-14, Wu X et al. (2011) J Virol 85:4578-4585, Doria-Rose N A et al. (2012) J Virol 86:8319-8323, Thenin S et al. (2012) J Gen Virol 93:1495-1505 and Ringe R et al. (2012) Virology 426:34-41). Some of these residues and glycans, such as N156, F159, N160, K168, K169 and K171, are directly contacted by the bnAb. However, others such as Y173, N190, N194 and N197 do not interact with PG9 in the crystal structure with scaffolded V1/V2 loops and are hypothesized to have an indirect effect on local residue positioning. In addition, elements of V3 (P299), C2 (1215), C4 (1423) and gp41 (G589) and various glycosylation sites throughout gp120 have been implicated in modulating PG9 recognition. Although the structural information here does not have the resolution to distinguish the role that these additional residues play in forming the PG9 epitope, the molecular envelope and fitted models do indicate that additional contacts might be present. Applicants have already noted potential interactions with a second N160 glycan on the PG9 Fab. Based on the 18 Å EM reconstruction and modeling, other interactions are also plausible for PG9 with the conserved V2 strands C and D and some residues of V3 that might extend towards the neighboring V1/V2 loops to mediate inter-subunit interactions, as previously suggested (Rusert P et al. (2011) J Exp Med 208:1419-1433). Further structural studies of the PG9: HIV Env trimer at higher resolution will be required to clearly define the role of these residues, as well as shed light on the exact orientation at which the V1/V2 base connects to the gp120 core. Yet another critical element that remains to be determined is the exact position of V3, which could not confidently be modeled at this resolution.

It remains puzzling that despite recognition by PG9 of its epitope in the BG505 SOSIP.664 trimeric context, the ~30 nM binding affinity measured is not higher than that for binding to the BG505 gp120 monomer. To date, only a few gp120 monomers have been shown to bind PG9, and recognition of these special sequences in a monomeric context remains poorly understood (Pejchal R et al. (2010) Proc Natl Acad Sci USA 107:11483-11488, McLellan J S et al. (2011) Nature 23:336-343, Doores K J & Burton D R (2010) J Virol 84:10510-10521, Doria-Rose N A et al. (2012) J Virol 86:8319-8323, Davenport T M et al. (2011) J Virol 85:7095-7107, Phogat S K et al. (2011) US20110262488). In addition, the binding affinity is still ~20 times lower than the corresponding median neutralization $IC_{50}$ of 0.23 µg/ml or 1.5 nM of PG9 (Walker L M et al. (2009) Science 326:285-289). This discrepancy is not unique to PG9; it is also observed for other antibodies, such as PGT 27, which binds the SOSIP.664 trimer with approximately 70 nM affinity despite having an apparent binding affinity of 46 nM for a gp120 outer domain (eODmV3), a 6 nM affinity for HIV-$1_{JR-FL}$ gp120 core with full-length V3 and a median neutralization $IC_{50}$ of 0.08 µg/ml or 0.5 nM against viruses neutralized with an $IC_{50}$<50 µg ml$^{-1}$ (Walker L M et al. (2011) Nature 477:466-470, Pejchal R et al. (2011) Science 334:1097-1103).

Antigens capable of presenting epitopes in a trimeric context are urgently needed to develop as potential immunogens. Indeed, studies comparing neutralizing and non-neutralizing Abs against the HIV-1 Env CD4bs have revealed the importance of epitope recognition in the context of the functional Env trimer (Chen L, et al. (2009) Science 326:1123-1127). Even if the residues contacted upon recognition are all displayed on gp120 monomers, such as the CD4bs, an epitope may have limited accessibility and access in the Env trimer. For PG9, the situation is even more complex as the full epitope is only formed after assembly of the trimeric Env structure. Thus, the PG9-BG505 SOSIP.664 trimer structure reported here constitutes a major advance, as it represents a new paradigm in recognition of HIV-1 Env, where only one Fab binds to the trimer and interacts asymmetrically with two of the three gp20 protomers. This soluble SOSIP trimer not only binds PG9, but also shows a higher degree of stability when compared to gp120 monomers and previous SOSIP constructs (Leavitt S A et al. (2004) Curr Protein Pept Sci 5:1-8) that make it an ideal reagent for elucidating the structure of other bnAb: trimer complexes that have so far remained elusive. Thus, this Env trimer has highly desirable properties that enable presentation of quaternary epitopes that are being increasingly identified from analysis of broadly neutralizing antibodies generated during the course of natural infection, and, hence, inform on design of optimal trimers as vaccine candidates. In addition, the structural information described indicates that the BG505SOSIP.664 represents an excellent candidate immunogen and vaccine.

Protein expression and purification. The PG9 Fab was expressed recombinantly following a protocol similar to that previously described (Pejchal R et al. (2010) Proc Natl Acad Sci USA 107:11483-11488). To ensure a maximum level of tyrosine sulfation, the heavy and light chain genes were co-transfected in 293F cells with a gene encoding tyrosyl-protein sulfotransferase 1 (TPST1). The secreted PG9 Fab was harvested 6-7 days post-transfection and the supernatant was directly loaded on an anti-human λ light chain affinity matrix (CaptureSelect Fab λ; BAC). Following elution with 100 mM glycine, pH 2.7, the sample was exchanged to buffer containing 20 mM sodium acetate, pH 5.6, and loaded onto a MonoS cation exchange column (GE Healthcare). After a gradient elution with sodium chloride, PG9 Fab was further purified by size-exclusion chromatography in a buffer containing 20 mM Tris, pH 8.0 and 150 mM sodium chloride. PG9 Fab glycan mutant was generated by mutation-PIPE polymerase chain reaction (PCR) and the resulting DNA was sequenced to ensure the correct introduction of the desired mutations. The high level of purity of all PG9 Fabs was confirmed by ESI-TOF high accuracy mass spectrometry.

The BG505 gp120 monomer and BG505 SOSIP.664 trimer were expressed and purified as previously described (Pejchal R et al. (2011) Science 334:1097-1103). Briefly, following expression in 293S cells (GnT I-deficient), the secreted BG505 constructs were harvested from the supernatant. The BG505 gp120 monomer was purified using a GNL affinity matrix, while the BG505 SOSIP.664 trimer was purified using a 2G12-coupled affinity matrix. Following elution, both constructs were purified to size homogeneity using either a Superdex 200 or Superose 6 SEC matrix (GE Healthcare).

Size-exclusion chromatography coupled with multi-angle light scattering (SEC-MALS). To obtain a pure PG9 Fab: BG505 SOSIP.664 trimer sample, PG9 Fab was added in a six-times molar excess over the trimer. Following 15 minutes incubation on ice, the sample was loaded on a Superose 6 10/30 SEC column (GE Healthcare), which was coupled in-line on an AKTA Avant FPLC system (GE Healthcare) with the following calibrated detectors: 1) HPI 1050 Hewlett-Packard UV detector (Norwalk, Conn.); 2) MiniDawn Treos multi-angle light scattering (MALS) detector (Wyatt Corporation, CA); 3) quasi-elastic light scattering (QELS) detector (Wyatt Corporation, CA); 4) Optilab T-reX refractive index (RI) detector (Wyatt Corporation, CA). Analysis of the light scattering data coupled to $UV_{280}$ and refractive index protein concentration measurements allowed determination of the molar mass of the eluting protein using the protein conjugate template in Astra V, as previously reported for KNH1144.664 SOSIP (Depetris R S et al. (2012) J Biol Chem 287:24239-24254).

Small-angle X-ray scattering (SAXS). The purified PG9: BG505 SOSIP.664 complex isolated from the SEC-UV/MALS/RI experiment was concentrated to 0.16, 0.34 and 0.65 mg/ml and these samples were subsequently studied by SAXS at the Stanford Synchrotron Radiation Lightsource (SSRL) BIO-SAXS beamline 4-2. For each concentration, 15 exposures of two seconds each were collected and the resulting scattering curves were buffer-subtracted. Using the program PRIMUS (Konarev P V et al. (2003) J Appl Cryst 36:1277-1282), the SAXS data were inspected and indicated no signs of aggregation, long-range interactions or radiation damage. An ideal scattering curve was generated by merging the low resolution data collected from a dilute sample (0.34 mg/ml) with the larger angle data of the more concentrated sample (0.65 mg/ml). Scattering data up to $q=0.2$ $Å^{-1}$ was included. Agreement between $R_G$ and I(0) values determined from the Guinier plot [log(I(q)) vs. $q^2$] and the pair-distribution function, P(r) further confirmed the good quality of the data. As such, determination of the $D_{max}$ overall shape, excluded volume and molar mass were confidently performed through analysis of the P(r) function, Kratky plots [$I(q)q^2$ vs. q] and Porod invariant. Ab initio shape determination of the monodisperse sample was performed using the program GASBOR with P1 symmetry (Svergun D I et al. (2001) Biophys J 80:2946-2953). Ten independent reconstructions were calculated and subsequently aligned and averaged using the program DAMAVER to yield a final probability map of the low-resolution envelope (Volkov V V & Svergun D I (2003) J Appl Cryst 36:860-864).

Electron microscopy and sample preparation. The purified PG9 Fab: BG505 SOSIP.664 complex was recovered from the SEC-UV/MALS/RI experiment and analyzed by electron microscopy. 3 μL of 0.03 mg/mL complex was applied for 5 seconds onto a carbon coated 400 Cu mesh grid that had been glow discharged at 20 mA for 30 seconds, then negatively stained with Nano-W for 30 seconds. Data were collected using a FEI Tecnai F20 electron microscope operating at 120 keV using an electron dose of 30 $e^-/Å^2$ and a magnification of 100,000× that resulted in a pixel size of 1.09 Å at the specimen plane. Images were acquired with a Gatan 4 k×4 k CCD camera using a nominal defocus range of 500 to 900 nm in 5° tilt increments from 0 to 55°. Protein G bound PG9 Fab: BG505 SOSIP.664 sample was prepared by adding 50 equivalents of Protein G to 0.2 mg/mL of the PG9 Fab: BG505 SOSIP.664 sample, and incubating on ice for 4 hours. The sample was diluted to 5 fold by volume. The grid was prepared and data were collected as stated above.

Image processing. Particles were picked automatically using DoG Picker and put into a particle stack using the Appion software package (Voss N R et al. (2009) J Struct Biol 166:205-213, Lander G C et al. (2009) J Struct Biol 166:95-102). Initial reference free 2D class averages were calculated using particles binned by 5 via the Xmipp Clustering 2D Alignment (Sorzano C O et al. (2010) J Struct Biol 171:197-206) and sorted into 440 classes. Good particles were selected into a substack, binned by four then another round of reference free alignment was carried out using the Xmipp Clustering and 2D alignment and IMAGIC softwares (van Heel M et al. (1996) J Struct Biol 116:17-24). A template stack of 154 images of 2D class averages was used to generate an ab initio 3D model, using an unliganded trimer (EMDB 5019 (Liu J et al. (2008) Nature 455:109-113) as the initial model for 89 iterations without imposing symmetry. The Fab density was visible after 10 iterations. To account for model bias, the identical 3D reconstruction procedure was carried out using a naïve reconstruction of the unliganded BG505 SOSIP.664 trimer. The final volumes for the EMDB 5019 trimer and BG505 SOSIP.664 trimer reconstructions were nearly identical. The same reconstruction procedure with C3 symmetry imposition was carried out to build confidence in the asymmetric model using the EMDB 5019 trimer. The C3 symmetrized volume placed three separate blobs of density in a C3 symmetric fashion around where the constant region of the Fab should be, indicating that the model is not C3 symmetric. Using the final map from the EMDB 5019 based reconstruction, further refinement was carried out against raw particles binned by 2, without imposing symmetry for 80 cycles. The resolution of the final map from 33.431 particles is ~18.1 Å as determined by an FSC cut-off at 0.5. The protein G bound PG9 Fab: BG505 SOSIP.664 data set was sorted by the aforementioned 2D classification, and 3D volume refinement methods. A template stack of 55 class averages was used to refine the protein G absent PG9 reconstruction for 49 iterations to generate an ab initio model. The final ab initio volume was used as the initial model for a 22 iteration refinement using 6,506 raw particles binned by 2. EMAN (Ludtke S J et al. (1999) J Struct Biol 128:82-97) was used for all 3D reconstructions.

Isothermal Titration Calorimetry (ITC). A MicroCal iTC200 instrument (GE Healthcare) was used to perform isothermal titration calorimetry measurements. All proteins tested were extensively dialyzed against 20 mM Tris, 150 mM NaCl, pH 8.0 buffer prior to the titration experiment. PG9 Fab was in the syringe at concentrations ranging between 30-200 μM, depending on the binding partner, while the BG505 gp120 monomer or SOSIP.664 trimer was in the cell at concentrations ranging between 3-10 μM. The protein and glycoprotein concentrations were determined by UV absorbance at 280 nm using calculated extinction coefficients (Gasteiger E et al. (2005) The Proteomics Protocols Handbook, ed Walker J M (Humana Press), pp 571-607). Experiments were carried out in triplicate at 25° C. and consisted of 12 injections of 3.5 μl each, with injection duration of 5 seconds, injection interval of 180 seconds and reference power of 5 μcals. Fitting of the integrated titration peaks with Origin 7.0 software using a single-site binding model allowed direct determination of the reaction affinity constant (Kd) and molar reaction enthalpy (ΔH). In addition, the change in Gibbs free energy, ΔG and the entropic change, ΔS were derived from the basic thermodynamic relationships ΔG=RT ln Kd and ΔG=ΔH−TΔS, respectively.

Differential Scanning Calorimetry (DSC). Thermal denaturation was probed with a VP-DSC calorimeter (GE Healthcare). Prior to carrying out the experiments, all samples were extensively dialyzed against Dulbeco's phosphate buffer saline. Protein concentration was subsequently adjusted to 0.1-0.3 mg/ml as assessed by UV absorbance at 280 nm using theoretical extinction coefficients (Gasteiger E et al. (2005) The Proteomics Protocols Handbook, ed Walker J M (Humana Press), pp 571-607). In the case where complexes were analyzed by DSC, the ligand (either PG9 or sCD4) was present in at least two times molar excess over the amount of glycoprotein. After loading of the protein sample in the cell, thermal denaturation was probed at a scan rate of 90° C./hour. Following buffer correction, normalization and baseline subtraction, data analysis was performed using the Origin 7.0 software. Data were fit using a non-two-state model, which ensues from the asymmetry of some of the peaks suggesting the presence of unfolding intermediates.

TABLE 1

Molar mass analysis of unliganded and PG9-bound BG505.664 SOSIP as assessed by SEC-UV/MALS/RI and SAXS.

| | Expected $MM_{protein}$ of BG505.664 SOSIP trimer (g/mol) | Estimated $MM_{glycan}$ of BG505.664 SOSIP trimer (g/mol) | Expected $MM_{protein}$ of PG9 Fab (g/mol) | Expected total $MM_{glcoprotein}$ (g/mol) | $MM_{glcoprotein}$ from SEC-UV/MALS/RI (g/mol) | $MM_{glcoprotein}$ from SAXS (g/mol) | Hydrodynamic radius, $r_H$ (nm) | Radius of gyration, $r_g$ (nm) |
|---|---|---|---|---|---|---|---|---|
| Unliganded BG505.664 SOSIP | 225,233 | 118,000 | 49,037 | 343,233 | 357,200 ± 25,000* | ND* | 8.1 | ND* |
| PG9 Fab + BG505.664 SOSIP | | | | 392,270 (trimer + 1 Fab) | 387,000 ± 31,000* | 393,000 | 8.6 | 5.7 |

ND = SAXS
Not determined.
*Associated error as determined by Astra V.

TABLE 2

Thermodynamic parameters of binding measured by isothermal titration calorimetry.

| Binding experiment | ΔG# (kcal mol⁻¹) | ΔH (kcal mol⁻¹) | −TΔS (kcal mol⁻¹) | $K_D$* (nM) | N& |
|---|---|---|---|---|---|
| PG9 WT into BG505 monomer | −10.2 | −27.4 | 17.2 | 31 ± 2 | 0.4 |
| PG9 mutant into BG505 monomer | −10.5 | −23.5 | | | |
| PG9 WT into BG505 SOSIP trimer | −10.1 | −20.6 | | | |
| PG9 mutant into BG505 SOSIP trimer | −8.8 | −23.7 | | | |

The change in Gibbs free energy (ΔG) was determined using the relationship: $ΔG_{binding}$ = RTlnK$_d$ (de Azevedo WF, Jr. & Dias R (2008) Experimental approaches to evaluate the thermodynamics of protein-drug interactions. Curr Drug Targets 9: 1071-1076).
*Associated errors are the standard deviation calculated from three independent measurements.
&The stoichiometry of binding (N) is directly affected by protein concentration measurements, sample impurity and glycan heterogeneity on gp120 that are incompatible with PG9 binding. For the heavily glycosylated gp120 monomer/trimer, discrepancies in glycoprotein concentrations determined from different techniques (UV$_{280}$, BCA, Bradford) result in variations in N of ±0.15.

Example 2

Supersite of Immune Vulnerability on the Glycosylated Face of HIV-1 Envelope Glycoprotein gp120

Sera from a proportion of HIV-infected donors exhibit potent neutralizing antibody activity against globally diverse viruses, suggesting an AIDS vaccine is feasible. A substantial fraction of antibodies in such sera recognize an epitope dependent on a glycan at Asparagine 332 (N332) on the HIV-1 gp120 surface glycoprotein. Here, Applicants elucidate how broadly neutralizing antibody (bnAb) PGT 135 recognizes its N332-dependent epitope from its crystal structure with gp1120, CD4 and Fab 17b at 3.1 Å resolution. PGT135 interacts with three glycans at N332, N392 and N386, and uses two long CDR loops (H1, H3) to reach through the glycan shield so as to access the gp120 protein surface around V4. This mode of recognition contrasts with other bNabs PGT 128 and 2G12, which also recognize N332-dependent epitopes but engage different constellations of the surrounding sugars. Electron microscopy reveals that PGT135 may more readily accommodate the conformational and chemical diversity of the HIV-1 N-linked glycans through some flexibility in its angle of engagement. Thus, in contrast to the CD4 binding site, another bnAb target on gp20, the N332-dependent epitope is much more extensive and accessible, allowing for multiple binding modes and varied angles of approach, thereby representing a supersite of vulnerability on HIV-1 for neutralization by antibodies of the immune system.

The human humoral immune system initially generates strain-specific neutralizing antibodies to HIV-1 that recognize only a fraction of the massively diverse mutational variants of its envelope glycoprotein (Env)(Weiss, R. A. et al. Nature 316, 69-72 (1985)). In the infected host, the virus diversifies extensively and escapes from these narrowly focused antibodies. Strong selection pressure drives variation in its exposed surfaces, including its five hypervariable loops (V1-V5) and around 27 N-linked glycans that cover most of the gp120 envelope glycoprotein surface (Wei, X. et al. Nature 422, 307-312 (2003)). Despite this extraordinary sequence variation and "evolving glycan shield", broadly neutralizing activity is found in 5-25% of donor sera after 2-3 years of infection (Scheid, J. F. et al. Science 333, 1633-1637, (2011), Stamatatos, L et al. Nat. Med. 15, 866-870 (2009)). However, by this time, the virus has firmly established itself, overwhelming even broadly neutralizing responses. Nevertheless, elicitation of such responses by a vaccine prior to virus exposure may lead to prophylactic protection against HIV-1.

Given that neutralizing antibody selection pressure shifts glycosylation sites on the virus during the course of infection (Wei, X. et al. Nature 422, 307-312 (2003)), it is reasonable to assume that these antibodies may not only be targeting protein surfaces near glycans, but also the glycans themselves. This notion is supported by observations of serum neutralizing activity that is dependent on the presence of the glycan attached to N332 (Walker, L. M. et al. Proc. Natl. Acad. Sci. U.S.A. 108, 20125-20129 (2011), Gray, E. S. et al. J. Virol. 85, 4828-4840 (2011)) and by the recent discovery of several broadly neutralizing antibodies (bnAb) that interact with gp120 in a glycan-dependent manner. Three antibodies, 2G12 (Calarese, D. A. et al. Science 300, 2065-2071 (2003)), PGT 128 (Pejchal, R. et al. Science 334, 1097-1103 (2011)) and PG9 (McLellan, J. S. et al. Nature 480, 336-343 (2011)), have been structurally characterized in complex with individual glycans, a gp120 outer domain fragment, and a scaffolded glycopeptide, respectively. 2G12 recognizes the outer tips of a cluster of high mannose glycans at N295, N332, N339 and N392 through an unusual domain exchange of its $V_H$ regions that leads to dimerization of the Fabs and formation of an extended combining region for multivalent binding of glycans. PGT 128 and PG9, on the other hand, are able to penetrate the glycan shield using very long CDR loops that reach the protein surface and contact small β-strand segments of the protein in addition to extensive interactions with two glycans. A number of other glycan-dependent bNabs, including PG16 and PGT 121-123, 130-131 and 142-145, await structural characterization in complex with Env (Walker, L. M. et al. Science 326, 285-289 (2009), Walker, L. M. et al. Nature 477, 466-470 (2011)).

Here, Applicants report on structural and functional analysis of PGT 135, an N332 glycan binding bnAb isolated from an individual whose serum has one of the highest neutralization breadths known (Walker, L. M. et al. Nature 477, 466-470 (2011), Zhu, J. et al. Front. Microbiol. 3, 315 (2012)). The PGT 135 epitope includes three glycans and protein segments that enable interaction with HIV-1 Env trimers in a flexible manner, revealing a major site of vulnerability on the glycosylated face of gp120.

Structural Characterization of PGT135 Mode of Binding to gp120.

To elucidate the interaction with gp120, PGT135 Fab complexes with a number of gp120 constructs and other ligands were tested for crystallization. Crystals of a quaternary complex (i.e. four protein components) of PGT 135 with JR-FL core gp20, CD4 D1D2 and Fab 17b Fab diffracted to 3.1 Å resolution, while unliganded Fab135 crystals diffracted to 1.75 Å. The JR-FL gp120 monomeric core binds to PGT 135 Fab with high affinity [82 nM by ITC], but the corresponding virus is only weakly neutralized by PGT 135 IgG unless specific mutations are introduced into the V1/V2 loop (Tong, T. et al. J. Virol. 86, 3574-3587 (2012)).

The overall structure shows that CD4, 17b and PGT 135 are bound to gp20 in nearly orthogonal orientations (FIG. 11A). When the gp120/PGT 135 complex was partially deglycosylated by endoglycosidase H prior to crystallization, only single N-acetylglucosamine (GlcNAc) moieties were observed in the electron density of the quaternary complex at N339, N362, N448, N262 and N276, whereas high mannose (Man) glycans interacting with PGT 135 were protected and density was observed for $GlcNAc_2Man$ at N386, $GlcNAc_2Man_6$ at N332 and $GlcNAc_2Man_8$ at N392. When compared to its unliganded structure, PGT 135 does not undergo any large conformational changes [0.4 Å Cα root-mean-square deviation (RMSD) between Fab variable domains]. The gp120 structure in the PGT135-CD4-17bgp120$_{JRFL}$ complex is also highly similar to that in the CD4-17b-gp120$_{HXBC}$ complex$_{14}$ (0.5 Å Cα RMSD), suggesting that PGT 135 does not induce any further conformational changes when it binds to gp20. This inference is corroborated by ITC data: the ΔG, ΔH and TΔS values for PGT 135 binding to unliganded gp120 and to the gp120-CD4 complex were nearly equivalent.

PGT 135 engages gp120 primarily via a long 18-residue CDR H3 loop that has 10 amino acid insertions after position 100 (n.b. the average human CDR H3 is 13 residues using the Kabat definition of H95-H102$_{15}$), and a CDR H1 loop containing a rare 5 amino-acid insertion not present in the predicted germline sequence; both CDR loops protrude from the $V_H$ surface by nearly 20 Å, comparable to the length of high mannose N-linked glycans. These extended $V_H$ CDR loops in unliganded PGT 135 converge to form a highly hydrophobic horseshoe-shaped surface consisting of $Trp_{34}$ from CDR H1, $Trps_3$ from H2, and $Val_{100}$-FMLVPIle$_{100F}$ from H3. A salt bridge between $Arg_{54}$ on the tip of H2 and $Glu_{33}$ near the top of the H1 loop insertion helps keep these loops in place. These features remain intact after binding to gp120. PGT 135 buries a complex epitope consisting of 438 Å$^2$ of protein and 1010 Å$^2$ of glycan surface on gp120 (FIG. 11), which is larger than the typical antibody footprint (~700-900 Å$^2$). 83% percent of the protein-protein buried surface involves side chains on gp120, in contrast to PG9 and PGT 128 that rely primarily on backbone interactions with V1/V2 and V3, respectively, to form main-chain β-strand associations (Pejchal, R. et al. Science 334, 1097-1103 (2011), McLellan, J. S. et al. Nature 480, 336-343 (2011)). The CDR H1 and H3 tips primarily contact gp120 protein along β-strand 19, which connects the V4 loop to β-strand 20, as part of the bridging sheet (FIG. 11B). In addition, the tips of these loops contact the adjacent β-strand 13, between V3 and α-helix 2, where $His_{330}$ is particularly important for binding and neutralization. On the gp120 V4 loop, Glu409 interacts with CDRs L2 and H3, forming a protein-protein interaction zone that is discontinuous from the rest of the contacts. The C(DR H1 insertion allows access to the protein surface around the N386 glycan (GlcNAc$_2$Man), which separates the PGT 135 epitope from the CD4 binding site. Trp$_{34}$ on the tip of CDR H1 insertion interacts with the N386 glycan. Coincidentally, bnAb b12 also contacts residues near the N386 glycan via CDR H3 Trp$_{100}$, which is in a similar relative position to PGT 135 H1 Trp$_{34}$ (Zhou, T. et al. Nature 445, 732-737 (2007)). Deletion of the H1 insertion significantly reduces PGT135 binding and neutralization of different HIV-1 isolates, suggesting that this extended loop is important for the antibody-antigen interaction.

The large glycan binding surface of PGT 135 is created by the CDR loops draping themselves across the entire length of the N-linked glycans at N392 (547 Å$^2$) and N332 (365 Å$^2$), where multiple van der Waals interactions and hydrogen bonds are made from the mannose tips to the GlcNAc stem (FIG. 11, FIG. 12A). The N386 glycan interaction is significantly less (99 Å$^2$, two van der Waals interactions with H1) than with N392 and N332, but nonetheless critical for neutralization of a number of HIV-1 strains (FIG. 12D). Interestingly, the N392 and N332 glycans interact with opposite faces of PGT135 CDR H3 in a bifurcated manner reminiscent of bnAb PG9 and PGT 128 binding to dual glycans on epitope-scaffolded V1/V2 (PG9) or gp120 outer domain (PGT 128), respectively (FIG. 12A). However, unlike these other bNabs, whose interacting glycans are on adjacent β-strands, the two glycans interacting with PGT 135 CDR H3 are on independent β-strands separated by β-strand 19 (FIG. 11B). V$_L$ also contacts the N332 glycan via CDR L3 on one side of Vt., whereas CDR L2, and V$_L$ framework regions 2-3 on the opposite side interact with the N392 glycan (FIG. 11).

Glycan Specificity of PGT 135.

N-linked glycans exhibit multiple levels of heterogeneity, from variable positioning of the glycosylation sequons on gp120 to conformational flexibility to differential processing by Golgi enzymes (Kasturi, L. et al. Biochem. J. 323, 415-419 (1997), Rudd, P. M. & Dwek, R. A. Crit. Rev. Biochem. Mol. Biol. 32, 1-100 (1997)). To understand how PGT 135 achieves relatively broad neutralizing activity despite dependence on such heterogeneous glycans, Applicants employed virus neutralization and binding assays based on virus and gp120s from different strains with various N-linked glycosylation knockouts, along with glycan arrays and different expression systems (FIGS. 12B-D).

Pseudoviruses prepared from mammalian 293T cells (complex, hybrid and oligomannose glycans) or 293S cells (Man$_{5-9}$GlcNAc$_2$ oligomannose glycans) had similar PGT 135 neutralization profiles (FIG. 12C). These results are consistent with the crystal structure, which shows interaction only with an oligomannose glycan patch on gp120 (Sanders, R. W. et al. J. Virol. 76, 7293-7305 (2002)) that would be present when gp120 is expressed in either cell line. In contrast to 2G12 and PGT 128, PGT 135 also neutralizes pseudoviruses from cells treated with N-butyldeoxynojirimycin (NB-DNJ), which results in either missing or glucosylated D1 arms of N-linked glycans (Fischer, P. B. et al. J. Virol. 69, 5791-5797 (1995)). This observation is also consistent with the crystal structure because PGT 135 does not interact with the N332 glycan D1 arm and only with the second mannose residue of the N392 glycan D1 arm, which would not be affected by NB-DNJ treatment (FIG. 12A). Also in contrast to 2G12 and PGT 128, adding kifunensine to the expression system, which limits glycan processing to Man$_9$GlcNAc$_2$, results in loss of neutralization by PGT 135. Again, the crystal structure is compatible with this outcome: modeling an additional mannose residue to the D2 arm of the Man$_8$ glycan at N392 would result in a severe steric clash. The D2 arm of the Man$_6$ glycan at N332 is also sterically crowded, but may be able to accommodate a terminal mannose with some slight adjustment.

Glycan array binding assays show that PGT 135 recognizes Man$_{7-9}$ glycans exclusively and binds to these with lower affinity than 2G12 and PGT128 (FIG. 12B). The pattern of binding to these glycans is dependent on the density and conformation of the presented glycans; in a different glycan array format using non-covalently immobilized N-linked glycans as neoglycolipids, only Man$_8$ and Man$_7$ glycans without the terminal D2 mannose are recognized. The array analyses and kifunensine effect described above can be reconciled if binding to glycans other than N392, most likely N332, can occur via Man$_8$ or Man$_9$.

Virus neutralization and binding assays revealed differential effects of these N-linked glycosylation sites on PGT 135 activity against different isolates of HIV-1 (FIG. 12D). Not surprisingly, N332 and N392 are required for all isolates tested because most of the antibody contacts are to these glycans. However, the requirement for N295 and N386 glycans, as well as His330 residue, on gp120, is strain dependent. Although the N295 glycan does not contact PGT 135 in the context of the JR-FL core gp120, these data suggest it may be recruited by the antibody in the context of other HIV-1 strains so that the epitope would be modified and strain dependent. Thus, although the PGT 135 interaction is highly specific for particular glycoforms on gp120, it may also be promiscuous by exploiting a neighboring N295 glycan for recognition of some HIV-1 strains. By targeting the oligomannose patch on gp120 where the required glycoforms are present, while tolerating a certain range of alternate glycan positions, PGT 135 may acquire broad neutralizing breadth despite the heterogeneity seen in the Env glycan populations. Overall, the data point towards two general requirements for PGT 135 binding, with the caveat that any given isolate may deviate from the most common pattern of recognition: 1) high mannose glycans within the context of the tightly clustered high mannose patch on gp120 and 2) a D2 arm on the glycan at N392 lacking at least the terminal mannose residue.

Structural Explanation for Neutralization Breadth of PGT 135.

PGT 135 can neutralize 33% of HIV-1 isolates at an IC$_{50}$<50 ug ml$_{-1}$ using a 162 cross-clade virus panel, which is comparable to bnAb b12 (34%), but less than PGT 128 (72%) (Walker, L. M. et al. Proc. Natl. Acad. Sci. U.S.A. 108, 20125-20129 (2011)), although PGT 135 and 128 both recognize epitopes critically dependent upon the same highly conserved N332 glycan (Walker, L. M. et al. Proc. Natl. Acad. Sci. U.S.A. 108, 20125-20129 (2011)). The variability of important residues and glycan sites was examined using 3045 aligned gp120 sequences (Los Alamos HIV Database). The sequence conservation of the essential elements necessary for gp120 binding agrees well with neutralization breadth. For PGT 128, glycans at N332 (73% conserved) and N301 (92% conserved) are critical for neutralization; both glycan motifs are present together in 69% of the sequences, which is close to the observed 72% neutralization breadths. For PGT 135, glycans at N332, N392, N295, N386, and His330 (73%, 79%, 59%, 87%, and 71% conserved, respectively) are all important for neutralization. His330, N332 and N392 are all required for neutralization of all isolates tested (FIG. 7D) and these three sites are found concurrently in 50% of the sequences. However, PGT 135 recognition also requires N295 and N386 glycans in a strain-dependent manner. His330, glycans at N332, N392, and either N295 or N386 are found in 31% or 42% of the sequences, while His330 along with all four glycan motifs (332, 392, 295, and 386) is present in 26% of the sequences, which approximates to the observed neutralization of 33% of test isolates by PGT135 (Walker, L. M. et al. Proc. Natl. Acad. Sci. U.S.A. 108, 20125-20129 (2011)).

PGT 135 Interaction with Trimer.

PGT 135 Fab binding to a glycosylated clade A BG505 SOSIP.664 gp140 trimer$_{20}$ was characterized by electron microscopy (EM). Three Fabs were bound per trimer, with the gp120 protomers in a more closed conformation (FIG. 13A) than the more open conformation seen with CD4 binding site ligands (Liu, J. et al. Nature 455, 109-113, (2008)). The PGT 135 angle of approach to the gp120 epitope prevents any clash with neighboring gp120 protomers or interference with the CD4 binding site (FIG. 13A). The 2D class averages show that PGT 135 occupies a distinct epitope from PGT 128, which also recognizes the N332 glycan (FIG. 13B), but significant variance is observed in the orientation of Fab PGT 135 relative to the trimer (FIG. 13C). Principal component analysis (PCA) of the variance clearly illustrates some flexibility in the Fab PGT 135 interaction with the trimer compared to PGT 128 (FIG. 13D). This increased variance for PGT 135 may represent a distribution of different angles of approach due to some slight shift between the interacting glycans or with the glycoforms it contacts (FIG. 13D). The use of alternative angles of approach may therefore reflect an immunologic countermeasure to some natural variation in the N-linked glycans that decorate the Env surfaces of different HIV-1 isolates.

Definition of a Glycan Containing Broadly Neutralizing Supersite.

PGT 135, 2G12 and PGT 128 are all dependent on the N332 glycan but have distinct binding motifs and quite different angles of approach to the oligomannose patch on gp120 that contains N332, and yet their neutralization activity is not compromised (FIG. 14A). Furthermore, PGT 135 also tolerates some variability in how it approaches and recognizes heterogeneous glycans (FIG. 13D). This scenario contrasts with antibodies whose binding footprints overlap the CD4 binding site where small differences in angle and relative position result in clashes with neighboring gp120s (Chen, L. et al. Science 326, 1123-1127 (2009)) and very different extents of neutralization from VRC01 (bnAb, 93% breadth) to F105 (non-neutralizing) (Scheid, J. F. et al. Science 333, 1633-1637, (2011)). Thus, these N332-dependent antibodies define a novel and unexpectedly broad supersite for neutralization (FIG. 14B), which encompasses conserved glycans at N295, N301, N332, N339, N386, and N392, the protein surface made by β-strands 16, 17, 19 and portions of the V3 strand backbone between N301 and N332 (FIG. 14B). For all of the N332-dependent antibodies, contacts with the highly conserved glycans mediate most of the binding, but the PGT 135 epitope contains the most substantial protein component in size and number of segments. While PGT 135 has undetectable affinity for the gp120 protein surface by itself since it cannot bind to deglycosylated gp120, and low affinity for glycans compared to PGT 128 and 2G12, it has 10-100 nM affinity for glycosylated gp120 where all these elements are combined. This complex binding mode may allow some of the individual elements on gp120, such as the N386 glycan or contact residues other than H330, to be dispensable or for other contacts to compensate in different isolates, thereby enhancing the neutralization breadth of PGT 135.

Although three different bNabs recognize the same N332 glycan, they contact chemically distinct surrounding surfaces. 2G12 binds to the glycan tips and is, therefore, highly dependent on the presence of the terminal mannose residues in a particular linkage. In contrast, PGT 135 and PGT 128 recognize the complete glycan at N332, but from completely opposite sides. Surprisingly, the glycan location and orientation is largely unchanged in the PGT 135 and PGT 128 structures, suggesting that each antibody recognizes a distinct and opposite face of the glycan. PGT 135 recognizes the more apolar B faces of the sugars, consistent with the more hydrophobic character of its CDR loops, whereas PGT 128 predominantly contacts the more polar A faces. The different faces of the N332 glycan are an important determinant for antibody recognition of this supersite.

The discovery of bNabs in a SHIV-infected macaque that depend on the N332 glycan, in addition to those described above in infected humans (Walker, L. M. et al. Proc. Natl. Acad. Sci. U.S.A. 108, 20125-20129 (2011). Gray, E. S. et al. J. Virol. 85, 4828-4840 (2011)), raises the prospect that suitable immunogens that display these combined glycan and protein epitopes in an appropriate configuration can be tested as vaccine candidates in animal models for re-elicitation of similar glycan-dependent antibodies. It is still not clear why the N332 glycan is so dominant in this interaction, but one possibility is that it is not only highly conserved (73%) and predominantly oligomannose, but also conformationally restrained by adjacent sugars. Indeed, the glycan N332 conformation is nearly identical in the crystal structures of PGT 128 (Pejchal, R. et al. Science 334, 1097-1103 (2011)) and PGT 135, suggesting that the immune system is presented with a comparatively well-ordered glycan shield, at least around N332. Thus, to mimic this supersite using rational vaccine design, such as epitope scaffolding (Azoitei, M. L. et al. Science 334, 373-376 (2011), Guenaga, J. et al. PLoS ONE 6, e16074 (2011)), and thereby create vaccine immunogens, one should carefully consider how to reconstitute a faithful representation of the glycan canopy with glycoforms that are similar to those in the intact Env trimer.

Multiple protein complexes containing various combinations of ligands and gp120 based on different HIV-1 sequences were screened for crystallization. Glycosylation on gp120 was controlled through expression in HEK 293S GnT1$_{-/-}$ (293S) cells and by partial deglycosylation using endoglycosidase H (Roche) after protein complex formation. A complex of PGT 135 Fab bound to a partially deglycosylated gp120-Fab 17b-CD4 complex crystallized in 16% w/v PEG MME 2000, Tris pH 7.87, and diffracted to 3.1 Å. Unliganded PGT 135 crystallized in 20% (w/v) PEG 8000, 0.1 M CHES, pH 9.5, with diffraction to 1.75 Å resolution. The structures were solved by molecular replacement with diffraction data collected at the Advanced Light Source beamline 5.0.2. and the Advanced Photon Source beamline 231D-B, respectively. Glycan binding was carried out on three different glycan array formats: high-mannose glycans printed on i) NHS activated slides from Schotts, ii) high-density NHS activated slides from ADA Technologies (Blixt, O. et al. Proc. Natl. Acad. Sci. U.S.A. 101, 17033-17038 (2004)) or iii) neoglycolipid microarrays (Palma. A. S. et al. J. Biol. Chem. 281, 5771-5779 (2006)). A glycosylated BG505 SOSIP.664 trimer was produced in 293S cells. Negative stain EM data on PGT 135 Fab in complex with this trimer were collected using a FEI Tecnai F20 electron microscope. The flexibility of the Fab PGT 135 interaction with the Env trimer was analyzed using 2D principal component analysis of class averages obtained from EM.

The detailed structural analysis of antibody binding to the BG505SOSIP.664 protein indicates that the structure is likely to be similar to that of the Envelope protein on the surface of the HIV particle. This indicates that the BG505SOSP.664 is a excellent candidate immunogen and vaccine and starting point for the design of improved vaccine candidates.

Cells and Proteins.

The reagent ARP3119, monoclonal antibody CA13, was obtained from the Centre for AIDS Reagents, NIBSC HPA UK, supported by the EC FP6/7 Europrise Network of Excellence, and NGIN consortia and the Bill and Melinda Gates GHRC-CAVD Project and was donated by Ms. C. Arnold. A sample of 17b IgG protein was obtained from Dr. James Robinson.

Expression and Purification of Soluble CD4.

The first two domains (D1D2) of CD4, followed by a $His_6$ tag (SEQ ID NO: 4), were cloned into vector pET26b and expressed in *E. coli* BL-21 DE3* cells in LB media. The supernatant was concentrated, and dialyzed extensively against 20 mM Tris, 0.5 M NaCl, pH 8, then applied to a 5 ml HiTap IMAC HP Nickel (GE) column, and eluted with a gradient of 0-100% 1.5M glycine in 20 mM Tris-acetate, 500 mM NaCl, pH 8.0. The eluted protein was dialyzed against 0.2M Tris-Cl, 150 mM NaCl, and finally purified by SEC on a Superdex75, 10/30 column.

Full-Length Antibody Expression.

PGT135 full-length antibody and antibody variants were produced in FreeStyle™ 293F cells (Invitrogen) by transfection of plasmids containing expression constructs for light chain and heavy chain and pAdVAntage™ Vector (Promega) using 293Fectin (Invitrogen). Supernatants were harvested 96 hours after transfection. Antibodies were purified using ProteinA Sepharose™ (GE Healthcare).

Expression and Purification of PGT 135 and 17b Fab.

PGT 135 Fab was expressed using a baculovirus system with SF9 cells as described previously in Pejchal, R. et al. Science 334, 1097-1103 (2011). PGT 135 was purified from the cell supernatant first by anti-human lambda affinity chromatography followed by cation exchange chromatography as previously described. Typically, two peaks are observed from the cation exchange chromatography, one containing aggregated and the other containing monomeric Fab. Therefore, size exclusion chromatography (SEC) was used to isolate the pure monomeric Fab using Superdex 200® (GE Healthcare). Fab 17b was obtained from digesting IgG 17b with papain using a previously described protocol from Calarese, D. A. et al. Science 300, 2065-2071 (2003).

Expression and Purification of JRFL Gp120 Core.

A JRFL gp120 core containing a short (mini) V3 region (residues 305-320 deleted and replaced by a proline residue as described in Pejchal, R. et al. Science 334, 1097-1103 (2011)) was cloned into a phCMV3 vector with an IgK secretion signal. This plasmid was used to transfect HEK 293S GnT1−/− (293S) cells using 293Fectin (Invitrogen) under serum free conditions. The protein was purified first through a *Galanthus nivalis* lectin column, followed by SEC with Superdex 200™ (GE Healthcare).

Expression and Purification of BG505 SOSIP.

664 trimer. The HIV-1 clade A BG505 Env sequence and the construction of SOSIP.664 trimers (Sanders, R. W. et al. J. Virol. 76, 8875-8889 (2002)) using the Env sequence of BG505.W6M.ENV.C2 (GenBank Accession ABA61516/DQ208458) designed with a T332N mutation$_{28}$ is described in Julien, J. P. et al. Proc. Natl. Acad. Sci. U.S.A., 2013. The BG505 SOSIP.664 trimer was expressed and purified as previously described in Pejchal. R. et al. Science 334, 1097-1103 (2011). Briefly, following expression in 293S cells, the secreted BG505 trimer was harvested from the supernatant. The BG505 SOSIP.664 trimer was purified using a 2G12-coupled affinity matrix followed by passage through a sizing column.

Formation of Protein Complexes and Partial Deglycosylation.

Many combinations of ligandgp120 complexes, with and without deglycosylation, were tested in crystal trials. Generally, complexes were formed by combining gp120:ligands in a 1:1.2 molar ratio before being purified by SEC. To decrease heterogeneity, deglycosylation was carried out with endoglycosidase H (Roche) in 200 mM NaCl, 50 mM NaOAc pH 5.7 for 15 minutes at 37° C. on preformed gp120-PGT 135 binary complexes. Deglycosylation was performed on postcomplexed as opposed to unliganded gp120 because fully deglycosylated gp120 does not bind PGT 135. As removal of glycans did not result in crystals of the Fab 135-gp120 binary complex, non-competing ligands, Fab17b and CD4, were added to the crystallization screens.

Crystallization and Data Collection.

Purified protein samples were concentrated to 8-12 mg/ml and passed through a 0.22 un filter before being screened for crystallization using the IAVI-JCSG-TSRI CrystalMation robot (Rigaku). 384 crystallization conditions (JCSG Core Suite) were screened at 20° C. with drops consisting of 100 nl of protein and 100 nl of crystallization reagent. Additionally, custom crystal optimization screens were used with the Oryx8 Crystallization robot (Douglas Instruments). Optimization screens were made using an Alchemist instrument (Rigaku). Unliganded PGT 135 Fab produced large crystals with dimensions 0.3×0.4 mm when grown over a period of 28 days at 20° C. in a crystallization reagent consisting of 20% (w/v) PEG 8000, 0.1 M CHES, pH 9.5. Crystals were harvested and cryoprotected by a brief immersion in 70% well buffer, 30% glycerol, followed by immediate flash-cooling in liquid nitrogen. Data were collected at APS beamline 231D-B. The crystal diffracted to a resolution of 1.75 Å with an overall $R_{sym}$ of 6.0% and an overall completeness of 96.1%. Data were processed with HKL-2000 (Otwinowski, Z. & Minor, W. Methods Enzymol. 276, 307-326, (1997)). The data were indexed, integrated and scaled in orthorhombic space group $P2_12_12$ with unit cell parameters: a=85.9 Å, b=138.2 Å, c=42.3 Å. Quaternary complexes of PGT 135 were shown by SEC and SDS PAGE to contain PGT 135 Fab, 17b Fab, soluble CD4 and partially deglycosylated gp120 core. Fractions of the SEC elution peak were collected, concentrated and screened individually and only the center of the main peak yielded thin, overlapping plate crystals with dimensions of 0.45×0.05 mm in a crystallization reagent consisting of 20% PEG 2000, 0.1 M Tris pH 7.0 (JCSG CoreSuite I Well C07) using Applicants' automated CrystalMation robotic system (Rigaku). An optimization screen was made around this condition and large single crystals were obtained from 16% w/v PEG MME 2000, Tris pH 7.87 using the Oryx8 Crystallization robot. Data were collected at the ALS beamline 5.0.2, and were processed and scaled with HKL-2000 (Otwinowski, Z. & Minor, W. Methods Enzymol. 276, 307-326, (1997)). The crystal diffracted to 3.1 Å resolution with an overall $R_{sym}$ of 6.3% and an overall completeness of 99.7%. The data were indexed, integrated and scaled in monoclinic space group C2 with unit cell parameters: a=218.4 Å, b=92.2 Å, c=88.2 Å, and ©=104.8°.

Structure Determination and Refinement.

The unliganded PGT 135 structure was determined by the molecular replacement method using Phaser with an unrelated Fab structure (PDB ID: 3KYM) as an initial model. For the quaternary complex, multiple components were used for phasing: 17b Fab (PDB ID: 2NXY), soluble CD4 (PDB ID: 2NXY), gp120 core (PDB ID: 2NXY) and high-resolution unliganded PGT 135 Fab as determined in this present study. Model building was carried out using Coot-0.6.2 and refinement was implemented with the Phenix program (Adams, P. D. et al. Acta Crystallogr. Sect. D. Biol. Crystallogr. 66, 213-221 (2010)). This antibody features a rare 5 amino-acid insertion in the CDR H1 loop. The Kabat numbering system (Wu, T. T. & Kabat, E. A. J. Exp. Med. 132, 211-250 (1970)), which was developed long before there was much structural information on antibodies, only allows for insertions after residue 35. Thus, while the coordinates have been numbered with a 7 amino-acid insertion (35A-35G) at position 35, the five residues that actually form the structural insertion are at positions 33-35B. Because of the lower resolution for the complex structure, the higher resolution structure for PGT 135, as well as the previously published structure of gp120-17b-CD4 complex (PDB 2NXY), was used to generate constraints during the refinement. Final R.sub.cryst and R.sub.free values for the unliganded structure are 20.7% and 24.5%, and for the complex structure are 23.9% and 28.6%. Energy minimized rotamers of high mannose glycan models were obtained from glycam.ccrc.uga.edu/glylib and used as initial models during refinement. Glycan nomenclature and geometry were monitored throughout the refinement with the PDB CArbohydrate REsidue check (PDBCARE) online tool (www.glvcosciences.de) (Lutteke, T. & von der Lieth, C. W. BMC Bioinformatics 5, 69 (2004)) and compared against optimal torsion angles derived from curated structures of glycans (Petrescu, A. J. et al. Glycobiology 9, 343-352 (1999)). Buried molecular surface areas were analyzed with the Molecular Surface Package (Connolly, M. L., J. Mol. Graph. 11, 139-141, (1993)) using a 1.7.ANG. probe radius and standard van der Waals radii, and van der Waals contacts and hydrogen bonds were evaluated with CONTACSYM (Sheriff, S. et al., J. Mol. Biol. 197, 273-296 (1987), Sheriff, S. et al., Proc. Natl. Acad. Sci. U.S.A. 84, 8075-8079 (1987)) and HBPLUS (McDonald, I. K. & Thornton, J. M., J. Mol. Biol. 238, 777-793 (1994)). Surface potential and electrostatics were calculated using APBS (Baker, N. A. et al., Proc. Natl. Acad. Sci. U.S.A. 98, 10037-10041 (2001)) and all structural visualizations were generated with PyMOL (The PyMOL Molecular Graphics System, Version 1.2r3pre, Schrodinger, LLC.). For the Fabs, the residues were renumbered according to the Kabat scheme (Martin, A. C., Proteins 25, 130-133 (1996)) and gp120 is numbered following the Hxbc scheme (Ratner, L. et al., AIDS Res. Hum. Retroviruses 3, 57-69 (1987)).

Germline Model.

The predicted germline sequence was obtained from Calarese, D. A. et al. Science 300, 2065-2071 (2003), a previously published study of the PGT antibodies. The structure of unliganded PGT 135 was then modified to match the sequence of the germline in Coot with no further modifications as a rough schematic model for the germline antibody.

SDS-PAGE.

Protein preparations and complexes were analyzed routinely with SDS-PAGE. All gels used were 4-20% gradient MINI-Protean TGX gels (BioRad) that were stained either with Coomasie blue or Silverquest (Invitrogen). Western staining was performed using CA13 (Reagent number ARP3119), a mouse monoclonal antibody that recognizes the C1 region of gp120, as the primary antibody, and Immunopure Goat anti-Mouse IgG, (H+L), Peroxidase Conjugated (ThermoScientific) as the secondary antibody.

Isothermal Titration Calorimetry.

Isothermal titration calorimetry (ITC) binding experiments were performed using a MicroCal iTC200 instrument (GE). All proteins were extensively dialyzed against a buffer containing 20 mM Tris, 150 mM NaCl, pH 8.0 before conducting the titrations. Subsequently, protein concentrations were adjusted and confirmed by using calculated extinction coefficients and absorbance at 280 nm. In the syringe, the ligand was PGT135 Fab, 17b Fab, or soluble CD4, at concentrations ranging between 50-100 µM. The gp120mV3 monomer was in the cell at a concentration of 5-10 µM. Two-protein binding experiments were performed with the following parameters: cell thermostatting at 25° C. 16 injections of 2.5 µl each, injection interval of 180 s, injection duration of 5 s, and reference power of 5 µcals. Three protein binding experiments by ITC were performed by using the sample from the first two protein binding experiment in the cell and subsequently adding PGT 135 Fab, 17b Fab, or soluble CD4 as a third component in the three-protein binding titration. To accurately determine thermodynamic parameters, the concentration of the two-protein complex was re-calculated based on the dilution from the first experiment (approximately ~88% of the initial concentration). To derive the affinity constants ($K_A$), the molar reaction enthalpy ($\Delta H$) and the stoichiometry of binding (N), Origin 7.0 software was used by fitting the integrated titration peaks using a single-site binding model. The entropic change $\Delta S$ was calculated from the definition of change in Gibbs free energy: $\Delta G = RT \ln K_A = \Delta H - T\Delta S$ where R is the gas constant and T is the temperature. The results show that PGT 135 binding to gp120 does not contribute to the large conformational changes associated with receptor binding and may therefore rely on a neutralization mechanism distinct from CD4 binding site antibodies. Indeed, the overall proximity of the PGT 135 epitope to the V4 loop suggests that PGT 135 may neutralize the virus in a similar manner to an anti-FLAG antibody, which neutralizes recombinant virus containing a FLAG insert in the V4 loop (Yang, X. et al. J. Virol. 80, 11404-11408 (2006)) in a mechanism that relies on overall, nonspecific steric coverage of the virion instead of blocking functionally important surfaces such as the CD4 binding site.

Generation of Pseudovirus.

Pseudovirus was generated in HEK 293T or GnT1_-/-_ deficient 293S cells as described previously (Li, M. et al., J. Virol. 79, 10108-10125 (2005)). Glycosidase inhibitors were added at the time of transfection and were used alone or in combination at the following concentrations as described in Pejchal, R. et al. Science 334, 1097-1103 (2011): 25 { M kifunensine and 2 mM N-butyldeoxynojirimycin (NB-DNJ).

Neutralization Assays.

Neutralization activity of antibodies against pseudovirus in TZM-bl cells was determined as described previously (Li, M. et al. J. Virol. 79, 10108-10125 (2005)).

Antibody and Envelope Mutations.

Mutations in the PGT heavy chain, the HIV-1 envelope glycoprotein and the JRFLmV3 construct were introduced using QuikChange site-directed mutagenesis (Stratagene, La Jolla, Calif.). Mutations were verified by DNA sequencing (Eton Biosciences, La Jolla, Calif.).

JR-FLmV3 Glycan Mutant Binding ELISAs.

JR-FLmV3 glycan mutants were expressed in 293S cells. Glycoproteins from the crude supernatant were captured onto ELISA plates using mAb 17b. Serial dilutions of biotinylated PGT 135 were added and antibody binding was probed with alkaline phosphatase conjugated streptavidin (Jackson, diluted to 1:1000) and visualized with p-nitrophenol phosphate substrate (Sigma) at 405 nm.

gp120 Binding ELISAs.

Recombinant gp120 (250 ng) was immobilised directly onto flat bottom microtitre plates (Costar type 3690, Corning Inc.) at 4° C. overnight. Antibody binding was determined as described above.

High Density High-Mannose Array Printing.

$Man_7GlcNAc_2$-Gly, $Man_5GlcNAc_2$-Gly, and $Man_9$ $GlcNAc_2Gly$ were printed in replicates of six onto NHS-activated glass slides (from ADA Technologies, Inc) at a concentration of 100 ∫ M as previously described in Pejchal, R. et al. Science 334, 1097-1103 (2011) using a 27 Micro-GridII contact microarray printing robot. Printing efficiency was determined by measuring ConA binding.

Binding of Antibodies to High-Density High-Mannose Array.

Binding of PGT 135, PGT128 and 2G12 antibodies was measured at 30 ∫ g/mL and detected using goat-anti-human-Fc©-R-PE (15 ∫ g/mL, Jackson). Arrays were scanned for R-PE fluorescence on a ProScanArray HT (PerkinElmer) confocal slide scanner at 70PMT90LP. Signal intensities were collected using Imagene (BioDiscovery) image analysis software and calculated using the mean intensity of 4 replicate spotted samples.

Comparison of PGT135 Binding to Low Density (Schott Slides) and High Density (ADA Slides) Glycan Microarrays.

Glycan microarray analysis was initially carried out on high mannose glycans printed on NHS-activated slides obtained from Schott as in Pejchal, R. et al. Science 334, 1097-1103 (2011) but binding of PGT135 could not be detected. However, PGT135 glycan binding could be detected using the glycan array imprinted on higher density NHS-activated slides from ADA Technologies, Inc. As a comparison, Applicants show that binding of PGT 128 was greatly enhanced using the high density slides and strong binding on the array could still be detected at 1 g/mL.

Neoglycolipid (NGL) Microarray Analyses.

Analysis with neoglycolipid arrays was carried out as described previously in Pejchal, R. et al., Science 334, 1097-1103 (2011). PGT 135 was pre-complexed with biotinylated anti-human-IgG (Vector) at a 1:3 ratio, w/w, before applying onto the slides at a final concentration of 10 μg/ml. Binding was detected with Alexa-Fluor 647 labelled streptavidin (Molecular Probes) at 1 μg/ml. Included for comparison are the results with human 2G12 (Polymun Scientific) taken from an earlier experiment performed using a different version of microarrays (Dunlop, D. C. et al., Glycobiology 20, 812-823 (2010)), PGT128 and plant lectin ConA in Pejchal, R. et al., Science 334, 1097-1103 (2011).

Electron Microscopy and Image Processing.

PGT135 Fab in complex with the BG505 SOSIP.664 trimer used for electron microscopy studies were prepared as previously described in Pejchal, R. et al., Science 334, 1097-1103 (2011). Particles were picked automatically using DoG Picker and put into a particle stack using the Appion software package (Lander, G. C. et al., J. Struct. Biol. 166, 95-102 (2009), Voss, N. R. et al. J. Struct. Biol. 166, 205-213 (2009)). Initial reference-free 2D class averages were calculated using particles binned by 4 via the Xmipp Clustering 2D Alignment (Sorzano, C. O. et al., J. Struct. Biol. 171, 197-206 (2010)), and IMAGIC software programs (van Heel, M. et al., J. Struct. Biol. 116, 17-24 (1996)). Particles were further classified into reference-free 2D class averages and refined using Refine2d in the EMAN package (Ludtke, S. J. et al., J. Struct. Biol. 128, 82-97 (1999)). An ab initio 3D model was generated by refining the EM map of an unliganded BG505 SOSIP.664 trimer for 29 iterations, against the 2D class averages from the last Refine2d iterations. This initial model was used for the final 75 iteration 3D refinement against 8,831 raw particles binned by 2 using EMAN (Ludtke, S. J. et al., J. Struct. Biol. 128, 82-97 (1999)). C3 symmetry was imposed throughout the reconstruction process. The final 3D reconstruction has a resolution of 20 Å by an FSC cut-off at 0.5.

Fitting of Gp120/PGT135 Crystal Structure into the EM Density.

Due to the high B-values in the constant region of the PGT135 Fab, initial rigid body fitting of the crystal structure was done with only the gp120 and the variable region of the PGT135 Fab. This structure was manually fit into the EM density and refined using the UCSF Chimera 'Fit in Map' function. The gp120/PGT135 crystal structure with the full Fab was then aligned to the fitted structure using the 'Match' command. The fitting of trimeric gp120/PGT135 crystal structure was further refined using the 'Fit in Map' function resulting in a final correlation value of 0.91.

Analysis of Fab Dynamics.

Candidate top views of PGT135/trimer and PGT 128/trimer particles were subjected to two rounds of reference-free 2 D class averaging using Xmipp Clustering 2D Alignment (Sorzano, C. O. et al. J. Struct. Biol. 171, 197-206 (2010)). 2D class averages with the clearest top views of gp20 were selected from the PGT135 and PGT128 alignments to be used as a template for the respective datasets. A circular mask was applied to conceal the Fabs, and the remaining particles from the second round of reference free 2D alignments were re-classified via IMAGIC Multi Reference Alignment, and IMAGIC Multivariate Statistical Analysis programs (van Heel, M. et al., J. Struct. Biol. 116, 17-24 (1996)). The 164 and 160 aligned particles for PGT135 and PGT128 respectively, from best the 2D class average for each were selected for 2D principal component analysis (PCA). The PCA analysis was carried out through the Sparx package (Hohn, M. et al., J. Struct. Biol. 157, 47-55 (2007)) using the first 5 eigenvectors. UCSF Chimera was used to create morph movies between the average image and each of the eigenvectors to visualize the flexibility.

Example 3

Cleaved, Soluble HIV-1 Env Trimers Presenting Multiple bNAb Epitopes

Soluble Env trimers that mimic the native viral spike may induce broadly neutralizing antibodies (bNabs). One guide to spike-mimetic strategies is how well multiple bNAb epitopes are presented and, conversely, irrelevant epitopes occluded. A true spike-mimetic should also be cleaved between gp120 and gp41, as this event modifies trimer antigenicity.

Applicants deleted the MPER from cleaved, stabilized SOSIP gp140 trimers, to reduce aggregation and facilitate structural studies. Screening multiple Env proteins for stability, expression levels and bNAb reactivity focused attention on the BG505 (clade A) sequence. Mutagenesis restored additional bNAb epitopes. The BG505 SOSIP.664 gp140 was expressed and the trimer fraction purified. Antigenicity was determined using SPR, ELISA (His-tagged variants), and ITC and EM studies, as well as neutralization assays were performed.

The BG505 SOSIP.664 trimers were highly stable over a multi-week period at 4° C. Their melting temperature, assessed by DSC, was now uniform, and higher than for previous SOSIP designs. The trimers bound the following bNabs efficiently in ELISA and/or SPR assays: CD4bs: CD4-IgG2, VRC01, VRC03, VRC06, HJ16, 3BNC60, 3BNC117, 12A12, 1NC9, NIH45-46, 8ANC195, PGV04; CD4i (+sCD4): X5, 412d, 17b; V1/V2 quaternary: PG9, PG16, PGT145; Glycan-OD sites: 2G12, PGT135, PGT136; V3-N332 site: PGT121, PGT122, PGT123, PGT125, PGT126, PGT128, PGT130. In contrast, non-neutralizing MAbs generally reacted poorly, including: CD4bs: F91, F105, 15e, b6; CD4i: X5, 412d, 17b; gp41 cluster I/II: 7B2, 98-6, D50. Also, CD4bs NAb b12 bound the trimers weakly; b12 does not neutralize HIV-1 BG505 despite reacting well with monomeric gp120. In contrast, the weakly neutralizing V3 MAb 19b bound the trimers well, and there was some reactivity with the gp41 cluster I MAb F240. Negative stain EM reconstructions showed that BG505 SOSIP.664 trimers have a similar morphology to previous cryo-EM images of viral Env, and allowed the bPGT128, PGT135, PGT 122, 2G12, PG9 and PGV04 epitopes to be characterized on trimer-bNAb complexes.

The array of bNAb epitopes and the absence of most non-neutralizing epitopes together imply the BG505 SOSIP.664 trimers are credible mimics of native Env spikes. Their stability and antigenicity renders them suitable for structural studies (high resolution cryo-EM, x-ray crystallography), as well as for evaluation as immunogens in macaques and, perhaps, eventually humans. Further, the BG505SOSIP.664 protein represents a substrate for further improvements in immunogen design that improve the mimicry of the native envelope protein found on the HIV particle. These improvements would likely consist of changes in the sequence of the BG505SOSIP.664 sequence to further improve binding of broadly neutralizing antibodies while limiting the binding of non-neutralizing antibodies.

Example 4

HIV-1 Isolate BG505.W6M.ENV.C2 from Kenya Envelope Glycoprotein (Env) Gene, Complete Cds (GenBank: DQ208458.1)

```
LOCUS       DQ208458 2583 bp DNA linear VRL 3 Jan. 2006
DEFINITION  HIV-1 isolate EG505.W6M.ENV.C2 from Kenya envelope glycoprotein
            (env) gene, complete cds.
ACCESSION   DQ208458
VERSION     DQ208458.1 GI: 77025198
KEYWORDS    .
SOURCE      Human immunodeficiency virus 1 (HIV-1)
ORGANISM    Human immunodeficiency virus 1
            Viruses; Retro-transcribing viruses; Retroviridae;
            Orthoretrovirinae; Lentivirus; Primate lentivirus group.
REFERENCE   1 (bases 1 to 2583)
AUTHORS     Wu, X., Parast, A. B., Richardson, B. A., Nduati, R., John-Stewart,
            G., Mbori-Ngacha, D., Rainwater, S. M. and Overbaugh, J.
TITLE       Neutralization escape variants of human immunodeficiency virus
            type 1 are transmitted from mother to infant
JOURNAL     J. Virol. 80 (2), 835-844 (2006)
PUBMED      16378685
REMARK      Erratum: [J Virol. 2006 March; 80(5): 2585]
REFERENCE   2 (bases 1 to 2583)
AUTHORS     Wu, X., Parast, A. B., Richardson, B. A., Nduati, R., John-Stewart,
            G., Mbori-Ngacha, D., Rainwater, S. M. J. and Overbaugh, J.
TITLE       Direct Submission
JOURNAL     Submitted (19 Sep. 2005) Human Biology, Fred. Hutchinson Cancer
            Research Center, 1100 Fairview Ave N., Seattle, WA 98109, USA
FEATURES    Location/Qualifiers
source      1 . . . 2583
            /organism = "Human immunodeficiency virus 1"
            /proviral
            /mol_type = "genomic DNA"
            /isolate = "BG505.W6M.ENV.C2"
            /isolation_source = "infant"
            /db_xref = "taxon: 11676"
            /country = "Kenya"
            /note = "subtype: A"
gene        1 . . . 2583
            /gene = "env"
CDS         1 . . . 2583
            /gene = "env"
            /codon_start = 1
            /product = "envelope glycoprotein"
            /protein_id = "ABA61516.1"
            /db_xref = "GI: 77025199"
```

(SEQ ID NO: 5)

/translation = "MRVMGIQRNCQHLFRWGTMILGMIIICSAAENLWVTVYYGVPVW

KDAETTLFCASDAKAYETEKHNVWATHACVPTDPNPQEIHLENVTEEFNMWKNNMVEQ

MHTDIISLWDQSLKPCVKLTPLCVTLQCTNVTNNITDDMRGELKNCSFNMTTELRDKK

QKVYSLFYRLDVVQINENQGNRSNNSNKEYRLINCNTSAITQACPKVSFEPIPIHYCA

PAGFAILKCKDKKFNGTGPCPSVSTVQCTHGIKPVVSTQLLLNGSLAEEEVMIRSENI

TNNAKNILVQFNTPVQINCTRPNNNTRKSIRIGPGQAFYATGDIIGDIRQAHCTVSKA

```
TWNETLGKVVKQLRKHFGNNTIIRFANSSGGDLEVTTHSFNCGGEFFYCNTSGLFNST
WISNTSVQGSNSTGSNDSITLPCRIKQIINMWQRIGQAMYAPPIQGVIRCVSNITGLI
LTRDGGSTNSTTETFRPGGGDMRDNWRSELYKYKVVKIEPLGVAPTRAKRRVVGREKR
AVGIGAVELGFLGAAGSTMGAASMTLTVQARNLLSGIVQQQSNLLRAIEAQQHLLKLT
VWGIKQLQARVLAVERYLRDQQLLGIWGCSGKLICTTNVPWNSSWSNRNLSEIWDNMT
WLQWDKEISNYTQIIYGLLEESQNQQEKNEQDLLALDKWASLWNWFDISNWLWYIKIF
IMIVGGLIGLRIVFAVLSVIHRVRQGYSPLSFQTHTPNPRGLDRPERIEEEDGEQDRG
RSTRLVSGFLALAWDDLRSLCLFCYHRLRDFILIAARIVELLGHSSLKGLRLGWEGLK
YLWNLLAYWGRELKISAINLFDTIAIAVAEWTDRVIEIGQRLCRAFLHIPRRIRQGLE
RALL"
ORIGIN
```
(SEQ ID NO: 6)

```
   1 atgagagtga tggggataca gaggaattgt cagcacttat tcagatgggg aactatgatc
  61 ttggggatga taataatctg tagtgcagca gaaaacttgt gggtcactgt ctactatggg
 121 gtacctgtgt ggaaagacgc agagaccacc ttattttgtg catcagatgc taaagcatat
 181 gagacagaaa agcataatgt ctgggctaca catgcctgtg tacccacaga ccccaaccca
 241 caagaaatac atttggaaaa tgtgactgaa gagtttaaca tgtggaaaaa taacatggta
 301 gagcagatgc atacagatat catcagtcta tgggaccaaa gcctaaagcc atgtgtaaag
 361 ttaacccctc tctgcgttac tctacagtgt accaatgtca ccaataatat cactgatgac
 421 atgaggggag aattaaaaaa ctgctctttc aatatgacca cagagctaag ggataagaaa
 481 cagaaggttt attcactttt ttatagacta gatgtagtac aaattaacga gaatcaaggt
 541 aataggagta ataatagtaa caaggagtat agattaataa attgtaatac ctcagccatt
 601 acacaggctt gtccaaaggt atcctttgag ccaattccca tacattattg tgccccagct
 661 ggttttgcga tcctaaagtg taaggataag aagttcaatg gaacagggcc atgcccaagt
 721 gtcagcacag tacaatgcac acatggaatc aagccagtag tatcaactca actgctgtta
 781 aatggcagtc tagcagaaga gaggtaatg attagatctg aaaatatcac aaacaatgcc
 841 aaaaacatac tagtacaatt aacacgcctg tgcaaattaa ttgtaccag acctaacaac
 901 aatacaagga aaagtatacg tataggacca ggacaagcat tctatgcaac aggggacata
 961 ataggggata agacaagc acattgtact gtcagtaaag caacatggaa tgaaactttg
1021 ggaaagtgg tcaaacaatt aagaaaacac tttgggaaca cacaataat aagatttgct
1081 aattcctcag gagggatct agaagtcaca acacatagtt ttaattgtgg aggagaattt
1141 ttctattgta acacatcagg cctgttcaat agcacttgga ttagcaatac cagcgtgcag
1201 gggtcaaata gcacggggtc aaatgacagt ataactctcc catgcagaat aaagcaaatt
1261 ataaatatgt ggcagagaat aggacaagca atgtatgccc ctcccatcca aggagtaata
1321 agatgtgtat caaacattac agggctaata ttaacaagag atggtgggag tactaatagt
1381 acaactgaaa ccttcagacc tggaggagga gatatgaggg acaattggag aagtgaatta
1441 tataagtata agtagtaaa aattgaacca ctaggagtag cacccaccag ggcaaagaga
1501 agagtggtgg ggagagaaaa aagagcagtt gaataggag ctgtcttcct tgggttctta
1561 ggagcagcag gaagcactat gggcgcggcg tcaatgacgc tgacggtaca ggccagaaat
1621 ttattatctg gcatagtgca acagcaaagc aatttgctga gggctataga ggctcaacaa
```

```
1681    catctgttga aactcacggt ctggggcatt aaacagctcc aggcaagggt cctggctgtg 1741    gaaagatacc taagggatca acagcttcta ggaatttggg gctgctctgg aaaactcatc 1801    tgcaccacta atgtgccctg gaactctagt tggagtaata gaaacctgag tgagatatgg 1861    gacaacatga cctggctgca atgggataaa gaaattagca attacacaca gataatatat 1921    gggctacttg aagaatcgca aaaccagcag gaaaagaatg aacaagactt attggcattg 1981    gataagtggg caagtctgtg gaattggttt gacatatcaa actggctgtg gtatataaaa 2041    atatttataa tgatagtagg aggcttaata ggattaagaa tagtttttgc tgtgctttct 2101    gtaatacata gagttaggca gggatactca cctttgtcgt ttcagaccca taccccaaac 2161    ccaaggggac tcgacaggcc cgaaagaatc gaagaagaag atggagagca agacagaggc 2221    agatcgacgc gattagtgag cggattctta gctcttgcct gggacgatct gaggagcctg 2281    tgcctcttct gctaccaccg attgagagac ttcatcttga ttgcagcgag gattgtggaa 2341    cttctgggac acagcagtct caaggggttg agactggggt gggaaggcct caagtatctg 2401    tggaatctcc tggcatattg gggtcgggaa ctaaaaatta gtgctattaa tttgtttgat 2461    accatagcaa tagcagtagc tgagtggaca gatagggtta tagaaatagg acaaagactt 2521    tgtagagctt ttctccacat acctagaaga atcagacagg gcctcgaaag ggctttgcta 2581    taa
        ***
```

Example 5

A Next-Generation Cleaved, Soluble HIV-1 Env Trimer, BG505 SOSIP.664 Gp140, Expresses Multiple Epitopes for Broadly Neutralizing but not Non-Neutralizing Antibodies (Sanders et al., PLOS Pathogens, 9:1-20, 2013)

A desirable but as yet unachieved property of a human immunodeficiency virus type 1 (HIV-1) vaccine candidate is the ability to induce broadly neutralizing antibodies (bNabs). One approach to the problem is to create trimeric mimics of the native envelope glycoprotein (Env) spike that expose as many bNAb epitopes as possible, while occluding those for nonneutralizing antibodies (non-Nabs). Here, Applicants describe the design and properties of soluble, cleaved SOSIP.664 gp140 trimers based on the subtype A transmitted/founder strain, BG505. These trimers are highly stable, more so even than the corresponding gp120 monomer, as judged by differential scanning calorimetry. They are also homogenous and closely resemble native virus spikes when visualized by negative stain electron microscopy (EM). Applicants used several techniques, including ELISA and surface plasmon resonance (SPR), to determine the relationship between the ability of monoclonal antibodies (MAbs) to bind the soluble trimers and neutralize the corresponding virus. In general, the concordance was excellent, in that virtually all bNabs against multiple neutralizing epitopes on HIV-1 Env were highly reactive with the BG505 SOSIP.664 gp140 trimers, including quaternary epitopes (CH01, PG9, PG16 and PGT145). Conversely, non-Nabs to the CD4-binding site, CD4-induced epitopes or gp41$_{ECTO}$ did not react with the trimers, even when their epitopes were present on simpler forms of Env (e.g. gp120 monomers or dissociated gp41 subunits). Three non-neutralizing MAbs to V3 epitopes did, however, react strongly with the trimers but only by ELISA, and not at all by SPR and to only a limited extent by EM. These new soluble trimers are useful for structural studies and are being assessed for their performance as immunogens.

A protective HIV-1 vaccine is badly needed, but no candidate has yet provided an adequate level of protection against infection. Most existing vaccines provide immune protection by inducing neutralizing antibodies, also a goal of many HIV-1 immunogen design projects. The trimeric envelope protein complex on the HIV-1 surface is the only relevant target for neutralizing antibodies, and is the basis for most strategies aimed at their induction. However, making a soluble, recombinant envelope protein complex that adequately mimics the structure present on the virus has been challenging. Here, Applicants describe a newly designed and engineered Env protein that has the appropriate properties. This protein, termed BG505 SOSIP.664 gp140, binds most of the known neutralizing antibodies but generally does not bind antibodies that lack neutralization activity. Its appearance in negative stain electron micrographs also resembles native envelope complexes.

One approach to creating a preventative vaccine against human immunodeficiency virus type 1 (HIV-1) infection is to design an immunogen capable of inducing adequate titers of broadly neutralizing antibodies (bNabs) [Burton D F, et al., (2004) Nat Immunol 5:233-236]. Nabs prevent HIV-1 from infecting target cells by binding to the viral envelope glycoprotein (Env) complex, a trimeric structure comprising three gp120 and three gp41 subunits held together by meta-stable, non-covalent interactions. Induction of Nabs therefore requires the use of an Env-based immunogen. Of these, the most widely tested have been monomeric gp120 subunits, which failed to induce bNabs and did not prevent infection [Flynn N M, et al. (2005) J Infect Dis 191: 654-665, Gilbert P B, et al. (2005) J Infect Dis 191: 666-677, Pitisuttithum P, et al. (2006) J Infect Dis 194: 1661-1671]. A better mimic of the native, trimeric Env spike may be a superior immunogen for bNAb induction [Burton D F et al., (2004) Nat Immunol 5:233-236, Binley J M, et al. (2000) J Virol 74: 627-643, Sanders R W, et al. (2002) J Virol 76: 8875-8889, Sanders R W (2011) Expert Rev Vaccines 10: 1117-1120, Forsell M N, et al. (2009) Curr Opin HIV AIDS 4: 380-387]. However, creating a true mimic of an Env trimeric spike has proven challenging. Most approaches to making Env trimers involve truncating the gp41 component to remove the hydrophobic transmembrane region, yielding soluble gp140 proteins containing three gp120 and gp41 ectodomain (gp41ECTO) subunits [Earl P L, et al. (1994) J Virol 68: 3015-3026]. Soluble gp140 trimers are highly unstable, perhaps because the inherently labile nature of the Env complex is exacerbated by the removal of the transmembrane region. Accordingly, gp140 trimers rapidly disintegrate into individual gp120 and gp41ECTO subunits unless preventative steps are taken. Two different methods have been used to stabilize gp140 trimers. The most widely used involves eliminating the cleavage site between gp120 and $gp41_{ECTO}$ and, in some cases, adding an additional trimer-stabilizing motif to the C-terminus of $gp41_{ECTO}$, with or without other modifications [Earl P L, et al. (1994) J Virol 68: 3015-3026, Earl P L, et al. (2001) J Virol 75: 645-653, Gao F, et al. (2005) J Virol 79: 1154-1163, Kovacs J M et al. (2012) Proc Natl Acad Sci USA 109: 12111-12116, Nkolola J P, et al. (2011) J Virol 84: 3270-3279, Spearman P, et al. (2011) J Infect Dis 203: 1165-1173, Srivastava I K, et al. (2003) J Virol 77: 11244-11259, Yang X, et al. (2000) J Virol 74: 5716-5725, Yang X, et al. (2000) J Virol 74: 4746-4754, Yang X, et al. (2002) J Virol 76:4634-4642, Yang X, et al. (2001) J Virol 75: 1165-1171]. Trimer-forming constructs such as these are generally referred to as uncleaved gp140s (gp140UNC). Applicants' alternative approach involves making fully cleaved trimers but stabilizing them by introducing specific mutations, namely a disulfide bond to covalently link gp120 to $gp41_{ECTO}$ and an Ile/Pro change at residue 559 to strengthen interactions between the gp41 subunits [Binley J M, et al. (2000) J Virol 74: 627-643, Sanders R W, et al. (2002) J Virol 76: 8875-8889]. The resulting trimers are designated SOSIP gp140s. Cleaved and uncleaved trimers are known to be antigenically distinct, in that the latter consistently express the epitopes for various non-neutralizing antibodies (non-Nabs) that are occluded on cleaved trimers, irrespective of whether the Env proteins are soluble or expressed on the cell surface [Binley J M, et al. (2000) J Virol 74: 627-643, Dey A K. et al. (2009) Virology 385: 275-281, Pancera M, Wyatt R (2005) Virology 332: 145-156, Si Z, et al. (2003) AIDS Res Hum Retroviruses 19: 217-226].

Here, Applicants describe a new version of SOSIP gp140 trimers based on the subtype A transmitted/founder (T/F) virus sequence BG505, modified to introduce some bNAb epitopes. The membrane-proximal external region (MPER) was also deleted to improve trimer solubility and reduce aggregate formation [Khayat R, et al. (2013) J Virol 87:9865-72, Klasse P J, et al. (2013) J Virol 87:9873-85]. The BG505 SOSIP.664 gp140 trimers can be produced efficiently and are homogenous and stable. Applicants show here that they express the epitopes for multiple bNabs, but very few for non-neutralizing antibodies (non-Nabs), when analyzed by ELISA, surface plasmon resonance (SPR), isothermal calorimetry (ITC) and negative stain electron microscopy (EM). Their antigenic properties mimic those of the native Env complexes on the BG505 virus, as judged by the outcome of virusneutralization assays, and they structurally resemble the native complexes when viewed by negative stain EM. These new trimers are the basis for a range of studies of Env structure, alone and as complexes with bNabs. They have already been used to characterize the epitopes for several bNabs, including PG9, PGT 122 and PGT135 [Julien J P, et al. (2013) PLoS Pathog 9: e1003342, Kong L, et al. (2013) Nat Struct Mol Biol 20: 796-803, Julien J P, et al. (2013) Proc Natl Acad Sci USA 110: 4351-4356]. The BG505 SOSIP.664 trimers may also be useful as immunogens.

Design of BG505 SOSIP.664 Gp140 Trimers.

Here, Applicants describe the production and properties of stable and homogenous SOSIP gp140 trimers that express multiple bNAb epitopes, based on the BG505 env gene. HIV-1 BG505, a subtype A T/F virus, was isolated from an infant 6-weeks after birth in a mother-infant transmission study [Wu X, et al. (2006) J Virol 80: 835-844]. The env sequence was then selected in silico based on its similarity to sequences in the individual from whom the bNabs PG9 and PG16 were isolated [Hoffenberg S, et al. (2013) J Virol 87: 5372-5383]. The monomeric BG505 gp120 protein has the unusual property of binding PG9, although it does not bind efficiently to PG16, and not at all to PGT 145; the latter two bNabs appear to be more dependent on the quaternary structure of the Env trimer [Julien J P, et al. (2013) Proc Natl Acad Sci USA 110: 4351-4356, Hoffenberg S, et al. (2013) J Virol 87: 5372-5383].

Figure 15A:
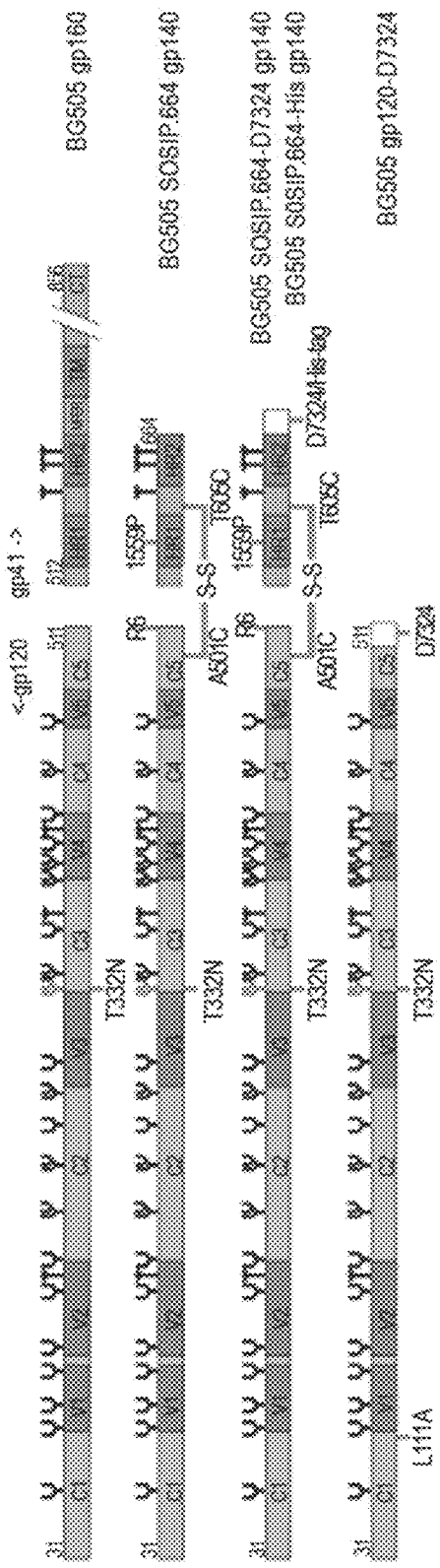

Various sequence modifications (see Methods and legend to FIG. 15A) were made to the wild type BG505 sequence to create the protein designated BG505 SOSIP.664 gp140 (FIG. 15A). These alterations included the SOS and I559P changes required for trimer stability, the deletion of the MPER to improve homogeneity and solubility, and the introduction of a T332N substitution to create the epitopes for several bNabs that depend on the presence of this glycan [Binley J M, et al. (2000) J Virol 74: 627-643, Sanders R W, et al. (2002) J Virol 76: 8875-8889, Klasse P J, et al. (2013) J Virol 87(17): 9873-85, Walker L M, et al. (2011) Nature 477: 466-470, Binley J M, et al. (2002) J Virol 76: 2606-2616]. Applicants also generated two variants with either a D7324-epitope tag or a His-tag located immediately downstream from residue 664, to permit the oriented immobilization of trimers on ELISA plates or SPR chips [Bontjer I, et al. (2010) J Biol Chem 285: 36456-36470, Eggink D, et al. (2010) Virology 401: 236-247, Hoorelbeke B, et al. (2013) FEBS Lett 587: 860-866]. These proteins are designated SOSIP.664-D7324 gp140 and SOSIP. 664-His gp140, respectively (FIG. 15A). For comparison, Applicants expressed and purified a monomeric BG505 gp120 protein containing the same T332N knock-in substitution made to the SOSIP.664 gp140 trimer, as well as the D7324 epitope introduced into the C5 region (see Methods) (FIG. 15A). The BG505 WT.664-His gp140 construct serves as a source of $gp41_{ECTO}$-His for ELISA studies (see Methods).

Biochemical and Biophysical Characterization of BG505 SOSIP.664 Gp140 Trimers.

The BG505 SOSIP.664 construct was expressed transiently in HEK293T, or in some experiments CHO-K, cells together with co-transfected Furin to boost the level of cleavage [Binley J M, et al. (2000) J Virol 74: 627-643, Binley J M, et al. (2002) J Virol 76: 2606-2616]. The two cell substrates yielded trimers of similar quality and antigenicity. The secreted Env proteins were affinity-purified using the 2G12 bNAb, followed by SEC on a Superdex 200 26/60 column to isolate trimers (FIG. 15B). The SEC profile showed that a predominant, trimer-containing peak eluted at 144 ml, while a smaller peak at 164 ml contained SOSIP gp140 monomers. The SEC profile was confirmed by a BN-PAGE analysis followed by Coomassie Blue dye staining; trimers predominated and some gp140 monomers were present, but there were no appreciable amounts of dimers or higher m. wt. aggregates (FIG. 15D). An analytical Superose 6 column assessment of the SEC-purified BG505 SOSIP.664 gp140 trimers showed that they remained trimeric and neither aggregated nor dissociated into gp120 or SOSIP gp140 monomers (FIG. 15C). These results were confirmed by BN-PAGE (FIG. 15E). The lack of aggregates most likely reflects the beneficial effect of deleting the MPER to make the SOSIP.664 variant [Khayat R, et al. (2013) J Virol 87:9865-72, Klasse P J, et al. (2013) J Virol 87:9873-85]. A single gp140 band was seen on an SDS-PAGE gel performed under non-reducing conditions, with no evidence for the formation of aberrant inter-protomer disulfide-bonds (FIG. 15F). Coomassie blue- or silver-stained SDS-PAGE gels showed that the gp140 band was essentially fully converted (0.95%) to gp120 and $gp41_{ECTO}$ when a reducing agent was present, confirming that the trimers were cleaved efficiently (FIG. 15F,G). Western blotting with anti-gp120 and anti-gp41 MAbs yielded a similar conclusion (data not shown).

Applicants used differential scanning calorimetry (DSC) to assess the thermal stability of the purified, HEK293T cell-expressed BG505 SOSIP.664 gp140 trimers. The DSC profile showed one distinct unfolding peak with a thermal denaturation midpoint (Tm) of 68.1 C (FIG. 16A). This finding was similar to ones made previously using the same trimers, but produced in HEK293S cells defective for GlcNAc transferase I (GnT1) and, hence, bearing only oligomannose glycans [Julien J P, et al. (2013) Proc Natl Acad Sci USA 110: 4351-4356]. Of note is that the BG505 SOSIP.664 gp140 trimers are substantially more stable than the corresponding gp120 monomers, which unfold in two phases (Tm, 53.5 C and 63.4 C; FIG. 16B), and also than YU2 gp120 (Tm, 59.2 C [Brower E T, et al. (2010) Biochemistry 49: 2359-2367, Leavitt S A, et al. (2004) Curr Protein Pept Sci 5: 1-8]) or 92UG031 gp120 (Tm, 58.4 C [Brower E T, et al. (2010) Biochemistry 49: 2359-2367]). The BG505 SOSIP.664 trimers are also more stable than the corresponding trimers from KNH1144 (Tm of 51.3° C. for the first thermal transition [Julien J P, et al. (2013) Proc Natl Acad Sci USA 110: 4351-4356]), and than JR-FL SOSIP.R6 trimers ("R6" disclosed as SEQ ID NO: 2) (which dissociate at about 50° C. [Sanders R W, et al. (2002) J Virol 76: 8875-8889]). Applicants conclude that the BG505 SOSIP.664 gp140 trimers have high thermal stability.

The overall morphology of SEC-purified, BG505 SOSIP.664 gp140 trimers was studied by negative stain EM (FIG. 16C). A 3D reconstruction at 24 Å resolution showed that compact and homogeneous trimers were consistently present, as described previously for the same trimers produced in HEK293S cells [Julien J P, et al. (2013) Proc Natl Acad Sci USA 110: 4351-4356]. Applicants obtained similar results with the SOSIP.664-D7324 and SOSIP.664-His gp140 proteins, indicating that the C-terminal tags did not perturb the overall trimer structure (data not shown). Additional EM images of trimer-bNAb complexes are described below.

Neutralization of the Parental BG505.T332N Virus.

To study the antigenic properties of the BG505 SOSIP.664 gp140 trimers, Applicants first tested a large panel of MAbs for their capacity to neutralize the corresponding Env-pseudotyped virus in a TZM-bl cell-based neutralization assay. The epitope clusters recognized by the MAbs cover most of the surface of the Env trimer [van Gils M J, Sanders R W (2013) Virology 435: 46-56] except the MPER, which was truncated in the SOSIP.664 construct. Note that the test virus contains the T332N knock-in change to allow comparison with antigenicity data obtained using the BG505 SOSIP.664 gp140 trimers; this change may account for any discrepancies from data described elsewhere using the unmodified BG505 virus [Hoffenberg S, et al. (2013) J Virol 87: 5372-5383].

Most of the known bNabs neutralized the BG505.T332N virus efficiently (FIG. 17). This outcome was true of bNabs to the CD4bs (VRC01, VRC03, VRC06, VRC06b, PGV04, HJ16, 3BNC60, 3BNC117, 12A12, 45-46, 45-46W, 1NC9, 8ANC195, CH31, CH103, CH106 and also CD4-IgG2); the N332-glycan dependent V3 cluster (PGT121-123, PGT125-130); the N332-glycan dependent outer domain cluster (PGT135, PGT136, 2G12); 3BC315 and 3BC176; and the quaternary-dependent V1/V2 epitopes (CH01, PG9, PG16, PGT145). Neutralization by PGT136 was modest (IC50, 26.600 ng/ml). Note that the CD4bs MAb b12 did not neutralize BG505 ($IC_{50}$ 30,000 ng/ml; FIG. 17), implying that it is a non-NAb for this subtype A virus [Hoffenberg S, et al. (2013) J Virol 87: 5372-5383]. The Duke University Central Laboratory has classified BG505.T332N as a Tier 2 virus, based on the use of Env-pseudotyped viruses in the TZM-bl cell assay.

Several test MAbs did not neutralize BG505.T332N ($IC_{50}$>30,000 ng/ml), including b6, 15e, F91 and F105 to the CD4bs; 17b, 412d, X5 and A32 to CD4-induced epitopes; 447-52D, 39F, 19b and 14e to V3; F240 and 7B2 directed to gp41. Applicants confirmed that their epitopes were present on at least one form of BG505 Env protein (e.g., gp120 monomers or $gp41_{ECTO}$), showing that their inability to neutralize the virus was not due to a sequence-dependent lack of the epitope (data not shown, and see below). The CD4i MAbs 17b and 412d also did not neutralize the BG505.T332N virus when sCD4 was also present (data not shown). For the V3 MAbs 19b and 14e, Applicants also performed extended pre-incubation experiments (16 h) before adding the MAb-virus mixtures to the target cells. Even in this assay format, the two V3 MAbs had no measurable neutralization activity, indicating that they do not inactivate the Env spike (data not shown).

Antigenic Analysis of BG505 SOSIP.664 Gp140 Trimers by ELISA.

Applicants used several methods to quantify the binding of bNabs and non-Nabs to wild type or epitope-tagged versions of BG505 SOSIP.664 gp140 trimers and, in some cases, the cognate SOSIP gp140 monomers, gp120 monomers, or $gp41_{ECTO}$ proteins. First, Applicants immobilized 2G12 affinity- and SEC-purified SOSIP.664-D7324 trimers onto ELISA plates and monitored the binding of a large panel of MAbs (FIGS. 3-5). The immobilized trimers were recognized efficiently by all of the bNabs against the CD4bs, the N332-glycan dependent V3 cluster or the N332-glycan dependent outer domain cluster that neutralized the corresponding virus (see above). The 3BC315 and 3BC176 bNabs bind to an incompletely characterized, but probably glycan-independent, epitope that is induced, to an extent, by CD4 binding [Klein F, et al. (2012) J Exp Med 209: 1469-1479]. They do not bind to any soluble Env protein tested to date, including uncleaved soluble gp140 trimers [Klein F, et al. (2012) J Exp Med 209: 1469-1479]. However, both bNabs interacted efficiently in ELISA with the BG505 SOSIP.664-D7324 gp140 trimers, but not the corresponding gp120 monomers (FIG. 17, FIG. 18C, and data not shown).

The bNabs that recognize quaternary-preferring epitopes are particularly useful tools for gauging whether soluble Env trimers adopt an appropriate conformation. This bNab category includes CH01, PG9, PG16 and PGT145 against epitopes that appear to span the V1/V2 domains of two gp120s within a single trimer [Julien et al. (2013) Proc Natl Acad Sci USA 110: 4351-4356]. Although these bNabs can bind a small subset of monomeric gp120s or uncleaved trimeric gp140s, any such interactions tend to be rare and weak, particularly for PG16 and PGT145 [Kovacs J M, et al. (2012) Proc Natl Acad Sci USA 109: 12111-12116, Julien et al. (2013) Proc Natl Acad Sci USA 110: 4351-4356, Hoffenberg S, et al. (2013) J Virol 87: 5372-5383, Davenport T M, et al. (2011) J Virol 85: 7095-7107]. Here, Applicants show that CH01, PG9, PG16 and PGT145 all bound efficiently to the BG505 SOSIP.664 gp140 trimers in ELISA (FIG. 17, FIG. 18D). In contrast, only PG9 reacted well with monomeric BG505 gp120, while CHOI and PGT145 were completely non-reactive and PG16 bound weakly. Applicants have also found that PG16 and PGT145 do not bind to BG505 SOSIP.664 gp40 trimer mutants that lack the glycans attached to N156 or N160, or to wild-type trimers produced in HEK293T cells treated with the mannosidase inhibitor kifunensine (data not shown). These findings are consistent with the known involvement of hybrid or complex glycans at N156 or N160 in the PG16 and PGT145 epitopes [Walker L M, et al. (2011) Nature 477: 466-470, Walker L M, et al. (2009) Science 326: 285-289].

To further study the influence of trimerization on the PG9, PG16 and PGT145 epitopes, Applicants fractionated 2G12 affinity purified SOSIP.664-D7324 gp140 proteins by SEC and analyzed the column fractions by ELISA (FIG. 18E). Both PG16 and PGT145 bound almost exclusively to the trimer-containing fractions, whereas PG9 bound more strongly to the trimers, but also recognized the SOSIP.664-D7324 gp140 monomers. This reactivity pattern is broadly consistent with previous observations on BG505 gp120 monomers [Hoffenberg S. et al. (2013) J Virol 87: 5372-5383]. In contrast, the CD4bs non-Nab b6 bound preferentially to the SOSIP.664-D7324 gp140 monomers, although some binding to trimers was also seen (see below).

For HIV-1 to be neutralized, a NAb must bind to a sufficient number of the native, functional, trimeric spikes present on the virus surface [Klasse P J, Sattentau Q J (2002) J Gen Virol 83: 2091-2108, Parren P W, et al. (1998) J Virol 72: 3512-3519]. Non-Nabs fail to neutralize because their epitopes are either absent from these trimers, or not accessible at the right time. A soluble gp140 trimer that mimics native, functional spikes should, therefore expose few or, ideally, no epitopes for non-Nabs. Accordingly, Applicants assessed various non-Nabs for their abilities to bind wild type or epitope-tagged versions of BG505 SOSIP.664 gp140 trimers. Several non-Nabs to CD4bs epitopes (F91, F105, b6, 15e) did not bind the SOSIP.664-D7324 trimers or did so only weakly. However, all of them reacted strongly with the corresponding gp120 monomers and/or SOSIP.664 gp140 monomers (FIG. 17 and FIG. 19A). The diminished or absent reactivity of these non-Nabs with the trimers does not, therefore, reflect the absence of the epitope due to sequence variation, but rather the structural constraints present on "native-like" trimers.

Applicants next investigated the binding of CD4i MAbs 17b, 412d, X5 and A32, which were all unable to neutralize the corresponding virus in the presence or absence of sCD4 (FIG. 17 and data not shown). None of these four non-Nabs bound to the BG505 SOSIP.664-D7324 gp140 trimers. When sCD4 was present, the 17b epitope was induced on the trimers (as were the similar 412d and X5 epitopes, to lesser extents), indicating that CD4-induced conformational changes had taken place (FIG. 17 and FIG. 19B, and data not shown). The 17b, 412d and X5 MAbs were also gp120 monomer-reactive but only when sCD4 was present (FIG. 17 and FIG. 19B, and data not shown). In contrast, the A32 MAb to a different category of CD4i epitope failed to bind the trimers even in the presence of sCD4, but bound strongly to the gp120 monomers in the absence of sCD4 and even more so when sCD4 was added (FIG. 17 and FIG. 19). The induction by sCD4 of conformational changes in the BG505 SOSIP.664-D7324 trimers, measured by ELISA, is consistent with the conformational changes seen in the EM images of sCD4/17b-complexes of the non-tagged trimers (see below).

Non-Nabs F240 and 7B2 against cluster I gp41$_{ECTO}$ epitopes were minimally reactive with the SOSIP.664-D7324 or SOSIP.664-His gp140 trimers, but bound strongly to the corresponding WT.664-His (gp41$_{ECTO}$) protein. Hence, these cluster I epitopes are present on BG505 gp41$_{ECTO}$, but occluded by trimer formation (FIG. 17 and FIG. 19C).

In contrast to the above observations, the anti-V3 MAbs 39F, 19b and 14e, which did not neutralize the BG505.T332N virus, bound strongly to the BG505 SOSIP.664-D7324 gp140 trimers in ELISA, although less well than to the corresponding gp120 monomer (FIG. 17 and FIG. 19D). Applicants note, however, that 19b and 14e bound only marginally to the same trimers in SPR- or EM based assays (see below).

The following MAbs were also non-reactive for binding to BG505 SOSIP.664 gp40 trimers by ELISA: D50 (gp41 cluster II), 98-6 (gp41 cluster II), 48d (gp120 CD4i), 8K8 (gp41 HR1), DN9 (gp41 HR1), CH58 (gp120 V2), CH59 (gp120 V2), HG107 (gp20 V2), HG120 (gp120 V2). However, Applicants could obtain no evidence for their reactivity with any other form of BG505 Env protein; i.e., gp120 monomer, SOSIP gp140 monomer or gp41$_{ECTO}$-His (data not shown). Applicants therefore conclude that the epitopes for these MAbs are absent from BG505 Env proteins due to sequence variation, negating their value for assessing trimer antigenicity.

Figure 6:
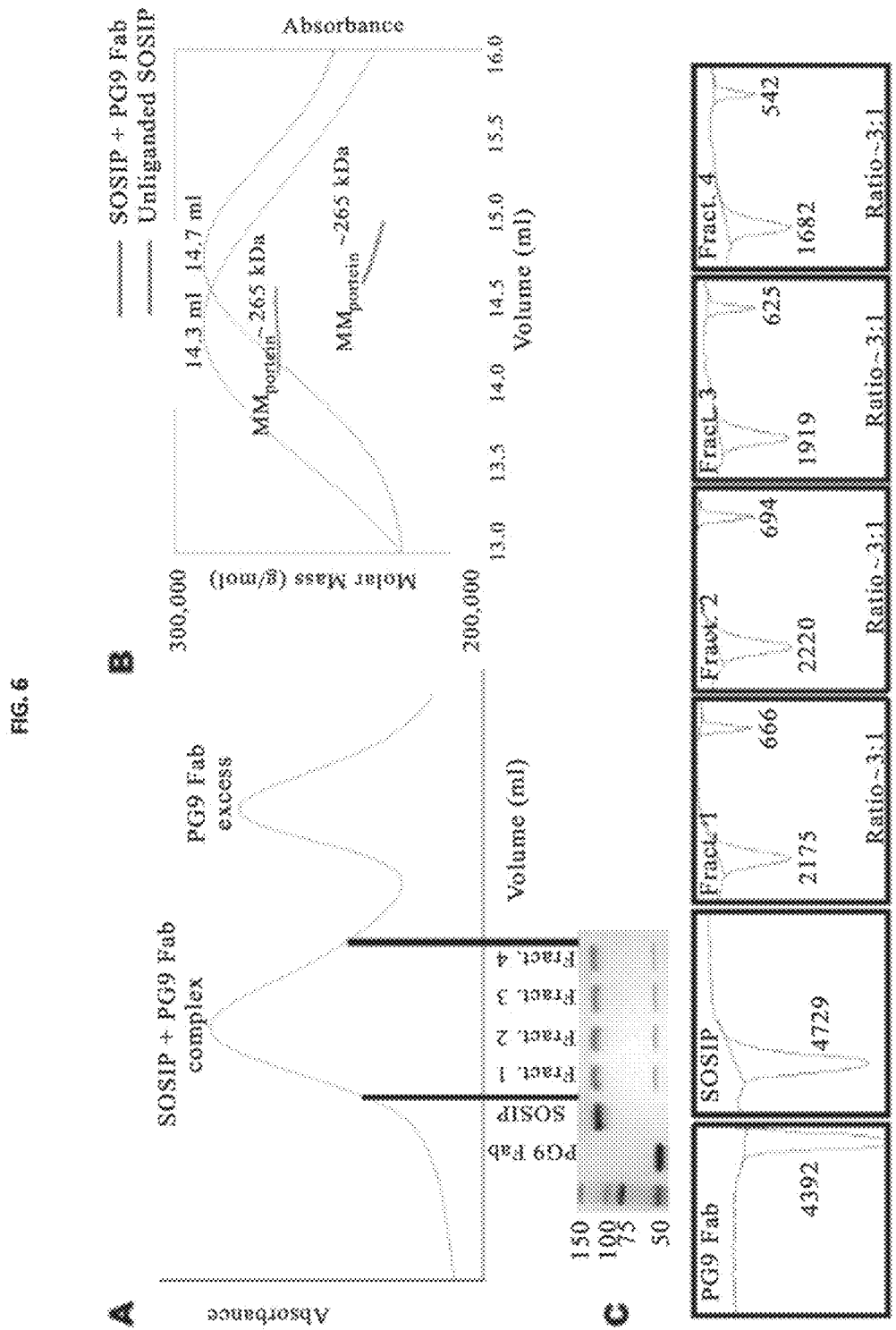
FIG. 6 depicts purification of the PG9 Fab: BG505 SOSIP.664 complex. A. Size exclusion chromatography (SEC) profile showing the separation of a homogeneous PG9 Fab: BG505 SOSIP.664 complex in the presence of excess PG9 Fab. B. The observed shift in elution volume and in molar mass of the protein (MMprotein) for the PG9 complex with BG505 SOSIP.664 trimer (red) as compared to the unliganded trimer (blue) indicates that one PG9 Fab binds to the trimer. The horizontal line under each peak corresponds to the MMprotein of the eluting sample as determined by SEC-UV/MALS/RI. C. Non-reducing SDS-PAGE gel analysis of the eluting SEC fractions. PG9 Fab and BG505 SOSIP.664 showed similar staining in control lanes for the same amount of protein. ImageJ (72) was used to determine that in the eluting samples, there were three gp140 protomers for each PG9 Fab (3:1 ratio).

Applicants plotted the EC50 values for MAbs to the SOSIP.664-D7324 gp140 trimers against the IC50 values for neutralization of the corresponding BG505.T332N Env-pseudovirus (FIG. 6). The resulting Spearman's correlation coefficient, r, was 0.65 (95% confidence interval 0.45-0.79), which was highly significant (P<0.0001). Thus, the BG505 SOSIP.664 gp140 trimer is an excellent antigenic mimic of the functional native BG505.T332N Env spike.

Most non-Nabs did not bind the SOSIP.664-D7324 gp140 trimers in ELISAs, or did so only weakly compared to their reactivity with monomeric proteins. The most striking outliers were the V3 non-Nabs 39F, 14e and 19b, which did bind strongly in this assay (FIG. 19D). The bNAb 2G12 bound more strongly to trimers in ELISA than would be predicted by its neutralization capacity. This outcome might be attributable to the specific enrichment of 2G12-reactive soluble trimers during the affinity purification process, given that other, less 2G12-reactive Env spikes will contribute to infection during neutralization assays. When 2G12, 39F, 14e and 19b were excluded from the correlation, the r-value increased to 0.88 (95% confidence interval 0.80-0.94; P<0.0001).

Antigenic analysis of BG505 SOSIP.664 gp140 trimers by surface plasmon resonance. Applicants next investigated the binding of a subset of representative bNabs and non-Nabs using surface plasmon resonance (SPR). In this assay, binding of MAbs to BG505 SOSIP.664-His gp140 trimers, immobilized via His-Ni$^{2+}$ interaction on NTA chips, again generally agreed well with their capacity to neutralize the corresponding Env-pseudovirus (FIG. 21A-C). Thus, bNabs 2G12 and PGT135 to glycan-dependent epitopes on the outer domain of gp120, bound to high and intermediate levels, respectively, in the SPR assay. The PGV04 bNAb (CD4bs) bound strongly with markedly slow dissociation, the V1V2- and quaternary-structuredependent bNabs PG9, PG16, and PGT145 all bound to intermediate levels, while the V3- and N332-dependent bNabs PGT121, PGT123, and PGT128 bound to intermediate or high extents with distinctive kinetics. In contrast, the CD4bs non-Nab b6 reacted only marginally with the trimers in the SPR assay, while b12 (CD4bs) and F240 (gp41 cluster I) did not bind detectably. The V3-specific non-NAb 14e, which did bind strongly to BG505 SOSIP.664-D7324 gp140 trimers in ELISA, was only marginally reactive with the corresponding His-tagged trimers by SPR; the low signals for 14e contrast markedly with those for the V3- and N332-dependent bNabs (e.g., the plateau values were 60-70 RU and 750 RU for 14e and PGT128, respectively). Moreover, the plateau signal for 14e at 1,000 nM (150,000 ng/ml) was only twice that for b6 (30 RU).

An even starker contrast between effective binding and complete lack of interaction was observed when Fabs were used instead of IgG molecules: the PGV04 Fab (bNAb) bound to an intermediate level (when the three times lower mass contribution to the resonance is taken into account), whereas there was no detectable binding of the (non-NAb) Fabs b6, b12 or F240 (FIG. 21D). Soluble CD4 (of a similar mass to Fabs) bound to a somewhat higher level than the PGV04 Fab, but with markedly faster association and dissociation kinetics (FIG. 21D).

The converse SPR approach of immobilizing the Env-reactive Abs and allowing the untagged BG505 SOSIP.664 gp140 trimers (at 200 nM; 78,000 ng/ml) to bind from the solution phase yielded broadly similar results for the subset of MAbs tested in this way (FIG. 21E). Thus, strong responses were obtained for trimer binding to immobilized 2G12 or PGT128. The BG505 SOSIP.664 trimers did not bind detectably to the immobilized b12 or F240 IgG (non-Nabs) in this SPR format, but a low level of binding to the b6 IgG (also a non-NAb) was observed. The extent of trimer-b6 binding was greater than in the converse SPR set-up, perhaps because the intrinsically weak paratope-gp120 binding is compensated for by the avidity effect of potentially trivalent interactions with the captured IgG; the 2.7-fold larger mass of the trimer compared to IgG should also be taken into account when assessing the degree of binding.

Antigenic analysis of BG505 SOSIP.664 gp140 trimers by isothermal titration calorimetry. To determine the thermodynamic binding characteristics of the BG505 SOSIP.664 gp40 trimers, Applicants performed isothermal titration calorimetry (ITC) experiments using PGT121 Fab, PGT128 Fab and the domain-exchanged 2G12 IgG. All three antibodies have previously been shown to be dependent on the high-mannose glycan at position N332 for Env recognition [Walker L M, et al. (2011) Nature 477: 466-470, Calarese D A, et al. (2003) Science 300: 2065-2071, Scanlan C N, et al. (2002) J Virol 76: 7306-7321, Sanders R W, et al. (2002) J Virol 76: 7293-7305, Pejchal R, et al. (2011) Science 334: 1097-1103]. PGT121, PGT128 and 2G12 all bound the BG505 SOSIP.664 trimer with nanomolar affinities (151 nM=7550 ng/ml; 5.7 nM=284 ng/ml; and 16.0 nM=2400 ng/ml, respectively) and near identical stoichiometries of 2.3-2.4 (Table 3; FIG. 22). These binding stoichiometries are three-fold higher than the value of 0.8 previously reported for PG9 binding (affinity 11 nM=550 ng/ml) to the same construct (Table 3) [Julien J P, et al. (2013) Proc Natl Acad Sci USA 110: 4351-4356]. The data therefore imply that three PGT121 Fabs. PGT128 Fabs or 2G12 IgG molecules bind per trimer, which is consistent with their recognition of N332-dependent epitopes on the outer domain of gp120. In contrast, only a single PG9 Fab recognizes the N160-dependent epitope at the membrane-distal apex of each trimer [Julien J P, et al. (2013) Proc Natl Acad Sci USA 110: 4351-4356]. Taken together, the ITC binding data further confirm that the BG505 SOSIP.664 gp140 trimers properly display the high affinity binding sites for the glycan-dependent bNabs, PGT121, PGT 128, 2G12 and PG9.

Antigenic analysis of BG505 SOSIP.664 gp140 trimers by electron microscopy. Applicants used negative stain electron microscopy (EM) to characterize the binding of the CD4bs bNAb PGV04 to the BG505 SOSIP.664 gp140 trimer (FIG. 23A). The reconstruction at 23-A resolution shows that PGV04 binds the soluble trimers in a manner similar to other CD4bs-directed bNabs with virion associated Env, in that it approaches the gp120 protomers from the side [Tran E E, et al. (2012) PLoS Pathog 8: e1002797]. Applicants compared the complex formed between PGV04 and BG505 SOSIP.664 trimers with other such bNAb-trimer complexes. Recent studies with the same trimers, albeit expressed in glycan processing-deficient GnT12/2 HEK293S cells and not, as here, HEK293T, have shown how the PGT122 and PGT135 bNabs bind to their N332 glycan-dependent epitopes. Thus, their angle of approach differs from how PGV04 encounters the CD4bs, but all three bNabs saturate the three available binding sites on the trimer (FIG. 23C) [Julien J P, et al. (2013) PLoS Pathog 9: e1003342, Kong L, et al. (2013) Nat Struct Mol Biol 20: 796-803]. In contrast, and as noted above, the quaternary preferring, N160 glycan-specific bNAb PG9, only binds to one epitope per trimer (FIG. 23C) [Julien J P, et al. (2013) Proc Natl Acad Sci USA 110: 4351-4356]. Images of the BG505 SOSIP.664 trimers in complex with sCD4 and 17b show that conformational changes are induced (FIG. 23B) that are consistent with ones described for SOSIP trimers based on the JRFL and KNH1144 genotypes [Khayat R, et al. (2013) J Virol 87: 9865-72, Klasse P J, et al. (2013) J Virol 87:9873-85, Harris A, et al. (2011) Proc Natl Acad Sci USA 108: 11440-11445], and for the full length, virus-associated BaL Env spike [Liu J, et al. (2008) Nature 455: 109-113]. Collectively, the new and recently published negative stain EM data show that BG505 SOSIP.664 trimers, derived from HEK293T or HEK293S cells, express multiple different bNAb epitope clusters, and also undergo conformational changes when they bind sCD4 [Julien J P, et al. (2013) PLoS Pathog 9: e1003342, Kong L, et al. (2013) Nat Struct Mol Biol 20: 796-803. Julien J P, et al. (2013) Proc Natl Acad Sci USA 110: 4351-4356].

Applicants also collected images of mixtures of the BG505 SOSIP.664 gp140 trimers with non-Nabs b6, 14e. 19b and F240, added as Fabs and in molar excess (Table 4; FIG. 24). Essentially none (<3%) of the trimers bound to F240, while about 6% could be seen to have a single b6 Fab attached (Table 4; FIG. 24). Hence the EM images are concordant with the ELISA and SPR data for F240. The ELISA-reactive V3 non-Nabs 14e and 19b bound the trimers to only a limited extent by EM (Table 4). Thus, about 179% of the trimers were occupied by one, or (about 217%) by or two (about 2%) 14e Fabs, and about 39% by one (about 30% by one), two (about 8% by two,) or about 1% by three (about 1%) 19b Fabs.

TABLE 3

Thermodynamic parameters of PGT121, PGT128, 2G12 and PG9 binding to
BG505 SOSIP.664 gp140 trimers measured by isothermal titration calorimetry.

| Binding experiment | $\Delta G^{a,b}$ (kcal mol$^{-1}$) | $\Delta H^a$ (kcal mol$^{-1}$) | $-T\Delta S^a$ (kcal mol$^{-1}$) | $K_d^a$ (nm) | $K_d^a$ (ng/ml) | $N^{a,c}$ | $K_{d2}^{a,d}$ (nM) |
|---|---|---|---|---|---|---|---|
| PGT121 Fab into BG505 SOSIP.664 | −9.3 | −29.9 | 20.6 | 151 | 7550 | 2.4 | N/A |
| PGT128 Fab into BG505 SOSIP.664 | −11.2 | −22.8 | 11.6 | 5.7 | 285 | 2.3 | 20,000$^e$ |
| 2G12 IgG into BG505 SOSIP.664 | −10.6 | −39.0 | 28.4 | 16.0 | 2400 | 2.4 | 12,300$^e$ |
| PG9 Fab into BG505 SOSIP.664$^f$ | −10.9 | −18.7 | 7.8 | 11.0 | 550 | 0.8 | N/A |

$^a$The reported values are averages from at least two independent measurements. The associated errors are approximately 10% of the average. Representative isotherms are shown in FIG. 22.
$^b$The change in Gibbs free energy ($\Delta G$) was determined using the relationship: $\Delta G_{binding} = RT\ln K_d$ [de Azevedo W F, Jr., Dias R (2008) Curr Drug Targets 9: 1071-1076].
$^c$The stoichiometry of binding (N) is directly affected by errors in protein concentration measurements, sample impurity and heterogeneity of gp140 glycans.
$^d$Dissociation constant associated with a second (low affinity) binding event.
$^e$The binding isotherms do not allow the stoichiometry and enthalpy associated with the second binding event to be determined accurately.
$^f$Data previously described elsewhere [Julien J P, et al. (2013) ProcNatl Acad Sci USA 110: 4351-4356].

Overall, the observations made with the non-Nabs b6, 14e, 19b and F240 contrast markedly with the EM images of the same trimers in complexes with bNabs PGT122, PGT135 and PGV04, where there was full occupancy (i.e., three Fabs bound) in >50% of the images and no occupancy (i.e., no Fabs bound) in only <3% of the images (not shown).

Antigenic Analysis of BG505 SOSIP.664 Gp140 Trimers: Summary.

Taken together, the various antigenicity assays show that every MAb that neutralizes the BG505.T332N virus efficiently also bound strongly to the soluble BG505 SOSIP.664 gp140 trimers (wild type and/or epitope tagged), except for MAbs to MPER epitopes that were not present in the trimer construct (data not shown) (FIG. 25). Applicants conclude that the trimers display a range of bNAb epitopes from multiple different clusters. In contrast, non-NAb epitopes are generally structurally occluded and not displayed on the SOSIP trimer (FIG. 25).

Applicants describe here the design and properties of a next generation, fully cleaved and highly stable soluble gp140 trimer based on the BG505 subtype A sequence. EM imaging shows that the BG505 SOSIP.664 gp140 trimers are homogeneous and that their architecture is very similar to that of native Env spikes on virions. Applicants used a range of techniques to assess the antigenic properties of the soluble trimers, particularly their abilities to bind bNabs and non-Nabs and the relationship between trimer binding and virus neutralization. The various techniques were generally concordant, with one notable exception relating to V3 MAbs. Overall, there were few discrepancies between the antigenicity of the trimers and the neutralization sensitivity of the corresponding BG505.T332N virus. Thus, in general, all the bNabs that neutralized the virus also bound to the soluble trimers, with the obvious exception of bNabs to the MPER, a region that was eliminated from the trimers to improve their biophysical properties. The presence of so many bNAb epitopes on a soluble, generally homogenous and highly stable trimer is highly beneficial for structural studies, and may also be valuable for their immunogenicity properties. Whether the favorable antigenic profile translates into the induction of bNabs will be determined experimentally.

In contrast to bNabs, non-Nabs were rarely strongly reactive with the BG505 SOSIP.664 gp140 trimers, even when their epitopes were present on less complex forms of BG505 Env (e.g., gp120 or gp140 monomers, or gp41$_{ECTO}$). This finding was particularly striking for non-Nabs against the CD4bs, such as F91 and F105, and implies that the steric constraints on MAb access to this region of virion-associated Env also applies to the soluble trimers. The same argument applies to the various CD4i epitopes, which were inaccessible on the soluble trimers unless sCD4 was also bound, and to non-NAb epitopes in gp41$_{ECTO}$. Applicants note that the A32 epitope, while present and further induced by sCD4 on BG505 gp120 monomers, was absent from the trimers whether sCD4 was present or not. This observation may be relevant to arguments that the A32 epitope is an important target for ADCC mediated killing of infected cells [Ferrari G, et al. (2011) J Virol 85:7029-7036]. The only discordance between the trimer-binding and virus-neutralization assays involved the V3 region of gp120. Thus, the V3 non-Nabs 19b, 14e and 39F bound efficiently to the D7324-tagged trimers in the capture ELISA. However, the outcomes of the SPR and negative stain EM assays were quite different, in that, in these assays, the V3 MAbs were only minimally reactive with His-tagged, D7324-tagged or non-tagged trimers. One explanation may be that the capture onto the ELISA plate via the D7324 antibody might induce some local unfolding of the trimers. As Applicants think it unlikely that the low level of binding of 19b and 14e seen by EM can explain the rather strong binding in ELISA, Applicants favor this explanation but acknowledge that it is speculative in nature. Applicants do, however, note that, at high concentrations, some binding of a subset of other non-Nabs can be observed in ELISA (FIG. 19). It is therefore also possible there is some conformational heterogeneity in the trimer population, with a minor subset displaying some non-NAb epitopes. Negative stain EM does show that some trimers can bind one or (very rarely) two non-NAb Fabs (FIG. 24). Another possibility is that the trimers are flexible, allowing different conformations to be sampled over time in a way that registers more strongly in an ELISA than in other binding assays [Ferrari G, et al. (2011) J Virol 85:7029-7036].

TABLE 4

Binding of non-Nabs to BG505 SOSIP.664 gp140 trimers as observed by negative stain EM.[a]

| Fab | Total particles | Trimer alone | | 1 Fab bound | | 2 Fabs bound | | 3 Fabs bound | |
|---|---|---|---|---|---|---|---|---|---|
| | | particles | % | particles | % | particles | % | particles | % |
| b6 | 5964 | 5610 | 94 | 354 | 6 | 0 | 0 | 0 | 0 |
| 14e | 26908 | 21854 | 81 | 4444 | 17 | 610 | 2 | 0 | 0 |
| 19b | 40833 | 25111 | 61 | 12457 | 30 | 3054 | 8 | 211 | 1 |
| F240 | 6417 | 6263 | 98 | 154 | 2 | 0 | 0 | 0 | 0 |

[a]Representative class averages are shown in FIG. 24.

Applicants note that an absolute stoichiometry of <3 (i.e., 2.4) was found for 2G12 IgG in the ITC binding experiments, whereas a value of 3 might have been expected for trimers that had been affinity-purified on a 2G12-IgG column. The discrepancy might arise from errors in glycoprotein concentration measurements. Sample impurity can also contribute to lower apparent binding stoichiometries. However, another possibility is that some gp120 protomers on a trimer do not express the 2G12 epitope due to variation in the glycosylation process. The presence of one or two 2G12 epitopes per trimer is probably sufficient for binding to the 2G12 affinity column. Of note is that ITC also yielded trimer binding stoichiometries of 2.3 to 2.4 for the glycan-dependent Fabs PGT121 and PGT128, whereas Fab PGT 22, which is very similar to PGT121, saturated all three binding sites on the trimer as visualized by EM (FIG. 23B). The explanation(s) might be similar to those suggested for 2G12.

In the ITC experiments, a weak secondary binding event could be seen for the PGT128 and 2G12 bNabs, in addition to the saturating high-affinity event. PGT128 and 2G12 have high affinities for mimetic (i.e., non-Env) oligomannose glycan substrates, and might therefore interact weakly with other oligomannose glycans on the SOSIP.664 gp140 trimers, in addition to their high-affinity epitopes. Whether such low affinity binding events imply that high concentrations of these antibodies would react with secondary binding sites on the virion-associated Env trimer, and hence contribute to neutralization, is not yet known.

Across the entire bNAb and non-NAb test panel, there was an excellent concordance between the outcomes of trimer-reactivity (by ELISA) and virus-neutralization assays. Thus, a formal correlation plot yielded a highly significant r-value of 0.65 (P<0.0001). Such an outcome would not be the case for Env binding assays using gp120 monomers or uncleaved gp40 trimers, because of their strong reactivity with multiple non-Nabs [Binley J M, et al. (2000) J Virol 74: 627-643, Dey A K, et al. (2009) Virology 385: 275-281, Pancera M, Wyatt R (2005) Virology 332: 145-156, Si Z, et al. (2003) AIDS Res Hum Retroviruses 19: 217-226]. The V3 non-Nabs were the predominant outliers in the correlation analysis and, as noted above, their strong ELISA reactivity is not supported by the SPR and EM studies. One other outlier was the 2G12 bNAb. Here, the discrepancy is likely to be rooted in the use of a 2G12-affinity column for purifying the BG505 SOSIP.664 gp140 trimers (D7324-tagged or not). Thus, the column is likely to select for a trimer sub-population that has a high affinity for 2G12. In contrast, the virions used in neutralization assays undergo no such 2G12-selection procedure and would have a more "average" affinity for this bNAb. When 2G12 and the V3 MAbs were excluded, the r-value for the trimer reactivity and neutralization correlation increased to 0.88 (P<0.0001). Overall, Applicants are encouraged by the general occlusion and/or absence of non-NAb epitopes on the BG505 SOSIP.664 gp140 trimers, not only because of their antigenic, and arguably structural, fidelity with respect to virion-associated trimers, but also for immunogenicity studies. Thus, when the goal is to induce bNabs, non-NAb epitopes represent a distraction to the immune system that is best avoided. Less sophisticated Env immunogens that do not mimic the native spike efficiently induce non-Nabs, if and when this is a desired outcome [Gilbert P B, et al. (2005) J Infect Dis 191: 666-677, Montefiori D C, et al. (2012) J Infect Dis 206: 431-441]. It is possible that the exposure of some V3-associated non-NAb epitopes on the BG505 SOSIP.664 trimers under certain experimental conditions in vitro (e.g., in the ELISA) might also occur when they are used as immunogens. While V3 is not an important neutralization site for primary viruses, some V3 Abs are active against a subset of viruses in vitro. Hence, any induction of V3 Abs in vivo might be useful under some circumstances. A converse argument, however, is that V3 is an immunodominant epitope cluster that may distract the immune system from focusing on more worthwhile targets elsewhere on the trimer. If so, it would be best to mask or stabilize the V3 region on a new variant of BG505 SOSIP.664 gp140 trimers, for example by introducing a glycan site(s) at an appropriate position [Garrity R R, et al. (1997) J Immunol 159:279-289]. Care would need to be taken, however, to occlude only undesirable regions of V3 (e.g., the 19b/14e sites) without affecting nearby areas that contribute to genuine bNAb epitopes, such as those for PGT121-123 and PGT125-130. Applicants also note that glycan-masking might introduce unwanted neo-epitopes. Additional structural information that would help guide future SOSIP gp140 trimer re-designs is being actively sought.

It may never be possible to make a soluble gp140 trimer that precisely mimics the native Env spike, because deleting the transmembrane and cytoplasmic domains (and, in the case of SOSIP.664 trimers, also the MPER) will have at least some impact on trimer structure. Thus, point substitutions in gp41 HR1, HR2, MPER and the intracytoplasmic tail, as well as the length of the cytoplasmic tail, can influence the interaction of antibodies with the gp120 moieties of trimers on virions and infected or transfected cells [Kalia V, et al. (2005) J Virol 79: 2097-2107, Vzorov A N, Compans R W (2000) J Virol 74: 8219-8225, Klasse P J, et al. (1993) Virology 196:332-337, Blish C A, et al. (2008) PLoS Med 5: e9, Back N K, et al. (1993) J Virol 67: 6897-6902]. Nonetheless, the BG505 SOSIP.664 gp140 trimers, as assessed by a variety of different antigenicity assays, do seem to come very close to being a faithful Env-spike mimetic.

The BG505 SOSIP.664 gp140 trimers have already been already useful for structure-based studies aimed at defining bNAb-Env interactions [Julien J P, et al. (2013) PLoS Pathog 9: e1003342, Kong L, et al. (2013) Nat Struct Mol Biol 20: 796-803, Julien J P, et al. (2013) Proc Natl Acad Sci USA 110: 4351-4356], as were the corresponding trimers based on the KNH1144 env gene [Pejchal R, et al. (2011) Science 334: 1097-1103, Harris A, et al. (2011) Proc Natl Acad Sci USA 108: 11440-11445, Harris A K, et al. (2013) J Virol 87: 7191-7196]. The BG505 trimers are also substrates for ongoing efforts aimed at defining crystal or high-resolution EM structures of the Env trimer. In addition, Applicants are assessing their immunogenicity in rabbits, guinea pigs and macaques, as well as determining how to make them in the much larger quantities, and of the appropriate quality, required for any future testing in humans. A high priority will also be to identify additional genotypes that yield SOSIP.664 trimers with the same favorable properties as the ones described here. Among hypotheses to explore is that the T/F and/or pediatric status of the BG505 isolate is relevant to the trimers' homogeneity and stability; a second relates to the presence of certain trimer-stabilizing residues associated with thermal stability. Thus, the M535, N543 and K567 residues that are present in BG505 SOSIP.664 have been reported to contribute to the trimerization efficiency of soluble gp140 and the thermal stability of Env trimers on virus particles [Dey A K, et al. (2007) Virology 360:199-208, Leaman D P, Zwick M B (2013) PLoS Pathog 29:e1003184].

Construct Design.

The BG505 (BG505.W6M.ENV.C2) env gene (GenBank accession nos. ABA61516 and DQ208458) is derived from a subtype A T/F virus isolated from a 6-week old, HIV-1-infected infant [Wu X, et al. (2006) J Virol 80: 835-844]. It has 73% identity to the proposed PG9-sensitive progenitor virus from the PG9 bNAb donor, based on computational analysis of the most recent common ancestor sequence [Hoffenberg S, et al. (2013) J Virol 87: 5372-5383]. The BG505 gp120 monomer binds PG9, which is unusual given the quaternary nature of the PG9-Env interaction [Hoffenberg S, et al. (2013) J Virol 87: 5372-5383]. To make the BG505 SOSIP.664 gp140 construct, Applicants introduced the following sequence changes (FIG. 1A): A501C and T605C (gp120-gp41ECTO disulfide bond [Binley J M, et al. (2000) J Virol 74: 627-643]); I559P in $gp41_{ECTO}$ (trimer-stabilizing [Sanders R W, et al. (2002) J Virol 76: 8875-8889]); REKR (SEQ ID NO: 1) to RRRRRR (SEQ ID NO: 2) in gp120 (cleavage enhancement [Binley J M. et al. (2002) J Virol 76: 2606-2616]); T332N in gp120 (introduction of epitopes dependent on glycan-332); stop codon at gp41ECTO residue 664 (improvement of homogeneity and solubility [Khayat R, et al. (2013) J Virol 87(17):9865-72, Klasse P J, et al. (2013) J Virol 87(17):9873-85]). The codon optimized gene for BG505 SOSIP.664 gp140 was obtained from Genscript (Piscataway, N.J.) and cloned into pPPI4 using PstI and NotI [Binley J M, et al. (2000) J Virol 74: 627-643].

Variants of the BG505 SOSIP.664 gp140 trimers bearing either a His-tag or a D7324 epitope-tag sequence at the C-terminus of $gp41_{ECTO}$ were also made by adding the amino acid sequences GSGSGGSGHHHHHHHH (SEQ ID NO: 7) or GSAPTKAKRRVVQREKR, (SEQ ID NO: 8) respectively, after residue 664 in gp41ECTO and preceding the stop codon. These proteins are designated SOSIP.664-His gp140 and SOSIP.664-D7324 gp140. Applicants also made a His-tagged gp140 with the C501 and C605 cysteines replaced by their original residues, and with P559 similarly reverted to the original isoleucine (BG505 WT.664-His gp140). When expressed in the presence of excess furin to ensure efficient precursor cleavage, the absence of the SOS disulfide bond means the gp140 trimer is unstable and dissociates to gp120 and a trimeric form of His-tagged gp41ECTO (BG505 gp41ECTO-His); the latter can be used in a NiNTAcapture enzyme-linked immunosorbent assay (ELISA; see below).

A monomeric BG505 gp120 with a similar sequence to the gp120 components of the gp140 trimers was designed by: introducing a stop codon into the SOSIP.664 construct at residue 512; reverting the optimized cleavage site to wild type (RRRRRR (SEQ ID NO: 2) changed to REKR (SEQ ID NO: 1 at residues 508-511); reverting the A501C change; introducing the D7324 epitope into the C5 region (R500K+G507Q); and making a L111A substitution to decrease gp120 dimer formation [Hoffenberg S, et al. (2013) J Virol 87: 5372-5383, 63]. A slightly modified version of BG505 gp120 that has been described previously [Julien J P, et al. (2013) PLoS Pathog 9: e1003342] was used in DSC experiments. For this modification, the BG505 gp120 gene was cloned downstream of an IgK secretion signal in a phCMV3 plasmid and upstream of a His-tag. The cleavage site was mutated to prevent the His-tag from being cleaved off, leading to the following C-terminal sequence: RAKRRV-VGSEKSGHHHHHH (SEQ ID NO: 9).

The BG505 gp160 clone for generating Env-pseudoviruses for neutralization assays has been described elsewhere [Hoffenberg S, et al. (2013) J Virol 87: 5372-5383]. Applicants modified this clone by inserting the same T332N substitution that is present in the BG505 SOSIP.664 trimers, and refer to the resulting virus as BG505.T332N.

Env Protein Expression.

The Env proteins from various env genes described above were expressed in wild type, adherent HEK293T cells or the 293F variant that is adapted for suspension cultures, or in CHO-K1 cells, essentially as described [Julien J P, et al. (2013) PLoS Pathog 9: e1003342, Julien J P, et al. (2013) Proc Natl Acad Sci USA 110: 4351-4356, 46, 64]. HEK293T and CHO-K1 cells were maintained in Dulbecco's modified Eagle's medium (DMEM) supplemented with 10% fetal calf serum (FCS), penicillin (100 U/ml), streptomycin (100 mg/ml), Glutamax (Invitrogen), non-essential amino acids (0.1 mM), sodium pyruvate (0.1 mM) and HEPES (0.1 mM). For gp140 trimer production, HEK293T or CHO-K1 cells were seeded at a density of $5.5 \times 10^4$/ml in a Corning Hyperflask. After 3 days, when the cells had reached a density of $1.0 \times 10^6$/ml, they were transfected using polyethyleneimine (PEI) as described elsewhere [Kirschner M, et al. (2006) Protein Expr Purif 48:61-68]. Briefly, PEIMAX (1.0 mg/ml) in water was mixed with expression plasmids for Env and Furin [Binley J M, et al. (2000) J Virol 74: 627-643] in OPTI-MEM. For one Corning Hyperflask, 600 μg of Env plasmid, 150 μg of Furin plasmid and 3 mg of PEIMAX were added in 550 ml of growth media. Culture supernatants were harvested 72 h after transfection. BG505 gp120 used in differential scanning calorimetry (DSC) experiments was produced in HEK293F cells using a protocol similar to that previously described [Julien J P, et al. (2013) PLoS Pathog 9: e1003342].

Env Protein Purification.

Env proteins were purified from the supernatants by affinity chromatography using either a 2G12 column or a Galanthus nivalis (GN)-lectin column [Julien J P, et al. (2013) PLoS Pathog 9: e1003342, Julien J P, et al. (2013) Proc Natl Acad Sci USA 110: 4351-4356, 46, 64]. Briefly, transfection supernatants were vacuum filtered through 0.2-μm filters and then passed (0.5-1 ml/min flow rate) over the column. The 2G12 column was made from CNBr-activated Sepharose 4B beads (GE Healthcare) coupled to the bNAb 2G12 (Polymun Sciences, Klosterneuburg, Austria). Purification using this column was performed as follows: the beads were washed with 2 column volumes of buffer (0.5 M NaCl, 20 mM Tris, pH 8.0) before eluting bound Env proteins using 1 column volume of 3 M $MgCl_2$. The eluted proteins were immediately buffer exchanged into 75 mM NaCl, 10 mM Tris, pH 8.0, using Snakeskin dialysis tubing (10K WCMO) (Thermo Scientific). The buffer-exchanged proteins were further concentrated using Vivaspin columns with a 30-kDa cut off (GE Healthcare). For GN-lectin affinity purification, the wash buffer was Dulbecco's phosphate buffer saline (DPBS) supplemented with 0.5 M NaCl was used, and elution was carried out using DPBS supplemented with 1 M methyl mannopyranoside.

In both cases, the affinity-purified Env proteins were further purified to size homogeneity using size exclusion chromatography (SEC) on a Superdex 200 26/60 column (GE Healthcare). A Superose 6 column was sometimes used for analytical or preparative purposes. The trimer fractions and, occasionally also the SOSIP gp140 monomer fractions, were collected and pooled. Protein concentrations were determined using either a bicinchonic acid-based assay (BCA assay; Thermo Scientific, Rockford, Ill.) or $UV_{280}$ absorbance using theoretical extinction coefficients [66].

SDS-PAGE and Blue Native-PAGE.

Env proteins were analyzed using SDS-PAGE and BN-PAGE [Sanders R W, et al. (2002) J Virol 76: 8875-8889, Schulke N, et al. (2002) J Virol 76:7760-7776] and stained using Coomassie blue or silver stain. The input material was mixed with loading dye and directly loaded onto a 4-12% Bis-Tris NuPAGE gel or a 10% Tris-Glycine gel (Invitrogen). The gels were run for 1.5 h at 200 V (0.07 A) using 50 mM MOPS, 50 mM Tris, pH 7.7 as the running buffer (Invitrogen).

Differential Scanning Calorimetry (DSC).

Thermal denaturation was probed with a VP-DSC calorimeter (GE Healthcare). Before carrying out the experiments, all samples were extensively dialyzed against phosphate-buffered saline (PBS). The protein concentration was subsequently adjusted to 0.1-0.3 mg/ml, as described above. After loading the protein sample into the cell, thermal denaturation was probed at a scan rate of 90 C/h. Buffer correction, normalization and baseline subtraction procedures were applied before the data were analyzed using Origin 7.0 software. The data were fitted using a non-two-state model, as the asymmetry of some of the peaks suggested the presence of unfolding intermediates.

Antibodies and Fabs.

Antibody concentrations are generally recorded in ng/ml for neutralization assays and trimer binding ELISAs, but in nM for ITC and SPR experiments. Since the molecular mass of an average IgG molecule is approximately 150,000 Da, the conversion factors for IgG are: 1000 ng/ml=6.7 nM and 1.0 nM=150 ng/ml. For Fabs, the conversion factors are: 1000 ng/ml=20 nM and 1.0 nM=50 ng/ml.

MAbs were obtained as gifts, or purchased, from the following sources: John Mascola and Peter Kwong (VRC01, VRC03, VRC06, VRC06b, X5, F105); Dennis Burton (PGV04, PG9, PG16, PGT121-123, PGT125-128, PGT130, PGT135, PGT136, PGT145, b6, b12, F240); Polymun Scientific (447-52D, 2G12); Michel Nussenzweig (3BNC60, 3BNC117, 12A12, 45-46, 45-46W, 1NC9, 8ANC195, 3BC176, 3BC315); Michael Zwick (8K8, DN9); Barton Haynes (CHO 1, CH31, CH58, CH59, CH103, CH106, HG107, HG120); James Robinson (39F, 17b, 48d, 412d, A32, 19b, 14e, F91, 15e, 7B2). William Olson of Progenics Pharmaceuticals provided soluble CD4 (sCD4) and CD4-IgG2. The following reagents were obtained through the NIH AIDS Reagent Program, Division of AIDS, NIAID, NIH: D50 from Dr. Patricia Earl; 98-6 from Dr. Susan Zolla-Pazner; HJ16 from Dr. Antonio Lanzavecchia.

Fab PGT121, PGT128 and PGV04, as well as IgG 2G12 used in isothermal titration calorimetry (ITC) and electron microscopy (EM) experiments, were produced following a protocol similar to that previously described [Julien J P, et al. (2013) PLoS Pathog 9: e1003342, Julien J P, et al. (2013) Proc Natl Acad Sci USA 110: 4351-4356]. Briefly, heavy and light chain genes were transfected in HEK293F cells using 293Fectin (Invitrogen). Secreted Fab or IgG were harvested 6-7 days posttransfection. The supernatant was directly loaded on either an anti-human λ light chain affinity matrix (CaptureSelect Fab 1; BAC) for PGT121 and PGT128 Fabs, an anti-human K light chain affinity matrix (CaptureSelect Fab k; BAC) for PGV04 Fab or on a Protein A column for 2G12 IgG. Elution was performed using a buffer containing 100 mM glycine, pH 2.7. The PGT121, PGT128 and PGV04 Fabs were subjected to MonoS (GE Healthcare) cation exchange chromatography to eliminate light chain dimers. All antibodies were subsequently purified to size homogeneity by gel filtration chromatography using a Superdex 200 column (GE Healthcare) in a buffer containing 150 mM NaCl, 20 mM Tris, pH 8.0.

The b6, F240, 14e and 19b Fab' fragments used in EM and SPR experiments were produced by IgG digestion at 37 C for 1 h with the enzyme IdeS in a buffer containing 150 mM NaCl, 20 mM Bis-tris, pH 6.0. A reduction and alkylation reaction involving the addition of 10 mM dithiothreitol for 1 h, followed by 5 mM iodoacetamide, produced Fab' from $(Fab')_2$. Subsequently, the Fab' was purified away from the Fc fragment and undigested IgG using a Protein A affinity column.

Neutralization Assays.

For Env-pseudovirus production, HEK293T cells ($2\times10^5$) were seeded at 2 ml per well in a 6-well tissue culture plate (Corning). After 1 d, the cells reached a confluence of 90-95%. Prior to transfection, the culture medium was refreshed using 2 ml of supplemented medium and the cells were transfected using Lipofectamine 2000 (Invitrogen). For one well, 1.6 µg of BG505.T332N plasmid and 2.4 µg of pSG3ΔEnv plasmid (obtained through the AIDS Research and Reference Reagent Program, Division of AIDS, NIAID, NIH from Drs. John C. Kappes and Xiaoyun Wu) were mixed in 250 µl of OPTI-MEM. A 10-µl aliquot of lipofectamine 2000 was mixed with 240 µl of OPTI-MEM immediately before addition to the solution containing the expression plasmids. After incubation for 20 min at room temperature, the mixture was added to the cells to initiate transfection. Culture supernatants were harvested 48 h later.

The TZM-bl reporter cell line, which stably expresses high levels of CD4 and the coreceptors CCR5 and CXCR4 and contains the luciferase and β-galactosidase genes under the control of the HIV-1 long-terminal-repeat promoter, was obtained through the NIH AIDS Research and Reference Reagent Program, Division of AIDS, NIAID, NIH (John C. Kappes, Xiaoyun Wu, and Tranzyme Inc. Durham, N.C.) [Derdeyn C A, et al. (2000) J Virol 74: 8358-8367, Wei X, et al. (2003) Nature 422: 307-312]. One day prior to infection, $1.7\times10^4$ TZM-bl cells per well were plated on a 96-well plate in DMEM containing 10% FCS, 16 MEM nonessential amino acids, penicillin and streptomycin (both at 100 U/ml), and incubated at 37 C in an atmosphere containing 5% $CO_2$ for 48 h. A fixed amount of virus (5 ng/ml of p24-antigen equivalent) was incubated for 30 min at room temperature with serial 1 in 3 dilutions of each test MAb [Bontjer I, et al. (2009) J Virol 83: 368-383, Eggink D, et al. (2009) J Biol Chem 284: 26941-26950]. This mixture was added to the cells and 40 µg/ml DEAE, in a total volume of 200 µl. Two days later, the medium was removed. The cells were washed once with PBS (150 mM NaCl, 50 mM sodium phosphate, pH 7.0) and lysed in Reporter Lysis Buffer (Promega, Madison, Wis.). Luciferase activity was measured using a Luciferase Assay kit (Promega, Madison, Wis.) and a Glomax Luminometer according to the manufacturer's instructions (Turner BioSystems, Sunnyvale, Calif.). All infections were performed in duplicate. Uninfected cells were used to correct for background luciferase activity. The infectivity of each mutant without inhibitor was set at 100%. Nonlinear regression curves were determined and 50% inhibitory concentrations ($IC_{50}$) were calculated using a sigmoid function in Prism software version 5.0.

D7324-Capture ELISA for Monomeric and Trimeric BG505 Env Proteins.

ELISAs were performed as described previously [Eggink D, et al. (2010) Virology 401: 236-247, Melchers M, et al. (2012) J Virol 86: 2488-2500, Melchers M, et al. (2011) Retrovirology 8: 48], with minor modifications. Microlon 96-well plates (Greiner Bio-One, Alphen aan den Rijn, The Netherlands) were coated overnight with Ab D7324 (Aalto Bioreagents, Dublin, Ireland) at 10 µg/ml in 0.1 M $NaHCO_3$, pH 8.6 (100 pd/well). After washing and blocking steps, purified, D7324-tagged BG505 Env proteins were added at 100 ng/ml in TBS/10% FCS for 2 h. Unbound Env proteins were washed away, and TBS (150 mM NaCl, 20 mM Tris) plus 2% skimmed milk was added to further block non-specific protein-binding sites. Serially diluted MAbs or CD4-IgG2 in TBS/2% skimmed milk were then added for 2 h followed by 3 washes with TBS. In some cases, sCD4 (10 µg/ml) was added during the incubation with a test MAb. Horseradish peroxidase labeled goat-anti-human immunoglobulin G (IgG) (Jackson Immunoresearch, Suffolk, England) was added for 60 min at a 1:3000 dilution (final concentration 0.33 µg/ml) in TBS/2% skimmed milk, followed by 5 washes with TBS/0.05% Tween-20. Colorimetric detection was performed using a solution containing 1% 3,3',5,5'-tetramethylbenzidine (Sigma-Aldrich, Zwijndrecht, The Netherlands), 0.01% $H_2O_2$, 100 mM sodium acetate and 100 mM citric acid. Color development was stopped using 0.8 M $H_2SO_4$ when appropriate, and absorption was measured at 450 nm. In most experiments, SEC-purified BG505 gp120-D7324 or SOSIP.664-D7324 gp140 trimers (or sequence variants specified elsewhere) were used for the above assays. However, when specifically indicated, unpurified D7324-tagged BG505 SOSIP.664 gp140 (or mutants) were used instead.

Ni-NTA-Capture ELISA for BG505 Env Proteins.

Supernatants from cells transiently expressing SOSIP.664-His gp140 or gp41$_{ECTO}$-His proteins were diluted 1:2 in TBS/10% FCS and incubated for 2 h with $Ni^{2+}$-nitrilotriacetic acid (Ni-NTA) coated Hissorb 96-well plates (Qiagen, Venlo, The Netherlands) [Bontjer I, et al. (2010) J Biol Chem 285: 36456-36470, Eggink D, et al. (2010) Virology 401: 236-247, Melchers M. et al. (2012) J Virol 86: 2488-2500, Melchers M, et al. (2011) Retrovirology 8: 48]. The subsequent procedures were exactly as described above for the D7324-capture ELISA.

Surface Plasmon Resonance.

MAb binding to trimers at 20 C was detected by two SPRbased methods using a Biacore 3000 instrument (GE Healthcare). In the first approach, His-tagged trimers were immobilized on Ni-NTA chips and the binding of solution-phase MAbs was recorded. After removing metallic contaminants via a pulse of EDTA (350 mM) in running buffer (150 mM NaCl, 10 mM Hepes, pH 7.4 plus 0.005% Tween20) for 1 min at a flow rate of 30 ml/min, the chip was loaded with $Ni^{2+}$ by injecting $NiCl_2$ (2.5 mM) for 1 min at a flow rate of 10 ml/min, resulting in a response of about 50 RU. For all steps between the high EDTA pulses, the running buffer was supplemented with 50 mM EDTA. Purified SOSIP.664-His gp140 trimers (10,000 ng/ml) were injected at 10 µl/min for 2-3 min to capture the equivalent of about 500 RU (=$R_L$). Control channels received neither trimer nor $NiCl_2$. However, control cycles were performed by flowing the analyte over $Ni^{2+}$-loaded NTA in the absence of trimer; there were no indications of non-specific binding. The analyte (IgG at 1,000 nM (150,000 ng/ml) or Fab at 500 nM (25,000 ng/ml)) was injected into the trimer sample and control channels at a flow rate of 50 l/min. Association was recorded for 300 s, and dissociation for 600 s. After each cycle of interaction, the NTA-chip surface was regenerated with a pulse of EDTA (350 mM) for 1 min at a flow rate of 30 µl/min, followed by 3 washes with running buffer. A high flow rate of analyte solution (50 µl/min) was used to minimize mass-transport limitation; ln(dY/dX) plots for the association phase were linear with negative slopes, indicating that the binding was largely kinetically limited. Both control-channel and zero-analyte responses were subtracted.

In the second approach, Env-reactive MAbs were captured onto the chip by an immobilized anti-Fc Ab and the binding of solution phase, untagged BG505 SOSIP.664 gp140 trimers was recorded. Affinity-purified goat anti-human IgG Fc (A80-104A, Bethyl Laboratories, Inc.) was diluted to 50 µg/ml in sodium acetate (pH 4.5) and then amine-coupled to dextran, reaching levels about $10^4$ RU, in all four channels of CM5 chips. Env-reactive Abs were added (1 mg/ml in sodium acetate, pH 4.5) to three channels on each chip, at a flow rate of 5 µl/ml, and captured to response levels of 800-900 RU; the fourth channel served as a control surface. BG505 SOSIP.664 gp40 trimers at 200 nM (78,000 ng/ml) in running buffer (150 mM NaCl, 10 mM Hepes, pH 7.4, 3 mM EDTA plus 0.005% Tween20; note the higher EDTA concentration) were injected at a flow rate of 30 µl/min. Association was recorded for 300 s, and dissociation for 600 s.

Isothermal Titration Calorimetry.

ITC was performed using an Auto-iTC 200 instrument (GE Healthcare) using a protocol similar to one previously described [Julien J P, et al. (2013) PLoS Pathog 9: e1003342, Julien J P, et al. (2013) Proc Natl Acad Sci USA 110: 4351-4356]. Briefly, prior to conducting the titrations, proteins were dialyzed against Tris-saline buffer (150 mM NaCl, 20 mM Tris, pH 8.0). Absorbance at 280 nm using calculated extinction coefficients served to determine and adjust protein concentrations [Gasteiger E G A, et al. (2005) In: Walker J M, editor. The Proteomics Protocols Handbook: Humana Press. pp. 571-607]. The ligand present in the syringe was PGT121 Fab, PGT128 Fab or 2G12 IgG at concentrations ranging between 113 LM and 167 µM, while the BG505 SOSIP.664 trimer was present in the cell at a concentration of 4.3 µM. In each binding experiment, a 5 µcal reference power determination preceded the first injection of 0.5 µl, which was followed by 15 injections of 2.5 µl each at intervals of 180 s. Origin 7.0 software was used to derive the affinity constants (Kd), the molar reaction enthalpy (ΔH) and the stoichiometry of binding (N), by fitting the integrated titration peaks via a single-site binding model (PGT121) or a two-site binding model (PGT128 and 2G12). All measured and derived thermodynamic parameters of binding are reported in Table 3.

Electron Microscopy.

SEC-purified BG505 SOSIP.664 gp140 trimers, either alone or as Fab complexes (with b6, F240, 14e, 19b, PGV04, sCD4/17b), were analyzed by negative stain EM. A 3 µL aliquot containing about 0.03 mg/mL of the trimer or Fab-trimer complex was applied for 5 s onto a carbon-coated 400 Cu mesh grid that had been glow discharged at 20 mA for 30 s, then negatively stained with Uranyl formate or Nano-W (Nanoprobes) for 30 s. Data were collected using a FEI Tecnai F20 or T12 electron microscope operating at 120 keV, with an electron dose of about 55 $e^-/A^2$ and a magnification of 52,000× that resulted in a pixel size of 2.05 A at the specimen plane. Images were acquired with a Gatan US4000 CCD or Tietz TemCam-F416 CMOS camera using a nominal defocus range of 900 to 1300 nm.

Image Processing and 3D Reconstruction.

Particles were picked automatically using DoG Picker and put into a particle stack using the Appion software package [Voss N R, et al. (2009) J Struct Biol 166: 205-213, Lander G C, et al. (2009) J Struct Biol 166: 95-102]. Initial, reference-free, two-dimensional (2D) class averages were calculated using particles binned by five via the Xmipp Clustering 2D Alignment [Sorzano C O, et al. (2010) J Struct Biol 171: 197-206] and sorted into classes. Particles corresponding to trimers or complexes were selected into a substack and binned by four before another round of reference-free alignment was carried out using the Xmipp Clustering and 2D alignment and IMAGIC software systems [van Heel M, et al. (1996) J Struct Biol 116: 17-24]. To analyze the interactions of the non-neutralizing Fabs (b6, F240, 14e, 19b) with BG505 SOSIP. 664 gp140 trimers, the reference-free 2D class averages were examined. The Fabs were clearly visualized if they are bound to the trimer, allowing the percentage of bound trimers relative to unbound trimers to be tabulated.

For Fab-containing complexes, the unliganded trimer (EMDB 5019; [Liu J, et al. (2008) Nature 455: 109-113]) was used as the initial model and refined against reference-free 2D class averages for 89 iterations without imposing symmetry. Fab densities were visible after 3 iterations. This model was then refined against raw particles for an additional 89 cycles with C3 symmetry imposed. For the unliganded BG505 SOSIP.664 gp140 trimer, an ab initio common lines model was calculated from reference-free 2D class averages in EMAN2 [Tang G, et al. (2007) J Struct Biol 157: 38-46]. The final volumes for the EMDB 5019 trimer and BG505 SOSIP.664 gp140 trimer reconstructions were nearly identical. EMAN [Ludtke S J. et al. (1999) J Struct Biol 128: 82-97] was used for all 3D reconstructions. For the 3D average of BG505 SOSIP.664 with PGV04, 32,867 particles were included in the final reconstruction. For the 3D average of BG505 SOSIP.664 in complex with sCD4 and 17b, 22,145 particles were included in the final reconstruction. For the 3D average of unliganded BG505, 15,352 particles were included in the final reconstruction.

Example 6

Immunogenicity of BG505 SOSIP.664 Trimers

BG505 is a founder virus. Primary infections often generate strong autologous NAb responses that, over several years, sometimes broaden into bNabs (maybe ~25% of cases). BG505 SOSIP.664 gp140 trimers have a favorable antigenic profile and structure (as per the other talks). A question is whether these trimers mimic the primary infection scenario. Immunogenicity studies may show how to design better or additional native-like trimers for eventual bNAb induction.

Three animal experiments were conducted (two in rabbits, one in macaques). Sera were analyzed for Nabs in-house using a Tzm-bl assay. The Tzm-bl assay data was generally concordant among test labs.

FIG. 26 shows that HIV-1 BG505.T332N has a Tier 2 phenotype, with FIG. 26A showing assays performed with sera from 8 subtype A infected subjects and FIG. 26B showing assays with Tier 1-specific MAbs.

A rabbit study was performed to demonstrate the immunogenicity of BG505 SOSIP.664 trimers. BG505 SOSIP.664 gp140 trimers vs. BG505 gp120 monomers, from 293S cells (also uncleaved YU2 gp140-Foldon), were in an ISCOMATRIX adjuvant. Immunizations (30 µg protein/dose) were at weeks 0, 4 and 20. A strong autologous response was seen after a 3rd immunization. BG505 SOSIP.664 trimers were superior to gp120 monomers in inducing an immune response.

In another rabbit study, BG505 SOSIP.664 gp140 trimers were made in 293T cells, 293S cells or 293S cells+EndoH digestion (hence different glycan profiles), all in an ISCOMATRIX adjuvant. Immunizations (30 µg protein/dose) were at weeks 0, 4 and 20. A strong autologous response was seen after a 3rd immunization. There was no obvious influence of glycan profile on an NAb response.

A macaque study was performed to demonstrate the immunogenicity of BG505 SOSIP.664 trimers. BG505 SOSIP.664 gp140 trimers vs. BG505 gp120 monomers, from 293T cells, were in an ISCOMATRIX adjuvant. Immunizations (100 µg protein/dose) were at weeks 0, 4, 12, 24. A strong autologous response seen after a 4th immunization. BG505 SOSIP.664 trimers were superior to gp120 monomers.

FIG. 27 depicts an autologous (BG505; Tier-2) Nabs in rabbits and macaques, specifically BG505 SOSIP.664 gp140 trimers vs. BG505 gp120 monomers (also YU2 uncleaved gp140-Foldon in rabbits) (Tzm-bl assay, Sera from weeks 20-24, after 3 or 4 immunizations).

FIG. 28 depicts a heterologous Tier-2 NAb responses in rabbits and macaques, specifically BG505 SOSIP.664 gp140 trimers vs. BG505 gp120 monomers vs. YU2 uncleaved gp140-Foldon (Tzm-bl assay, Sera from week 20, after 3 immunizations).

FIG. 29 depicts a heterologous Tier-1B NAb responses in rabbits, specifically BG505 SOSIP.664 gp140 trimers vs. BG505 gp1120 monomers vs. YU2 uncleaved gp140-Foldon.

FIG. 30 depicts a heterologous Tier-1A NAb responses in rabbits, specifically BG505 SOSIP.664 gp140 trimers vs. BG505 gp120 monomers vs. YU2 uncleaved gp140-Foldon (AMC; Tzm-bl assay, Sera from week 20, after 3 immunizations).

The BG505 SOSIP.664 trimers provides a consistent, strong neutralization of the autologous Tier-2 BG505-T332N virus (18 of 19 animals; titers from 50-3000) in the Tzm-bl assay (not previously seen for other Envs), cross-neutralization of Tier-1A and -1B viruses, no/minimal cross-neutralization of Tier-2 viruses (including within subtype A) and a NAb profile (potency but not breadth) similar to primary HIV-1 infection—consistent with response to a native-like trimer from a founder virus.

SOSIP trimers are a platform for rational, structure-aided immunogen design aimed at inducing bNabs. Strategies include: removing/silencing unwanted immunodominant epitopes that induce non-Nabs and/or purely autologous Nabs, testing multiple trimers based on evolving sequences that lead to bNAb induction (BG505 and other longitudinal, intra-patient series) and trying a cocktail of trimers from the same or different subtypes.

The invention is further described by the following numbered paragraphs:

1. An engineered or non-naturally occurring HIV-1 envelope glycoprotein isolated from a BG505 virus and having a SOSIP mutation.

2. The glycoprotein of paragraph 1, wherein the glycoprotein is a BG505 SOSIP.664 trimer.

3. The glycoprotein of paragraph 2, wherein the glycoprotein is a modification of BG505 SOSIP.664.

4. The glycoprotein of paragraph 3, wherein the modification improves purification, stability, binding to broadly neutralizing antibodies, and/or limits binding to non-neutralizing antibodies.

5. The glycoprotein of paragraph 3 or 4, wherein the modification is (a) a replacement of signal sequence by the tPA leader to enhance secretion (b) mutations A501C and T605C (SOS) to stabilize gp20-gp41 association, (c) mutation REKR(508-511)RRRRRR (SEQ ID NOS 1 and 2, respectively) to enhance cleavage (d) mutation I559P to facilitate trimerization, (e) a truncation at position 664 to prevent MPER-mediated aggregation and/or (f) T332N to create 2G12, PGT125-PGT131 epitopes or any combination thereof.

6. The glycoprotein of paragraph 3, wherein the sequence of the glycoprotein comprises (SEQ ID NO: 3)
MDAMKRGLCCVLLLCGAVFVSPSQEIHARFRRGARAENLWVTVYYGVPVW
KDAETTLFCASDAKAYETEKHNVWATHACVPTDPNPQEIHLENVTEEFNM
WKNNMVEQMHTDIISLWDQSLKPCVKLTPLCVTLQCTNVTNNITDDMRGE
LKNCSFNMTTELRDKKQKVYSLFYRLDVVQINENQGNRSNNSNKEYRLIN
CNTSAITQACPKVSFEPIPIHYCAPAGFAILKCKDKKFNGTGPCPSVSTV
QCTHGIKPVVSTQLLLNGSLAEEEVMIRSENITNNAKNILVQFNTPVQIN
CTRPNNNTRKSIRIGPGQAFYATGDIIGDIRQAHCNVSKATWNETLGKVV
KQLRKHFGNNTIIRFANSSGGDLEVTTHSFNCGGEFFYCNTSGLFNSTWI
SNTSVQGSNSTGSNDSITLPCRIKQIINMWQRIGQAMYAPPIQGVIRCVS
NITGLILTRDGGSTNSTTETFRPGGGDMRDNWRSELYKYKVVKIEPLGVA
PTRCKRRVVGRRRRRRAVGIGAVFLGFLGAAGSTMGAASMTLTVQARNLL
SGIVQQQSNLLRAPEAQQHLLKLTVWGIKQLQARVLAVERYLRDQQLLGI
WGCSGKLICCTNVPWNSSWSNRNLSEIWDNMTWLQWDKEISNYTQIIYGL
LEESQNQQEKNEQDLLALD\*.

7. A method of eliciting an immune response comprising administering to a mammal the glycoprotein of any one of paragraphs 1 to 6.

8. The method of paragraph 7 further comprising an adjuvant.

9. The method of paragraph 8 wherein the adjuvant comprises a lecithin.

10. The method of paragraph 9 wherein the adjuvant is a lecithin is combined with an acrylic polymer, a lecithin coated oil droplet in an oil-in-water emulsion or a lecithin and an acrylic polymer in an oil-in-water emulsion.

11. The method of paragraph 8 wherein the adjuvant comprises alum.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An engineered or non-naturally occurring HIV-1 envelope glycoprotein isolated from a BG505 virus and having a SOSIP mutation
    wherein the glycoprotein is a BG505 SOSIP.664 gp140 trimer
    and
    wherein the SOSIP mutation comprises one or more mutations of the wild type amino acid alanine (A) or by wild type amino acid threonine (T) substitution with cysteine (C) (SOS mutation) and/or a mutation of the wild type amino acid isoleucine (I) by substitution with proline (P) (IP mutation);
    wherein the BG505 SOSIP.664 gp140 trimer is more compact than a KNH1144 SOSIP.664G trimer isolated from with respect to envelope volume; and
    wherein the BG505 SOSIP.664 gp140 trimer has a thermal denaturation midpoint (TM) of about 68 C.

2. An engineered or non-naturally occurring HIV-1 envelope glycoprotein isolated from a BG505 virus and having a SOSIP mutation, wherein the SOSIP mutation comprises a:

(a) mutation of the wild type amino acid threonine (T) by substitution with asparagine (N) to create 2G12, and PGT125, PGT126, PGT127, PGT128, PGT129, PGT130, and/or PGT 131 epitopes;
(b) mutation of the wild type amino acid isoleucine (I) by substitution with proline (P) to facilitation trimerization; or
(c) mutations of the wild type sequence REKR (SEQ ID NO: 1) at amino acid positions by substitution with RRRRRR (SEQ ID NO: 2) to enhance cleavage;
or any combination thereof.

3. An engineered or non-naturally occurring HIV-1 envelope comprising the amino acid sequence of SEQ ID NO: 3.

4. The glycoprotein of claim 1, wherein the SOSIP mutation comprises a mutation of the wild type amino acid alanine (A) at position 498 of SEQ ID NO: 5 by substitution with cysteine (C) (SOS mutation).

5. The glycoprotein of claim 1, wherein the SOSIP mutation comprises a mutation of the wild type amino acid threonine (T) at position 602 of SEQ ID NO: 5 by substitution with cysteine (C) (SOS mutation).

6. The glycoprotein of claim 1, wherein the SOSIP mutation comprises a mutation of the wild type amino acid isoleucine (I) at position 556 of SEQ ID NO: 5 by substitution with proline (P) (IP mutation).

7. The glycoprotein of claim 1,
wherein the SOSIP mutation comprises a mutation of the wild type amino acid alanine (A) at position 498 of SEQ ID NO: 5 by substitution with cysteine (C) and of the wild type amino acid threonine (T) at position 602 of SEQ ID NO: 5 by substitution with cysteine (C) (SOS mutation) and a mutation of the wild type amino acid isoleucine (I) at position 556 of SEQ ID NO: 5 by substitution with proline (P) (IP mutation).

8. The glycoprotein of claim 2, wherein the SOSIP mutation comprises a mutation of the wild type amino acid threonine (T) at position 330 of SEQ ID NO: 5 by substitution with asparagine (N).

9. The glycoprotein of claim 2, wherein the SOSIP mutation comprises a mutation of the wild type amino acid isoleucine (I) at position 556 of SEQ ID NO: 5 by substitution with proline (P).

10. The glycoprotein of claim 2, wherein the SOSIP mutation comprises mutations of the wild type sequence REKR (SEQ ID NO: 1) at amino acid positions 505-508 of SEQ ID NO: 5 by substitution with RRRRRR (SEQ ID NO: 2).

11. The glycoprotein of claim 2, wherein the SOSIP mutation comprises a
(a) mutation of the wild type amino acid threonine (T) at position 330 of SEQ ID NO: 5 by substitution with asparagine (N);
(b) mutation of the wild type amino acid isoleucine (I) at position 556 of SEQ ID NO: 5 by substitution with proline (P); and
(c) mutations of the wild type sequence REKR (SEQ ID NO: 1) at amino acid positions 505-508 of SEQ ID NO: 5 by substitution with RRRRRR (SEQ ID NO: 2).

12. The glycoprotein of claim 3 consisting essentially of the amino acid sequence of SEQ ID NO: 3.

13. The glycoprotein of claim 3 consisting of the amino acid sequence of SEQ ID NO: 3.

14. A method of eliciting an immune response comprising administering to a mammal the glycoprotein of claim 1.

15. The method of claim 14 further comprising an adjuvant.

16. The method of claim 15 wherein the adjuvant comprises alum.

17. A method of eliciting an immune response comprising administering to a mammal the glycoprotein of claim 3.

18. The method of claim 17 further comprising an adjuvant.

19. The method of claim 18 wherein the adjuvant comprises alu

* * * * *

SEQUENCE LISTING

```
<160> NUMBER OF SEQ ID NOS: 17

<210> SEQ ID NO 1
<211> LENGTH: 4
<212> TYPE: PRT
<213> ORGANISM: Human immunodeficiency virus 1

<400> SEQUENCE: 1

Arg Glu Lys Arg
1

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Arg Arg Arg Arg
1               5

<210> SEQ ID NO 3
<211> LENGTH: 669
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 3

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ala Glu Asn Leu Trp Val Thr Val Tyr Tyr Gly Val Pro
        35                  40                  45

Val Trp Lys Asp Ala Glu Thr Thr Leu Phe Cys Ala Ser Asp Ala Lys
50                  55                  60

Ala Tyr Glu Thr Glu Lys His Asn Val Trp Ala Thr His Ala Cys Val
65                  70                  75                  80

Pro Thr Asp Pro Asn Pro Gln Glu Ile His Leu Glu Asn Val Thr Glu
                85                  90                  95

Glu Phe Asn Met Trp Lys Asn Asn Met Val Glu Gln Met His Thr Asp
            100                 105                 110

Ile Ile Ser Leu Trp Asp Gln Ser Leu Lys Pro Cys Val Lys Leu Thr
        115                 120                 125

Pro Leu Cys Val Thr Leu Gln Cys Thr Asn Val Thr Asn Asn Ile Thr
130                 135                 140

Asp Asp Met Arg Gly Glu Leu Lys Asn Cys Ser Phe Asn Met Thr Thr
145                 150                 155                 160

Glu Leu Arg Asp Lys Lys Gln Lys Val Tyr Ser Leu Phe Tyr Arg Leu
                165                 170                 175

Asp Val Val Gln Ile Asn Glu Asn Gln Gly Asn Arg Ser Asn Asn Ser
            180                 185                 190

Asn Lys Glu Tyr Arg Leu Ile Asn Cys Asn Thr Ser Ala Ile Thr Gln
        195                 200                 205

Ala Cys Pro Lys Val Ser Phe Glu Pro Ile Pro Ile His Tyr Cys Ala
210                 215                 220

Pro Ala Gly Phe Ala Ile Leu Lys Cys Lys Asp Lys Lys Phe Asn Gly
225                 230                 235                 240

Thr Gly Pro Cys Pro Ser Val Ser Thr Val Gln Cys Thr His Gly Ile
                245                 250                 255

Lys Pro Val Val Ser Thr Gln Leu Leu Leu Asn Gly Ser Leu Ala Glu
            260                 265                 270

Glu Glu Val Met Ile Arg Ser Glu Asn Ile Thr Asn Asn Ala Lys Asn
        275                 280                 285

Ile Leu Val Gln Phe Asn Thr Pro Val Gln Ile Asn Cys Thr Arg Pro
290                 295                 300

Asn Asn Asn Thr Arg Lys Ser Ile Arg Ile Gly Pro Gly Gln Ala Phe
305                 310                 315                 320

Tyr Ala Thr Gly Asp Ile Ile Gly Asp Ile Arg Gln Ala His Cys Asn
                325                 330                 335

Val Ser Lys Ala Thr Trp Asn Glu Thr Leu Gly Lys Val Val Lys Gln
            340                 345                 350

Leu Arg Lys His Phe Gly Asn Asn Thr Ile Ile Arg Phe Ala Asn Ser
        355                 360                 365

Ser Gly Gly Asp Leu Glu Val Thr Thr His Ser Phe Asn Cys Gly Gly
370                 375                 380
```

```
Glu Phe Phe Tyr Cys Asn Thr Ser Gly Leu Phe Asn Ser Thr Trp Ile
385                 390                 395                 400

Ser Asn Thr Ser Val Gln Gly Ser Asn Ser Thr Gly Ser Asn Asp Ser
            405                 410                 415

Ile Thr Leu Pro Cys Arg Ile Lys Gln Ile Ile Asn Met Trp Gln Arg
            420                 425                 430

Ile Gly Gln Ala Met Tyr Ala Pro Pro Ile Gln Gly Val Ile Arg Cys
        435                 440                 445

Val Ser Asn Ile Thr Gly Leu Ile Leu Thr Arg Asp Gly Gly Ser Thr
    450                 455                 460

Asn Ser Thr Thr Glu Thr Phe Arg Pro Gly Gly Gly Asp Met Arg Asp
465                 470                 475                 480

Asn Trp Arg Ser Glu Leu Tyr Lys Tyr Lys Val Val Lys Ile Glu Pro
                485                 490                 495

Leu Gly Val Ala Pro Thr Arg Cys Lys Arg Arg Val Val Gly Arg Arg
            500                 505                 510

Arg Arg Arg Arg Ala Val Gly Ile Gly Ala Val Phe Leu Gly Phe Leu
        515                 520                 525

Gly Ala Ala Gly Ser Thr Met Gly Ala Ala Ser Met Thr Leu Thr Val
    530                 535                 540

Gln Ala Arg Asn Leu Leu Ser Gly Ile Val Gln Gln Ser Asn Leu
545                 550                 555                 560

Leu Arg Ala Pro Glu Ala Gln Gln His Leu Leu Lys Leu Thr Val Trp
                565                 570                 575

Gly Ile Lys Gln Leu Gln Ala Arg Val Leu Ala Val Glu Arg Tyr Leu
            580                 585                 590

Arg Asp Gln Gln Leu Leu Gly Ile Trp Gly Cys Ser Gly Lys Leu Ile
        595                 600                 605

Cys Cys Thr Asn Val Pro Trp Asn Ser Ser Trp Ser Asn Arg Asn Leu
    610                 615                 620

Ser Glu Ile Trp Asp Asn Met Thr Trp Leu Gln Trp Asp Lys Glu Ile
625                 630                 635                 640

Ser Asn Tyr Thr Gln Ile Ile Tyr Gly Leu Leu Glu Glu Ser Gln Asn
                645                 650                 655

Gln Gln Glu Lys Asn Glu Gln Asp Leu Leu Ala Leu Asp
            660                 665

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5

<210> SEQ ID NO 5
<211> LENGTH: 860
<212> TYPE: PRT
<213> ORGANISM: Human immunodeficiency virus 1

<400> SEQUENCE: 5

Met Arg Val Met Gly Ile Gln Arg Asn Cys Gln His Leu Phe Arg Trp
1               5                   10                  15
```

```
Gly Thr Met Ile Leu Gly Met Ile Ile Cys Ser Ala Ala Glu Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Gln Cys Thr Asn Val Thr Asn Asn Ile Thr Asp Asp Met Arg Gly Glu
    130                 135                 140

Leu Lys Asn Cys Ser Phe Asn Met Thr Thr Glu Leu Arg Asp Lys Lys
145                 150                 155                 160

Gln Lys Val Tyr Ser Leu Phe Tyr Arg Leu Asp Val Val Gln Ile Asn
                165                 170                 175

Glu Asn Gln Gly Asn Arg Ser Asn Asn Ser Asn Lys Glu Tyr Arg Leu
            180                 185                 190

Ile Asn Cys Asn Thr Ser Ala Ile Thr Gln Ala Cys Pro Lys Val Ser
        195                 200                 205

Phe Glu Pro Ile Pro Ile His Tyr Cys Ala Pro Ala Gly Phe Ala Ile
    210                 215                 220

Leu Lys Cys Lys Asp Lys Lys Phe Asn Gly Thr Gly Pro Cys Pro Ser
225                 230                 235                 240

Val Ser Thr Val Gln Cys Thr His Gly Ile Lys Pro Val Val Ser Thr
                245                 250                 255

Gln Leu Leu Leu Asn Gly Ser Leu Ala Glu Glu Val Met Ile Arg
            260                 265                 270

Ser Glu Asn Ile Thr Asn Asn Ala Lys Asn Ile Leu Val Gln Phe Asn
        275                 280                 285

Thr Pro Val Gln Ile Asn Cys Thr Arg Pro Asn Asn Asn Thr Arg Lys
    290                 295                 300

Ser Ile Arg Ile Gly Pro Gly Gln Ala Phe Tyr Ala Thr Gly Asp Ile
305                 310                 315                 320

Ile Gly Asp Ile Arg Gln Ala His Cys Thr Val Ser Lys Ala Thr Trp
                325                 330                 335

Asn Glu Thr Leu Gly Lys Val Val Lys Gln Leu Arg Lys His Phe Gly
            340                 345                 350

Asn Asn Thr Ile Ile Arg Phe Ala Asn Ser Ser Gly Gly Asp Leu Glu
        355                 360                 365

Val Thr Thr His Ser Phe Asn Cys Gly Gly Glu Phe Phe Tyr Cys Asn
    370                 375                 380

Thr Ser Gly Leu Phe Asn Ser Thr Trp Ile Ser Asn Thr Ser Val Gln
385                 390                 395                 400

Gly Ser Asn Ser Thr Gly Ser Asn Asp Ser Ile Thr Leu Pro Cys Arg
                405                 410                 415

Ile Lys Gln Ile Ile Asn Met Trp Gln Arg Ile Gly Gln Ala Met Tyr
            420                 425                 430

Ala Pro Pro Ile Gln Gly Val Ile Arg Cys Val Ser Asn Ile Thr Gly
```

```
                    435                 440                 445
Leu Ile Leu Thr Arg Asp Gly Gly Ser Thr Asn Ser Thr Thr Glu Thr
            450                 455                 460
Phe Arg Pro Gly Gly Gly Asp Met Arg Asp Asn Trp Arg Ser Glu Leu
465                 470                 475                 480
Tyr Lys Tyr Lys Val Lys Ile Glu Pro Leu Gly Val Ala Pro Thr
                    485                 490                 495
Arg Ala Lys Arg Val Val Gly Arg Glu Lys Arg Ala Val Gly Ile
            500                 505                 510
Gly Ala Val Phe Leu Gly Phe Leu Gly Ala Ala Gly Ser Thr Met Gly
            515                 520                 525
Ala Ala Ser Met Thr Leu Thr Val Gln Ala Arg Asn Leu Leu Ser Gly
            530                 535                 540
Ile Val Gln Gln Gln Ser Asn Leu Leu Arg Ala Ile Glu Ala Gln Gln
545                 550                 555                 560
His Leu Leu Lys Leu Thr Val Trp Gly Ile Lys Gln Leu Gln Ala Arg
                    565                 570                 575
Val Leu Ala Val Glu Arg Tyr Leu Arg Asp Gln Gln Leu Leu Gly Ile
            580                 585                 590
Trp Gly Cys Ser Gly Lys Leu Ile Cys Thr Thr Asn Val Pro Trp Asn
            595                 600                 605
Ser Ser Trp Ser Asn Arg Asn Leu Ser Glu Ile Trp Asp Asn Met Thr
            610                 615                 620
Trp Leu Gln Trp Asp Lys Glu Ile Ser Asn Tyr Thr Gln Ile Ile Tyr
625                 630                 635                 640
Gly Leu Leu Glu Glu Ser Gln Asn Gln Gln Glu Lys Asn Glu Gln Asp
                    645                 650                 655
Leu Leu Ala Leu Asp Lys Trp Ala Ser Leu Trp Asn Trp Phe Asp Ile
            660                 665                 670
Ser Asn Trp Leu Trp Tyr Ile Lys Ile Phe Ile Met Ile Val Gly Gly
            675                 680                 685
Leu Ile Gly Leu Arg Ile Val Phe Ala Val Leu Ser Val Ile His Arg
            690                 695                 700
Val Arg Gln Gly Tyr Ser Pro Leu Ser Phe Gln Thr His Thr Pro Asn
705                 710                 715                 720
Pro Arg Gly Leu Asp Arg Pro Glu Arg Ile Glu Glu Asp Gly Glu
                    725                 730                 735
Gln Asp Arg Gly Arg Ser Thr Arg Leu Val Ser Gly Phe Leu Ala Leu
            740                 745                 750
Ala Trp Asp Asp Leu Arg Ser Leu Cys Leu Phe Cys Tyr His Arg Leu
            755                 760                 765
Arg Asp Phe Ile Leu Ile Ala Ala Arg Ile Val Glu Leu Leu Gly His
            770                 775                 780
Ser Ser Leu Lys Gly Leu Arg Leu Gly Trp Glu Gly Leu Lys Tyr Leu
785                 790                 795                 800
Trp Asn Leu Leu Ala Tyr Trp Gly Arg Glu Leu Lys Ile Ser Ala Ile
                    805                 810                 815
Asn Leu Phe Asp Thr Ile Ala Ile Ala Val Ala Glu Trp Thr Asp Arg
            820                 825                 830
Val Ile Glu Ile Gly Gln Arg Leu Cys Arg Ala Phe Leu His Ile Pro
            835                 840                 845
Arg Arg Ile Arg Gln Gly Leu Glu Arg Ala Leu Leu
            850                 855                 860
```

<210> SEQ ID NO 6
<211> LENGTH: 2583
<212> TYPE: DNA
<213> ORGANISM: Human immunodeficiency virus 1

<400> SEQUENCE: 6

```
atgagagtga tggggataca gaggaattgt cagcacttat tcagatgggg aactatgatc      60
ttggggatga taataatctg tagtgcagca gaaaacttgt gggtcactgt ctactatggg     120
gtacctgtgt ggaaagacgc agagaccacc ttattttgtg catcagatgc taaagcatat     180
gagacagaaa agcataatgt ctgggctaca catgcctgtg tacccacaga ccccaaccca     240
caagaaatac atttggaaaa tgtgactgaa gagtttaaca tgtggaaaaa taacatggta     300
gagcagatgc atacagatat catcagtcta tgggaccaaa gcctaaagcc atgtgtaaag     360
ttaaccccctc tctgcgttac tctacagtgt accaatgtca ccaataatat cactgatgac     420
atgaggggag aattaaaaaa ctgctctttc aatatgacca cagagctaag ggataagaaa     480
cagaaggttt attcactttt ttatagacta gatgtagtac aaattaacga gatcaaggt     540
aataggagta taatagtaa caaggagtat agattaataa attgtaatac ctcagccatt     600
acacaggctt gtccaaaggt atcctttgag ccaattccca tacattattg tgccccagct     660
ggttttgcga tcctaaagtg taaggataag aagttcaatg gaacagggcc atgcccaagt     720
gtcagcacag tacaatgcac acatggaatc aagccagtag tatcaactca actgctgtta     780
aatggcagtc tagcagaaga gaggtaatg attagatctg aaaatatcac aaacaatgcc     840
aaaaacatac tagtacaatt taacacgcct gtgcaaatta attgtaccag acctaacaac     900
aatacaagga aaagtatacg tataggacca ggacaagcat tctatgcaac aggggacata     960
atagggataa agacaagca cattgtact gtcagtaaag caacatggaa tgaaactttg    1020
ggaaaggtgg tcaaacaatt aagaaaacac tttgggaaca cacaataat aagatttgct    1080
aattcctcag gaggggatct agaagtcaca acacatagtt ttaattgtgg aggagaattt    1140
ttctattgta acacatcagg cctgttcaat agcacttgga ttagcaatac agcgtgcag    1200
gggtcaaata gcacggggtc aaatgacagt ataactctcc catgcagaat aaagcaaatt    1260
ataaatatgt ggcagagaat aggacaagca atgtatgccc ctcccatcca aggagtaata    1320
agatgtgtat caaacattac agggctaata ttaacaagag atggtgggag tactaatagt    1380
acaactgaaa ccttcagacc tggaggagga gatatgaggg acaattggag aagtgaatta    1440
tataagtata agtagtaaaa aattgaacca ctaggagtag cacccaccag gcaaagaga    1500
agagtggtgg ggagagaaaa aagagcagtt ggaataggag ctgtcttcct tgggttctta    1560
ggagcagcag gaagcactat gggcgcggcg tcaatgacgc tgacggtaca ggccagaaat    1620
ttattatctg gcatagtgca acagcaaagc aatttgctga ggctataga ggctcaacaa    1680
catctgttga actcacggt ctggggcatt aaacagctcc aggcaagggt cctggctgtg    1740
gaaagatacc taagggatca acagcttcta ggaatttggg gctgctctgg aaaactcatc    1800
tgcaccacta atgtgccctg gaactctagt tggagtaata aaaacctgag tgagatatgg    1860
gacaacatga cctggctgca atgggataaa gaaattagca attacacaca gataatatat    1920
gggctacttg aagaatcgca gaaccagcag gaaaagaatg aacaagactt attggcattg    1980
gataagtggg caagtctgtg gaattggttt gacatatcaa actggctgtg gtatataaaa    2040
atatttataa tgatagtagg aggcttaata ggattaagaa tagttttgc tgtgctttct    2100
```

-continued

```
gtaatacata gagttaggca gggatactca cctttgtcgt ttcagaccca taccccaaac    2160
ccaaggggac tcgacaggcc cgaaagaatc gaagaagaag atggagagca agacagaggc    2220
agatcgacgc gattagtgag cggattctta gctcttgcct gggacgatct gaggagcctg    2280
tgcctcttct gctaccaccg attgagagac ttcatcttga ttgcagcgag gattgtggaa    2340
cttctgggac acagcagtct caaggggttg agactggggt gggaaggcct caagtatctg    2400
tggaatctcc tggcatattg gggtcgggaa ctaaaaatta gtgctattaa tttgtttgat    2460
accatagcaa tagcagtagc tgagtggaca gatagggtta tagaaatagg acaaagactt    2520
tgtagagctt ttctccacat acctagaaga atcagacagg gcctcgaaag ggctttgcta    2580
taa                                                                  2583
```

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ser Gly Ser Gly Gly Ser Gly His His His His His His His His
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Ala Pro Thr Lys Ala Lys Arg Arg Val Val Gln Arg Glu Lys
1               5                   10                  15

Arg

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ala Lys Arg Arg Val Val Gly Ser Glu Lys Ser Gly His His His
1               5                   10                  15

His His His

<210> SEQ ID NO 10
<211> LENGTH: 1569
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (21)..(1550)

<400> SEQUENCE: 10

```
ggcgcgccga attcgccacc atg cct atg ggc agc ctg cag cct ctg gcc aca    53
```

```
                    Met Pro Met Gly Ser Leu Gln Pro Leu Ala Thr
                    1               5                   10 ctg tac ctg ctg ggc atg ctg gtg gcc tct gtg ctg gcc gcc gag aac      101
Leu Tyr Leu Leu Gly Met Leu Val Ala Ser Val Leu Ala Ala Glu Asn
            15                  20                  25 ctg tgg gtg aca gtg tac tac ggc gtg ccc gtg tgg aag gac gcc gag      149
Leu Trp Val Thr Val Tyr Tyr Gly Val Pro Val Trp Lys Asp Ala Glu
        30                  35                  40 aca acc ctg ttc tgc gcc agc gac gcc aag gcc tac gag aca gag aag      197
Thr Thr Leu Phe Cys Ala Ser Asp Ala Lys Ala Tyr Glu Thr Glu Lys
    45                  50                  55 cac aac gtg tgg gcc acc cac gcc tgc gtg cca acc gac cct aac ccc      245
His Asn Val Trp Ala Thr His Ala Cys Val Pro Thr Asp Pro Asn Pro
60                  65                  70                  75 cag gaa atc cac ctg gaa aac gtg acc gaa gag ttc aac atg tgg aag      293
Gln Glu Ile His Leu Glu Asn Val Thr Glu Glu Phe Asn Met Trp Lys
                80                  85                  90 aac aac atg gtg gaa cag atg cac acc gac atc atc agc ctg tgg gac      341
Asn Asn Met Val Glu Gln Met His Thr Asp Ile Ile Ser Leu Trp Asp
            95                  100                 105 cag agc ctg aag ccc tgc gtg aag ctg acc ccc ctg tgc gtg acc ctg      389
Gln Ser Leu Lys Pro Cys Val Lys Leu Thr Pro Leu Cys Val Thr Leu
        110                 115                 120 cag tgc acc aac gtg acc aac aac atc acc gac gac atg cgg ggc gag      437
Gln Cys Thr Asn Val Thr Asn Asn Ile Thr Asp Asp Met Arg Gly Glu
    125                 130                 135 ctg aag aac tgc agc ttc aac atg acc acc gag ctg cgg gac aag aaa      485
Leu Lys Asn Cys Ser Phe Asn Met Thr Thr Glu Leu Arg Asp Lys Lys
140                 145                 150                 155 cag aag gtg tac agc ctg ttc tac cgg ctg gac gtg gtg cag atc aac      533
Gln Lys Val Tyr Ser Leu Phe Tyr Arg Leu Asp Val Val Gln Ile Asn
                160                 165                 170 gag aac cag ggc aac aga agc aac aac agc aac aaa gag tac cgg ctg      581
Glu Asn Gln Gly Asn Arg Ser Asn Asn Ser Asn Lys Glu Tyr Arg Leu
            175                 180                 185 atc aac tgc aac acc agc gcc atc acc cag gcc tgc ccc aag gtg tcc      629
Ile Asn Cys Asn Thr Ser Ala Ile Thr Gln Ala Cys Pro Lys Val Ser
        190                 195                 200 ttc gag ccc atc ccc atc cac tac tgc gcc cct gcc ggc ttc gcc atc      677
Phe Glu Pro Ile Pro Ile His Tyr Cys Ala Pro Ala Gly Phe Ala Ile
    205                 210                 215 ctg aag tgc aag gac aag aag ttc aac ggc acc ggc ccc tgc ccc agc      725
Leu Lys Cys Lys Asp Lys Lys Phe Asn Gly Thr Gly Pro Cys Pro Ser
220                 225                 230                 235 gtg tcc aca gtg cag tgt acc cac ggc atc aag ccc gtg gtc tcc acc      773
Val Ser Thr Val Gln Cys Thr His Gly Ile Lys Pro Val Val Ser Thr
                240                 245                 250 cag ctg ctg ctg aac ggc agc ctg gcc gaa gag gaa gtg atg atc aga      821
Gln Leu Leu Leu Asn Gly Ser Leu Ala Glu Glu Glu Val Met Ile Arg
            255                 260                 265 agc gag aac atc acc aac aac gcc aag aac atc ctg gtg cag ttc aac      869
Ser Glu Asn Ile Thr Asn Asn Ala Lys Asn Ile Leu Val Gln Phe Asn
        270                 275                 280 acc ccc gtg cag att aac tgc acc cgg ccc aac aac aac acc aga aag      917
Thr Pro Val Gln Ile Asn Cys Thr Arg Pro Asn Asn Asn Thr Arg Lys
    285                 290                 295 agc atc cgg atc ggc cca ggc cag gcc ttc tac gcc acc ggc gac atc      965
Ser Ile Arg Ile Gly Pro Gly Gln Ala Phe Tyr Ala Thr Gly Asp Ile
300                 305                 310                 315
```

```
atc ggc gac atc cgg cag gcc cac tgc acc gtg tcc aag gcc acc tgg      1013
Ile Gly Asp Ile Arg Gln Ala His Cys Thr Val Ser Lys Ala Thr Trp
            320                 325                 330 aac gag aca ctg ggc aag gtg gtg aaa cag ctg cgg aag cac ttc ggg      1061
Asn Glu Thr Leu Gly Lys Val Val Lys Gln Leu Arg Lys His Phe Gly
            335                 340                 345 aac aac acc atc atc cgc ttc gcc aac agc tct ggc ggc gac ctg gaa      1109
Asn Asn Thr Ile Ile Arg Phe Ala Asn Ser Ser Gly Gly Asp Leu Glu
            350                 355                 360 gtg acc acc cac agc ttc aac tgt ggc ggc gag ttc ttc tac tgc aat      1157
Val Thr Thr His Ser Phe Asn Cys Gly Gly Glu Phe Phe Tyr Cys Asn
            365                 370                 375 acc tcc ggc ctg ttc aac agc acc tgg atc agc aat acc agc gtg cag      1205
Thr Ser Gly Leu Phe Asn Ser Thr Trp Ile Ser Asn Thr Ser Val Gln
380                 385                 390                 395 ggc agc aac agc acc ggc agc aac gac agc atc acc ctg ccc tgc cgg      1253
Gly Ser Asn Ser Thr Gly Ser Asn Asp Ser Ile Thr Leu Pro Cys Arg
                400                 405                 410 atc aag cag atc atc aat atg tgg cag cgg att ggc cag gct atg tac      1301
Ile Lys Gln Ile Ile Asn Met Trp Gln Arg Ile Gly Gln Ala Met Tyr
            415                 420                 425 gcc cca ccc atc cag ggc gtg atc aga tgc gtg tcc aat atc acc ggc      1349
Ala Pro Pro Ile Gln Gly Val Ile Arg Cys Val Ser Asn Ile Thr Gly
            430                 435                 440 ctg atc ctg acc cgg gac ggc ggc tct acc aac agc acc acc gaa acc      1397
Leu Ile Leu Thr Arg Asp Gly Gly Ser Thr Asn Ser Thr Thr Glu Thr
445                 450                 455 ttc aga ccc ggc gga ggc gac atg aga gac aac tgg cgg agc gag ctg      1445
Phe Arg Pro Gly Gly Gly Asp Met Arg Asp Asn Trp Arg Ser Glu Leu
460                 465                 470                 475 tac aag tac aaa gtg gtg aaa atc gag ccc ctg ggc gtg gcc ccc acc      1493
Tyr Lys Tyr Lys Val Val Lys Ile Glu Pro Leu Gly Val Ala Pro Thr
                480                 485                 490 aga gcc aag aga aga gtg gtc gga agc gag aag tcc ggc cac cac cac      1541
Arg Ala Lys Arg Arg Val Val Gly Ser Glu Lys Ser Gly His His His
            495                 500                 505 cat cac cac tgagcggccg cttaattaa                                     1569
His His His
        510

<210> SEQ ID NO 11
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
```

```
                        85                  90                  95
Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
            115                 120                 125

Thr Asn Asn Ile Thr Asp Asp Met Arg Gly Glu Leu Lys Asn Cys Ser
            130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190

Ser Ala Ile Thr Gln Ala Cys Pro Lys Val Ser Phe Glu Pro Ile Pro
            195                 200                 205

Ile His Tyr Cys Ala Pro Ala Gly Phe Ala Ile Leu Lys Cys Lys Asp
            210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Val Met Ile Arg Ser Glu Asn Ile Thr
            260                 265                 270

Asn Asn Ala Lys Asn Ile Leu Val Gln Phe Asn Thr Pro Val Gln Ile
            275                 280                 285

Asn Cys Thr Arg Pro Asn Asn Asn Thr Arg Lys Ser Ile Arg Ile Gly
            290                 295                 300

Pro Gly Gln Ala Phe Tyr Ala Thr Gly Asp Ile Ile Gly Asp Ile Arg
305                 310                 315                 320

Gln Ala His Cys Thr Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
            355                 360                 365

Phe Asn Cys Gly Gly Glu Phe Phe Tyr Cys Asn Thr Ser Gly Leu Phe
            370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415

Asn Met Trp Gln Arg Ile Gly Gln Ala Met Tyr Ala Pro Pro Ile Gln
            420                 425                 430

Gly Val Ile Arg Cys Val Ser Asn Ile Thr Gly Leu Ile Leu Thr Arg
            435                 440                 445

Asp Gly Gly Ser Thr Asn Ser Thr Thr Glu Thr Phe Arg Pro Gly Gly
            450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Arg Arg
                485                 490                 495

Val Val Gly Ser Glu Lys Ser Gly His His His His His
            500                 505                 510
```

<210> SEQ ID NO 12
<211> LENGTH: 2091
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (21)..(2072)

<400> SEQUENCE: 12

```
ggcgcgccga attcgccacc atg cct atg ggc agc ctg cag cct ctg gcc aca        53
                     Met Pro Met Gly Ser Leu Gln Pro Leu Ala Thr
                      1               5                  10 ctg tac ctg ctg ggc atg ctg gtg gcc tct gtg ctg gcc gcc gag aac         101
Leu Tyr Leu Leu Gly Met Leu Val Ala Ser Val Leu Ala Ala Glu Asn
             15                  20                  25 ctg tgg gtg aca gtg tac tac ggc gtg ccc gtg tgg aag gac gcc gag         149
Leu Trp Val Thr Val Tyr Tyr Gly Val Pro Val Trp Lys Asp Ala Glu
         30                  35                  40 aca acc ctg ttc tgc gcc agc gac gcc aag gcc tac gag aca gag aag         197
Thr Thr Leu Phe Cys Ala Ser Asp Ala Lys Ala Tyr Glu Thr Glu Lys
     45                  50                  55 cac aac gtg tgg gcc acc cac gcc tgc gtg cca acc gac cct aac ccc         245
His Asn Val Trp Ala Thr His Ala Cys Val Pro Thr Asp Pro Asn Pro
 60                  65                  70                  75 cag gaa atc cac ctg gaa aac gtg acc gaa gag ttc aac atg tgg aag         293
Gln Glu Ile His Leu Glu Asn Val Thr Glu Glu Phe Asn Met Trp Lys
                 80                  85                  90 aac aac atg gtg gaa cag atg cac acc gac atc atc agc ctg tgg gac         341
Asn Asn Met Val Glu Gln Met His Thr Asp Ile Ile Ser Leu Trp Asp
             95                 100                 105 cag agc ctg aag ccc tgc gtg aag ctg acc ccc ctg tgc gtg acc ctg         389
Gln Ser Leu Lys Pro Cys Val Lys Leu Thr Pro Leu Cys Val Thr Leu
        110                 115                 120 cag tgc acc aac gtg acc aac aac atc acc gac gac atg cgg ggc gag         437
Gln Cys Thr Asn Val Thr Asn Asn Ile Thr Asp Asp Met Arg Gly Glu
    125                 130                 135 ctg aag aac tgc agc ttc aac atg acc acc gag ctg cgg gac aag aaa         485
Leu Lys Asn Cys Ser Phe Asn Met Thr Thr Glu Leu Arg Asp Lys Lys
140                 145                 150                 155 cag aag gtg tac agc ctg ttc tac cgg ctg gac gtg gtg cag atc aac         533
Gln Lys Val Tyr Ser Leu Phe Tyr Arg Leu Asp Val Val Gln Ile Asn
                160                 165                 170 gag aac cag ggc aac aga agc aac aac agc aac aaa gag tac cgg ctg         581
Glu Asn Gln Gly Asn Arg Ser Asn Asn Ser Asn Lys Glu Tyr Arg Leu
            175                 180                 185 atc aac tgc aac acc agc gcc atc acc cag gcc tgc ccc aag gtg tcc         629
Ile Asn Cys Asn Thr Ser Ala Ile Thr Gln Ala Cys Pro Lys Val Ser
        190                 195                 200 ttc gag ccc atc ccc atc cac tac tgc gcc cct gcc ggc ttc gcc atc         677
Phe Glu Pro Ile Pro Ile His Tyr Cys Ala Pro Ala Gly Phe Ala Ile
    205                 210                 215 ctg aag tgc aag gac aag aag ttc aac ggc acc ggc ccc tgc ccc agc         725
Leu Lys Cys Lys Asp Lys Lys Phe Asn Gly Thr Gly Pro Cys Pro Ser
220                 225                 230                 235 gtg tcc aca gtg cag tgt acc cac ggc atc aag ccc gtg gtg tcc acc         773
Val Ser Thr Val Gln Cys Thr His Gly Ile Lys Pro Val Val Ser Thr
                240                 245                 250
```

-continued

| | |
|---|---|
| cag ctg ctg ctg aac ggc agc ctg gcc gaa gag gaa gtg atg atc aga<br>Gln Leu Leu Leu Asn Gly Ser Leu Ala Glu Glu Glu Val Met Ile Arg<br>255 260 265 | 821 |
| agc gag aac atc acc aac aac gcc aag aac atc ctg gtg cag ttc aac<br>Ser Glu Asn Ile Thr Asn Asn Ala Lys Asn Ile Leu Val Gln Phe Asn<br>270 275 280 | 869 |
| acc ccc gtg cag att aac tgc acc cgg ccc aac aac aac acc aga aag<br>Thr Pro Val Gln Ile Asn Cys Thr Arg Pro Asn Asn Asn Thr Arg Lys<br>285 290 295 | 917 |
| agc atc cgg atc ggc cca ggc cag gcc ttc tac gcc acc ggc gac atc<br>Ser Ile Arg Ile Gly Pro Gly Gln Ala Phe Tyr Ala Thr Gly Asp Ile<br>300 305 310 315 | 965 |
| atc ggc gac atc cgg cag gcc cac tgc acc gtg tcc aag gcc acc tgg<br>Ile Gly Asp Ile Arg Gln Ala His Cys Thr Val Ser Lys Ala Thr Trp<br>320 325 330 | 1013 |
| aac gag aca ctg ggc aag gtg gtg aaa cag ctg cgg aag cac ttc ggg<br>Asn Glu Thr Leu Gly Lys Val Val Lys Gln Leu Arg Lys His Phe Gly<br>335 340 345 | 1061 |
| aac aac acc atc atc cgc ttc gcc aac agc tct ggc ggc gac ctg gaa<br>Asn Asn Thr Ile Ile Arg Phe Ala Asn Ser Ser Gly Gly Asp Leu Glu<br>350 355 360 | 1109 |
| gtg acc acc cac agc ttc aac tgt ggc ggc gag ttc ttc tac tgc aat<br>Val Thr Thr His Ser Phe Asn Cys Gly Gly Glu Phe Phe Tyr Cys Asn<br>365 370 375 | 1157 |
| acc tcc ggc ctg ttc aac agc acc tgg atc agc aat acc agc gtg cag<br>Thr Ser Gly Leu Phe Asn Ser Thr Trp Ile Ser Asn Thr Ser Val Gln<br>380 385 390 395 | 1205 |
| ggc agc aac agc acc ggc agc aac gac agc atc acc ctg ccc tgc cgg<br>Gly Ser Asn Ser Thr Gly Ser Asn Asp Ser Ile Thr Leu Pro Cys Arg<br>400 405 410 | 1253 |
| atc aag cag atc atc aat atg tgg cag cgg att ggc cag gct atg tac<br>Ile Lys Gln Ile Ile Asn Met Trp Gln Arg Ile Gly Gln Ala Met Tyr<br>415 420 425 | 1301 |
| gcc cca ccc atc cag ggc gtg atc aga tgc gtg tcc aat atc acc ggc<br>Ala Pro Pro Ile Gln Gly Val Ile Arg Cys Val Ser Asn Ile Thr Gly<br>430 435 440 | 1349 |
| ctg atc ctg acc cgg gac ggc ggc tct acc aac agc acc acc gaa acc<br>Leu Ile Leu Thr Arg Asp Gly Gly Ser Thr Asn Ser Thr Thr Glu Thr<br>445 450 455 | 1397 |
| ttc aga ccc ggc gga ggc gac atg aga gac aac tgg cgg agc gag ctg<br>Phe Arg Pro Gly Gly Gly Asp Met Arg Asp Asn Trp Arg Ser Glu Leu<br>460 465 470 475 | 1445 |
| tac aag tac aaa gtg gtg aaa atc gag ccc ctg ggc gtg gcc ccc acc<br>Tyr Lys Tyr Lys Val Val Lys Ile Glu Pro Leu Gly Val Ala Pro Thr<br>480 485 490 | 1493 |
| aga gcc aag aga aga gtg gtc gga agc gag aag tcc gcc gtg ggc atc<br>Arg Ala Lys Arg Arg Val Val Gly Ser Glu Lys Ser Ala Val Gly Ile<br>495 500 505 | 1541 |
| ggc gcc gtg ttt ctg gga ttc ctg ggc gct gcc ggc tct aca atg gga<br>Gly Ala Val Phe Leu Gly Phe Leu Gly Ala Ala Gly Ser Thr Met Gly<br>510 515 520 | 1589 |
| gcc gcc agc atg aca ctg acc gtg cag gcc aga aac ctg ctg tcc ggc<br>Ala Ala Ser Met Thr Leu Thr Val Gln Ala Arg Asn Leu Leu Ser Gly<br>525 530 535 | 1637 |
| atc gtg cag cag cag agc aac ctg ctg aga gcc atc gag gcc cag cag<br>Ile Val Gln Gln Gln Ser Asn Leu Leu Arg Ala Ile Glu Ala Gln Gln<br>540 545 550 555 | 1685 |
| cat ctc ctc aaa ctc aca gtc tgg ggc atc aag cag ctg cag gcc agg<br>His Leu Leu Lys Leu Thr Val Trp Gly Ile Lys Gln Leu Gln Ala Arg<br>560 565 570 | 1733 |

```
gtg ctg gcc gtg gag aga tac ctg cgg gat cag cag ctc ctc ggc atc       1781
Val Leu Ala Val Glu Arg Tyr Leu Arg Asp Gln Gln Leu Leu Gly Ile
            575                 580                 585 tgg ggc tgc agc ggc aag ctg atc tgc acc acc aac gtg ccc tgg aac       1829
Trp Gly Cys Ser Gly Lys Leu Ile Cys Thr Thr Asn Val Pro Trp Asn
        590                 595                 600 tcc agc tgg tcc aac cgg aac ctg agc gag atc tgg gac aac atg acc       1877
Ser Ser Trp Ser Asn Arg Asn Leu Ser Glu Ile Trp Asp Asn Met Thr
605                 610                 615 tgg ctg cag tgg gac aaa gag atc agc aac tac acc cag atc atc tac       1925
Trp Leu Gln Trp Asp Lys Glu Ile Ser Asn Tyr Thr Gln Ile Ile Tyr
620                 625                 630                 635 ggc ctg ctg gaa gag agc cag aac cag cag gaa aag aac gaa cag gat       1973
Gly Leu Leu Glu Glu Ser Gln Asn Gln Gln Glu Lys Asn Glu Gln Asp
            640                 645                 650 ctc ctg gct ctc gat aag tgg gcc agc ctg tgg aat tgg ttc gac atc       2021
Leu Leu Ala Leu Asp Lys Trp Ala Ser Leu Trp Asn Trp Phe Asp Ile
        655                 660                 665 agc aac tgg ctg tgg tac atc aag ggc agc ggc cac cac cac cat cac       2069
Ser Asn Trp Leu Trp Tyr Ile Lys Gly Ser Gly His His His His His
    670                 675                 680 cac tgagcggccg cttaattaa                                              2091
His
```

```
<210> SEQ ID NO 13
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
                85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
        115                 120                 125

Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190
```

```
Ser Ala Ile Thr Gln Ala Cys Pro Lys Val Ser Phe Glu Pro Ile Pro
            195                 200                 205
Ile His Tyr Cys Ala Pro Ala Gly Phe Ala Ile Leu Lys Cys Lys Asp
    210                 215                 220
Lys Lys Phe Asn Gly Thr Gly Pro Cys Pro Ser Val Ser Thr Val Gln
225                 230                 235                 240
Cys Thr His Gly Ile Lys Pro Val Val Ser Thr Gln Leu Leu Leu Asn
                245                 250                 255
Gly Ser Leu Ala Glu Glu Glu Val Met Ile Arg Ser Glu Asn Ile Thr
            260                 265                 270
Asn Asn Ala Lys Asn Ile Leu Val Gln Phe Asn Thr Pro Val Gln Ile
        275                 280                 285
Asn Cys Thr Arg Pro Asn Asn Asn Thr Arg Lys Ser Ile Arg Ile Gly
    290                 295                 300
Pro Gly Gln Ala Phe Tyr Ala Thr Gly Asp Ile Ile Gly Asp Ile Arg
305                 310                 315                 320
Gln Ala His Cys Thr Val Ser Lys Ala Thr Trp Asn Glu Thr Leu Gly
                325                 330                 335
Lys Val Val Lys Gln Leu Arg Lys His Phe Gly Asn Asn Thr Ile Ile
            340                 345                 350
Arg Phe Ala Asn Ser Ser Gly Gly Asp Leu Glu Val Thr Thr His Ser
        355                 360                 365
Phe Asn Cys Gly Gly Glu Phe Phe Tyr Cys Asn Thr Ser Gly Leu Phe
    370                 375                 380
Asn Ser Thr Trp Ile Ser Asn Thr Ser Val Gln Gly Ser Asn Ser Thr
385                 390                 395                 400
Gly Ser Asn Asp Ser Ile Thr Leu Pro Cys Arg Ile Lys Gln Ile Ile
                405                 410                 415
Asn Met Trp Gln Arg Ile Gly Gln Ala Met Tyr Ala Pro Pro Ile Gln
            420                 425                 430
Gly Val Ile Arg Cys Val Ser Asn Ile Thr Gly Leu Ile Leu Thr Arg
        435                 440                 445
Asp Gly Gly Ser Thr Asn Ser Thr Thr Glu Thr Phe Arg Pro Gly Gly
    450                 455                 460
Gly Asp Met Arg Asp Asn Trp Arg Ser Glu Leu Tyr Lys Tyr Lys Val
465                 470                 475                 480
Val Lys Ile Glu Pro Leu Gly Val Ala Pro Thr Arg Ala Lys Arg Arg
                485                 490                 495
Val Val Gly Ser Glu Lys Ser Ala Val Gly Ile Gly Ala Val Phe Leu
            500                 505                 510
Gly Phe Leu Gly Ala Ala Gly Ser Thr Met Gly Ala Ala Ser Met Thr
        515                 520                 525
Leu Thr Val Gln Ala Arg Asn Leu Leu Ser Gly Ile Val Gln Gln Gln
    530                 535                 540
Ser Asn Leu Leu Arg Ala Ile Glu Ala Gln His Leu Leu Lys Leu
545                 550                 555                 560
Thr Val Trp Gly Ile Lys Gln Leu Gln Ala Arg Val Leu Ala Val Glu
                565                 570                 575
Arg Tyr Leu Arg Asp Gln Leu Leu Gly Ile Trp Gly Cys Ser Gly
            580                 585                 590
Lys Leu Ile Cys Thr Thr Asn Val Pro Trp Asn Ser Ser Trp Ser Asn
        595                 600                 605
Arg Asn Leu Ser Glu Ile Trp Asp Asn Met Thr Trp Leu Gln Trp Asp
```

```
                    610                 615                 620
Lys Glu Ile Ser Asn Tyr Thr Gln Ile Ile Tyr Gly Leu Leu Glu Glu
625                 630                 635                 640

Ser Gln Asn Gln Gln Glu Lys Asn Glu Gln Asp Leu Leu Ala Leu Asp
                645                 650                 655

Lys Trp Ala Ser Leu Trp Asn Trp Phe Asp Ile Ser Asn Trp Leu Trp
                660                 665                 670

Tyr Ile Lys Gly Ser Gly His His His His His His
            675                 680

<210> SEQ ID NO 14
<211> LENGTH: 2193
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (21)..(2174)

<400> SEQUENCE: 14
ggcgcgccga attcgccacc atg ccc atg gga tcc ctg cag cct ctg gcc aca        53
                      Met Pro Met Gly Ser Leu Gln Pro Leu Ala Thr
                      1               5                   10 ctg tat ctg ctg ggc atg ctg gtg gcc tct gtg ctg gcc gct ggc aat         101
Leu Tyr Leu Leu Gly Met Leu Val Ala Ser Val Leu Ala Ala Gly Asn
            15                  20                  25 ctg tgg gtc acc gtg tac tac ggc gtg ccc gtg tgg aag gac gcc gag         149
Leu Trp Val Thr Val Tyr Tyr Gly Val Pro Val Trp Lys Asp Ala Glu
        30                  35                  40 aca acc ctg ttc tgc gcc agc gac gcc aag gcc tac gag aca gag aag         197
Thr Thr Leu Phe Cys Ala Ser Asp Ala Lys Ala Tyr Glu Thr Glu Lys
    45                  50                  55 cac aac gtg tgg gcc acc cac gcc tgc gtg cca acc gac cct aac ccc         245
His Asn Val Trp Ala Thr His Ala Cys Val Pro Thr Asp Pro Asn Pro
60                  65                  70                  75 cag gaa atc cac ctg gaa aac gtg acc gaa gag ttc aac atg tgg aag         293
Gln Glu Ile His Leu Glu Asn Val Thr Glu Glu Phe Asn Met Trp Lys
                80                  85                  90 aac aac atg gtg gaa cag atg cac acc gac atc atc agc ctg tgg gac         341
Asn Asn Met Val Glu Gln Met His Thr Asp Ile Ile Ser Leu Trp Asp
            95                  100                 105 cag agc ctg aag ccc tgc gtg aag ctg acc ccc ctg tgc gtg acc ctg         389
Gln Ser Leu Lys Pro Cys Val Lys Leu Thr Pro Leu Cys Val Thr Leu
        110                 115                 120 cag tgc acc aac gtg acc aac aac atc acc gac gac atg cgg ggc gag         437
Gln Cys Thr Asn Val Thr Asn Asn Ile Thr Asp Asp Met Arg Gly Glu
    125                 130                 135 ctg aag aac tgc agc ttc aac atg acc acc gag ctg cgg gac aag aaa         485
Leu Lys Asn Cys Ser Phe Asn Met Thr Thr Glu Leu Arg Asp Lys Lys
140                 145                 150                 155 cag aag gtg tac agc ctg ttc tac cgg ctg gac gtg gtg cag atc aac         533
Gln Lys Val Tyr Ser Leu Phe Tyr Arg Leu Asp Val Val Gln Ile Asn
                160                 165                 170 gag aac cag ggc aac aga agc aac aac agc aac aaa gag tac cgg ctg         581
Glu Asn Gln Gly Asn Arg Ser Asn Asn Ser Asn Lys Glu Tyr Arg Leu
            175                 180                 185 atc aac tgc aac acc agc gcc atc acc cag gcc tgc ccc aag gtg tcc         629
Ile Asn Cys Asn Thr Ser Ala Ile Thr Gln Ala Cys Pro Lys Val Ser
        190                 195                 200
```

-continued

| | | |
|---|---|---|
| ttc gag ccc atc ccc atc cac tac tgc gcc cct gcc ggc ttc gcc atc<br>Phe Glu Pro Ile Pro Ile His Tyr Cys Ala Pro Ala Gly Phe Ala Ile<br>205                     210                     215 | 677 |
| ctg aag tgc aag gac aag aag ttc aac ggc acc ggc ccc tgc ccc agc<br>Leu Lys Cys Lys Asp Lys Lys Phe Asn Gly Thr Gly Pro Cys Pro Ser<br>220                     225                     230                 235 | 725 |
| gtg tcc aca gtg cag tgt acc cac ggc atc aag ccc gtg gtg tcc acc<br>Val Ser Thr Val Gln Cys Thr His Gly Ile Lys Pro Val Val Ser Thr<br>                   240                     245                     250 | 773 |
| cag ctg ctg ctg aac ggc agc ctg gcc gaa gag gaa gtg atg atc aga<br>Gln Leu Leu Leu Asn Gly Ser Leu Ala Glu Glu Glu Val Met Ile Arg<br>             255                     260                     265 | 821 |
| agc gag aac atc acc aac aac gcc aag aac atc ctg gtg cag ttc aac<br>Ser Glu Asn Ile Thr Asn Asn Ala Lys Asn Ile Leu Val Gln Phe Asn<br>             270                     275                     280 | 869 |
| acc ccc gtg cag att aac tgc acc cgg ccc aac aac aac acc aga aag<br>Thr Pro Val Gln Ile Asn Cys Thr Arg Pro Asn Asn Asn Thr Arg Lys<br>285                     290                     295 | 917 |
| agc atc cgg atc ggc cca ggc cag gcc ttc tac gcc acc ggc gac atc<br>Ser Ile Arg Ile Gly Pro Gly Gln Ala Phe Tyr Ala Thr Gly Asp Ile<br>300                     305                     310                 315 | 965 |
| atc ggc gac atc cgg cag gcc cac tgc acc gtg tcc aag gcc acc tgg<br>Ile Gly Asp Ile Arg Gln Ala His Cys Thr Val Ser Lys Ala Thr Trp<br>                   320                     325                     330 | 1013 |
| aac gag aca ctg ggc aag gtg gtg aaa cag ctg cgg aag cac ttc ggg<br>Asn Glu Thr Leu Gly Lys Val Val Lys Gln Leu Arg Lys His Phe Gly<br>             335                     340                     345 | 1061 |
| aac aac acc atc atc cgc ttc gcc aac agc tct ggc ggc gac ctg gaa<br>Asn Asn Thr Ile Ile Arg Phe Ala Asn Ser Ser Gly Gly Asp Leu Glu<br>                   350                     355                     360 | 1109 |
| gtg acc acc cac agc ttc aac tgt ggc ggc gag ttc ttc tac tgc aat<br>Val Thr Thr His Ser Phe Asn Cys Gly Gly Glu Phe Phe Tyr Cys Asn<br>      365                     370                     375 | 1157 |
| acc tcc ggc ctg ttc aac agc acc tgg atc agc aat acc agc gtg cag<br>Thr Ser Gly Leu Phe Asn Ser Thr Trp Ile Ser Asn Thr Ser Val Gln<br>380                     385                     390                     395 | 1205 |
| ggc agc aac agc acc ggc agc aac gac agc atc acc ctg ccc tgc cgg<br>Gly Ser Asn Ser Thr Gly Ser Asn Asp Ser Ile Thr Leu Pro Cys Arg<br>                   400                     405                     410 | 1253 |
| atc aag cag atc atc aat atg tgg cag cgg att ggc cag gct atg tac<br>Ile Lys Gln Ile Ile Asn Met Trp Gln Arg Ile Gly Gln Ala Met Tyr<br>             415                     420                     425 | 1301 |
| gcc cca ccc atc cag ggc gtg atc aga tgc gtg tcc aat atc acc ggc<br>Ala Pro Pro Ile Gln Gly Val Ile Arg Cys Val Ser Asn Ile Thr Gly<br>                   430                     435                     440 | 1349 |
| ctg atc ctg acc cgg gac ggc ggc tct acc aac agc acc acc gaa acc<br>Leu Ile Leu Thr Arg Asp Gly Gly Ser Thr Asn Ser Thr Thr Glu Thr<br>445                     450                     455 | 1397 |
| ttc aga ccc ggc gga ggc gac atg aga gac aac tgg cgg agc gag ctg<br>Phe Arg Pro Gly Gly Gly Asp Met Arg Asp Asn Trp Arg Ser Glu Leu<br>460                     465                     470                     475 | 1445 |
| tac aag tac aaa gtg gtg aaa atc gag ccc ctg ggc gtg gcc ccc acc<br>Tyr Lys Tyr Lys Val Val Lys Ile Glu Pro Leu Gly Val Ala Pro Thr<br>                   480                     485                     490 | 1493 |
| aga gcc aag aga aga gtg gtc gga agc gag aag tcc gcc gtg gga atc<br>Arg Ala Lys Arg Arg Val Val Gly Ser Glu Lys Ser Ala Val Gly Ile<br>             495                     500                     505 | 1541 |
| ggc gcc gtg ttt ctg gga ttc ctg ggc gct gcc ggc tct aca atg gga<br>Gly Ala Val Phe Leu Gly Phe Leu Gly Ala Ala Gly Ser Thr Met Gly | 1589 |

```
                510                 515                 520
gcc gcc agc atg aca ctg acc gtg cag gcc aga aac ctg ctg tcc ggc    1637
Ala Ala Ser Met Thr Leu Thr Val Gln Ala Arg Asn Leu Leu Ser Gly
        525                 530                 535 atc gtg cag cag cag agc aac ctg ctg aga gcc atc gag gcc cag cag    1685
Ile Val Gln Gln Gln Ser Asn Leu Leu Arg Ala Ile Glu Ala Gln Gln
540                 545                 550                 555 cat ctc ctc aaa ctc aca gtc tgg ggc atc aag cag ctg cag gcc agg    1733
His Leu Leu Lys Leu Thr Val Trp Gly Ile Lys Gln Leu Gln Ala Arg
                560                 565                 570 gtg ctg gcc gtg gag aga tac ctg cgg gat cag cag ctc ctc ggc atc    1781
Val Leu Ala Val Glu Arg Tyr Leu Arg Asp Gln Gln Leu Leu Gly Ile
            575                 580                 585 tgg ggc tgc agc ggc aag ctg atc tgc acc acc aac gtg ccc tgg aac    1829
Trp Gly Cys Ser Gly Lys Leu Ile Cys Thr Thr Asn Val Pro Trp Asn
        590                 595                 600 tcc agc tgg tcc aac cgg aac ctg agc gag atc tgg gac aat atg acc    1877
Ser Ser Trp Ser Asn Arg Asn Leu Ser Glu Ile Trp Asp Asn Met Thr
605                 610                 615 tgg ctg cag tgg gac aaa gag atc agc aac tac acc cag atc atc tac    1925
Trp Leu Gln Trp Asp Lys Glu Ile Ser Asn Tyr Thr Gln Ile Ile Tyr
620                 625                 630                 635 ggc ctg ctg gaa gag agc cag aac cag cag gaa aag aac gag cag gac    1973
Gly Leu Leu Glu Glu Ser Gln Asn Gln Gln Glu Lys Asn Glu Gln Asp
                640                 645                 650 ctg ctg gcc ctg gac aag tgg gcc tcc ctg tgg aat tgg ttc gac atc    2021
Leu Leu Ala Leu Asp Lys Trp Ala Ser Leu Trp Asn Trp Phe Asp Ile
            655                 660                 665 tcc aac tgg ctg tgg tac atc aag ggc agc ggc ggc atg aag cag atc    2069
Ser Asn Trp Leu Trp Tyr Ile Lys Gly Ser Gly Gly Met Lys Gln Ile
        670                 675                 680 gag gac aag atc gaa gag atc gag tct aag atc aag aag att gag aac    2117
Glu Asp Lys Ile Glu Glu Ile Glu Ser Lys Ile Lys Lys Ile Glu Asn
685                 690                 695 gag atc gcc cgc atc aag aaa ctg atc ggc gag agc ggc cac cac cac    2165
Glu Ile Ala Arg Ile Lys Lys Leu Ile Gly Glu Ser Gly His His His
                700                 705                 710                 715 cat cac cat tgagcggccg cttaattaa                                   2193
His His His <210> SEQ ID NO 15
<211> LENGTH: 718
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
                20                  25                  30

Tyr Tyr Gly Val Pro Val Trp Lys Asp Ala Glu Thr Thr Leu Phe Cys
            35                  40                  45

Ala Ser Asp Ala Lys Ala Tyr Glu Thr Glu Lys His Asn Val Trp Ala
        50                  55                  60

Thr His Ala Cys Val Pro Thr Asp Pro Asn Pro Gln Glu Ile His Leu
65                  70                  75                  80
```

-continued

```
Glu Asn Val Thr Glu Phe Asn Met Trp Lys Asn Asn Met Val Glu
             85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
            115                 120                 125

Thr Asn Asn Ile Thr Asp Asp Met Arg Gly Glu Leu Lys Asn Cys Ser
130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190

Ser Ala Ile Thr Gln Ala Cys Pro Lys Val Ser Phe Glu Pro Ile Pro
            195                 200                 205

Ile His Tyr Cys Ala Pro Ala Gly Phe Ala Ile Leu Lys Cys Lys Asp
            210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Val Met Ile Arg Ser Glu Asn Ile Thr
            260                 265                 270

Asn Asn Ala Lys Asn Ile Leu Val Gln Phe Asn Thr Pro Val Gln Ile
            275                 280                 285

Asn Cys Thr Arg Pro Asn Asn Asn Thr Arg Lys Ser Ile Arg Ile Gly
            290                 295                 300

Pro Gly Gln Ala Phe Tyr Ala Thr Gly Asp Ile Ile Gly Asp Ile Arg
305                 310                 315                 320

Gln Ala His Cys Thr Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
            355                 360                 365

Phe Asn Cys Gly Gly Glu Phe Phe Tyr Cys Asn Thr Ser Gly Leu Phe
            370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415

Asn Met Trp Gln Arg Ile Gly Gln Ala Met Tyr Ala Pro Pro Ile Gln
            420                 425                 430

Gly Val Ile Arg Cys Val Ser Asn Ile Thr Gly Leu Ile Leu Thr Arg
            435                 440                 445

Asp Gly Gly Ser Thr Asn Ser Thr Thr Glu Thr Phe Arg Pro Gly Gly
450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Arg Arg
                485                 490                 495

Val Val Gly Ser Glu Lys Ser Ala Val Gly Ile Gly Ala Val Phe Leu
```

```
                      500                 505                 510
Gly Phe Leu Gly Ala Ala Gly Ser Thr Met Gly Ala Ala Ser Met Thr
            515                 520                 525

Leu Thr Val Gln Ala Arg Asn Leu Leu Ser Gly Ile Val Gln Gln Gln
        530                 535                 540

Ser Asn Leu Leu Arg Ala Ile Glu Ala Gln Gln His Leu Leu Lys Leu
545                 550                 555                 560

Thr Val Trp Gly Ile Lys Gln Leu Gln Ala Arg Val Leu Ala Val Glu
                565                 570                 575

Arg Tyr Leu Arg Asp Gln Gln Leu Leu Gly Ile Trp Gly Cys Ser Gly
            580                 585                 590

Lys Leu Ile Cys Thr Thr Asn Val Pro Trp Asn Ser Ser Trp Ser Asn
        595                 600                 605

Arg Asn Leu Ser Glu Ile Trp Asp Asn Met Thr Trp Leu Gln Trp Asp
610                 615                 620

Lys Glu Ile Ser Asn Tyr Thr Gln Ile Ile Tyr Gly Leu Leu Glu Glu
625                 630                 635                 640

Ser Gln Asn Gln Gln Glu Lys Asn Glu Gln Asp Leu Leu Ala Leu Asp
                645                 650                 655

Lys Trp Ala Ser Leu Trp Asn Trp Phe Asp Ile Ser Asn Trp Leu Trp
            660                 665                 670

Tyr Ile Lys Gly Ser Gly Gly Met Lys Gln Ile Glu Asp Lys Ile Glu
        675                 680                 685

Glu Ile Glu Ser Lys Ile Lys Lys Ile Glu Asn Glu Ile Ala Arg Ile
690                 695                 700

Lys Lys Leu Ile Gly Glu Ser Gly His His His His His His
705                 710                 715

<210> SEQ ID NO 16
<211> LENGTH: 2154
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (21)..(2135)

<400> SEQUENCE: 16
ggcgcgccga attcgccacc atg ccc atg gga tcc ctg cag cct ctg gcc aca       53
                      Met Pro Met Gly Ser Leu Gln Pro Leu Ala Thr
                       1               5                  10 ctg tat ctg ctg ggc atg ctg gtg gcc tct gtg ctg gcc gct ggc aat       101
Leu Tyr Leu Leu Gly Met Leu Val Ala Ser Val Leu Ala Ala Gly Asn
         15                  20                  25 ctg tgg gtc acc gtg tac tac ggc gtg ccc gtg tgg aag gac gcc gag       149
Leu Trp Val Thr Val Tyr Tyr Gly Val Pro Val Trp Lys Asp Ala Glu
     30                  35                  40 aca acc ctg ttc tgc gcc agc gac gcc aag gcc tac gag aca gag aag       197
Thr Thr Leu Phe Cys Ala Ser Asp Ala Lys Ala Tyr Glu Thr Glu Lys
 45                  50                  55 cac aac gtg tgg gcc acc cac gcc tgc gtg cca acc gac cct aac ccc       245
His Asn Val Trp Ala Thr His Ala Cys Val Pro Thr Asp Pro Asn Pro
 60                  65                  70                  75 cag gaa atc cac ctg gaa aac gtg acc gaa gag ttc aac atg tgg aag       293
Gln Glu Ile His Leu Glu Asn Val Thr Glu Glu Phe Asn Met Trp Lys
                 80                  85                  90
```

```
                                         -continued
aac aac atg gtg gaa cag atg cac acc gac atc atc agc ctg tgg gac      341
Asn Asn Met Val Glu Gln Met His Thr Asp Ile Ile Ser Leu Trp Asp
            95                  100                 105 cag agc ctg aag ccc tgc gtg aag ctg acc ccc ctg tgc gtg acc ctg      389
Gln Ser Leu Lys Pro Cys Val Lys Leu Thr Pro Leu Cys Val Thr Leu
        110                 115                 120 cag tgc acc aac gtg acc aac aac atc acc gac gac atg cgg ggc gag      437
Gln Cys Thr Asn Val Thr Asn Asn Ile Thr Asp Asp Met Arg Gly Glu
    125                 130                 135 ctg aag aac tgc agc ttc aac atg acc acc gag ctg cgg gac aag aaa      485
Leu Lys Asn Cys Ser Phe Asn Met Thr Thr Glu Leu Arg Asp Lys Lys
140                 145                 150                 155 cag aag gtg tac agc ctg ttc tac cgg ctg gac gtg gtg cag atc aac      533
Gln Lys Val Tyr Ser Leu Phe Tyr Arg Leu Asp Val Val Gln Ile Asn
            160                 165                 170 gag aac cag ggc aac aga agc aac aac agc aac aaa gag tac cgg ctg      581
Glu Asn Gln Gly Asn Arg Ser Asn Asn Ser Asn Lys Glu Tyr Arg Leu
        175                 180                 185 atc aac tgc aac acc agc gcc atc acc cag gcc tgc ccc aag gtg tcc      629
Ile Asn Cys Asn Thr Ser Ala Ile Thr Gln Ala Cys Pro Lys Val Ser
    190                 195                 200 ttc gag ccc atc ccc atc cac tac tgc gcc cct gcc ggc ttc gcc atc      677
Phe Glu Pro Ile Pro Ile His Tyr Cys Ala Pro Ala Gly Phe Ala Ile
205                 210                 215 ctg aag tgc aag gac aag aag ttc aac ggc acc ggc ccc tgc ccc agc      725
Leu Lys Cys Lys Asp Lys Lys Phe Asn Gly Thr Gly Pro Cys Pro Ser
220                 225                 230                 235 gtg tcc aca gtg cag tgt acc cac ggc atc aag ccc gtg gtg tcc acc      773
Val Ser Thr Val Gln Cys Thr His Gly Ile Lys Pro Val Val Ser Thr
            240                 245                 250 cag ctg ctg ctg aac ggc agc ctg gcc gaa gag gaa gtg atg atc aga      821
Gln Leu Leu Leu Asn Gly Ser Leu Ala Glu Glu Glu Val Met Ile Arg
        255                 260                 265 agc gag aac atc acc aac aac gcc aag aac atc ctg gtg cag ttc aac      869
Ser Glu Asn Ile Thr Asn Asn Ala Lys Asn Ile Leu Val Gln Phe Asn
    270                 275                 280 acc ccc gtg cag att aac tgc acc cgg ccc aac aac aac acc aga aag      917
Thr Pro Val Gln Ile Asn Cys Thr Arg Pro Asn Asn Asn Thr Arg Lys
285                 290                 295 agc atc cgg atc ggc cca ggc cag gcc ttc tac gcc acc ggc gac atc      965
Ser Ile Arg Ile Gly Pro Gly Gln Ala Phe Tyr Ala Thr Gly Asp Ile
300                 305                 310                 315 atc ggc gac atc cgg cag gcc cac tgc acc gtg tcc aag gcc acc tgg     1013
Ile Gly Asp Ile Arg Gln Ala His Cys Thr Val Ser Lys Ala Thr Trp
            320                 325                 330 aac gag aca ctg ggc aag gtg gtg aaa cag ctg cgg aag cac ttc ggg     1061
Asn Glu Thr Leu Gly Lys Val Val Lys Gln Leu Arg Lys His Phe Gly
        335                 340                 345 aac aac acc atc atc cgc ttc gcc aac agc tct ggc ggc gac ctg gaa     1109
Asn Asn Thr Ile Ile Arg Phe Ala Asn Ser Ser Gly Gly Asp Leu Glu
    350                 355                 360 gtg acc acc cac agc ttc aac tgt ggc ggc gag ttc ttc tac tgc aat     1157
Val Thr Thr His Ser Phe Asn Cys Gly Gly Glu Phe Phe Tyr Cys Asn
365                 370                 375 acc tcc ggc ctg ttc aac agc acc tgg atc agc aat acc agc gtg cag     1205
Thr Ser Gly Leu Phe Asn Ser Thr Trp Ile Ser Asn Thr Ser Val Gln
380                 385                 390                 395 ggc agc aac agc acc ggc agc aac gac agc atc acc ctg ccc tgc cgg     1253
Gly Ser Asn Ser Thr Gly Ser Asn Asp Ser Ile Thr Leu Pro Cys Arg
            400                 405                 410
```

```
atc aag cag atc atc aat atg tgg cag cgg att ggc cag gct atg tac    1301
Ile Lys Gln Ile Ile Asn Met Trp Gln Arg Ile Gly Gln Ala Met Tyr
            415                 420                 425 gcc cca ccc atc cag ggc gtg atc aga tgc gtg tcc aat atc acc ggc    1349
Ala Pro Pro Ile Gln Gly Val Ile Arg Cys Val Ser Asn Ile Thr Gly
        430                 435                 440 ctg atc ctg acc cgg gac ggc ggc tct acc aac agc acc acc gaa acc    1397
Leu Ile Leu Thr Arg Asp Gly Gly Ser Thr Asn Ser Thr Thr Glu Thr
    445                 450                 455 ttc aga ccc ggc gga ggc gac atg aga gac aac tgg cgg agc gag ctg    1445
Phe Arg Pro Gly Gly Gly Asp Met Arg Asp Asn Trp Arg Ser Glu Leu
460                 465                 470                 475 tac aag tac aaa gtg gtg aaa atc gag ccc ctg ggc gtg gcc ccc acc    1493
Tyr Lys Tyr Lys Val Val Lys Ile Glu Pro Leu Gly Val Ala Pro Thr
                480                 485                 490 aga gcc aag aga aga gtg gtc gga cgc gag aag cgg gcc gtg gga att    1541
Arg Ala Lys Arg Arg Val Val Gly Arg Glu Lys Arg Ala Val Gly Ile
            495                 500                 505 gga gcc gtg ttt ctg gga ttc ctg ggc gct gcc ggc tct aca atg gga    1589
Gly Ala Val Phe Leu Gly Phe Leu Gly Ala Ala Gly Ser Thr Met Gly
        510                 515                 520 gcc gcc agc atg aca ctg acc gtg cag gcc aga aac ctg ctg tcc ggc    1637
Ala Ala Ser Met Thr Leu Thr Val Gln Ala Arg Asn Leu Leu Ser Gly
    525                 530                 535 atc gtg cag cag cag agc aac ctg ctg aga gcc atc gag gcc cag cag    1685
Ile Val Gln Gln Gln Ser Asn Leu Leu Arg Ala Ile Glu Ala Gln Gln
540                 545                 550                 555 cat ctc ctc aaa ctc aca gtc tgg ggc atc aag cag ctg cag gcc agg    1733
His Leu Leu Lys Leu Thr Val Trp Gly Ile Lys Gln Leu Gln Ala Arg
                560                 565                 570 gtg ctg gcc gtg gag aga tac ctg cgg gat cag cag ctc ctc ggc atc    1781
Val Leu Ala Val Glu Arg Tyr Leu Arg Asp Gln Gln Leu Leu Gly Ile
            575                 580                 585 tgg ggc tgc agc ggc aag ctg atc tgc acc acc aac gtg ccc tgg aac    1829
Trp Gly Cys Ser Gly Lys Leu Ile Cys Thr Thr Asn Val Pro Trp Asn
        590                 595                 600 tcc agc tgg tcc aac cgg aac ctg agc gag atc tgg gac aat atg acc    1877
Ser Ser Trp Ser Asn Arg Asn Leu Ser Glu Ile Trp Asp Asn Met Thr
    605                 610                 615 tgg ctg cag tgg gac aaa gag atc agc aac tac acc cag atc atc tac    1925
Trp Leu Gln Trp Asp Lys Glu Ile Ser Asn Tyr Thr Gln Ile Ile Tyr
620                 625                 630                 635 ggc ctg ctg gaa gag agc cag aac cag cag gaa aag aac gag cag gac    1973
Gly Leu Leu Glu Glu Ser Gln Asn Gln Gln Glu Lys Asn Glu Gln Asp
                640                 645                 650 ctg ctg gcc ctg gac aag tgg gcc tcc ctg tgg aat tgg ttc gac atc    2021
Leu Leu Ala Leu Asp Lys Trp Ala Ser Leu Trp Asn Trp Phe Asp Ile
            655                 660                 665 tcc aac tgg ctg tgg tac atc aag atc ttc atc atg atc gtg ggc gga    2069
Ser Asn Trp Leu Trp Tyr Ile Lys Ile Phe Ile Met Ile Val Gly Gly
        670                 675                 680 ctg atc ggc ctg cgg atc gtg ttt gcc gtg ctg agc gtg atc tcc ggc    2117
Leu Ile Gly Leu Arg Ile Val Phe Ala Val Leu Ser Val Ile Ser Gly
    685                 690                 695 cac cac cac cat cac cac tgagcggccg cttaattaa                       2154
His His His His His His
700                 705
```

<210> SEQ ID NO 17

<211> LENGTH: 705
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
                85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
        115                 120                 125

Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190

Ser Ala Ile Thr Gln Ala Cys Pro Lys Val Ser Phe Glu Pro Ile Pro
        195                 200                 205

Ile His Tyr Cys Ala Pro Ala Gly Phe Ala Ile Leu Lys Cys Lys Asp
    210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Val Met Ile Arg Ser Glu Asn Ile Thr
            260                 265                 270

Asn Asn Ala Lys Asn Ile Leu Val Gln Phe Asn Thr Pro Val Gln Ile
        275                 280                 285

Asn Cys Thr Arg Pro Asn Asn Asn Thr Arg Lys Ser Ile Arg Ile Gly
    290                 295                 300

Pro Gly Gln Ala Phe Tyr Ala Thr Gly Asp Ile Ile Gly Asp Ile Arg
305                 310                 315                 320

Gln Ala His Cys Thr Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
        355                 360                 365

Phe Asn Cys Gly Gly Glu Phe Phe Tyr Cys Asn Thr Ser Gly Leu Phe
```

```
                370             375             380
Asn Ser Thr Trp Ile Ser Asn Thr Ser Val Gln Gly Ser Asn Ser Thr
385                 390                 395                 400
Gly Ser Asn Asp Ser Ile Thr Leu Pro Cys Arg Ile Lys Gln Ile Ile
                405                 410                 415
Asn Met Trp Gln Arg Ile Gly Gln Ala Met Tyr Ala Pro Pro Ile Gln
                420                 425                 430
Gly Val Ile Arg Cys Val Ser Asn Ile Thr Gly Leu Ile Leu Thr Arg
                435                 440                 445
Asp Gly Gly Ser Thr Asn Ser Thr Thr Glu Thr Phe Arg Pro Gly Gly
                450                 455                 460
Gly Asp Met Arg Asp Asn Trp Arg Ser Glu Leu Tyr Lys Tyr Lys Val
465                 470                 475                 480
Val Lys Ile Glu Pro Leu Gly Val Ala Pro Thr Arg Ala Lys Arg Arg
                485                 490                 495
Val Val Gly Arg Glu Lys Arg Ala Val Gly Ile Gly Ala Val Phe Leu
                500                 505                 510
Gly Phe Leu Gly Ala Ala Gly Ser Thr Met Gly Ala Ala Ser Met Thr
                515                 520                 525
Leu Thr Val Gln Ala Arg Asn Leu Leu Ser Gly Ile Val Gln Gln Gln
                530                 535                 540
Ser Asn Leu Leu Arg Ala Ile Glu Ala Gln Gln His Leu Leu Lys Leu
545                 550                 555                 560
Thr Val Trp Gly Ile Lys Gln Leu Gln Ala Arg Val Leu Ala Val Glu
                565                 570                 575
Arg Tyr Leu Arg Asp Gln Gln Leu Leu Gly Ile Trp Gly Cys Ser Gly
                580                 585                 590
Lys Leu Ile Cys Thr Thr Asn Val Pro Trp Asn Ser Ser Trp Ser Asn
                595                 600                 605
Arg Asn Leu Ser Glu Ile Trp Asp Asn Met Thr Trp Leu Gln Trp Asp
                610                 615                 620
Lys Glu Ile Ser Asn Tyr Thr Gln Ile Ile Tyr Gly Leu Leu Glu Glu
625                 630                 635                 640
Ser Gln Asn Gln Gln Glu Lys Asn Glu Gln Asp Leu Leu Ala Leu Asp
                645                 650                 655
Lys Trp Ala Ser Leu Trp Asn Trp Phe Asp Ile Ser Asn Trp Leu Trp
                660                 665                 670
Tyr Ile Lys Ile Phe Ile Met Ile Val Gly Gly Leu Ile Gly Leu Arg
                675                 680                 685
Ile Val Phe Ala Val Leu Ser Val Ile Ser Gly His His His His
                690                 695                 700
His
705
```

UNITED STATES PATENT AND TRADEMARK OFFICE
CERTIFICATE OF CORRECTION

PATENT NO. : 9,738,688 B2
APPLICATION NO. : 14/072209
DATED : August 22, 2017
INVENTOR(S) : Michael Caulfield et al.

It is certified that error appears in the above-identified patent and that said Letters Patent is hereby corrected as shown below:

On the Title Page

Item (54) and in the Specification, Column 1, Line 1, please correct the title to read:
--NOVEL HIV-1 ENVELOPE GLYCOPROTEIN--

Signed and Sealed this
Third Day of April, 2018

Andrei Iancu
*Director of the United States Patent and Trademark Office*